United States Patent
Yohn et al.

(10) Patent No.: US 9,428,779 B2
(45) Date of Patent: Aug. 30, 2016

(54) TRANSFORMATION OF ALGAE FOR INCREASING LIPID PRODUCTION

(75) Inventors: Christopher Yohn, San Diego, CA (US); April Brand, San Diego, CA (US); Michael Mendez, San Diego, CA (US); Craig A. Behnke, San Diego, CA (US)

(73) Assignee: SAPPHIRE ENERGY, INC., San Diego, CA (US)

( * ) Notice: Subject to any disclaimer, the term of this patent is extended or adjusted under 35 U.S.C. 154(b) by 738 days.

(21) Appl. No.: 13/576,821

(22) PCT Filed: Feb. 1, 2011

(86) PCT No.: PCT/US2011/023406
§ 371 (c)(1),
(2), (4) Date: Sep. 5, 2012

(87) PCT Pub. No.: WO2011/097261
PCT Pub. Date: Aug. 11, 2011

(65) Prior Publication Data
US 2012/0322157 A1    Dec. 20, 2012

Related U.S. Application Data

(60) Provisional application No. 61/301,141, filed on Feb. 3, 2010.

(51) Int. Cl.
C12P 7/64 (2006.01)
C07K 14/405 (2006.01)
C12N 15/82 (2006.01)

(52) U.S. Cl.
CPC ............ *C12P 7/6463* (2013.01); *C07K 14/405* (2013.01); *C12N 15/8247* (2013.01); *C12P 7/6409* (2013.01)

(58) Field of Classification Search
None
See application file for complete search history.

(56) References Cited

FOREIGN PATENT DOCUMENTS

WO    WO 2008/151149 A2    12/2008

OTHER PUBLICATIONS

However, Friedberg (Automated protein function prediction—the genomic challenge. Brief. Bioinformatics. 7:225-242, 2006).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Shigeno et al (Disease-related potential of mutations in transcriptional cofactors CREB-binding protein and p300 in leukemias. Cancer Letters 213:11-20, 2004).*
GenBank Accession No. XM_0019692667.
Merchant et al., "The Chlamydomonas Genome Reveals the Evolution of Key Animal and Plant Functions." Science, 2007, vol. 318, pp. 245-251.
Rosenberg et al., "A green light for engineered algae: redirecting metabolism to fuel a biotechnology revolution." Current Opinion in Biotechnology, 2008, vol. 19, pp. 430-436.
Bi et al., "Global transcription profiling reveals differential responses to chronic nitrogen stress and putative nitrogen regulatory components in Arabidopsis." BMC Genomics, 2007, vol. 8:281. pp. 1-17.
Hema et al., "Chlamydomonas reinhardtii, a model system for functional validation of abiotic stress responsive genes." Planta, 2007, vol. 226, pp. 655-670.
Hu et al., "Microalgal triacylglycerols as feedstocks for biofuel production: perspectives and advances." The Plant Journal, 2008, vol. 54, pp. 621-639.
Ohlrogge et al., "Lipid Biosynthesis." The Plant Cell, 1995, vol. 7, pp. 957-970.
Wang et al., "RNA-Seq: a revolutionary tool for transcriptomics." Nature Reviews/Genetics, 2009, vol. 10, pp. 57-63.

* cited by examiner

*Primary Examiner* — Medina A Ibrahim
*Assistant Examiner* — Wayne Zhong
(74) *Attorney, Agent, or Firm* — Sapphire Energy, Inc.

(57) ABSTRACT

The present disclosure provides novel proteins that when over expressed in algae result in an increase or change in fatty acid and/or glycerol lipid production and/or accumulation, without a substantial decrease in the growth rate of the alga or the break down of algal components, such as chlorophyll. The present disclosure also describes methods of using the novel proteins to increase or change the production and/or accumulation of fatty acids and/or glycerol lipids in algae. In addition, these proteins are useful tools in obtaining information about the fatty acid and triacyglyceride (TAG) synthetic pathways in algae.

25 Claims, 73 Drawing Sheets

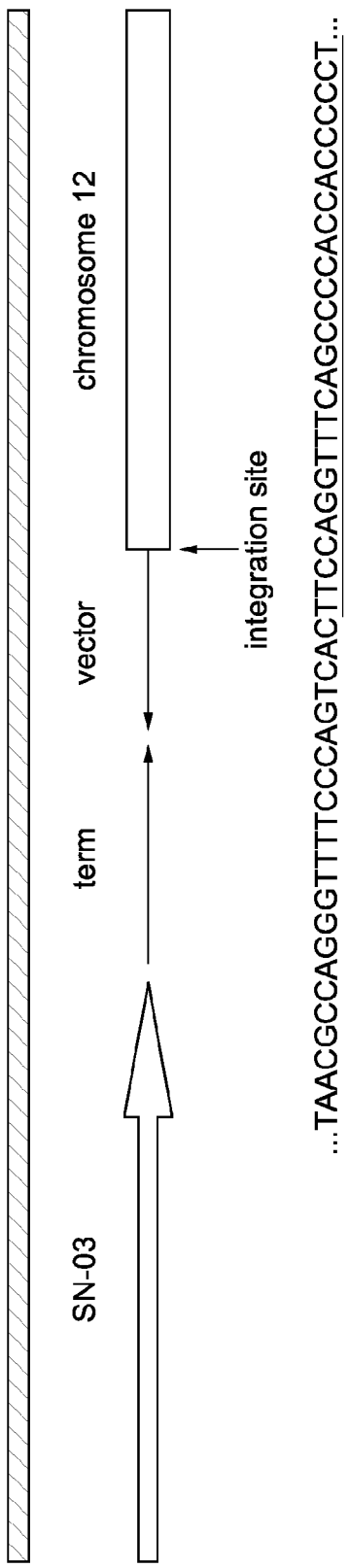
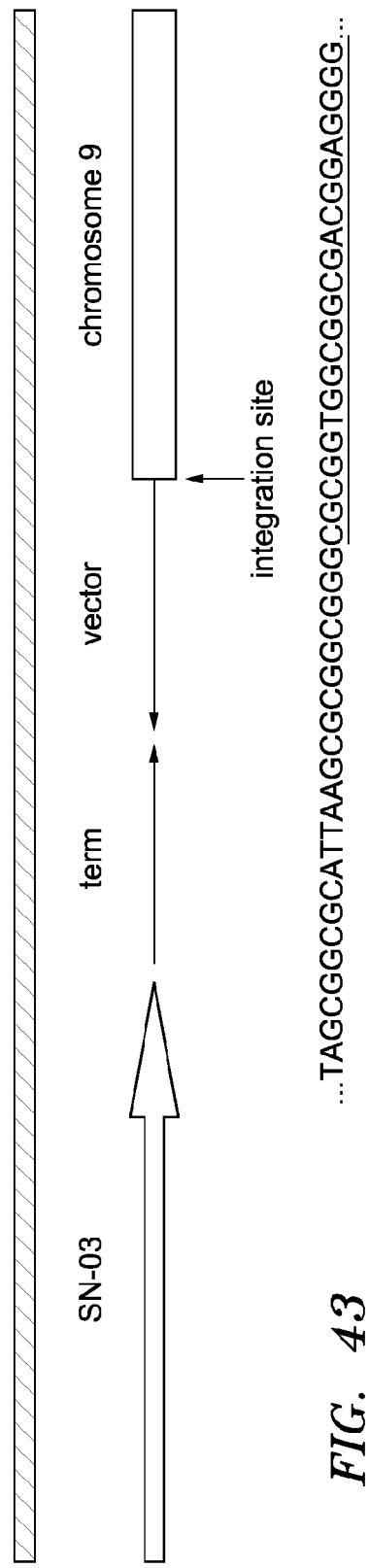
FIG. 43

```
                  10        20        30        40        50        60        70        80
                  |         |         |         |         |         |         |         |
Endo SN03   MQVYGYEVVGWEEAHAKEPKLPAADPYAPSQLVTPLDSQQQQQQQQPPPSAASKASPLGVPRHGQRTTFNVCVPLLAG   80
JGI  SN03   MQVYGYEVVGWEEAHAKEPKLPAADPYAPSQLVTPLDSQQQQQQQQPPPSAASKASPLGVPRHGQRTIFN----------   72

90       100       110       120       130       140       150       160
                  |         |         |         |         |         |         |         |
Endo SN03   GRQVLPPGTYRLPFRLQLPADLPGTFRLAGTPARTIGDVSYRNLSGEVSYGLQVEVRRPSSFASAAEQQQHQLAVLRADC  160
JGI  SN03   ---------------------------------------------VEVRRPSSFASAAEQQQHQLAVLRADC         99

170       180       190       200       210       220       230       240
                  |         |         |         |         |         |         |         |
Endo SN03   ELVIIQRAEAAQGPPAPEEHTSAGAAAARGPAAGGAEAAEAAAPVPCDEVVTLVPAFFFCCSSGGRVTVRLRPGRDGYVA  240
JGI  SN03   ELVIIQRAEAAQGPPAPEEHTSAGAAAARGPAAGGAEAAEAAAPVPCDEVVTLVPAFFFCCSSGGRVTVRLRPGRDGYVA  179

250       260       270       280       290       300       310       320
                  |         |         |         |         |         |         |         |
Endo SN03   GEAAEVVVEVDNRSNQEFRDVRLEVERRLTLVSNSAGGGSAGSSGSSGSSSSATAGLVPGCFTEEERIFKSKTTAALLPGA  320
JGI  SN03   GEAAEVVVEVDNRSNQEFRDVRLEVERRLTLVSNSAGGGSAGSSGSSGSSSSATAGLVPGCFTEEERIFKSKTT-----A  253

330       340       350       360       370       380       390       400
                  |         |         |         |         |         |         |         |
Endo SN03   CYLGANALRLPVPLPSNTPPSTSGALVRCSYTATVEVLPASATALRGAAPPRLRVPLTVFASAPSSFATAAARHAHLQQD  400
JGI  SN03   CYLGANALRLPVPLPSNTPPSTSGALVRCSYTATVEVLPASATALRGAAPPRLRVPLTVFASAPSSFATAAARHAHLQQD  333

410       420       430       440       450
                  |         |         |         |         |
Endo SN03   ASEQAPAHVLVVVPPVDVVLPAAAPQLPPTAEVNVKQHNGVAGANPMYAGP.  452
JGI  SN03   ASEQAPAHVLVVVPPVDVVLPAAAPQLPPTAEVNVKQHNGVAGANPMYAGP.  385
```

*FIG. 49*

SEQUENCE LISTING

```
<160> NUMBER OF SEQ ID NOS: 64

<210> SEQ ID NO 1
<211> LENGTH: 1155
<212> TYPE: DNA
<213> ORGANISM: Chlamydomonas reinhardtii

<400> SEQUENCE: 1
atgcaggtgt atgggtacga ggtcgtgggc tgggaggagg cgcacgcgaa ggagcccaag      60
ctcccggcgg cggacccata cgcccctagc cagctggtga caccctggga ctcacagcag     120
cagcaacagc agcagcaaca gccgccgccg ccatctgcgg cctccaaggc ttcgccactg     180
ggcgtgccca gacacggcca gcgaaccatc ttcaatgtgg aggtgcggcg tccgagcagt     240
ttcgcgtcgg cagccgaaca gcagcagcac cagttggcgg ttctgcgtgc tgattgcgag     300
ctcgtgatta tacagcgcgc ggaggcggcg cagggcccgc cagcccccga ggagcatacg     360
tcggctgggg cggcggcggc caggggccca gcagcaggcg gagctgaagc ggcggaggcg     420
gccgcgccgg tgccgtgcga tgaggtggtg accctggtgc cggccttctt cttctgctgc     480
agtagcggcg gccgcgtgac ggtgcggctg cggccggggc gggatggcta cgtggcaggc     540
gaggcggcgg aggtggtggt cgaggttgac aaccggtcga atcaggagtt tcgggatgtg     600
cggcttgaag tggagcgccg cctcacattg gtcagcaaca gcgccggcgg aggcggtagc     660
gccggcagca gcggcagcgg cagtagcagc gccaccgcgg ggcttgtgcc gggatgcttc     720
actgaagagg agcggatctt caagagcaag accacggcct gctacctggg agccaacgcg     780
ctgcggctgc cggtgcccct gccctccaac acgccgccct ccacctccgg cgcgcttgtg     840
cgctgctcct acaccgccac ggtggaggtg ctgccggcgt cggcgacagc gctgcgcggc     900
gcggcgccgc cgcggctgcg tgtgccgctg accgtgttcg catccgcgcc gagctcgttc     960
gccacggcgg cggcacggca tgctcacctg cagcaggacg caagcgagca agcgccggcg    1020
cacgtgttgg tggtggtgcc gcccgtggat gtagtgctcc ccgcagctgc gccgcagctg    1080
cctcccaccg ccgaggtaaa tgtcaaacag cacaacggcg tggctggcgc aaacccgatg    1140
```

```
tacgcgggcc cgtag                                                   1155
```

<210> SEQ ID NO 2
<211> LENGTH: 1149
<212> TYPE: DNA
<213> ORGANISM: Chlamydomonas reinhardtii

<400> SEQUENCE: 2

```
caggtgtatg ggtacgaggt cgtgggctgg gaggaggcgc acgcgaagga gcccaagctc     60
ccggcggcgg acccatacgc ccctagccag ctggtgacac ccttggactc acagcagcag    120
caacagcagc agcaacagcc gccgccgcca tctgcggcct ccaaggcttc gccactgggc    180
gtgcccagac acggccagcg aaccatcttc aatgtggagg tgcggcgtcc gagcagtttc    240
gcgtcggcag ccgaacagca gcagcaccag ttggcggttc tgcgtgctga ttgcgagctc    300
gtgattatac agcgcgcgga ggcggcgcag ggcccgccag cccccgagga gcatacgtcg    360
gctggggcgg cggcggccag gggcccagca gcaggcggag ctgaagcggc ggaggcggcc    420
gcgccggtgc cgtgcgatga ggtggtgacc ctggtgccgg ccttcttctt ctgctgcagt    480
agcggcggcc gcgtgacggt gcggctgcgg ccggggcggg atggctacgt ggcaggcgag    540
gcggcggagg tggtggtcga ggttgacaac cggtcgaatc aggagtttcg ggatgtgcgg    600
cttgaagtgg agcgccgcct cacattggtc agcaacagcg ccggcggagg cggtagcgcc    660
ggcagcagcg gcagcggcag tagcagcgcc accgcgggc ttgtgccggg atgcttcact    720
gaagaggagc ggatcttcaa gagcaagacc acggcctgct acctgggagc caacgcgctg    780
cggctgccgg tgcccctgcc ctccaacacg ccgcctcca cctccggcgc gcttgtgcgc    840
tgctcctaca ccgccacggt ggaggtgctg ccggcgtcgg cgacagcgct gcgcggcgcg    900
gcgccgccgc ggctgcgtgt gccgctgacc gtgttcgcat ccgcgccgag ctcgttcgcc    960
acggcggcgg cacggcatgc tcacctgcag caggacgcaa gcgagcaagc gccggcgcac   1020
gtgttggtgg tggtgccgcc cgtggatgta gtgctccccg cagctgcgcc gcagctgcct   1080
cccaccgccg aggtaaatgt caaacagcac aacggcgtgg ctggcgcaaa cccgatgtac   1140
gcgggcccg                                                         1149
```

<210> SEQ ID NO 3
<211> LENGTH: 1152
<212> TYPE: DNA
<213> ORGANISM: Artificial Sequence
<220> FEATURE:
<223> OTHER INFORMATION: codon optimized

<400> SEQUENCE: 3

```
atgcaagtgt atggttacga ggtggtgggt tggaggagg ctcatgctaa ggagcccaag     60
ctgcccgcgg ccgacccta cgccccatcc caactggtca ctccgctgga cagccagcag    120
cagcaacagc agcaacaaca accgccgccc cgtccgccg ccagcaaggc ctccccgctc    180
ggcgtgcctc gtcacggtca acgcacaatt ttcaacgtcg aggtccggcg tcccctcgtcc    240
ttcgcgtcgg cggcagagca acaacagcac cagctggccg tgctgcgggc ggactgcgag    300
ctcgtcatca tccagcgcgc ggaggccgcc caggcccac cagcccccga ggagcatacg    360
tccgccggtg ccgctgccgc tcgcgggcca gcggctgggg gtgctgaggc ggcggaggcg    420
gctgccccg tgccgtgcga cgaggtggtg acgctggtcc ccgccttctt tttctgctgc    480
tcgtccgggg gtcgcgtgac cgtgcgcctg cgccaggcc gcgacggtta cgtggctggc    540
gaggccgctg aggtcgtggt ggaggtggac aaccggagca accaggagtt ccgtgacgtg    600
```

```
cgcctggagg tcgagcgccg cctcacgctg gtgtcgaact cggcgggtgg cggcggctcg      660
gcggggtcct cgggctcggg cagctcgtcc gctacggccg gtctggtgcc aggctgcttc      720
acggaggagg agcggatctt caagtcgaag acgacagcgt gttacctggg cgcgaacgcc      780
ctgcgcctgc cggtccccct gcccagcaac accccgcctt ccacctcggg cgcgctggtg      840
cgttgcagct ataccgcgac cgtcgaggtg ctgccggcga gcgcgacggc gctgcgtggg      900
gccgctcccc cgcgtctccg tgtgccgctg accgtgttcg cgtccgcgcc ttcgtcgttc      960
gccaccgccg cagcccgcca cgcgcacctg caacaggacg ccagcgagca ggcaccggcc     1020
cacgtcctgg tggtggtgcc gcccgtggac gtggtgctgc cagccgccgc accccagctg     1080
cctcccaccg cggaggtgaa cgtgaagcag cacaacggcg tggcgggcgc caaccccatg     1140
tacgccggtc cc                                                         1152

<210> SEQ ID NO 4
<211> LENGTH: 1149
<212> TYPE: DNA
<213> ORGANISM: Artificial Sequence
<220> FEATURE:
<223> OTHER INFORMATION: codon optimized

<400> SEQUENCE: 4
caagtgtatg gttacgaggt ggtgggttgg gaggaggctc atgctaagga gcccaagctg       60
cccgcggccg acccctacgc cccatcccaa ctggtcactc cgctggacag ccagcagcag      120
caacagcagc aacaacaacc gccgccccg tccgccgcca gcaaggcctc cccgctcggc      180
gtgcctcgtc acggtcaacg cacaattttc aacgtcgagg tccggcgtcc ctcgtccttc      240
gcgtcggcgg cagagcaaca acagcaccag ctggccgtgc tgcgggcgga ctgcgagctc      300
gtcatcatcc agcgcgcgga ggccgcccag ggccaccag ccccgagga gcatacgtcc        360 gccggtgccg ctgccgctcg cgggccagcg gctgggggtg ctgaggcggc ggaggcggct      420
gcccccgtgc cgtgcgacga ggtggtgacg ctggtccccg ccttcttttt ctgctgctcg      480 tccggggtc gcgtgaccgt gcgcctgcgc ccaggccgcg acggttacgt ggctggcgag       540
gccgctgagg tcgtggtgga ggtggacaac cggagcaacc aggagttccg tgacgtgcgc      600
ctggaggtcg agcgccgcct cacgctggtg tcgaactcgg cgggtggcgg cggctcggcg      660
gggtcctcgg gctcgggcag ctcgtccgct acggccggtc tggtgccagg ctgcttcacg      720
gaggaggagc ggatcttcaa gtcgaagacg acagcgtgtt acctgggcgc gaacgccctg      780
cgcctgccgg tccccctgcc cagcaacacc ccgccttcca cctcgggcgc gctggtgcgt      840
tgcagctata ccgcgaccgt cgaggtgctg ccggcgagcg cgacggcgct gcgtggggcc      900
gctcccccgc gtctccgtgt gccgctgacc gtgttcgcgt ccgcgccttc gtcgttcgcc      960
accgccgcag cccgccacgc gcacctgcaa caggacgcca gcgagcaggc accggcccac     1020
gtcctggtgg tggtgccgcc cgtggacgtg gtgctgccag ccgccgcacc ccagctgcct     1080
cccaccgcgg aggtgaacgt gaagcagcac aacggcgtgg cgggcgccaa ccccatgtac     1140
gccggtccc                                                             1149

<210> SEQ ID NO 5
<211> LENGTH: 1212
<212> TYPE: DNA
<213> ORGANISM: Artificial Sequence
<220> FEATURE:
<223> OTHER INFORMATION: codon optimized
<220> FEATURE:
```

```
<221> NAME/KEY: misc_feature
<222> LOCATION: (1153)..(1158)
<223> OTHER INFORMATION: AgeI restriction site
<220> FEATURE:
<221> NAME/KEY: misc_feature
<222> LOCATION: (1159)..(1182)
<223> OTHER INFORMATION: FLAG Tag
<220> FEATURE:
<221> NAME/KEY: misc_feature
<222> LOCATION: (1183)..(1203)
<223> OTHER INFORMATION: MAT Tag
<220> FEATURE:
<221> NAME/KEY: misc_feature
<222> LOCATION: (1204)..(1209)
<223> OTHER INFORMATION: AgeI restriction site

<400> SEQUENCE: 5
atgcaagtgt atggttacga ggtggtgggt tgggaggagg ctcatgctaa ggagcccaag      60
ctgcccgcgg ccgacccta cgccccatcc caactggtca ctccgctgga cagccagcag     120
cagcaacagc agcaacaaca accgccgccc ccgtccgccg ccagcaaggc ctccccgctc     180
ggcgtgcctc gtcacggtca acgcacaatt ttcaacgtcg aggtccggcg tccctcgtcc     240
ttcgcgtcgg cggcagagca acaacagcac cagctggccg tgctgcgggc ggactgcgag     300
ctcgtcatca tccagcgcgc ggaggccgcc cagggcccac cagcccccga ggagcatacg     360
tccgccggtg ccgctgccgc tcgcgggcca gcggctgggg gtgctgaggc ggcggaggcg     420
gctgccccg tgccgtgcga cgaggtggtg acgctggtcc ccgccttctt tttctgctgc     480
tcgtccgggg gtcgcgtgac cgtgcgcctg cgcccaggcc gcgacggtta cgtggctggc     540
gaggccgctg aggtcgtggt ggaggtggac aaccggagca accaggagtt ccgtgacgtg     600
cgcctggagg tcgagcgccg cctcacgctg gtgtcgaact cggcgggtgg cggcggctcg     660
gcggggtcct cgggctcggg cagctcgtcc gctacggccg tctggtgcc aggctgcttc     720
acggaggagg agcggatctt caagtcgaag acgacagcgt gttacctggg cgcgaacgcc     780
ctgcgcctgc cggtccccct gcccagcaac accccgcctt ccacctcggg cgcgctggtg     840
cgttgcagct ataccgcgac cgtcgaggtg ctgccggcga gcgcgacggc gctgcgtggg     900
gccgctcccc cgcgtctccg tgtgccgctg accgtgttcg cgtccgcgcc ttcgtcgttc     960
gccaccgccg cagcccgcca cgcgcacctg caacaggacg ccagcgagca ggcaccggcc    1020
cacgtcctgg tggtggtgcc gcccgtggac gtggtgctgc cagccgccgc accccagctg    1080
cctcccaccg cggaggtgaa cgtgaagcag cacaacggcg tggcgggcgc caaccccatg    1140
tacgccggtc ccaccggtga ctacaaggac gacgacgaca agcacaacca ccgccataag    1200
cacaccggtt ga                                                        1212

<210> SEQ ID NO 6
<211> LENGTH: 384
<212> TYPE: PRT
<213> ORGANISM: Chlamydomonas reinhardtii

<400> SEQUENCE: 6

Met Gln Val Tyr Gly Tyr Glu Val Val Gly Trp Glu Glu Ala His Ala
1               5                   10                  15

Lys Glu Pro Lys Leu Pro Ala Ala Asp Pro Tyr Ala Pro Ser Gln Leu
            20                  25                  30

Val Thr Pro Leu Asp Ser Gln Gln Gln Gln Gln Gln Gln Gln Gln Pro
        35                  40                  45

Pro Pro Pro Ser Ala Ala Ser Lys Ala Ser Pro Leu Gly Val Pro Arg
    50                  55                  60
```

```
His Gly Gln Arg Thr Ile Phe Asn Val Glu Val Arg Arg Pro Ser Ser
 65                  70                  75                  80

Phe Ala Ser Ala Ala Glu Gln Gln His Gln Leu Ala Val Leu Arg
                 85                  90                  95

Ala Asp Cys Glu Leu Val Ile Ile Gln Arg Ala Glu Ala Gln Gly
            100                 105                 110

Pro Pro Ala Pro Glu Glu His Thr Ser Ala Gly Ala Ala Ala Arg
            115                 120                 125

Gly Pro Ala Ala Gly Gly Ala Glu Ala Glu Ala Ala Ala Pro Val
            130                 135                 140

Pro Cys Asp Glu Val Val Thr Leu Val Pro Ala Phe Phe Cys Cys
145                 150                 155                 160

Ser Ser Gly Gly Arg Val Thr Val Arg Leu Arg Pro Gly Arg Asp Gly
                165                 170                 175

Tyr Val Ala Gly Glu Ala Ala Glu Val Val Glu Val Asp Asn Arg
            180                 185                 190

Ser Asn Gln Glu Phe Arg Asp Val Arg Leu Glu Val Glu Arg Arg Leu
            195                 200                 205

Thr Leu Val Ser Asn Ser Ala Gly Gly Gly Ser Ala Gly Ser Ser
210                 215                 220

Gly Ser Gly Ser Ser Ala Thr Ala Gly Leu Val Pro Gly Cys Phe
225                 230                 235                 240

Thr Glu Glu Glu Arg Ile Phe Lys Ser Lys Thr Thr Ala Cys Tyr Leu
                245                 250                 255

Gly Ala Asn Ala Leu Arg Leu Pro Val Pro Leu Pro Ser Asn Thr Pro
            260                 265                 270

Pro Ser Thr Ser Gly Ala Leu Val Arg Cys Ser Tyr Thr Ala Thr Val
            275                 280                 285

Glu Val Leu Pro Ala Ser Ala Thr Ala Leu Arg Gly Ala Ala Pro Pro
290                 295                 300

Arg Leu Arg Val Pro Leu Thr Val Phe Ala Ser Ala Pro Ser Ser Phe
305                 310                 315                 320

Ala Thr Ala Ala Ala Arg His Ala His Leu Gln Gln Asp Ala Ser Glu
                325                 330                 335

Gln Ala Pro Ala His Val Leu Val Val Pro Pro Val Asp Val Val
            340                 345                 350

Leu Pro Ala Ala Ala Pro Gln Leu Pro Pro Thr Ala Glu Val Asn Val
            355                 360                 365

Lys Gln His Asn Gly Val Ala Gly Ala Asn Pro Met Tyr Ala Gly Pro
            370                 375                 380

<210> SEQ ID NO 7
<211> LENGTH: 403
<212> TYPE: PRT
<213> ORGANISM: Artificial Sequence
<220> FEATURE:
<223> OTHER INFORMATION: modified protein sequence
<220> FEATURE:
<221> NAME/KEY: MISC_FEATURE
<222> LOCATION: (384)..(385)
<223> OTHER INFORMATION: AgeI restriction site
<220> FEATURE:
<221> NAME/KEY: MISC_FEATURE
<222> LOCATION: (386)..(394)
<223> OTHER INFORMATION: FLAG Tag
<220> FEATURE:
<221> NAME/KEY: MISC_FEATURE
<222> LOCATION: (395)..(401)
```

<223> OTHER INFORMATION: MAT Tag
<220> FEATURE:
<221> NAME/KEY: MISC_FEATURE
<222> LOCATION: (402)..(403)
<223> OTHER INFORMATION: AgeI restriction site

<400> SEQUENCE: 7

```
Met Gln Val Tyr Gly Tyr Glu Val Val Gly Trp Glu Glu Ala His Ala
1               5                   10                  15
Lys Glu Pro Lys Leu Pro Ala Ala Asp Pro Tyr Ala Pro Ser Gln Leu
            20                  25                  30
Val Thr Pro Leu Asp Ser Gln Gln Gln Gln Gln Gln Gln Gln Gln Pro
        35                  40                  45
Pro Pro Pro Ser Ala Ala Ser Lys Ala Ser Pro Leu Gly Val Pro Arg
    50                  55                  60
His Gly Gln Arg Thr Ile Phe Asn Val Glu Val Arg Arg Pro Ser Ser
65                  70                  75                  80
Phe Ala Ser Ala Ala Glu Gln Gln Gln His Gln Leu Ala Val Leu Arg
                85                  90                  95
Ala Asp Cys Glu Leu Val Ile Ile Gln Arg Ala Glu Ala Ala Gln Gly
            100                 105                 110
Pro Pro Ala Pro Glu Glu His Thr Ser Ala Gly Ala Ala Ala Ala Arg
        115                 120                 125
Gly Pro Ala Ala Gly Gly Ala Glu Ala Glu Ala Ala Ala Ala Pro Val
    130                 135                 140
Pro Cys Asp Glu Val Val Thr Leu Val Pro Ala Phe Phe Cys Cys
145                 150                 155                 160
Ser Ser Gly Gly Arg Val Thr Val Arg Leu Arg Pro Gly Arg Asp Gly
                165                 170                 175
Tyr Val Ala Gly Glu Ala Ala Glu Val Val Glu Val Asp Asn Arg
            180                 185                 190
Ser Asn Gln Glu Phe Arg Asp Val Arg Leu Glu Val Glu Arg Arg Leu
        195                 200                 205
Thr Leu Val Ser Asn Ser Ala Gly Gly Gly Ser Ala Gly Ser Ser
    210                 215                 220
Gly Ser Gly Ser Ser Ser Ala Thr Ala Gly Leu Val Pro Gly Cys Phe
225                 230                 235                 240
Thr Glu Glu Glu Arg Ile Phe Lys Ser Lys Thr Thr Ala Cys Tyr Leu
                245                 250                 255
Gly Ala Asn Ala Leu Arg Leu Pro Val Pro Leu Pro Ser Asn Thr Pro
            260                 265                 270
Pro Ser Thr Ser Gly Ala Leu Val Arg Cys Ser Tyr Thr Ala Thr Val
        275                 280                 285
Glu Val Leu Pro Ala Ser Ala Thr Ala Leu Arg Gly Ala Ala Pro Pro
    290                 295                 300
Arg Leu Arg Val Pro Leu Thr Val Phe Ala Ser Ala Pro Ser Ser Phe
305                 310                 315                 320
Ala Thr Ala Ala Ala Arg His Ala His Leu Gln Gln Asp Ala Ser Glu
                325                 330                 335
Gln Ala Pro Ala His Val Leu Val Val Pro Val Asp Val Val
            340                 345                 350
Leu Pro Ala Ala Ala Pro Gln Leu Pro Pro Thr Ala Glu Val Asn Val
        355                 360                 365
Lys Gln His Asn Gly Val Ala Gly Ala Asn Pro Met Tyr Ala Gly Pro
    370                 375                 380
```

Thr Gly Asp Tyr Lys Asp Asp Asp Lys His Asn His Arg His Lys
385                 390                 395                 400

His Thr Gly

<210> SEQ ID NO 8
<211> LENGTH: 1356
<212> TYPE: DNA
<213> ORGANISM: Chlamydomonas reinhardtii

<400> SEQUENCE: 8

| | | | | | |
|---|---|---|---|---|---|
| atgcaggtgt | atgggtacga | ggtcgtgggc | tgggaggagg | cgcacgcgaa | ggagcccaag | 60 |
| ctcccggcgg | cggacccata | cgcccctagc | cagctggtga | cacccttgga | ctcacagcag | 120 |
| cagcaacagc | agcagcaaca | gccgccgccg | ccatctgcgg | cctccaaggc | ttcgccactg | 180 |
| ggcgtgccca | gacacggcca | gcgaaccatc | ttcaatgtat | gcgtcccact | gctggcgggc | 240 |
| gggcggcaag | tgctgccgcc | ggggacgtac | aggcttccct | tccggctgca | actccctgca | 300 |
| gatctgccag | ggacgtttcg | gctggccggc | acaccagcac | gcaccattgg | agacgtgagc | 360 |
| taccggaacc | tctctggcga | ggtcagctac | ggcttgcagg | tggaggtgcg | gcgtccgagc | 420 |
| agtttcgcgt | cggcagccga | acagcagcag | caccagttgg | cggttctgcg | tgctgattgc | 480 |
| gagctcgtga | ttatacagcg | cgcggaggcg | gcgcagggcc | gccagcccc | gaggagcat | 540 |
| acgtcggctg | gggcggcggc | ggccagggc | ccagcagcag | gcggagctga | agcggcggag | 600 |
| gcggccgcgc | cggtgccgtg | cgatgaggtg | gtgaccctgg | tgccggcctt | cttcttctgc | 660 |
| tgcagtagcg | gcggccgcgt | gacggtgcgg | ctgcggccgg | ggcgggatgg | ctacgtggca | 720 |
| ggcgaggcgg | cggaggtggt | ggtcgaggtt | gacaaccggt | cgaatcagga | gtttcgggat | 780 |
| gtgcggcttg | aagtggagcg | ccgcctcaca | ttggtcagca | acagcgccgg | cggaggcggt | 840 |
| agcgccggca | gcagcggcag | cggcagtagc | agcgccaccg | cggggcttgt | gccgggatgc | 900 |
| ttcactgaag | aggagcggat | cttcaagagc | aagaccacgg | ccgccctact | accgggagcc | 960 |
| tgctacctgg | agccaacgc | gctgcggctg | ccggtgcccc | tgcctccaa | cacgccgccc | 1020 |
| tccacctccg | gcgcgcttgt | gcgctgctcc | tacaccgcca | cggtggaggt | gctgccggcg | 1080 |
| tcggcgacag | cgctgcgcgg | gcggcgccg | ccgcggctgc | gtgtgccgct | gaccgtgttc | 1140 |
| gcatccgcgc | cgagctcgtt | cgccacgcg | cggcacggc | atgctcacct | gcagcaggac | 1200 |
| gcaagcgagc | aagcgccggc | gcacgtgttg | gtggtggtgc | cgcccgtgga | tgtagtgctc | 1260 |
| cccgcagctg | cgccgcagct | gcctccacc | gccgaggtaa | atgtcaaaca | gcacaacggc | 1320 |
| gtggctggcg | caaacccgat | gtacgcgggc | ccgtag | | | 1356 |

<210> SEQ ID NO 9
<211> LENGTH: 1350
<212> TYPE: DNA
<213> ORGANISM: Chlamydomonas reinhardtii

<400> SEQUENCE: 9

| | | | | | |
|---|---|---|---|---|---|
| caggtgtatg | ggtacgaggt | cgtgggctgg | gaggaggcgc | acgcgaagga | gcccaagctc | 60 |
| ccggcggcgg | acccatacgc | ccctagccag | ctggtgacac | ccttggactc | acagcagcag | 120 |
| caacagcagc | agcaacagcc | gccgccgcca | tctgcggcct | ccaaggcttc | gccactgggc | 180 |
| gtgcccagac | acggccagcg | aaccatcttc | aatgtatgcg | tcccactgct | ggcgggcggg | 240 |
| cggcaagtgc | tgccgccggg | gacgtacagg | cttcccttcc | ggctgcaact | ccctgcagat | 300 |
| ctgccaggga | cgtttcggct | ggccggcaca | ccagcacgca | ccattggaga | cgtgagctac | 360 |

-continued

```
cggaacctct ctggcgaggt cagctacggc ttgcaggtgg aggtgcggcg tccgagcagt    420
ttcgcgtcgg cagccgaaca gcagcagcac cagttggcgg ttctgcgtgc tgattgcgag    480
ctcgtgatta tacagcgcgc ggaggcggcg cagggcccgc cagcccccga ggagcatacg    540
tcggctgggg cggcggcggc caggggccca gcagcaggcg gagctgaagc ggcggaggcg    600
gccgcgccgg tgccgtgcga tgaggtggtg accctggtgc cggccttctt cttctgctgc    660
agtagcggcg gccgcgtgac ggtgcggctg cggccggggc gggatggcta cgtggcaggc    720
gaggcggcgg aggtggtggt cgaggttgac aaccggtcga atcaggagtt tcgggatgtg    780
cggcttgaag tggagcgccg cctcacattg gtcagcaaca gcgccggcgg aggcggtagc    840
gccggcagca gcggcagcgg cagtagcagc gccaccgcgg ggcttgtgcc gggatgcttc    900
actgaagagg agcggatctt caagagcaag accacggccg ccctactacc gggagcctgc    960
tacctgggag ccaacgcgct gcggctgccg gtgcccctgc cctccaacac gccgccctcc   1020
acctccggcg cgcttgtgcg ctgctcctac accgccacgg tggaggtgct gccggcgtcg   1080
gcgacagcgc tgcgcggcgc ggcgccgccg cggctgcgtg tgccgctgac cgtgttcgca   1140
tccgcgccga gctcgttcgc cacgcgcgcg gcacggcatg ctcacctgca gcaggacgca   1200
agcgagcaag cgccggcgca cgtgttggtg gtggtgccgc ccgtggatgt agtgctcccc   1260
gcagctgcgc cgcagctgcc tcccaccgcc gaggtaaatg tcaaacagca caacggcgtg   1320
gctggcgcaa acccgatgta cgcgggcccg                                    1350
```

<210> SEQ ID NO 10
<211> LENGTH: 1416
<212> TYPE: DNA
<213> ORGANISM: Artificial Sequence
<220> FEATURE:
<223> OTHER INFORMATION: modified nucleotide sequence
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (1357)..(1362)
<223> OTHER INFORMATION: AgeI restriction site
<220> FEATURE:
<221> NAME/KEY: misc_feature
<222> LOCATION: (1363)..(1386)
<223> OTHER INFORMATION: FLAG Tag
<220> FEATURE:
<221> NAME/KEY: misc_feature
<222> LOCATION: (1387)..(1407)
<223> OTHER INFORMATION: MAT Tag
<220> FEATURE:
<221> NAME/KEY: misc_feature
<222> LOCATION: (1408)..(1413)
<223> OTHER INFORMATION: XmaI/AgeI restriction site

<400> SEQUENCE: 10

```
ctcgagcagg tgtatgggta cgaggtcgtg ggctggagg aggcgcacgc gaaggagccc      60
aagctcccgg cggcggaccc atacgcccct agccagctgg tgacacccct ggactcacag    120
cagcagcaac agcagcagca acagccgccg ccgccatctg cggcctccaa ggcttcgcca    180
ctgggcgtgc ccagacacgg ccagcgaacc atcttcaatg tatgcgtccc actgctggcg    240
ggcgggcggc aagtgctgcc gccggggacg tacaggcttc ccttccggct gcaactccct    300
gcagatctgc cagggacgtt tcggctggcc ggcacaccag cacgcaccat tggagacgtg    360
agctaccgga acctctctgg cgaggtcagc tacggcttgc aggtggaggt gcggcgtccg    420
```

| | |
|---|---|
| agcagtttcg cgtcggcagc cgaacagcag cagcaccagt tggcggttct gcgtgctgat | 480 |
| tgcgagctcg tgattataca gcgcgcggag gcggcgcagg gccgccagc ccccgaggag | 540 |
| catacgtcgg ctggggcggc ggcggccagg ggcccagcag caggcggagc tgaagcggcg | 600 |
| gaggcggccg cgccggtgcc gtgcgatgag gtggtgaccc tggtgccggc cttcttcttc | 660 |
| tgctgcagta gcggcggccg cgtgacggtg cggctgcggc cggggcggga tggctacgtg | 720 |
| gcaggcgagg cggcggaggt ggtggtcgag gttgacaacc ggtcgaatca ggagtttcgg | 780 |
| gatgtgcggc ttgaagtgga gcgccgcctc acattggtca gcaacagcgc cggcggaggc | 840 |
| ggtagcgccg gcagcagcgg cagcggcagt agcagcgcca ccgcggggct tgtgccggga | 900 |
| tgcttcactg aagaggagcg gatcttcaag agcaagacca cggccgccct actaccggga | 960 |
| gcctgctacc tggagccaa cgcgctgcgg ctgccggtgc ccctgccctc caacacgccg | 1020 |
| ccctccacct ccggcgcgct tgtgcgctgc tcctacaccg ccacggtgga ggtgctgccg | 1080 |
| gcgtcggcga cagcgctgcg cggcgcggcg ccgccgcggc tgcgtgtgcc gctgaccgtg | 1140 |
| ttcgcatccg cgccgagctc gttcgccacg gcggcggcac ggcatgctca cctgcagcag | 1200 |
| gacgcaagcg agcaagcgcc ggcgcacgtg ttggtggtgg tgccgcccgt ggatgtagtg | 1260 |
| ctccccgcag ctgcgccgca gctgcctccc accgccgagt aaatgtcaa acagcacaac | 1320 |
| ggcgtggctg gcgcaaaccc gatgtacgcg ggcccgaccg gtgactacaa ggacgacgac | 1380 |
| gacaagcaca accaccgcca caagcacccc ggttaa | 1416 |

<210> SEQ ID NO 11
<211> LENGTH: 1356
<212> TYPE: DNA
<213> ORGANISM: Artificial Sequence
<220> FEATURE:
<223> OTHER INFORMATION: codon optimized

<400> SEQUENCE: 11

| | |
|---|---|
| atgcaagtgt atggttacga ggtggtgggt tgggaggagg ctcatgctaa ggagcccaag | 60 |
| ctgcccgcgg ccgacccta cgccccatcc caactggtca ctccgctgga cagccagcag | 120 |
| cagcaacagc agcaacaaca accgccgccc ccgtccgccg ccagcaaggc ctccccgctc | 180 |
| ggcgtgcctc gtcacggtca acgcacaatt ttcaacgtct gtgtgccact cctggctggg | 240 |
| gccgtcaag tgctccctcc cggcacctac cgcctgccct tccgcctcca gctgccggct | 300 |
| gacctgccag gcacgtttcg cctggccggc accccggcgc gcacgatcgg cgacgtgtcc | 360 |
| taccggaacc tgtccgggga ggtgagctac ggcctccagg tggaggtccg gcgtccctcg | 420 |
| tccttcgcgt cggcggcaga gcaacaacag caccagctgg ccgtgctgcg ggcggactgc | 480 |
| gagctcgtca tcatccagcg cgcggaggcc gccagggcc accagccccc cgaggagcat | 540 |
| acgtccgccg gtgccgctgc cgctcgcggg ccagcggctg ggggtgctga ggcggcggag | 600 |
| gcggctgccc ccgtgccgtg cgacgaggtg gtgacgctgg tccccgcctt ctttttctgc | 660 |
| tgctcgtccg ggggtcgcgt gaccgtgcgc ctgcgcccag gccgcgacgg ttacgtggct | 720 |
| ggcgaggccg ctgaggtcgt ggtggaggtg gacaaccgga gcaaccagga gttccgtgac | 780 |
| gtgcgcctgg aggtcgagcg ccgcctcacg ctggtgtcga actcggcggg tggcggcggc | 840 |
| tcggcggggt cctcgggctc gggcagctcg tccgctacgg ccggtctggt gccaggctgc | 900 |
| ttcacggagg aggagcggat cttcaagtcg aagacgacag cggcgctgct gccaggggcc | 960 |
| tgttacctgg gcgcgaacgc cctgcgcctg ccggtccccc tgcccagcaa caccccgcct | 1020 |
| tccacctcgg gcgcgctggt gcgttgcagc tataccgcga ccgtcgaggt gctgccggcg | 1080 |

-continued

| | |
|---|---|
| agcgcgacgg cgctgcgtgg ggccgctccc ccgcgtctcc gtgtgccgct gaccgtgttc | 1140 |
| gcgtccgcgc cttcgtcgtt cgccaccgcc gcagcccgcc acgcgcacct gcaacaggac | 1200 |
| gccagcgagc aggcaccggc ccacgtcctg gtggtggtgc cgcccgtgga cgtggtgctg | 1260 |
| ccagccgccg cacccagct gcctcccacc gcggaggtga acgtgaagca gcacaacggc | 1320 |
| gtggcgggcg ccaaccccat gtacgccggt ccctag | 1356 |

<210> SEQ ID NO 12
<211> LENGTH: 1350
<212> TYPE: DNA
<213> ORGANISM: Artificial Sequence
<220> FEATURE:
<223> OTHER INFORMATION: codon optimized

<400> SEQUENCE: 12

| | |
|---|---|
| caagtgtatg gttacgaggt ggtgggttgg gaggaggctc atgctaagga gcccaagctg | 60 |
| cccgcggccg acccctacgc cccatcccaa ctggtcactc cgctggacag ccagcagcag | 120 |
| caacagcagc aacaacaacc gccgccccg tccgccgcca gcaaggcctc cccgctcggc | 180 |
| gtgcctcgtc acggtcaacg cacaattttc aacgtctgtg tgccactcct ggctgggggc | 240 |
| cgtcaagtgc tccctcccgg cacctaccgc ctgcccttcc gcctccagct gccggctgac | 300 |
| ctgccaggca cgtttcgcct ggccggcacc ccggcgcgca cgatcggcga cgtgtcctac | 360 |
| cggaacctgt ccggggaggt gagctacggc ctccaggtgg aggtccggcg tccctcgtcc | 420 |
| ttcgcgtcgg cggcagagca acaacagcac cagctggccg tgctgcgggc ggactgcgag | 480 |
| ctcgtcatca tccagcgcgc ggaggccgcc cagggcccac cagccccga ggagcatacg | 540 |
| tccgccggtg ccgctgccgc tcgcgggcca gcggctgggg gtgctgaggc ggcggaggcg | 600 |
| gctgccccg tgccgtgcga cgaggtggtg acgctggtcc ccgccttctt tttctgctgc | 660 |
| tcgtccgggg gtcgcgtgac cgtgcgcctg cgcccaggcc gcgacggtta cgtggctggc | 720 |
| gaggccgctg aggtcgtggt ggaggtggac aaccggagca accaggagtt ccgtgacgtg | 780 |
| cgcctggagg tcgagcgccg cctcacgctg gtgtcgaact cggcgggtgg cggcggctcg | 840 |
| gcggggtcct cgggctcggg cagctcgtcc gctacggccg gtctggtgcc aggctgcttc | 900 |
| acggaggagg agcggatctt caagtcgaag acgacagcgg cgctgctgcc aggggcctgt | 960 |
| tacctgggcg cgaacgccct gcgcctgccg gtcccctgc ccagcaacac cccgccttcc | 1020 |
| acctcgggcg cgctggtgcg ttgcagctat accgcgaccg tcgaggtgct gccggcgagc | 1080 |
| gcgacgcgc tgcgtggggc cgctccccg cgtctccgtg tgccgctgac cgtgttcgcg | 1140 |
| tccgcgcctt cgtcgttcgc caccgccgca gcccgccacg cgcacctgca acaggacgcc | 1200 |
| agcgagcagg caccggccca cgtcctggtg gtggtgccgc ccgtggacgt ggtgctgcca | 1260 |
| gccgccgcac ccagctgcc tccaccgcg gaggtgaacg tgaagcagca caacggcgtg | 1320 |
| gcgggcgcca ccccatgta cgccggtccc | 1350 |

<210> SEQ ID NO 13
<211> LENGTH: 1416
<212> TYPE: DNA
<213> ORGANISM: Artificial Sequence
<220> FEATURE:
<223> OTHER INFORMATION: codon optimized
<220> FEATURE:
<221> NAME/KEY: misc_feature
<222> LOCATION: (1)..(6)
<223> OTHER INFORMATION: XhoI restriction site
<220> FEATURE:

<221> NAME/KEY: misc_feature
<222> LOCATION: (1357)..(1362)
<223> OTHER INFORMATION: AgeI restriction site
<220> FEATURE:
<221> NAME/KEY: misc_feature
<222> LOCATION: (1363)..(1386)
<223> OTHER INFORMATION: FLAG Tag
<220> FEATURE:
<221> NAME/KEY: misc_feature
<222> LOCATION: (1387)..(1407)
<223> OTHER INFORMATION: MAT Tag
<220> FEATURE:
<221> NAME/KEY: misc_feature
<222> LOCATION: (1408)..(1413)
<223> OTHER INFORMATION: XmaI/AgeI restriction site

<400> SEQUENCE: 13

```
ctcgagcaag tgtatggtta cgaggtggtg ggttgggagg aggctcatgc taaggagccc      60
aagctgcccg cggccgaccc ctacgcccca tcccaactgg tcactccgct ggacagccag     120
cagcagcaac agcagcaaca acaaccgccg ccccgtccg ccgccagcaa ggcctccccg      180
ctcggcgtgc ctcgtcacgg tcaacgcaca attttcaacg tctgtgtgcc actcctggct     240
gggggccgtc aagtgctccc tcccggcacc taccgcctgc ccttccgcct ccagctgccg     300
gctgacctgc caggcacgtt tcgcctggcc ggcaccccgg cgcgcacgat cggcgacgtg     360
tcctaccgga acctgtccgg ggaggtgagc tacggcctcc aggtggaggt ccggcgtccc     420
tcgtccttcg cgtcggcggc agagcaacaa cagcaccagc tggccgtgct gcgggcggac     480
tgcgagctcg tcatcatcca gcgcgcggag gccgcccagg gcccaccagc cccgaggag     540
catacgtccg ccggtgccgc tgccgctcgc gggccagcgg ctgggggtgc tgaggcggcg     600
gaggcggctg ccccccgtgcc gtgcgacgag gtggtgacgc tggtccccgc cttctttttc     660
tgctgctcgt ccggggggtcg cgtgaccgtg cgcctgcgcc caggccgcga cggttacgtg     720
gctggcgagg ccgctgaggt cgtggtggag gtggacaacc ggagcaacca ggagttccgt     780
gacgtgcgcc tggaggtcga gcgccgcctc acgctggtgt cgaactcggc gggtggcggc     840
ggctcggcgg ggtcctcggg ctcgggcagc tcgtccgcta cggccggtct ggtgccaggc     900
tgcttcacgg aggaggagcg gatcttcaag tcgaagacga cagcggcgct gctgccaggg     960
gcctgttacc tgggcgcgaa cgccctgcgc ctgccggtcc ccctgcccag caacaccccg    1020
ccttccacct cgggcgcgct ggtgcgttgc agctataccg cgaccgtcga ggtgctgccg    1080
gcgagcgcga cggcgctgcg tggggccgct ccccgcgtc tccgtgtgcc gctgaccgtg    1140
ttcgcgtccg cgccttcgtc gttcgccacc gccgcagccc gccacgcgca cctgcaacag    1200
gacgccagcg agcaggcacc ggcccacgtc ctggtggtgg tgccgcccgt ggacgtggtg    1260
ctgccagccg ccgcacccca gctgcctccc accgcggagg tgaacgtgaa gcagcacaac    1320
ggcgtggcgg gcgccaaccc catgtacgcc ggtcccaccg gtgactacaa ggacgacgac    1380
gacaagcaca ccaccgcca caagcaccc ggttaa                                1416
```

<210> SEQ ID NO 14
<211> LENGTH: 451
<212> TYPE: PRT
<213> ORGANISM: Chlamydomonas reinhardtii

<400> SEQUENCE: 14

```
Met Gln Val Tyr Gly Tyr Glu Val Val Gly Trp Glu Ala His Ala
1               5                   10                  15

Lys Glu Pro Lys Leu Pro Ala Ala Asp Pro Tyr Ala Pro Ser Gln Leu
            20                  25                  30
```

```
Val Thr Pro Leu Asp Ser Gln Gln Gln Gln Gln Gln Gln Pro
         35                  40                  45
Pro Pro Pro Ser Ala Ala Ser Lys Ala Ser Pro Leu Gly Val Pro Arg
 50                  55                  60
His Gly Gln Arg Thr Ile Phe Asn Val Cys Val Pro Leu Leu Ala Gly
 65                  70                  75                  80
Gly Arg Gln Val Leu Pro Pro Gly Thr Tyr Arg Leu Pro Phe Arg Leu
                 85                  90                  95
Gln Leu Pro Ala Asp Leu Pro Gly Thr Phe Arg Leu Ala Gly Thr Pro
                100                 105                 110
Ala Arg Thr Ile Gly Asp Val Ser Tyr Arg Asn Leu Ser Gly Glu Val
                115                 120                 125
Ser Tyr Gly Leu Gln Val Glu Val Arg Arg Pro Ser Ser Phe Ala Ser
130                 135                 140
Ala Ala Glu Gln Gln Gln His Gln Leu Ala Val Leu Arg Ala Asp Cys
145                 150                 155                 160
Glu Leu Val Ile Ile Gln Arg Ala Glu Ala Ala Gln Gly Pro Pro Ala
                165                 170                 175
Pro Glu Glu His Thr Ser Ala Gly Ala Ala Ala Arg Gly Pro Ala
                180                 185                 190
Ala Gly Gly Ala Glu Ala Ala Glu Ala Ala Ala Pro Val Pro Cys Asp
                195                 200                 205
Glu Val Val Thr Leu Val Pro Ala Phe Phe Cys Cys Ser Ser Gly
210                 215                 220
Gly Arg Val Thr Val Arg Leu Arg Pro Gly Arg Asp Gly Tyr Val Ala
225                 230                 235                 240
Gly Glu Ala Ala Glu Val Val Glu Val Asp Asn Arg Ser Asn Gln
                245                 250                 255
Glu Phe Arg Asp Val Arg Leu Glu Val Glu Arg Arg Leu Thr Leu Val
                260                 265                 270
Ser Asn Ser Ala Gly Gly Gly Ser Ala Gly Ser Ser Gly Ser Gly
    275                 280                 285
Ser Ser Ser Ala Thr Ala Gly Leu Val Pro Gly Cys Phe Thr Glu Glu
    290                 295                 300
Glu Arg Ile Phe Lys Ser Lys Thr Thr Ala Ala Leu Leu Pro Gly Ala
305                 310                 315                 320
Cys Tyr Leu Gly Ala Asn Ala Leu Arg Leu Pro Val Pro Leu Pro Ser
                325                 330                 335
Asn Thr Pro Pro Ser Thr Ser Gly Ala Leu Val Arg Cys Ser Tyr Thr
                340                 345                 350
Ala Thr Val Glu Val Leu Pro Ala Ser Ala Thr Ala Leu Arg Gly Ala
                355                 360                 365
Ala Pro Pro Arg Leu Arg Val Pro Leu Thr Val Phe Ala Ser Ala Pro
370                 375                 380
Ser Ser Phe Ala Thr Ala Ala Arg His Ala His Leu Gln Gln Asp
385                 390                 395                 400
Ala Ser Glu Gln Ala Pro Ala His Val Leu Val Val Pro Pro Val
                405                 410                 415
Asp Val Val Leu Pro Ala Ala Pro Gln Leu Pro Pro Thr Ala Glu
                420                 425                 430
Val Asn Val Lys Gln His Asn Gly Val Ala Gly Ala Asn Pro Met Tyr
                435                 440                 445
```

Ala Gly Pro
    450

<210> SEQ ID NO 15
<211> LENGTH: 471
<212> TYPE: PRT
<213> ORGANISM: Artificial Sequence
<220> FEATURE:
<223> OTHER INFORMATION: modified protein sequence
<220> FEATURE:
<221> NAME/KEY: MISC_FEATURE
<222> LOCATION: (1)..(2)
<223> OTHER INFORMATION: XhoI restriction site
<220> FEATURE:
<221> NAME/KEY: MISC_FEATURE
<222> LOCATION: (453)..(454)
<223> OTHER INFORMATION: AgeI restriction site
<220> FEATURE:
<221> NAME/KEY: MISC_FEATURE
<222> LOCATION: (455)..(462)
<223> OTHER INFORMATION: FLAG Tag
<220> FEATURE:
<221> NAME/KEY: MISC_FEATURE
<222> LOCATION: (463)..(469)
<223> OTHER INFORMATION: MAT Tag
<220> FEATURE:
<221> NAME/KEY: MISC_FEATURE
<222> LOCATION: (470)..(471)
<223> OTHER INFORMATION: XmaI/AgeI restriction site

<400> SEQUENCE: 15

Leu Glu Gln Val Tyr Gly Tyr Glu Val Val Gly Trp Glu Glu Ala His
1               5                   10                  15

Ala Lys Glu Pro Lys Leu Pro Ala Ala Asp Pro Tyr Ala Pro Ser Gln
            20                  25                  30

Leu Val Thr Pro Leu Asp Ser Gln Gln Gln Gln Gln Gln Gln Gln Gln
        35                  40                  45

Pro Pro Pro Pro Ser Ala Ala Ser Lys Ala Ser Pro Leu Gly Val Pro
    50                  55                  60

Arg His Gly Gln Arg Thr Ile Phe Asn Val Cys Val Pro Leu Leu Ala
65                  70                  75                  80

Gly Gly Arg Gln Val Leu Pro Pro Gly Thr Tyr Arg Leu Pro Phe Arg
                85                  90                  95

Leu Gln Leu Pro Ala Asp Leu Pro Gly Thr Phe Arg Leu Ala Gly Thr
            100                 105                 110

Pro Ala Arg Thr Ile Gly Asp Val Ser Tyr Arg Asn Leu Ser Gly Glu
        115                 120                 125

Val Ser Tyr Gly Leu Gln Val Glu Val Arg Arg Pro Ser Ser Phe Ala
    130                 135                 140

Ser Ala Ala Glu Gln Gln Gln His Gln Leu Ala Val Leu Arg Ala Asp
145                 150                 155                 160

Cys Glu Leu Val Ile Ile Gln Arg Ala Glu Ala Ala Gln Gly Pro Pro
                165                 170                 175

Ala Pro Glu Glu His Thr Ser Ala Gly Ala Ala Ala Arg Gly Pro
            180                 185                 190

Ala Ala Gly Gly Ala Glu Ala Ala Gly Ala Ala Ala Pro Val Pro Cys
        195                 200                 205

Asp Glu Val Val Thr Leu Val Pro Ala Phe Phe Phe Cys Cys Ser Ser
    210                 215                 220

Gly Gly Arg Val Thr Val Arg Leu Arg Pro Gly Arg Asp Gly Tyr Val
225                 230                 235                 240

Ala Gly Glu Ala Ala Glu Val Val Val Glu Val Asp Asn Arg Ser Asn

```
            245                 250                 255
Gln Glu Phe Arg Asp Val Arg Leu Glu Val Glu Arg Arg Leu Thr Leu
            260                 265                 270

Val Ser Asn Ser Ala Gly Gly Gly Ser Ala Gly Ser Ser Gly Ser
        275                 280                 285

Gly Ser Ser Ser Ala Thr Ala Gly Leu Val Pro Gly Cys Phe Thr Glu
    290                 295                 300

Glu Glu Arg Ile Phe Lys Ser Lys Thr Thr Ala Ala Leu Leu Pro Gly
305                 310                 315                 320

Ala Cys Tyr Leu Gly Ala Asn Ala Leu Arg Leu Pro Val Pro Leu Pro
                325                 330                 335

Ser Asn Thr Pro Pro Ser Thr Ser Gly Ala Leu Val Arg Cys Ser Tyr
            340                 345                 350

Thr Ala Thr Val Glu Val Leu Pro Ala Ser Ala Thr Ala Leu Arg Gly
            355                 360                 365

Ala Ala Pro Pro Arg Leu Arg Val Pro Leu Thr Val Phe Ala Ser Ala
    370                 375                 380

Pro Ser Ser Phe Ala Thr Ala Ala Arg His Ala His Leu Gln Gln
385                 390                 395                 400

Asp Ala Ser Glu Gln Ala Pro Ala His Val Leu Val Val Pro Pro
                405                 410                 415

Val Asp Val Val Leu Pro Ala Ala Pro Gln Leu Pro Pro Thr Ala
            420                 425                 430

Glu Val Asn Val Lys Gln His Asn Gly Val Gly Ala Asn Pro Met
            435                 440                 445

Tyr Ala Gly Pro Thr Gly Asp Tyr Lys Asp Asp Asp Lys His Asn
    450                 455                 460

His Arg His Lys His Pro Gly
465                 470

<210> SEQ ID NO 16
<211> LENGTH: 1215
<212> TYPE: DNA
<213> ORGANISM: Artificial Sequence
<220> FEATURE:
<223> OTHER INFORMATION: codon optimized
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (1156)..(1161)
<223> OTHER INFORMATION: AgeI restriction site
<220> FEATURE:
<221> NAME/KEY: misc_feature
<222> LOCATION: (1162)..(1185)
<223> OTHER INFORMATION: FLAG Tag
<220> FEATURE:
<221> NAME/KEY: misc_feature
<222> LOCATION: (1186)..(1206)
<223> OTHER INFORMATION: MAT Tag
<220> FEATURE:
<221> NAME/KEY: misc_feature
<222> LOCATION: (1207)..(1212)
<223> OTHER INFORMATION: AgeI restriction site

<400> SEQUENCE: 16
ctcgagcaag tgtatggtta cgaggtggtg ggttgggagg aggctcatgc taaggagccc      60
aagctgcccg cggccgaccc ctacgcccca tcccaactgg tcactccgct ggacagccag     120
cagcagcaac agcagcaaca acaaccgccg ccccgtccg ccgccagcaa ggcctccccg     180
```

```
ctcggcgtgc ctcgtcacgg tcaacgcaca attttcaacg tcgaggtccg gcgtccctcg      240
tccttcgcgt cggcggcaga gcaacaacag caccagctgg ccgtgctgcg ggcggactgc      300
gagctcgtca tcatccagcg cgcggaggcc gcccagggcc caccagcccc cgaggagcat      360
acgtccgccg gtgccgctgc cgctcgcggg ccagcggctg ggggtgctga ggcggcggag      420
gcggctgccc ccgtgccgtg cgacgaggtg gtgacgctgg tccccgcctt cttttctgc       480 tgctcgtccg ggggtcgcgt gaccgtgcgc ctgcgcccag gccgcgacgg ttacgtggct      540
ggcgaggccg ctgaggtcgt ggtggaggtg gacaaccgga gcaaccagga gttccgtgac      600
gtgcgcctgg aggtcgagcg ccgcctcacg ctggtgtcga actcggcggg tggcggcggc      660
tcggcggggt cctcgggctc gggcagctcg tccgctacgg ccgtctggt gccaggctgc       720 ttcacggagg aggagcggat cttcaagtcg aagacgacag cgtgttacct gggcgcgaac      780
gccctgcgcc tgccggtccc cctgcccagc aacacccgc cttccacctc gggcgcgctg       840
gtgcgttgca gctataccgc gaccgtcgag gtgctgccgg cgagcgcgac ggcgctgcgt      900
ggggccgctc cccgcgtct ccgtgtgccg ctgaccgtgt tcgcgtccgc gccttcgtcg       960
ttcgccaccg ccgcagcccg caccgcgacc ctgcaacagg acgccagcga gcaggcaccg     1020
gcccacgtcc tggtggtggt gccgcccgtg gacgtggtgc tgccagccgc cgcacccag     1080 ctgcctccca ccgcggaggt gaacgtgaag cagcacaacg cgtggcggg cgccaaccc     1140 atgtacgccg gtcccaccgg tgactacaag gacgacgacg acaagcacaa ccaccgccat     1200
aagcacaccg gttga                                                     1215

<210> SEQ ID NO 17
<211> LENGTH: 1215
<212> TYPE: DNA
<213> ORGANISM: Artificial Sequence
<220> FEATURE:
<223> OTHER INFORMATION: codon optimized
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (1156)..(1161)
<223> OTHER INFORMATION: AgeI restriction site
<220> FEATURE:
<221> NAME/KEY: misc_feature
<222> LOCATION: (1162)..(1185)
<223> OTHER INFORMATION: FLAG Tag
<220> FEATURE:
<221> NAME/KEY: misc_feature
<222> LOCATION: (1186)..(1206)
<223> OTHER INFORMATION: MAT Tag
<220> FEATURE:
<221> NAME/KEY: misc_feature
<222> LOCATION: (1207)..(1212)
<223> OTHER INFORMATION: AgeI restriction site

<400> SEQUENCE: 17
ctcgagcaag tgtatggtta cgaggtggtg ggttgggagg aggctcatgc taaggagccc       60
aagctgcccg cggccgaccc ctacgcccca tcccaactgg tcactccgct ggacagccag      120
cagcagcaac agcagcaaca acaaccgccg cccccgtccg ccgccagcaa ggcctccccg      180
ctcggcgtgc ctcgtcacgg tcaacgcaca attttcaacg tcgaggtccg gcgtccctcg      240
tccttcgcgt cggcggcaga gcaacaacag caccagctgg ccgtgctgcg ggcggactgc      300
gagctcgtca tcatccagcg cgcggaggcc gcccagggcc caccagcccc cgaggagcat      360
```

```
acgtccgccg gtgccgctgc cgctcgcggg ccagcggctg ggggtgctga ggcggcggag    420
gcggctgccc ccgtgccgtg cgacgaggtg gtgacgctgg tccccgcctt cttttctgc    480 tgctcgtccg ggggtcgcgt gaccgtgcgc ctgcgcccag gccgcgacgg ttacgtggct    540
ggcgaggccg ctgaggtcgt ggtggaggtg gacaaccgga gcaaccagga gttccgtgac    600
gtgcgcctgg aggtcgagcg ccgcctcacg ctggtgtcga actcggcggg tggcggcggc    660
tcggcggggt cctcgggctc gggcagctcg tccgctacgg ccgtctggt gccaggctgc    720 ttcacggagg aggagcggat cttcaagtcg aagacgacag cgtgttacct gggcgcgaac    780
gccctgcgcc tgccggtccc cctgccagc aacaccccgc cttccacctc gggcgcgctg    840
gtgcgttgca gctataccgc gaccgtcgag gtgctgccgg cgagcgcgac ggcgctgcgt    900
ggggccgctc ccccgcgtct ccgtgtgccg ctgaccgtgt tcgcgtccgc gccttcgtcg    960
ttcgccaccg ccgcagcccg ccacgcgcac ctgcaacagg acgccagcga gcaggcaccg    1020
gccaccgtcc tggtggtggt gccgcccgtg acgtggtgc tgccagccgc cgcaccccag    1080
ctgcctccca ccgcggaggt gaacgtgaag cagcacaacg cgtggcggg cgccaacccc    1140 atgtacgccg gtcccaccgg tgactacaag gacgacgacg acaagcacaa ccaccgccat    1200
aagcacaccg gttga                                                    1215
```

<210> SEQ ID NO 18
<211> LENGTH: 1215
<212> TYPE: DNA
<213> ORGANISM: Artificial Sequence
<220> FEATURE:
<223> OTHER INFORMATION: codon optimized
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (1156)..(1161)
<223> OTHER INFORMATION: AgeI restriction site
<220> FEATURE:
<221> NAME/KEY: misc_feature
<222> LOCATION: (1162)..(1185)
<223> OTHER INFORMATION: FLAG Tag
<220> FEATURE:
<221> NAME/KEY: misc_feature
<222> LOCATION: (1186)..(1206)
<223> OTHER INFORMATION: MAT Tag
<220> FEATURE:
<221> NAME/KEY: misc_feature
<222> LOCATION: (1207)..(1212)
<223> OTHER INFORMATION: AgeI restriction site

<400> SEQUENCE: 18

```
ctcgagcaag tgtatggtta cgaggtggtg ggttgggagg aggctcatgc taaggagccc    60
aagctgcccg cggccgaccc ctacgcccca tcccaactgg tcactccgct ggacagccag    120
cagcagcaac agcagcaaca acaaccgccg ccccgtccg ccgccagcaa ggcctccccg    180
ctcggcgtgc ctcgtcacgg tcaacgcaca attttcaacg tcgaggtccg gcgtccctcg    240
tccttcgcgt cggcggcaga gcaacaacag caccagctgg ccgtgctgcg ggcggactgc    300
gagctcgtca tcatccagcg cgcggaggcc gccagggcc accagcccc cgaggagcat    360 acgtccgccg gtgccgctgc cgctcgcggg ccagcggctg ggggtgctga ggcggcggag    420
gcggctgccc ccgtgccgtg cgacgaggtg gtgacgctgg tccccgcctt cttttctgc    480 tgctcgtccg ggggtcgcgt gaccgtgcgc ctgcgcccag gccgcgacgg ttacgtggct    540
ggcgaggccg ctgaggtcgt ggtggaggtg gacaaccgga gcaaccagga gttccgtgac    600
```

```
gtgcgcctgg aggtcgagcg ccgcctcacg ctggtgtcga actcggcggg tggcggcggc    660
tcggcggggt cctcgggctc gggcagctcg tccgctacgg ccggtctggt gccaggctgc    720
ttcacggagg aggagcggat cttcaagtcg aagacgacag cgtgttacct gggcgcgaac    780
gccctgcgcc tgccggtccc cctgcccagc aacaccccgc cttccacctc gggcgcgctg    840
gtgcgttgca gctataccgc gaccgtcgag gtgctgccgg cgagcgcgac ggcgctgcgt    900
ggggccgctc ccccgcgtct ccgtgtgccg ctgaccgtgt tcgcgtccgc gccttcgtcg    960
ttcgccaccg ccgcagcccg caccgcgacc ctgcaacagg acgccagcga gcaggcaccg   1020
gccaccgtcc tggtggtggt gccgcccgtg acgtggtgc tgccagccgc cgcaccccag    1080
ctgcctccca ccgcggaggt gaacgtgaag cagcacaacg gcgtggcggg cgccaacccc   1140
atgtacgccg gtcccaccgg tgactacaag gacgacgacg acaagcacaa ccaccgccat   1200
aagcacaccg gttga                                                    1215
```

<210> SEQ ID NO 19
<211> LENGTH: 406
<212> TYPE: PRT
<213> ORGANISM: Artificial Sequence
<220> FEATURE:
<223> OTHER INFORMATION: modified protein sequence
<220> FEATURE:
<221> NAME/KEY: MISC_FEATURE
<222> LOCATION: (1)..(2)
<223> OTHER INFORMATION: XhoI restriction site
<220> FEATURE:
<221> NAME/KEY: MISC_FEATURE
<222> LOCATION: (388)..(389)
<223> OTHER INFORMATION: AgeI restriction site
<220> FEATURE:
<221> NAME/KEY: MISC_FEATURE
<222> LOCATION: (390)..(397)
<223> OTHER INFORMATION: FLAG Tag
<220> FEATURE:
<221> NAME/KEY: MISC_FEATURE
<222> LOCATION: (398)..(404)
<223> OTHER INFORMATION: MAT Tag
<220> FEATURE:
<221> NAME/KEY: MISC_FEATURE
<222> LOCATION: (405)..(406)
<223> OTHER INFORMATION: AgeI restriction site

<400> SEQUENCE: 19

```
Leu Glu His Met Gln Val Tyr Gly Tyr Glu Val Val Gly Trp Glu Glu
1               5                   10                  15

Ala His Ala Lys Glu Pro Lys Leu Pro Ala Ala Asp Pro Tyr Ala Pro
            20                  25                  30

Ser Gln Leu Val Thr Pro Leu Asp Ser Gln Gln Gln Gln Gln Gln Gln
        35                  40                  45

Gln Gln Pro Pro Pro Pro Ser Ala Ala Ser Lys Ala Ser Pro Leu Gly
    50                  55                  60

Val Pro Arg His Gly Gln Arg Thr Ile Phe Asn Val Glu Val Arg Arg
65                  70                  75                  80

Pro Ser Ser Phe Ala Ser Ala Ala Glu Gln Gln Gln His Gln Leu Ala
                85                  90                  95

Val Leu Arg Ala Asp Cys Glu Leu Val Ile Ile Gln Arg Ala Glu Ala
            100                 105                 110

Ala Gln Gly Pro Pro Ala Pro Glu Glu His Thr Ser Ala Gly Ala Ala
        115                 120                 125

Ala Ala Arg Gly Pro Ala Ala Gly Gly Ala Glu Ala Ala Glu Ala Ala
    130                 135                 140
```

Ala Pro Val Pro Cys Asp Glu Val Val Thr Leu Val Pro Ala Phe Phe
145                 150                 155                 160

Phe Cys Cys Ser Ser Gly Gly Arg Val Thr Val Arg Leu Arg Pro Gly
            165                 170                 175

Arg Asp Gly Tyr Val Ala Gly Glu Ala Ala Glu Val Val Glu Val
        180                 185                 190

Asp Asn Arg Ser Asn Gln Glu Phe Arg Asp Val Arg Leu Glu Val Glu
            195                 200                 205

Arg Arg Leu Thr Leu Val Ser Asn Ser Ala Gly Gly Gly Ser Ala
        210                 215                 220

Gly Ser Ser Gly Ser Gly Ser Ser Ala Thr Ala Gly Leu Val Pro
225                 230                 235                 240

Gly Cys Phe Thr Glu Glu Glu Arg Ile Phe Lys Ser Lys Thr Thr Ala
            245                 250                 255

Cys Tyr Leu Gly Ala Asn Ala Leu Arg Leu Pro Val Pro Leu Pro Ser
            260                 265                 270

Asn Thr Pro Pro Ser Thr Ser Gly Ala Leu Val Arg Cys Ser Tyr Thr
            275                 280                 285

Ala Thr Val Glu Val Leu Pro Ala Ser Ala Thr Ala Leu Arg Gly Ala
        290                 295                 300

Ala Pro Pro Arg Leu Arg Val Pro Leu Thr Val Phe Ala Ser Ala Pro
305                 310                 315                 320

Ser Ser Phe Ala Thr Ala Ala Arg Thr Ala Thr Leu Gln Gln Asp
            325                 330                 335

Ala Ser Glu Gln Ala Pro Ala His Val Leu Val Val Pro Pro Val
        340                 345                 350

Asp Val Val Leu Pro Ala Ala Pro Gln Leu Pro Pro Thr Ala Glu
            355                 360                 365

Val Asn Val Lys Gln His Asn Gly Val Ala Gly Ala Asn Pro Met Tyr
            370                 375                 380

Ala Gly Pro Thr Gly Asp Tyr Lys Asp Asp Asp Lys His Asn His
385                 390                 395                 400

Arg His Lys His Thr Gly
                405

<210> SEQ ID NO 20
<211> LENGTH: 406
<212> TYPE: PRT
<213> ORGANISM: Artificial Sequence
<220> FEATURE:
<223> OTHER INFORMATION: modified protein sequence
<220> FEATURE:
<221> NAME/KEY: MISC_FEATURE
<222> LOCATION: (1)..(2)
<223> OTHER INFORMATION: XhoI restriction site
<220> FEATURE:
<221> NAME/KEY: MISC_FEATURE
<222> LOCATION: (388)..(389)
<223> OTHER INFORMATION: AgeI restriction site
<220> FEATURE:
<221> NAME/KEY: MISC_FEATURE
<222> LOCATION: (390)..(397)
<223> OTHER INFORMATION: FLAG Tag
<220> FEATURE:
<221> NAME/KEY: MISC_FEATURE
<222> LOCATION: (398)..(404)
<223> OTHER INFORMATION: MAT Tag
<220> FEATURE:
<221> NAME/KEY: MISC_FEATURE
<222> LOCATION: (405)..(406)
<223> OTHER INFORMATION: AgeI restriction site

<400> SEQUENCE: 20

```
Leu Glu His Met Gln Val Tyr Gly Tyr Glu Val Val Gly Trp Glu Glu
1               5                   10                  15
Ala His Ala Lys Glu Pro Lys Leu Pro Ala Ala Asp Pro Tyr Ala Pro
            20                  25                  30
Ser Gln Leu Val Thr Pro Leu Asp Ser Gln Gln Gln Gln Gln Gln Gln
        35                  40                  45
Gln Gln Pro Pro Pro Ser Ala Ala Ser Lys Ala Ser Pro Leu Gly
    50                  55                  60
Val Pro Arg His Gly Gln Arg Thr Ile Phe Asn Val Glu Val Arg Arg
65              70                  75                  80
Pro Ser Ser Phe Ala Ser Ala Ala Glu Gln Gln Gln His Gln Leu Ala
                85                  90                  95
Val Leu Arg Ala Asp Cys Glu Leu Val Ile Ile Gln Arg Ala Glu Ala
            100                 105                 110
Ala Gln Gly Pro Pro Ala Pro Glu Glu His Thr Ser Ala Gly Ala Ala
        115                 120                 125
Ala Ala Arg Gly Pro Ala Ala Gly Gly Ala Glu Ala Ala Glu Ala Ala
    130                 135                 140
Ala Pro Val Pro Cys Asp Glu Val Val Thr Leu Val Pro Ala Phe Phe
145                 150                 155                 160
Phe Cys Cys Ser Ser Gly Gly Arg Val Thr Val Arg Leu Arg Pro Gly
                165                 170                 175
Arg Asp Gly Tyr Val Ala Gly Glu Ala Ala Glu Val Val Glu Val
            180                 185                 190
Asp Asn Arg Ser Asn Gln Glu Phe Arg Asp Val Arg Leu Glu Val Glu
        195                 200                 205
Arg Arg Leu Thr Leu Val Ser Asn Ser Ala Gly Gly Gly Ser Ala
    210                 215                 220
Gly Ser Ser Gly Ser Gly Ser Ser Ser Ala Thr Ala Gly Leu Val Pro
225                 230                 235                 240
Gly Cys Phe Thr Glu Glu Glu Arg Ile Phe Lys Ser Lys Thr Thr Ala
                245                 250                 255
Cys Tyr Leu Gly Ala Asn Ala Leu Arg Leu Pro Val Pro Leu Pro Ser
            260                 265                 270
Asn Thr Pro Pro Ser Thr Ser Gly Ala Leu Val Arg Cys Ser Tyr Thr
        275                 280                 285
Ala Thr Val Glu Val Leu Pro Ala Ser Ala Thr Ala Leu Arg Gly Ala
    290                 295                 300
Ala Pro Pro Arg Leu Arg Val Pro Leu Thr Val Phe Ala Ser Ala Pro
305                 310                 315                 320
Ser Ser Phe Ala Thr Ala Ala Arg His Ala His Leu Gln Gln Asp
                325                 330                 335
Ala Ser Glu Gln Ala Pro Ala Thr Val Leu Val Val Pro Pro Val
    340                 345                 350
Asp Val Val Leu Pro Ala Ala Pro Gln Leu Pro Pro Thr Ala Glu
        355                 360                 365
Val Asn Val Lys Gln His Asn Gly Val Ala Gly Ala Asn Pro Met Tyr
    370                 375                 380
Ala Gly Pro Thr Gly Asp Tyr Lys Asp Asp Asp Lys His Asn His
385                 390                 395                 400
Arg His Lys His Thr Gly
```

```
<210> SEQ ID NO 21
<211> LENGTH: 406
<212> TYPE: PRT
<213> ORGANISM: Artificial Sequence
<220> FEATURE:
<223> OTHER INFORMATION: modified protein sequence
<220> FEATURE:
<221> NAME/KEY: MISC_FEATURE
<222> LOCATION: (1)..(2)
<223> OTHER INFORMATION: XhoI restriction site
<220> FEATURE:
<221> NAME/KEY: MISC_FEATURE
<222> LOCATION: (388)..(389)
<223> OTHER INFORMATION: AgeI restriction site
<220> FEATURE:
<221> NAME/KEY: MISC_FEATURE
<222> LOCATION: (390)..(397)
<223> OTHER INFORMATION: FLAG Tag
<220> FEATURE:
<221> NAME/KEY: MISC_FEATURE
<222> LOCATION: (398)..(404)
<223> OTHER INFORMATION: MAT Tag
<220> FEATURE:
<221> NAME/KEY: MISC_FEATURE
<222> LOCATION: (405)..(406)
<223> OTHER INFORMATION: AgeI restriction site

<400> SEQUENCE: 21
```

Leu Glu His Met Gln Val Tyr Gly Tyr Glu Val Val Gly Trp Glu Glu
1               5                   10                  15

Ala His Ala Lys Glu Pro Lys Leu Pro Ala Ala Asp Pro Tyr Ala Pro
            20                  25                  30

Ser Gln Leu Val Thr Pro Leu Asp Ser Gln Gln Gln Gln Gln Gln Gln
        35                  40                  45

Gln Gln Pro Pro Pro Pro Ser Ala Ala Ser Lys Ala Ser Pro Leu Gly
    50                  55                  60

Val Pro Arg His Gly Gln Arg Thr Ile Phe Asn Val Glu Val Arg Arg
65                  70                  75                  80

Pro Ser Ser Phe Ala Ser Ala Ala Glu Gln Gln Gln His Gln Leu Ala
                85                  90                  95

Val Leu Arg Ala Asp Cys Glu Leu Val Ile Ile Gln Arg Ala Glu Ala
            100                 105                 110

Ala Gln Gly Pro Pro Ala Pro Glu Glu His Thr Ser Ala Gly Ala Ala
        115                 120                 125

Ala Ala Arg Gly Pro Ala Ala Gly Gly Ala Glu Ala Ala Glu Ala Ala
    130                 135                 140

Ala Pro Val Pro Cys Asp Glu Val Val Thr Leu Val Pro Ala Phe Phe
145                 150                 155                 160

Phe Cys Cys Ser Ser Gly Gly Arg Val Thr Val Arg Leu Arg Pro Gly
                165                 170                 175

Arg Asp Gly Tyr Val Ala Gly Glu Ala Ala Glu Val Val Val Glu Val
            180                 185                 190

Asp Asn Arg Ser Asn Gln Glu Phe Arg Asp Val Arg Leu Glu Val Glu
        195                 200                 205

Arg Arg Leu Thr Leu Val Ser Asn Ser Ala Gly Gly Gly Ser Ala
    210                 215                 220

Gly Ser Ser Gly Ser Gly Ser Ser Ala Thr Ala Gly Leu Val Pro
225                 230                 235                 240

Gly Cys Phe Thr Glu Glu Glu Arg Ile Phe Lys Ser Lys Thr Thr Ala
                245                 250                 255

```
Cys Tyr Leu Gly Ala Asn Ala Leu Arg Leu Pro Val Pro Leu Pro Ser
                260                 265                 270

Asn Thr Pro Pro Ser Thr Ser Gly Ala Leu Val Arg Cys Ser Tyr Thr
            275                 280                 285

Ala Thr Val Glu Val Leu Pro Ala Ser Ala Thr Ala Leu Arg Gly Ala
        290                 295                 300

Ala Pro Pro Arg Leu Arg Val Pro Leu Thr Val Phe Ala Ser Ala Pro
305                 310                 315                 320

Ser Ser Phe Ala Thr Ala Ala Arg Thr Ala Thr Leu Gln Gln Asp
                325                 330                 335

Ala Ser Glu Gln Ala Pro Ala Thr Val Leu Val Val Pro Pro Val
            340                 345                 350

Asp Val Val Leu Pro Ala Ala Ala Pro Gln Leu Pro Pro Thr Ala Glu
        355                 360                 365

Val Asn Val Lys Gln His Asn Gly Val Ala Gly Ala Asn Pro Met Tyr
    370                 375                 380

Ala Gly Pro Thr Gly Asp Tyr Lys Asp Asp Asp Lys His Asn His
385                 390                 395                 400

Arg His Lys His Thr Gly
                405

<210> SEQ ID NO 22
<211> LENGTH: 21
<212> TYPE: DNA
<213> ORGANISM: Artificial Sequence
<220> FEATURE:
<223> OTHER INFORMATION: PCR primer

<400> SEQUENCE: 22
gacttctacg tgtgcctgga g                                            21

<210> SEQ ID NO 23
<211> LENGTH: 21
<212> TYPE: DNA
<213> ORGANISM: Artificial Sequence
<220> FEATURE:
<223> OTHER INFORMATION: PCR primer

<400> SEQUENCE: 23
catctgtcat caccagcctc t                                            21

<210> SEQ ID NO 24
<211> LENGTH: 24
<212> TYPE: DNA
<213> ORGANISM: Artificial Sequence
<220> FEATURE:
<223> OTHER INFORMATION: PCR primer

<400> SEQUENCE: 24
tatgcaagtg tatggttacg aggt                                         24

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
ggttgttgtt gctgctgttg                                              20
```

```
<210> SEQ ID NO 26
<211> LENGTH: 19
<212> TYPE: DNA
<213> ORGANISM: Artificial Sequence
<220> FEATURE:
<223> OTHER INFORMATION: PCR primer

<400> SEQUENCE: 26
ctcacgctgg tgtcgaact                                              19

<210> SEQ ID NO 27
<211> LENGTH: 21
<212> TYPE: DNA
<213> ORGANISM: Artificial Sequence
<220> FEATURE:
<223> OTHER INFORMATION: PCR primer

<400> SEQUENCE: 27
aggtaacacg ctgtcgtctt c                                           21

<210> SEQ ID NO 28
<211> LENGTH: 19
<212> TYPE: DNA
<213> ORGANISM: Artificial Sequence
<220> FEATURE:
<223> OTHER INFORMATION: PCR primer

<400> SEQUENCE: 28
ggaggtgaac gtgaagcag                                              19

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
tcctcaaccg gtgtgcttat                                             20

<210> SEQ ID NO 30
<211> LENGTH: 19
<212> TYPE: DNA
<213> ORGANISM: Artificial Sequence
<220> FEATURE:
<223> OTHER INFORMATION: PCR primer

<400> SEQUENCE: 30
cgagctcgtc atcatccag                                              19

<210> SEQ ID NO 31
<211> LENGTH: 18
<212> TYPE: DNA
<213> ORGANISM: Artificial Sequence
<220> FEATURE:
<223> OTHER INFORMATION: PCR primer

<400> SEQUENCE: 31
gaccagcgtc accacctc                                               18

<210> SEQ ID NO 32
<211> LENGTH: 24
<212> TYPE: DNA
<213> ORGANISM: Artificial Sequence
<220> FEATURE:
<223> OTHER INFORMATION: PCR Primer
```

-continued

<400> SEQUENCE: 32
agtcccatat ttacacaagg gcta                                    24

<210> SEQ ID NO 33
<211> LENGTH: 24
<212> TYPE: DNA
<213> ORGANISM: Artificial Sequence
<220> FEATURE:
<223> OTHER INFORMATION: PCR primer

<400> SEQUENCE: 33
tttcaaccaa aatgatatgc agtc                                    24

<210> SEQ ID NO 34
<211> LENGTH: 30
<212> TYPE: DNA
<213> ORGANISM: Artificial Sequence
<220> FEATURE:
<223> OTHER INFORMATION: PCR primer

<400> SEQUENCE: 34
taccgtactc accgtgcgag atactgctgc                              30

<210> SEQ ID NO 35
<211> LENGTH: 30
<212> TYPE: DNA
<213> ORGANISM: Artificial Sequence
<220> FEATURE:
<223> OTHER INFORMATION: PCR primer

<400> SEQUENCE: 35
cgcgcgcaaa aggctacttc ccctctacgg                              30

<210> SEQ ID NO 36
<211> LENGTH: 30
<212> TYPE: DNA
<213> ORGANISM: Artificial Sequence
<220> FEATURE:
<223> OTHER INFORMATION: PCR primer

<400> SEQUENCE: 36
ctctacgggc ccgcgtacat cgggtttgcg                              30

<210> SEQ ID NO 37
<211> LENGTH: 30
<212> TYPE: DNA
<213> ORGANISM: Artificial Sequence
<220> FEATURE:
<223> OTHER INFORMATION: PCR primer

<400> SEQUENCE: 37
atgcaggtgt atgggtacga ggtcgtgggc                              30

<210> SEQ ID NO 38
<211> LENGTH: 21
<212> TYPE: DNA
<213> ORGANISM: Chlamydomonas reinhardtii

<400> SEQUENCE: 38
tgtataatca cgagctccca a                                       21

<210> SEQ ID NO 39
<211> LENGTH: 21
<212> TYPE: DNA

<213> ORGANISM: Chlamydomonas reinhardtii

<400> SEQUENCE: 39
ttcttcagtg aagcatccct g        21

<210> SEQ ID NO 40
<211> LENGTH: 21
<212> TYPE: DNA
<213> ORGANISM: Chlamydomonas reinhardtii

<400> SEQUENCE: 40
ttttgacatt tacctcggca g        21

<210> SEQ ID NO 41
<211> LENGTH: 21
<212> TYPE: DNA
<213> ORGANISM: Chlamydomonas reinhardtii

<400> SEQUENCE: 41
tacattgaag atggttcgct g        21

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
ggtcgtgtcc acgaacttcc        20

<210> SEQ ID NO 43
<211> LENGTH: 19
<212> TYPE: DNA
<213> ORGANISM: Artificial Sequence
<220> FEATURE:
<223> OTHER INFORMATION: PCR primer

<400> SEQUENCE: 43
ctcacgctgg tgtcgaact        19

<210> SEQ ID NO 44
<211> LENGTH: 34
<212> TYPE: DNA
<213> ORGANISM: Artificial Sequence
<220> FEATURE:
<223> OTHER INFORMATION: PCR Primer

<400> SEQUENCE: 44
gactattaat ggtgttgggt cggtgttttt ggtc        34

<210> SEQ ID NO 45
<211> LENGTH: 28
<212> TYPE: DNA
<213> ORGANISM: Artificial Sequence
<220> FEATURE:
<223> OTHER INFORMATION: PCR Primer

<400> SEQUENCE: 45
agatctcagc tggaacactg cgcccagg        28

<210> SEQ ID NO 46
<211> LENGTH: 42
<212> TYPE: DNA
<213> ORGANISM: Artificial Sequence

```
<220> FEATURE:
<223> OTHER INFORMATION: PCR Primer

<400> SEQUENCE: 46
gcagtgttcc agctgagatc tagccggaac actgccagga ag                    42

<210> SEQ ID NO 47
<211> LENGTH: 33
<212> TYPE: DNA
<213> ORGANISM: Artificial Sequence
<220> FEATURE:
<223> OTHER INFORMATION: PCR Primer

<400> SEQUENCE: 47
gactggatcc ggtgtaacta agccagccca aac                              33

<210> SEQ ID NO 48
<211> LENGTH: 714
<212> TYPE: DNA
<213> ORGANISM: Trichoderma reesei

<400> SEQUENCE: 48
atggtcgagt cgtgccgccc ggctgcggag gtggagtcgg tggccgtgga gaagcgccag      60
acgattcagc cgggcaccgg ctacaacaac ggctatttct actcctactg gaacgacggc     120
cacggtggcg tcacctacac caacggcccc ggggtcagt tcagcgtgaa ctggtcgaac      180
tccggcaact tcgtgggtgg caagggttgg cagcccggca cgaagaacaa ggtgatcaac     240
ttcagcggca gctacaaccc taacggcaac agctacctgt ccgtgtacgg ttggtcccgc     300
aaccctctca tcgagtacta catcgtggag aacttcggca cctacaatcc gagcaccggc     360
gcgacaaagc tgggcgaggt cacctcggac ggcagcgtgt acgacatcta ccgcacacag     420
cgcgtcaacc agccctcgat catcggcacg gcaacgttct accagtattg gtccgtgcgg     480
cggaatcacc gcagctccgg ttcggtgaat acggccaacc atttcaacgc ttgggcccag     540
cagggcctga cgctgggcac aatggactac cagatcgtgg cggtggaggg ttacttcagc     600
tcgggctcgg ccagcatcac ctgtgagcac cggtgactaca aggacgacga cgacaagtcc     660
ggcgagaacc tgtactttca ggggcacaac caccgccata gcacaccgg ttaa            714

<210> SEQ ID NO 49
<211> LENGTH: 18
<212> TYPE: DNA
<213> ORGANISM: Artificial Sequence
<220> FEATURE:
<223> OTHER INFORMATION: PCR Primer

<400> SEQUENCE: 49
cgcagccggg cggcacga                                               18

<210> SEQ ID NO 50
<211> LENGTH: 1215
<212> TYPE: DNA
<213> ORGANISM: Artificial Sequence
<220> FEATURE:
<223> OTHER INFORMATION: codon optimized
<220> FEATURE:
<221> NAME/KEY: misc_feature
<222> LOCATION: (1)..(6)
<223> OTHER INFORMATION: XhoI restriction site
<220> FEATURE:
<221> NAME/KEY: misc_feature
<222> LOCATION: (1156)..(1161)
<223> OTHER INFORMATION: AgeI restriction site
<220> FEATURE:
```

```
<221> NAME/KEY: misc_feature
<222> LOCATION: (1162)..(1185)
<223> OTHER INFORMATION: FLAG Tag
<220> FEATURE:
<221> NAME/KEY: misc_feature
<222> LOCATION: (1186)..(1206)
<223> OTHER INFORMATION: MAT Tag
<220> FEATURE:
<221> NAME/KEY: misc_feature
<222> LOCATION: (1207)..(1212)
<223> OTHER INFORMATION: AgeI restriction site

<400> SEQUENCE: 50
ctcgagcaag tgtatggtta cgaggtggtg ggttgggagg aggctcatgc taaggagccc      60
aagctgcccg cggccgaccc ctacgcccca tcccaactgg tcactccgct ggacagccag     120
cagcagcaac agcagcaaca acaaccgccg cccccgtccg ccgccagcaa ggcctccccg     180
ctcggcgtgc ctcgtcacgg tcaacgcaca attttcaacg tcgaggtccg gcgtccctcg     240
tccttcgcgt cggcggcaga gcaacaacag caccagctgg ccgtgctgcg ggcggactgc     300
gagctcgtca tcatccagcg cgcggaggcc gcccagggcc accagcccc cgaggagcat      360
acgtccgccg gtgccgctgc cgctcgcggg ccagcggctg ggggtgctga ggcggcggag     420
gcggctgccc ccgtgccgtg cgacgaggtg gtgacgctgg tccccgcctt cttttctgc      480
tgctcgtccg ggggtcgcgt gaccgtgcgc ctgcgcccag gccgcgacgg ttacgtggct     540
ggcgaggccc tgaggtcgt ggtggaggtg gacaaccgga gcaaccagga gttccgtgac      600
gtgcgcctgg aggtcgagcg ccgcctcacg ctggtgtcga actcggcggg tggcggcggc     660
tcggcggggt cctcgggctc gggcagctcg tccgctacgg ccggtctggt gccaggctgc     720
ttcacggagg aggagcggat cttcaagtcg aagacgacag cgtgttacct gggcgcgaac     780
gccctgcgcc tgccggtccc cctgcccagc aacaccccgc cttccacctc gggcgcgctg     840
gtgcgttgca gctataccgc gaccgtcgag gtgctgccgg cgagcgcgac ggcgctgcgt     900
ggggccgctc ccccgcgtct ccgtgtgccg ctgaccgtgt tcgcgtccgc gccttcgtcg     960
ttcgccaccg ccgcagcccg ccacgcgcac ctgcaacagg acgccagcga gcaggcaccg    1020
gcccacgtcc tggtggtggt gccgcccgtg acgtggtgc tgccagccgc cgcaccccag    1080
ctgcctccca ccgcggaggt gaacgtgaag cagcacaacg gcgtggcggg cgccaacccc    1140
atgtacgccg gtcccaccgg tgactacaag gacgacgacg acaagcacaa ccaccgccat    1200
aagcacaccg gttga                                                    1215

<210> SEQ ID NO 51
<211> LENGTH: 383
<212> TYPE: PRT
<213> ORGANISM: Chlamydomonas reinhardtii

<400> SEQUENCE: 51

Gln Val Tyr Gly Tyr Glu Val Val Gly Trp Glu Glu Ala His Ala Lys
1               5                   10                  15

Glu Pro Lys Leu Pro Ala Ala Asp Pro Tyr Ala Pro Ser Gln Leu Val
            20                  25                  30

Thr Pro Leu Asp Ser Gln Gln Gln Gln Gln Gln Gln Gln Pro Pro
        35                  40                  45

Pro Pro Ser Ala Ala Ser Lys Ala Ser Pro Leu Gly Val Pro Arg His
    50                  55                  60

Gly Gln Arg Thr Ile Phe Asn Val Glu Val Arg Arg Pro Ser Ser Phe
65                  70                  75                  80
```

```
Ala Ser Ala Ala Glu Gln Gln Gln His Gln Leu Ala Val Leu Arg Ala
                85                  90                  95

Asp Cys Glu Leu Val Ile Ile Gln Arg Ala Glu Ala Ala Gln Gly Pro
            100                 105                 110

Pro Ala Pro Glu Glu His Thr Ser Ala Gly Ala Ala Ala Ala Arg Gly
        115                 120                 125

Pro Ala Ala Gly Gly Ala Glu Ala Ala Glu Ala Ala Pro Val Pro
    130                 135                 140

Cys Asp Glu Val Val Thr Leu Val Pro Ala Phe Phe Cys Cys Ser
145                 150                 155                 160

Ser Gly Gly Arg Val Thr Val Arg Leu Arg Pro Gly Arg Asp Gly Tyr
                165                 170                 175

Val Ala Gly Glu Ala Ala Glu Val Val Glu Val Asp Asn Arg Ser
            180                 185                 190

Asn Gln Glu Phe Arg Asp Val Arg Leu Glu Val Glu Arg Arg Leu Thr
                195                 200                 205

Leu Val Ser Asn Ser Ala Gly Gly Gly Ser Ala Gly Ser Ser Gly
    210                 215                 220

Ser Gly Ser Ser Ser Ala Thr Ala Gly Leu Val Pro Gly Cys Phe Thr
225                 230                 235                 240

Glu Glu Glu Arg Ile Phe Lys Ser Lys Thr Thr Ala Cys Tyr Leu Gly
                245                 250                 255

Ala Asn Ala Leu Arg Leu Pro Val Pro Leu Pro Ser Asn Thr Pro Pro
                260                 265                 270

Ser Thr Ser Gly Ala Leu Val Arg Cys Ser Tyr Thr Ala Thr Val Glu
    275                 280                 285

Val Leu Pro Ala Ser Ala Thr Ala Leu Arg Gly Ala Ala Pro Pro Arg
    290                 295                 300

Leu Arg Val Pro Leu Thr Val Phe Ala Ser Ala Pro Ser Ser Phe Ala
305                 310                 315                 320

Thr Ala Ala Ala Arg His Ala His Leu Gln Gln Asp Ala Ser Glu Gln
                325                 330                 335

Ala Pro Ala His Val Leu Val Val Pro Pro Val Asp Val Val Leu
            340                 345                 350

Pro Ala Ala Ala Pro Gln Leu Pro Pro Thr Ala Glu Val Asn Val Lys
                355                 360                 365

Gln His Asn Gly Val Ala Gly Ala Asn Pro Met Tyr Ala Gly Pro
    370                 375                 380

<210> SEQ ID NO 52
<211> LENGTH: 450
<212> TYPE: PRT
<213> ORGANISM: Chlamydomonas reinhardtii

<400> SEQUENCE: 52

Gln Val Tyr Gly Tyr Glu Val Val Gly Trp Glu Glu Ala His Ala Lys
1               5                   10                  15

Glu Pro Lys Leu Pro Ala Ala Asp Pro Tyr Ala Pro Ser Gln Leu Val
            20                  25                  30

Thr Pro Leu Asp Ser Gln Gln Gln Gln Gln Gln Gln Pro Pro
        35                  40                  45

Pro Pro Ser Ala Ala Ser Lys Ala Ser Pro Leu Gly Val Pro Arg His
    50                  55                  60

Gly Gln Arg Thr Ile Phe Asn Val Cys Val Pro Leu Leu Ala Gly Gly
65                  70                  75                  80
```

Arg Gln Val Leu Pro Pro Gly Thr Tyr Arg Leu Pro Phe Arg Leu Gln
                85                  90                  95

Leu Pro Ala Asp Leu Pro Gly Thr Phe Arg Leu Ala Gly Thr Pro Ala
            100                 105                 110

Arg Thr Ile Gly Asp Val Ser Tyr Arg Asn Leu Ser Gly Glu Val Ser
        115                 120                 125

Tyr Gly Leu Gln Val Glu Val Arg Arg Pro Ser Ser Phe Ala Ser Ala
    130                 135                 140

Ala Glu Gln Gln Gln His Gln Leu Ala Val Leu Arg Ala Asp Cys Glu
145                 150                 155                 160

Leu Val Ile Ile Gln Arg Ala Glu Ala Gln Gly Pro Pro Ala Pro
                165                 170                 175

Glu Glu His Thr Ser Ala Gly Ala Ala Ala Arg Gly Pro Ala Ala
                180                 185                 190

Gly Gly Ala Glu Ala Glu Ala Ala Pro Val Pro Cys Asp Glu
            195                 200                 205

Val Val Thr Leu Val Pro Ala Phe Phe Phe Cys Cys Ser Ser Gly Gly
        210                 215                 220

Arg Val Thr Val Arg Leu Arg Pro Gly Arg Asp Gly Tyr Val Ala Gly
225                 230                 235                 240

Glu Ala Ala Glu Val Val Glu Val Asp Asn Arg Ser Asn Gln Glu
                245                 250                 255

Phe Arg Asp Val Arg Leu Glu Val Glu Arg Arg Leu Thr Leu Val Ser
                260                 265                 270

Asn Ser Ala Gly Gly Gly Ser Ala Gly Ser Ser Gly Ser Gly Ser
            275                 280                 285

Ser Ser Ala Thr Ala Gly Leu Val Pro Gly Cys Phe Thr Glu Glu Glu
        290                 295                 300

Arg Ile Phe Lys Ser Lys Thr Thr Ala Ala Leu Leu Pro Gly Ala Cys
305                 310                 315                 320

Tyr Leu Gly Ala Asn Ala Leu Arg Leu Pro Val Pro Leu Pro Ser Asn
                325                 330                 335

Thr Pro Pro Ser Thr Ser Gly Ala Leu Val Arg Cys Ser Tyr Thr Ala
            340                 345                 350

Thr Val Glu Val Leu Pro Ala Ser Ala Thr Ala Leu Arg Gly Ala Ala
        355                 360                 365

Pro Pro Arg Leu Arg Val Pro Leu Thr Val Phe Ala Ser Ala Pro Ser
370                 375                 380

Ser Phe Ala Thr Ala Ala Arg His Ala His Leu Gln Gln Asp Ala
385                 390                 395                 400

Ser Glu Gln Ala Pro Ala His Val Leu Val Val Pro Pro Val Asp
                405                 410                 415

Val Val Leu Pro Ala Ala Pro Gln Leu Pro Pro Thr Ala Glu Val
            420                 425                 430

Asn Val Lys Gln His Asn Gly Val Ala Gly Ala Asn Pro Met Tyr Ala
            435                 440                 445

Gly Pro
    450

<210> SEQ ID NO 53
<211> LENGTH: 1149
<212> TYPE: DNA
<213> ORGANISM: Artificial Sequence
<220> FEATURE:

<223> OTHER INFORMATION: codon optimized

<400> SEQUENCE: 53

| | |
|---|---|
| caagtgtatg gttacgaggt ggtggggttgg gaggaggctc atgctaagga gcccaagctg | 60 |
| cccgcggccg accsctacgc cccatcccaa ctggtcactc cgctggacag ccagcagcag | 120 |
| caacagcagc aacaacaacc gccgcccccg tccgccgcca gcaaggcctc cccgctcggc | 180 |
| gtgcctcgtc acggtcaacg cacaattttc aacgtcgagg tccggcgtcc ctcgtccttc | 240 |
| gcgtcggcgg cagagcaaca acagcaccag ctggccgtgc tgcgggcgga ctgcgagctc | 300 |
| gtcatcatcc agcgcgcgga ggccgcccag ggcccaccag ccccgagga gcatacgtcc | 360 |
| gccggtgccg ctgccgctcg cgggccagcg gctgggggtg ctgaggcggc ggaggcggct | 420 |
| gccccgtgc cgtgcgacga ggtggtgacg ctggtccccg ccttcttttt ctgctgctcg | 480 |
| tccgggggtc gcgtgaccgt gcgcctgcgc ccaggccgcg acggttacgt ggctggcgag | 540 |
| gccgctgagg tcgtggtgga ggtggacaac cggagcaacc aggagttccg tgacgtgcgc | 600 |
| ctggaggtcg agcgccgcct cacgctggtg tcgaactcgg cgggtggcgg cggctcggcg | 660 |
| gggtcctcgg gctcgggcag ctcgtccgct acggccggtc tggtgccagg ctgcttcacg | 720 |
| gaggaggagc ggatcttcaa gtcgaagacg acagcgtgtt acctgggcgc gaacgccctg | 780 |
| cgcctgccgg tccccctgcc cagcaacacc ccgccttcca cctcgggcgc gctggtgcgt | 840 |
| tgcagctata ccgcgaccgt cgaggtgctg cggcgagcg cgacggcgct gcgtggggcc | 900 |
| gctcccccgc gtctccgtgt gccgctgacc gtgttcgcgt ccgcgccttc gtcgttcgcc | 960 |
| accgccgcag cccgcaccgc gaccctgcaa caggacgcca gcgagcaggc accggcccac | 1020 |
| gtcctggtgg tggtgccgcc cgtggacgtg tgctgccag ccgccgcacc ccagctgcct | 1080 |
| cccaccgcga aggtgaacgt gaagcagcac aacggcgtgg cgggcgccaa ccccatgtac | 1140 |
| gccggtccc | 1149 |

<210> SEQ ID NO 54
<211> LENGTH: 1149
<212> TYPE: DNA
<213> ORGANISM: Artificial Sequence
<220> FEATURE:
<223> OTHER INFORMATION: codon optimized

<400> SEQUENCE: 54

| | |
|---|---|
| caagtgtatg gttacgaggt ggtggggttgg gaggaggctc atgctaagga gcccaagctg | 60 |
| cccgcggccg accsctacgc cccatcccaa ctggtcactc cgctggacag ccagcagcag | 120 |
| caacagcagc aacaacaacc gccgcccccg tccgccgcca gcaaggcctc cccgctcggc | 180 |
| gtgcctcgtc acggtcaacg cacaattttc aacgtcgagg tccggcgtcc ctcgtccttc | 240 |
| gcgtcggcgg cagagcaaca acagcaccag ctggccgtgc tgcgggcgga ctgcgagctc | 300 |
| gtcatcatcc agcgcgcgga ggccgcccag ggcccaccag ccccgagga gcatacgtcc | 360 |
| gccggtgccg ctgccgctcg cgggccagcg gctgggggtg ctgaggcggc ggaggcggct | 420 |
| gccccgtgc cgtgcgacga ggtggtgacg ctggtccccg ccttcttttt ctgctgctcg | 480 |
| tccgggggtc gcgtgaccgt gcgcctgcgc ccaggccgcg acggttacgt ggctggcgag | 540 |
| gccgctgagg tcgtggtgga ggtggacaac cggagcaacc aggagttccg tgacgtgcgc | 600 |
| ctggaggtcg agcgccgcct cacgctggtg tcgaactcgg cgggtggcgg cggctcggcg | 660 |
| gggtcctcgg gctcgggcag ctcgtccgct acggccggtc tggtgccagg ctgcttcacg | 720 |
| gaggaggagc ggatcttcaa gtcgaagacg acagcgtgtt acctgggcgc gaacgccctg | 780 |

```
cgcctgccgg tccccctgcc cagcaacacc ccgccttcca cctcgggcgc gctggtgcgt    840
tgcagctata ccgcgaccgt cgaggtgctg ccggcgagcg cgacggcgct gcgtggggcc    900 gctccccgc gtctccgtgt gccgctgacc gtgttcgcgt ccgcgccttc gtcgttcgcc     960
accgccgcag cccgccacgc gcacctgcaa caggacgcca gcgagcaggc accggccacc   1020
gtcctggtgg tggtgccgcc cgtggacgtg gtgctgccag ccgccgcacc ccagctgcct   1080
cccaccgcgg aggtgaacgt gaagcagcac aacggcgtgg cgggcgccaa ccccatgtac   1140
gccggtccc                                                           1149
```

<210> SEQ ID NO 55
<211> LENGTH: 1149
<212> TYPE: DNA
<213> ORGANISM: Artificial Sequence
<220> FEATURE:
<223> OTHER INFORMATION: codon optimized

<400> SEQUENCE: 55

```
caagtgtatg gttacgaggt ggtgggttgg gaggaggctc atgctaagga gcccaagctg     60
cccgcggccg accctacgc cccatcccaa ctggtcactc cgctggacag ccagcagcag    120
caacagcagc aacaacaacc gccgcccccg tccgccgcca gcaaggcctc cccgctcggc    180
gtgcctcgtc acggtcaacg cacaattttc aacgtcgagg tccggcgtcc ctcgtccttc    240
gcgtcggcgg cagagcaaca acagcaccag ctggccgtgc tgcgggcgga ctgcgagctc    300
gtcatcatcc agcgcgcgga ggccgcccag ggcccaccag ccccgagga gcatacgtcc     360 gccggtgccg ctgccgctcg cgggccagcg gctggggtg ctgaggcggc ggaggcggct    420 gccccgtgc cgtgcgacga ggtggtgacg ctggtccccg ccttctttt ctgctgctcg     480 tccggggtc gcgtgaccgt gcgcctgcgc ccaggccgcg acggttacgt ggctggcgag    540
gccgctgagg tcgtggtgga ggtggacaac cggagcaacc aggagttccg tgacgtgcgc    600
ctggaggtcg agcgccgcct cacgctggtg tcgaactcgg cgggtggcgg cggctcggcg    660
gggtcctcgg gctcgggcag ctcgtccgct acggccggtc tggtgccagg ctgcttcacg    720
gaggaggagc ggatcttcaa gtcgaagacg acagcgtgtt acctgggcgc gaacgccctg    780
cgcctgccgg tccccctgcc cagcaacacc ccgccttcca cctcgggcgc gctggtgcgt    840
tgcagctata ccgcgaccgt cgaggtgctg ccggcgagcg cgacggcgct gcgtggggcc    900 gctccccgc gtctccgtgt gccgctgacc gtgttcgcgt ccgcgccttc gtcgttcgcc     960
accgccgcag cccgccaccgc gacctgcaa caggacgcca gcgagcaggc accggccacc   1020
gtcctggtgg tggtgccgcc cgtggacgtg gtgctgccag ccgccgcacc ccagctgcct   1080
cccaccgcgg aggtgaacgt gaagcagcac aacggcgtgg cgggcgccaa ccccatgtac   1140
gccggtccc                                                           1149
```

<210> SEQ ID NO 56
<211> LENGTH: 385
<212> TYPE: PRT
<213> ORGANISM: Artificial Sequence
<220> FEATURE:
<223> OTHER INFORMATION: modified protein sequence

<400> SEQUENCE: 56

```
His Met Gln Val Tyr Gly Tyr Glu Val Val Gly Trp Glu Glu Ala His
 1               5                   10                  15

Ala Lys Glu Pro Lys Leu Pro Ala Ala Asp Pro Tyr Ala Pro Ser Gln
```

```
            20                  25                  30
Leu Val Thr Pro Leu Asp Ser Gln Gln Gln Gln Gln Gln Gln
        35                  40                  45
Pro Pro Pro Pro Ser Ala Ala Ser Lys Ala Ser Pro Leu Gly Val Pro
 50                  55                  60
Arg His Gly Gln Arg Thr Ile Phe Asn Val Glu Val Arg Arg Pro Ser
 65                  70                  75                  80
Ser Phe Ala Ser Ala Ala Glu Gln Gln Gln His Gln Leu Ala Val Leu
                85                  90                  95
Arg Ala Asp Cys Glu Leu Val Ile Ile Gln Arg Ala Glu Ala Ala Gln
               100                 105                 110
Gly Pro Pro Ala Pro Glu Glu His Thr Ser Ala Gly Ala Ala Ala Ala
               115                 120                 125
Arg Gly Pro Ala Ala Gly Gly Ala Glu Ala Ala Glu Ala Ala Ala Pro
               130                 135                 140
Val Pro Cys Asp Glu Val Val Thr Leu Val Pro Ala Phe Phe Phe Cys
145                 150                 155                 160
Cys Ser Ser Gly Gly Arg Val Thr Val Arg Leu Arg Pro Gly Arg Asp
                165                 170                 175
Gly Tyr Val Ala Gly Glu Ala Ala Glu Val Val Glu Val Asp Asn
                180                 185                 190
Arg Ser Asn Gln Glu Phe Arg Asp Val Arg Leu Glu Val Glu Arg Arg
                195                 200                 205
Leu Thr Leu Val Ser Asn Ser Ala Gly Gly Gly Ser Ala Gly Ser
                210                 215                 220
Ser Gly Ser Gly Ser Ser Ala Thr Ala Gly Leu Val Pro Gly Cys
225                 230                 235                 240
Phe Thr Glu Glu Glu Arg Ile Phe Lys Ser Lys Thr Thr Ala Cys Tyr
                245                 250                 255
Leu Gly Ala Asn Ala Leu Arg Leu Pro Val Pro Leu Pro Ser Asn Thr
                260                 265                 270
Pro Pro Ser Thr Ser Gly Ala Leu Val Arg Cys Ser Tyr Thr Ala Thr
                275                 280                 285
Val Glu Val Leu Pro Ala Ser Ala Thr Ala Leu Arg Gly Ala Ala Pro
                290                 295                 300
Pro Arg Leu Arg Val Pro Leu Thr Val Phe Ala Ser Ala Pro Ser Ser
305                 310                 315                 320
Phe Ala Thr Ala Ala Arg Thr Ala Thr Leu Gln Gln Asp Ala Ser
                325                 330                 335
Glu Gln Ala Pro Ala His Val Leu Val Val Pro Val Asp Val
                340                 345                 350
Val Leu Pro Ala Ala Ala Pro Gln Leu Pro Pro Thr Ala Glu Val Asn
                355                 360                 365
Val Lys Gln His Asn Gly Val Ala Gly Ala Asn Pro Met Tyr Ala Gly
                370                 375                 380
Pro
385

<210> SEQ ID NO 57
<211> LENGTH: 385
<212> TYPE: PRT
<213> ORGANISM: Artificial Sequence
<220> FEATURE:
<223> OTHER INFORMATION: modified protein sequence
```

```
<400> SEQUENCE: 57

His Met Gln Val Tyr Gly Tyr Glu Val Gly Trp Glu Glu Ala His
1               5                   10                  15

Ala Lys Glu Pro Lys Leu Pro Ala Ala Asp Pro Tyr Ala Pro Ser Gln
                20                  25                  30

Leu Val Thr Pro Leu Asp Ser Gln Gln Gln Gln Gln Gln Gln Gln Gln
            35                  40                  45

Pro Pro Pro Pro Ser Ala Ala Ser Lys Ala Ser Pro Leu Gly Val Pro
        50                  55                  60

Arg His Gly Gln Arg Thr Ile Phe Asn Val Glu Val Arg Arg Pro Ser
65                  70                  75                  80

Ser Phe Ala Ser Ala Ala Glu Gln Gln Gln His Gln Leu Ala Val Leu
                85                  90                  95

Arg Ala Asp Cys Glu Leu Val Ile Ile Gln Arg Ala Glu Ala Ala Gln
                100                 105                 110

Gly Pro Pro Ala Pro Glu Glu His Thr Ser Ala Gly Ala Ala Ala
                115                 120                 125

Arg Gly Pro Ala Ala Gly Gly Ala Glu Ala Ala Glu Ala Ala Ala Pro
130                 135                 140

Val Pro Cys Asp Glu Val Val Thr Leu Val Pro Ala Phe Phe Phe Cys
145                 150                 155                 160

Cys Ser Gly Gly Arg Val Thr Val Arg Leu Arg Pro Gly Arg Asp
                165                 170                 175

Gly Tyr Val Ala Gly Glu Ala Ala Glu Val Val Glu Val Asp Asn
                180                 185                 190

Arg Ser Asn Gln Glu Phe Arg Asp Val Arg Leu Glu Val Glu Arg Arg
                195                 200                 205

Leu Thr Leu Val Ser Asn Ser Ala Gly Gly Gly Ser Ala Gly Ser
        210                 215                 220

Ser Gly Ser Gly Ser Ser Ser Ala Thr Ala Gly Leu Val Pro Gly Cys
225                 230                 235                 240

Phe Thr Glu Glu Glu Arg Ile Phe Lys Ser Lys Thr Thr Ala Cys Tyr
                245                 250                 255

Leu Gly Ala Asn Ala Leu Arg Leu Pro Val Pro Leu Pro Ser Asn Thr
            260                 265                 270

Pro Pro Ser Thr Ser Gly Ala Leu Val Arg Cys Ser Tyr Thr Ala Thr
        275                 280                 285

Val Glu Val Leu Pro Ala Ser Ala Thr Ala Leu Arg Gly Ala Ala Pro
        290                 295                 300

Pro Arg Leu Arg Val Pro Leu Thr Val Phe Ala Ser Ala Pro Ser Ser
305                 310                 315                 320

Phe Ala Thr Ala Ala Ala Arg His Ala His Leu Gln Gln Asp Ala Ser
                325                 330                 335

Glu Gln Ala Pro Ala Thr Val Leu Val Val Pro Pro Val Asp Val
                340                 345                 350

Val Leu Pro Ala Ala Ala Pro Gln Leu Pro Pro Thr Ala Glu Val Asn
            355                 360                 365

Val Lys Gln His Asn Gly Val Ala Gly Ala Asn Pro Met Tyr Ala Gly
        370                 375                 380

Pro
385

<210> SEQ ID NO 58
```

```
<211> LENGTH: 385
<212> TYPE: PRT
<213> ORGANISM: Artificial Sequence
<220> FEATURE:
<223> OTHER INFORMATION: modified protein sequence

<400> SEQUENCE: 58

His Met Gln Val Tyr Gly Tyr Glu Val Val Gly Trp Glu Glu Ala His
1               5                   10                  15

Ala Lys Glu Pro Lys Leu Pro Ala Ala Asp Pro Tyr Ala Pro Ser Gln
            20                  25                  30

Leu Val Thr Pro Leu Asp Ser Gln Gln Gln Gln Gln Gln Gln Gln Gln
        35                  40                  45

Pro Pro Pro Ser Ala Ala Ser Lys Ala Ser Pro Leu Gly Val Pro
    50                  55                  60

Arg His Gly Gln Arg Thr Ile Phe Asn Val Glu Val Arg Arg Pro Ser
65                  70                  75                  80

Ser Phe Ala Ser Ala Ala Glu Gln Gln Gln His Gln Leu Ala Val Leu
                85                  90                  95

Arg Ala Asp Cys Glu Leu Val Ile Ile Gln Arg Ala Glu Ala Ala Gln
            100                 105                 110

Gly Pro Pro Ala Pro Glu Glu His Thr Ser Ala Gly Ala Ala Ala Ala
        115                 120                 125

Arg Gly Pro Ala Ala Gly Gly Ala Glu Ala Ala Glu Ala Ala Ala Pro
    130                 135                 140

Val Pro Cys Asp Glu Val Val Thr Leu Val Pro Ala Phe Phe Phe Cys
145                 150                 155                 160

Cys Ser Ser Gly Gly Arg Val Thr Val Arg Leu Arg Pro Gly Arg Asp
                165                 170                 175

Gly Tyr Val Ala Gly Glu Ala Ala Glu Val Val Glu Val Asp Asn
            180                 185                 190

Arg Ser Asn Gln Glu Phe Arg Asp Val Arg Leu Glu Val Glu Arg Arg
        195                 200                 205

Leu Thr Leu Val Ser Asn Ser Ala Gly Gly Gly Ser Ala Gly Ser
    210                 215                 220

Ser Gly Ser Gly Ser Ser Ser Ala Thr Ala Gly Leu Val Pro Gly Cys
225                 230                 235                 240

Phe Thr Glu Glu Glu Arg Ile Phe Lys Ser Lys Thr Thr Ala Cys Tyr
                245                 250                 255

Leu Gly Ala Asn Ala Leu Arg Leu Pro Val Pro Leu Pro Ser Asn Thr
            260                 265                 270

Pro Pro Ser Thr Ser Gly Ala Leu Val Arg Cys Ser Tyr Thr Ala Thr
        275                 280                 285

Val Glu Val Leu Pro Ala Ser Ala Thr Ala Leu Arg Gly Ala Ala Pro
    290                 295                 300

Pro Arg Leu Arg Val Pro Leu Thr Val Phe Ala Ser Ala Pro Ser Ser
305                 310                 315                 320

Phe Ala Thr Ala Ala Ala Arg Thr Ala Thr Leu Gln Gln Asp Ala Ser
                325                 330                 335

Glu Gln Ala Pro Ala Thr Val Leu Val Val Pro Val Asp Val
            340                 345                 350

Val Leu Pro Ala Ala Pro Gln Leu Pro Pro Thr Ala Glu Val Asn
        355                 360                 365

Val Lys Gln His Asn Gly Val Ala Gly Ala Asn Pro Met Tyr Ala Gly
    370                 375                 380
```

Pro
385

<210> SEQ ID NO 59
<211> LENGTH: 500
<212> TYPE: DNA
<213> ORGANISM: Chlamydomonas reinhardtii

<400> SEQUENCE: 59

```
aggggaagta gccttttgcg cgcgtcgttc gggccgcggc gcttgcagca gtatctcgca      60
cggtgagtac ggtattccga ttcccggcag tcgcagaagc gtgatgaaac aggcaatagc     120
aggtatcgaa acggcctgcg gttgcgtgga agccgctgcg ctgttgtgtg atgcattgtt     180
aagttgcatg catagccctt gtgtaaatat gggactgcat atcattttgg ttgaagggc     240
agagggacga ccctgtgggt gcctcgggtc acggcgtggc cgaggtgcac ccttgctgcg     300
taggaaggcg tgtggcgtgc cttcggacgg cacgcagggc ggttgaagta aggcactggg     360
tcgtggtgtg ttcatttatg cgctccttca agtatcctgc ttatttgatg cgtgtttgat    420
tgctagcatt agcaatatgt actgtgaggc ctactttgct cgctgcacac cgcacacatg    480
gacggacgga attatggtct                                                 500
```

<210> SEQ ID NO 60
<211> LENGTH: 500
<212> TYPE: DNA
<213> ORGANISM: Chlamydomonas reinhardtii

<400> SEQUENCE: 60

```
ggaataacga cctgacgcga gcggggcaag aggcgccttc atgccgctac tgcaagtggt      60
catgaagaca gtcgcttctc gcgagacagc ccaaatgata tcaataagat gttacaaggc     120
cgatacctga agctgcagct caagagcgtg ccaaagggtc gctcccccct ccccactcag     180
tctggaacgg gcagcttcga gcgccttcaa tatgccttcg gggttgccgt taggcgcctt     240
gcctaccggg ctacaagggc gctctcatct tagcggcgtg atccctcaga tgtgcaaggg     300
ggaaacgcac cggggggcgg gggcggcagg ccgctgccaa ctgtgcctgc tggcctgctg     360
gccctgtcaa cgggtgtgcg tgctggttgg tatacgaacc ggcgcgggct gcggcgtgtt     420
cacgtgagcg gctcccgcat gcacccaacg tcgcccccctt ttctgttttc tgcctgccgc     480
ccgtgattga tgcccgtggc                                                 500
```

<210> SEQ ID NO 61
<211> LENGTH: 22
<212> TYPE: PRT
<213> ORGANISM: Chlamydomonas reinhardtii

<400> SEQUENCE: 61

Ala Arg His Ala His Leu Gln Gln Asp Ala Ser Glu Gln Ala Pro Ala
1               5                   10                  15

His Val Leu Val Val Val
            20

<210> SEQ ID NO 62
<211> LENGTH: 112
<212> TYPE: DNA
<213> ORGANISM: Unknown
<220> FEATURE:
<223> OTHER INFORMATION: unknown eukaryote

<400> SEQUENCE: 62

-continued

```
atcacagtgg gactccataa atttttctcg aaggaccagc agaaacgaga gaaaaaggac      60
agagtcccca gcgggctgaa ggggatgaaa cattaaagtc aaacaatatg aa             112

<210> SEQ ID NO 63
<211> LENGTH: 51
<212> TYPE: DNA
<213> ORGANISM: artificial sequence
<220> FEATURE:
<223> OTHER INFORMATION: synthesized

<400> SEQUENCE: 63
taacgccagg gttttcccag tcacttccag gtttcagccc caccacccc t               51

<210> SEQ ID NO 64
<211> LENGTH: 46
<212> TYPE: DNA
<213> ORGANISM: artificial sequence
<220> FEATURE:
<223> OTHER INFORMATION: synthesized

<400> SEQUENCE: 64
tagcggcgca ttaagcgcgg cgggcgcggt ggcggcgacg gagggg                    46
```

TRANSFORMATION OF ALGAE FOR INCREASING LIPID PRODUCTION

CROSS REFERENCE TO RELATED APPLICATION

This application is a national phase under 35 U.S.C. §371 of International Application Number PCT/US2011/023406 filed Feb. 1, 2011, U.S. Provisional Application No. 61/301,141, filed Feb. 3, 2010, the entire contents of both applications are incorporated by reference for all purposes.

INCORPORATION OF SEQUENCE LISTING

This application contains a Sequence Listing which has been submitted in ASCII format via EFS-Web and is hereby incorporated by reference in its entirety. Said ASCII copy, created on May 9, 2013, is named 0810US-UTL1_ST25.txt and is 88,159 bytes in size.

INCORPORATION BY REFERENCE

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

BACKGROUND

Microalgae represent a diverse group of micro-organisms adapted to various ecological habitats (for example, as described in Hu et al., Plant J (2008) vol. 54 (4) pp. 621-639). Many microalgae have the ability to produce substantial amounts (for example, 20-50% dry cell weight) of lipids, such as triacyl glycerols (TAGs) and diacylglycerols (DAGs), as storage lipids under stress conditions, such as nitrogen starvation. Under nitrogen starvation many microalgae exhibit decreased growth rate and break down of photo synthetic components, such as chlorophyll.

Fatty acids, the building blocks for TAGs and all other cellular lipids, are synthesized in the chloroplast using a single set of enzymes, in which acetyl CoA carboxylase (ACCase) is key in regulating fatty acid synthesis rates. However, the expression of genes involved in fatty acid synthesis is poorly understood in microalgae. Synthesis and sequestration of TAGs into cytosolic lipid bodies appears to be a protective mechanism by which algal cells cope with stress conditions.

Little is known about the regulation of lipids, such as TAG formation, at the molecular or cellular level. At the biochemical level, available information about fatty acid and TAG synthetic pathways in algae is still fragmentary. Knowledge regarding both the regulatory and structural genes involved in these pathways and the potential interactions between the pathways is lacking. Because fatty acids are common precursors for the synthesis of both membrane lipids and TAGs, how the algal cell coordinates the distribution of the precursors to the two distinct destinations or the inter-conversion between the two types of lipids needs to be elucidated. Many fundamental biological questions relating to the biosynthesis and regulation of fatty acids and lipids in algae need to be answered.

Much research has been conducted over the last few decades regarding using microalgae as an alternative and renewable source of lipid-rich biomass feedstock for bio fuels. Microalgae are an attractive model in that they are capable of producing substantial amounts of lipids such as TAGs and DAGs under stress conditions, such as nitrogen starvation. However, a decrease in growth of the microalgae under nitrogen starvation makes it harder to use microalgae in the large scale production of biofuels. While algae provide the natural raw material in the form of lipid-rich feedstock, our understanding of the details of lipid metabolism in order to enable the manipulation of the process physiologically and genetically is lacking.

Thus, a need exists to better understand the regulation of lipids, such as TAGs and DAGs, in algae at the molecular level. Furthermore, it would be useful to genetically manipulate algae such, that the algae are capable of producing substantial amounts of lipids without decreased growth rate and the break down of algal components, such as chlorophyll.

SUMMARY

Provided herein is an isolated polynucleotide comprising, (a) a nucleic acid sequence of SEQ ID NO: 9; or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 9. In one embodiment, the nucleic acid sequence of SEQ ID NO: 9 is codon optimized for nuclear expression in an algae. In another embodiment, the nucleic acid sequence of SEQ ID NO: 9 is codon optimized for chloroplast expression in an algae. In yet another embodiment, the codon-optimized nucleic acid sequence comprises the nucleotide sequence of SEQ ID NO: 12.

Also provided herein is an isolated polynucleotide comprising, (a) a nucleic acid sequence of SEQ ID NO: 12; or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 12.

Also provided herein is an isolated polynucleotide comprising, (a) a nucleic acid sequence of SEQ ID NO: 4; or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 4. In other embodiments, the nucleotide sequence comprises the sequence of SEQ ID NO: 53, SEQ ID NO: 54, or SEQ ID NO: 55.

Provided herein are isolated polynucleotides comprising the nucleic acid sequence of SEQ ID NO: 9, SEQ ID NO: 12, SEQ ID NO: 4, SEQ ID NO: 53, SEQ ID NO: 54, or SEQ ID NO: 55.

Also provided herein are isolated polynucleotides capable of transforming an organism, wherein the polynucleotides comprise a nucleic acid sequence of SEQ ID NO: 9, SEQ ID NO: 12, SEQ ID NO: 4, SEQ ID NO: 53, SEQ ID NO: 54, or SEQ ID NO: 55.

Provided herein is an isolated polynucleotide comprising a nucleotide sequence having at least 95% sequence identity to a nucleic acid sequence of SEQ ID NO: 9, SEQ ID NO: 12, or SEQ ID NO: 4, wherein the nucleotide sequence comprises at least one mutation comprising one or more nucleotide additions, deletions or substitutions. In one embodiment, the at least one mutation is in a coding region. In another embodiment, the at least one mutation results in one or more amino acid additions, deletions or substitutions in a protein encoded by the coding region. In another embodiment, the at least one mutation is in a regulator/ region. In yet another embodiment, the nucleotide sequence has at least 95% sequence identity to the nucleic acid sequence of SEQ ID NO: 4. In other embodiments, the nucleotide sequence comprises the sequence of SEQ ID NO: 53, SEQ ID NO: 54, or SEQ ID NO: 55.

Also provided herein, is an isolated polynucleotide encoding a protein comprising, (a) an amino acid sequence of SEQ ID NO: 52; or (b) a homolog of the amino acid sequence of SEQ ID NO: 52, wherein the homolog has at least 50%, at least 60%, at least 70%, at least 75%, at least 80%, at least 85%, at least 90%, at least 95%, at least 98%, or at least 99% sequence identity to the amino acid sequence of SEQ ID NO: 52.

Provided herein is an isolated polynucleotide encoding a protein comprising, (a) an amino acid sequence of SEQ ID NO: 56, SEQ ID NO: 57, or SEQ ID NO: 58.

Also provided herein is a vector comprising a polynucleotide comprising, (a) a nucleic acid sequence of SEQ ID NO: 9, SEQ ID NO: 12, SEQ ID NO: 4, SEQ ID NO: 53, SEQ ID NO: 54, or SEQ ID NO: 55; or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 9, SEQ ID NO: 12, SEQ ID NO: 4, SEQ ID NO: 53, SEQ ID NO: 54, or SEQ ID NO: 55. In one embodiment, the vector is an expression vector. In another embodiment, the vector further comprises a 5' regulatory region. In yet another embodiment, the 5' regulatory region further comprises a promoter. In an embodiment, the promoter is a constitutive promoter. In another embodiment, the promoter is an inducible promoter. In other embodiments, the inducible promoter is a light inducible promoter, a nitrate inducible promoter, or a heat responsive promoter. In other embodiments, the vector further comprises a 3' regulatory region.

Provided herein is a transformed organism comprising, (a) a nucleic acid sequence of SEQ ID NO: 9, SEQ ID NO: 12, SEQ ID NO: 4, SEQ ID NO: 53, SEQ ID NO: 54, or SEQ ID NO: 55; or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 9, SEQ ID NO: 12, SEQ ID NO: 4, SEQ ID NO: 53, SEQ ID NO: 54, or SEQ ID NO: 55.

Also provided herein is a trans formed organism comprising an amino acid sequence of SEQ ID NO: 52, SEQ ID NO: 56, SEQ ID NO: 57, or SEQ ID NO: 58.

Provided herein is a transformed organism comprising a polynucleotide wherein the transformed organism has a different fatty acid or glycerol lipid content, or profile than an untransformed organism and the polynucleotide comprises a nucleic acid sequence of SEQ ID NO: 9, SEQ ID NO: 12, SEQ ID NO: 4, SEQ ID NO: 53, SEQ ID NO: 54, or SEQ ID NO: 55.

Also provided herein is a photosynthetic organism comprising a polynucleotide comprising, (a) a nucleic acid sequence of SEQ ID NO: 9, SEQ ID NO: 12, or SEQ ID NO: 4, or (b) a nucleotide sequence having at least 95% identity to the nucleic acid sequence of SEQ ID NO: 9, SEQ ID NO: 12, or SEQ ID NO: 4, wherein the nucleotide sequence comprises at least one mutation comprising one or snore nucleotide additions, deletions or substitutions. In one embodiment, the at least one mutation is in a coding region. In other embodiments, the at least one mutation results in one or more amino acid additions, deletions or substitutions in a protein encoded by the coding region. In yet another embodiment, the at least one mutation is in a regulatory region. In an embodiment, the at least one mutation is in a 5' UTR. In another embodiment, the at least one mutation is in a 3' UTR. In yet another embodiment, the at least one mutation is in a promoter. In one embodiment, the nucleotide sequence has at least 95% identity to the nucleic acid of SEQ ID NO: 4. In other embodiments, the nucleotide sequence comprises the sequence of SEQ ID NO: 53, SEQ ID NO: 54, or SEQ ID NO: 55. In one embodiment, the organism is grown in an aqueous environment. In another embodiment, the organism is a vascular plant. In yet another embodiment, the organism is a non-vascular photosynthetic organism. In other embodiments, the organism is an alga or a bacterium. In one embodiment, the bacterium is a cyanobacterium. In yet another embodiment, the alga is a microalga. In other embodiments, the microalga is at least one of a *Chlamydomonas* sp. *Volvacales* sp., *Dunaliella* sp., *Scenedesmus* sp., *Chlorella* sp., *Hematococcus* sp., *Volvox* sp., or *Nannochloropsis* sp. In yet other embodiments, the microalga is at least one of *C. reinhardtii, N. oceanica, N. salina, D. salina, H. pluvaiis, S. dimorphus, D. viridis, N. oculata* or *D. tertiolecta*. In an embodiment, the *C. reinhardtii* is wild-type strain CC-1690 21 gr mt+.

Also provided herein is a method of changing a fatty acid or glycerol lipid content or profile in an organism comprising transforming the organism with a polynucleotide comprising a nucleic acid sequence of SEQ ID NO: 9, SEQ ID NO: 12, SEQ ID NO: 4, SEQ ID NO: 53, SEQ ID NO: 54, or SEQ ID NO: 55, or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 9, SEQ ID NO: 12, SEQ ID NO: 4, SEQ ID NO: 53, SEQ ID NO: 54, or SEQ ID NO: 55, wherein the change is compared to an untransformed organism. In some embodiments, the glycerol lipid content or profile of the organism is changed. In other embodiments, the glycerol lipid is TAG, DAG, a neutral storage lipid, or a polar lipid. In one embodiment, the glycerol lipid profile of the organism is changed. In another embodiment, the change is a shift in lipid metabolism from membrane lipid synthesis to storage of neutral lipids. In one embodiment, the organism is an evolved organism. In yet other embodiments, the organism to be transformed has been evolved to be salt tolerant, to be biocide resistant, to be resistant to sodium hypochlorite, or to be tolerant to pH levels above 9.0 as compared to an unevolved organism. In another embodiment, the organism is a previously or concurrently transformed organism. In other embodiments, the organism has been previously or concurrently transformed with a nucleotide sequence that when expressed results in the organism having increased salt tolerance, biocide resistance, sodium hypochlorite resistance, or pH tolerance, as compared to an untransformed organism, la some embodiments, the content of the fatty acid or glycerol lipid is increased in the organism. In other embodiments, the content of the fatty acid or glycerol lipid is decreased in the organism. In other embodiments, the fatty acid or glycerol lipid profile is different from that of the untransformed organism. In yet other embodiments, she change is measured by extraction, gravimetric extraction, or lipid dyes. In some embodiments, the extaction is Bligh-Dyer or MTBE. In other embodiments, the lipid dye is Bodipy, LipidTOXgreen, or Nile Red. In one embodiment, the organism is grown in an aqueous environment. In another embodiment, the organism is a vascular plant. In yet another embodiment, the organism is a non-vascular photosynthetic organism. In other embodiments, the organism is an alga or a bacterium. In one embodiment, the bacterium is a cyanobacterium. In another embodiment, the alga is a microalga. In some embodiments, the microalga is *Chlamydomonas* sp., *Volvacales* sp., *Dunaliella* sp., *Scenedesmus* sp., *Chlorella* sp., *Hematococcus* sp., *Volvox* sp., or *Nannochloropsis* sp. In other embodiments, the microalga is *C. reinhardtii, N. oceanica, N. salina, D. salina, H. pluvalis, S. dimorphus, D. viridis, N. oculata* or *D. tertiolecta*. In one embodiment, the *C. reinhardtii* is wild-type strain CC-1690 21 gr mt+. In another embodiment, the organism's nuclear genome is transformed. In yet another embodiment, the organism's chloroplast genome is transformed. In some embodiments, the organism is cultured in a media comprising a final $NH_4Cl$ concentration of at least about 0.5 mM to about 7.5 mM. In one embodiment, the organism is cultured in a media comprising a final $NH_4Cl$ concentration is at least about 7.5 mM. In other embodiments, the organism is cultured in a media comprising a final nitrate concentration of at least about 0.5 mM to about 7.5 mM. In one embodiment, the organism is cultured in a media comprising a final nitrate concentration of at least about 7.5 mM.

Provided herein is a method of producing a fatty acid or a glycerol lipid, comprising: i) transforming an organism with a polynucleotide comprising a nucleotide sequence encoding a protein capable of being expressed in the organism, wherein expression of the protein results in the production of or increased production of or an altered profile of the fatty acid or the glycerol lipid as compared to an untransformed organism, and wherein the nucleotide sequence comprises, (a) a nucleic acid sequence of SEQ ID NO: 9, SEQ ID NO: 12, SEQ ID NO: 4, SEQ ID NO: 53, SEQ ID NO: 54, or SEQ ID NO: 55, or (b) a nucleotide sequence with at least 50%, at least 60%, at least 70%, at least 75%, at least 80%, at least 85%, at least 90%, at least 95%, at least 98%, or at least 99% sequence identity to the nucleic acid sequence of SEQ ID NO: 9, SEQ ID NO: 32, SEQ ID NO: 4, SEQ ID NO: 53, SEQ ID NO: 54, or SEQ ID NO: 55. In some embodiments, the protein comprises the amino acid sequence of SEQ ID NO: 52, SEQ ID NO: 56, SEQ ID NO: 57, or SEQ ID NO: 58. In other embodiments, the fatty acid or glycerol lipid is stored in a lipid body, a cell membrane, an inter-thylakoid space, or a plastoglubuli of the organism. In still other embodiments, the organism is cultured in media comprising a final $NH_4Cl$ concentration of at least about 0.5 mM to about 7.5 mM. In another embodiment, the organism is cultured in media comprising a final $NH_4Cl$ concentration of at least about 7.5 mM.

In some embodiments, the organism is cultured in media comprising a final nitrate concentration of at least about 0.5 mM to about 7.5 mM. In another embodiment, the organism is cultured in media comprising a final nitrate concentration of at least about 7.5 mM. In other embodiments, the method further comprises collecting the fatty acid or glycerol lipid from a lipid body or a cell membrane of the organism. In yet other embodiments, the glycerol lipid is a triacylglycerol (TAG), a diacyglycerol (DAG), a glycosylglycerol lipid, a glycerophospholipid, a spingolipid, or other polar lipid. In one embodiment, the organism's nuclear genome is transformed. In another embodiment, the organism's chloroplast genome is transformed. In yet another embodiment, the organism's growth rate is not substantially decreased as compared to the untransformed organism. In some embodiments, the substantial decrease is about 2%, about 4%, about 6%, about 8%, about 10%, about 12%, about 14%, about 16%, about 18%, about 20%, about 22%, about 24%, about 26%, about 28%, or about 30%. In another embodiment, the organism's chlorophyll level is not substantially decreased as compared to the untransformed organism. In some embodiments, the substantial decrease is about 2%, about 4%, about 6%, about 8%, about 10%, about 12%, about 14%, about 16%, about 18%, about 20%, about 22%, about 24%, about 26%, about 28%, or about 30%.

Also provided herein is a method of screening for proteins involved in fatty acid or glycerol lipid metabolism in an organism comprising, (i) transforming the organism, with a polynucleotide comprising a nucleic acid sequence of SEQ ID NO: 9, SEQ ID NO: 12, SEQ ID NO: 4, SEQ ID NO: 53, SEQ ID NO: 54, or SEQ ID NO: 55, wherein the transformation results in expression of a polypeptide encoded by the corresponding nucleic acid sequence of SEQ ID NO: 9, SEQ ID NO: 12, SEQ ID NO: 4, SEQ ID NO: 53, SEQ ID NO: 54, or SEQ ID NO: 55, and (ii) observing a change in expression of an RNA in the transformed organism as compared to an untransformed organism. In one embodiment, the change is an increase in expression of the RNA in the transformed organism as compared to the untransformed organism. In another embodiment, the change is a decrease in expression of the RNA in the transformed organism as compared to the untransformed organism. In yet another embodiment, the organism is grown in an aqueous environment. In another embodiment, the organism is a vascular plant. In one embodiment, the organism is a non-vascular photosynthetic organism. In some embodiments, the organism is an alga or a bacterium. In one embodiment, the bacterium is a cyanobacterium. In another embodiment, the alga is a microalga. In some embodiments, the microalga is a *Chlamydomonas* sp., *Volvacales* sp., *Dunaliella* sp., *Scenedesmus* sp., *Chlorella* sp., *Hematococcus* sp., *Volvox* sp., or *Nannochloropsis* sp. In other embodiments, the microalga is a *C. reinhardtii, N. oceanica, N. salina, D. salina, H. pluvalis, S. dimorphus, D. viridis, N. oculata* or *D. tertiolecta*. In one embodiment, the *C. reinhardtii* is wild-type strain CC-1690 21 gr mt+. In another embodiment, the organism's nuclear genome is transformed. In yet another embodiment, the organism's chloroplast genome is transformed, in some embodiments, the change is measured by a microarray, RNA-Seq, or serial analysis of gene expression (SAGE). In other embodiments, the change is at least two fold or at least four fold as compared to an untransformed organism. In still other embodiments, the organism is grown in the presence or in the absence of nitrogen.

Provided herein is a method of screening for proteins involved in fatty acid or glycerol lipid metabolism in an organism comprising, (i) transforming the organism with a microRNA construct comprising a 21 nucleotide sequence directed towards any portion of a nucleic acid sequence of SEQ ID NO: 1 or SEQ ID NO: 8, or any portion of a 5' UTR (SEQ ID NO: 59) or a 3' UTR (SEQ ID NO: 60), and (ii) observing a change in expression of an RNA in the transformed organism as compared to an untransformed organism. In one embodiment, the change is an increase in expression of the RNA in the transformed organism as compared to the untransformed organism. In another embodiment, the change is a decrease in expression of the RNA in the transformed organism as compared to the untransformed organism. In yet another embodiment, the organism is grown in an aqueous environment. In one embodiment, the organism is a vascular plant. In another embodiment, the organism is a non-vascular photosynthetic organism. In some embodiments, the organism is an alga or a bacterium. In one embodiment, the bacterium is a cyanobacterium. In another embodiment the alga is a microalga. In some embodiments, the microalga is a *Chlamydomonas* sp.,

*Volvacales* sp., *Dunaliella* sp., *Scenedesmus* sp., *Chlorella* sp., *Hematococcus* sp., *Volvox* sp., or *Nannochloropsis* sp. In other embodiments, the microalga is a *C. reinhardtii, N. oceanica, N. salina, D. salina, H. pluvalis, S. dimorphus, D. viridis, N. oculata* or *D. tertiolecta*. In one embodiment, the *C. reinhardtii* is wild-type strain CC-1690 21 gr mt+. In another embodiment, the nuclear genome of the organism is transformed. In yet another embodiment, the chloroplast genome of the organism is transformed. In some embodiments, she change is measured by a microarray, RNA-Seq, or serial analysis of gene expression (SAGE). In yet other embodiments, the change is at least two fold or at least four fold as compared to an untransformed organism. In other embodiments, the organism is grown in the presence or in the absence of nitrogen.

BRIEF DESCRIPTION OF THE DRAWINGS

These and other features, aspects, and advantages of the present disclosure will become better understood with regard to the following description, appended claims and accompanying figures where:

FIG. 8A shows percent lipid levels in three algal strains (SE0004 is *Scenedesmus dimorphus*; SE0043 is *Dunaliella Salina*; and SE0050 is *Chlamydomonas reinhardtii*) in the presence and absence of nitrogen.

FIG. 8B shows percent lipid levels in the two algal strains shown in FIG. 8A with the addition of SE0003 (*Dunaliella salina*).

FIG. 8C shows growth of *Chlamydomonas reinhardtii* in the presence and absence of nitrogen.

FIG. 8D shows chlorophyll levels in *Chlamydomonas reinhardtii* in the presence and absence of nitrogen over a 9-day time course.

FIGS. 19A and B use Bodipy dye; FIG. 19C uses Lipid TOX green; and FIG. 19D uses Nile Red. Wild type is *Chlamydomonas reinhardtii* replicates and the numbers represent the various SN03 strains.

FIGS. 23A and B represent strains grown in TAP and FIG. 23C represents strains grown in HSM.

FIG. 43 shows the genomic integration site of the SN03 vector (as shown in FIG. 34) for two SN03 overexpression cell lines. The nucleic acid sequences of a portion of vector Ble2A-SN03 and a portion of the genomic sequence of *Chlamydomonas reinhardtii*, as described in Example 5, are shown in SEQ ID NO: 63 and SEQ ID NO: 64.

FIG. 49 shows a protein alignment of the U.S. Department of Energy (DOE) Joint Genome Institute (JGI) annotated SN03 sequence (SEQ ID NO: 6) and the endogenous SN03 sequence (SEQ ID NO: 14).

DETAILED DESCRIPTION

Figure 1A:
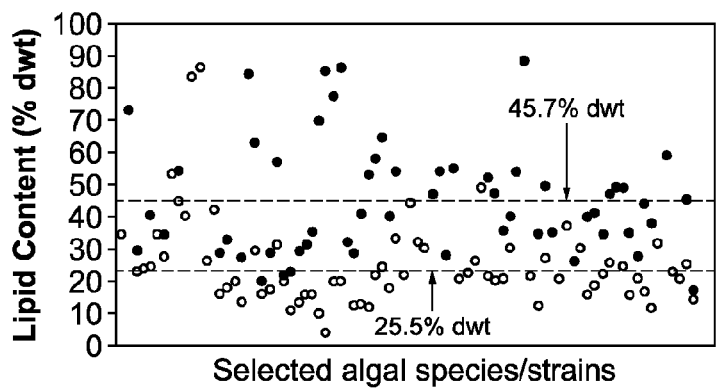
FIG. 1 shows cellular lipid content in various classes of microalgae and cyanobacteria under normal growth (NG) and stress conditions (SC), (a) green microalgae; (b) diatoms; (c) oleaginous species/strains from other eukaryotic algal taxa; and (d) cyanobacteria. Open circles: cellular lipid contents obtained under normal growth or nitrogen-replete conditions. Closed circles: cellular lipid contents obtained under nitrogen-depleted or other stress conditions. The differences in cellular lipid content between cultures under normal growth and stress growth, conditions were statistically significant for all three groups (a, b and c) of algae examined using Duncan's multiple range test with the ANOVA procedure.

The following detailed description is provided to aid those skilled in the art in practicing the present disclosure. Even so, this detailed description should not be construed to unduly limit the present disclosure as modifications and variations in the embodiments discussed herein can be made by those of ordinary skill in the art without departing from the spirit or scope of the present disclosure.

As used in this specification and the appended claims, the singular forms "a", "an" and "the" include plural reference unless the context clearly dictates otherwise.

Endogenous

An endogenous nucleic acid, nucleotide, polypeptide, or protein as described herein is defined in relationship to the host organism. An endogenous nucleic acid, nucleotide, polypeptide, or protein is one that naturally occurs in the host organism.

Exogenous

An exogenous nucleic acid, nucleotide, polypeptide, or protein as described herein is defined in relationship to the host organism. An exogenous nucleic acid, nucleotide, polypeptide, or protein is one that does not naturally occur in the host organism or is a different location in the host organism.

Nucleic Acid and Protein Sequences

The following nucleic acid and amino acid sequences are useful in the disclosed embodiments.

If a stop codon is not present at the end of a coding sequence, one of skill in the art would know to insert nucleotides encoding for a stop codon (TAA, TAG, or TGA) at the end of the nucleotide sequence. If an initial start codon (Met) is not present from the amino acid sequence, one of skill in the art would be able to include, at the nucleotide level, an initial ATG, so that the translated polypeptide would have the initial Met.

SEQ ID NO: 1 is the nucleotide sequence of SN03 annotated in the *Chlamydomonas reinhardtii* wild-type strain CC-1690 21gr mt+ genome (JGI protein ID #147817).

SEQ ID NO: 2 is the sequence of SEQ ID NO: 1 without an initial "atg" and a stop codon.

SEQ ID NO: 3 is the nucleotide sequence of SEQ ID NO: 1 codon optimized for expression in the nucleus of *Chlamydomonas reinhardtii*. There is no stop codon.

SEQ ID NO: 4 is the sequence of SEQ ID NO: 3 without an initial "atg",

SEQ ID NO: 5 is the nucleotide sequence of SEQ ID NO: 3 with the addition at the 3'end of an AgeI restriction site, a nucleotide sequence coding for a FLAG sag, a nucleotide sequence coding for a MAT tag, another AgeI restriction site, and a stop codon.

SEQ ID NO: 6 is the translated protein sequence of SEQ ID NO: 1.

SEQ ID NO: 7 is the translated protein sequence of SEQ ID NO: 5.

SEQ ID NO: 8 is the nucleotide sequence of the endogenous SN03 cDNA taken from *Chlamydomonas reinhardtii* wild-type strain CC-1690 21 gr mt+.

SEQ ID NO: 9 is the sequence of SEQ ID NO: 8 without an initial "atg" and a stop codon.

SEQ ID NO: 10 is the sequence of SEQ ID NO: 8 with an XhoI restriction site in place of the ATG at the 5' end, an AgeI restriction site after the final codon, a nucleotide sequence coding for a FLAG tag, a nucleotide sequence coding for a MAT tag, a six base pair sequence corresponding to the joining of XmaI and AgeI restriction sites, and a STOP codon at the 3' end.

SEQ ID NO: 11 is the sequence of SEQ ID NO: 8 codon optimized for expression in the nucleus of *Chlamydomonas reinhardtii*.

SEQ ID NO: 12 is the sequence of SEQ ID NO: 11 without an initial "atg" and a stop codon.

SEQ ID NO: 13 is the sequence of SEQ ID NO: 11 with an XhoI restriction site in place of the ATG at the 5' end, an AgeI restriction site after the final codon, a nucleotide sequence coding for a FLAG tag, a nucleotide sequence coding for a MAT tag, a six base pair sequence corresponding to the joining of XmaI and AgeI restriction sites, and a STOP codon at the 3" end.

SEQ ID NO: 14 is the translated protein of SEQ ID NO: 8.

SEQ ID NO: 15 is the translated protein sequence of SEQ ID NO: 13.

SEQ ID NO: 16 is the nucleotide sequence of SEQ ID NO: 50 with the codons for two of the histidine residues that make up the putative zinc finger domain altered to code for threonine; specifically nucleic acid numbers 982 and 983 are changed from a CA to an AC, and nucleic acids numbers 988 and 989 are changed from a CA to an AC.

SEQ ID NO: 17 is the nucleotide sequence of SEQ ID NO: 50 with the codons for one of the histidine residues that make up the putative zinc finger domain altered to code for threonine; specifically nucleic acid numbers 1024 and 1025 are changed from a CA to an AC.

SEQ ID NO: 18 is the nucleotide sequence of SEQ ID NO: 50 with the codons for three of the histidine residues that make up the putative zinc finger domain altered to code for threonine; specifically nucleic acid numbers 982 and 983 are changed from a CA to an AC, nucleic acids numbers 988 and 989 are changed from a CA to an AC, and nucleic acid numbers 1024 and 1025 are changed from a CA to an AC.

SEQ ID NO: 19 is the translated protein of SEQ ID NO: 16.

SEQ ID NO: 20 is the translated protein of SEQ ID NO: 17.

SEQ ID NO: 21 is the translated protein of SEQ ID NO: 18.

SEQ ID NOs: 22 to 37 are primer sequences.

SEQ ID NOs: 38-41 are miRNA target nucleotide sequences.

SEQ ID NOs: 42-47 are primer sequences.

SEQ ID NO: 48 is the nucleotide sequence of BD11.

SEQ ID NO: 49 is a primer sequence.

SEQ ID NO: 50 is the sequence of SEQ ID NO: 3 with an XhoI restriction site in place of the ATG at the 5' end, an AgeI restriction site after the final codon, a nucleotide sequence coding for a FLAG tag, a nucleotide sequence coding for a MAT tag, a six base pair sequence encoding an AgeI restriction site, and a STOP codon at the 3' end.

SEQ ID NO: 51 is the protein sequence of SEQ ID NO: 6 without the initial "M".

SEQ ID NO: 52 is the protein sequence of SEQ ID NO: 14 without the initial "M".

SEQ ID NO: 53 is a nucleotide sequence comprising a mutated putative zinc finger domain, SEQ ID NO: 54 is a nucleotide sequence comprising a mutated putative zinc finger domain, SEQ ID NO: 55 is a nucleotide sequence comprising a mutated putative zinc finger domain, SEQ ID NO: 56 is the translated protein sequence of SEQ ID NO: 53.

SEQ ID NO: 57 is the translated protein sequence of SEQ ID NO: 54.

SEQ ID NO: 58 is the translated protein sequence of SEQ ID NO: 55.

SEQ ID NO: 59 is a 5' untranslated (UTR) region.

SEQ ID NO: 60 is a 3' untranslated (UTR) region.

Media's Used and Levels of Ammonium

Tris-acetate-phosphate (TAP) media contains a final concentration of 7.5 mM $NH_4Cl$. High-salt-media (HSM) contains a final concentration of 7.5 mM $NH_4Cl$ (for example, as described in Harris (2009) The *Chlamydomonas* Sourcebook, Academic Press, San Diego, Calif.) Modified artificial seawater media (MASM) contains a final concentration of 11.8 mM $NaNO_3$ and 0.5 mM $NH_4Cl$. The final $NH_4Cl$ concentration in TAP or HSM media can be varied, for example, so that the final $NH_4Cl$ concentration is about 0.5 mM to about 7.5 mM.

The interrelation between the different nitrogen limitation phenotypes in algae (i.e., increased lipid, breakdown of photosystem, decreased growth, and mating induction) has long been assumed to be directly linked. Efforts to separate, for example, the lipid increase from reduced growth have met with failure, leading to the accepted hypothesis that nutrient flux is fixed and increasing usage for one pathway (e.g., lipid) always leads to a concomitant reduction in another pathway (e.g., growth). Under environmental stress, many algae modify their biosynthetic pathways to accumulate higher levels of lipid, with concurrent changes in the profile of accumulated lipids as well.

We have identified an mRNA encoding a protein (SN03) in *Chlamydomonas reinhardtii* wild-type strain CC-1690 21 gr mt+ whose expression is up regulated upon nitrogen starvation (stress conditions). SN03 acts as a lipid trigger; over expression of this protein in algae leads to increases in lipid levels with little impact on other nitrogen limitation phenotypes. Over-expression of this protein in algae results in an increase in total extractable fats and a change in the lipid profile that is similar to the change in profile induced by nitrogen starvation. Thus, we have triggered stress-induced lipid accumulation in the absence of external stress.

Algae are analyzed for total gravimetric lipids by methanol/methyl-tert-butyl ether (MTBE) extraction according to a modified Bligh Dyer method (as described in Matyash V., et al. (2008) journal of Lipid Research 49:1137-1146) or by the original Bligh Dyer method (as described in BLIGH and DYER. (1959) Can J Biochem Physiol vol. 37 (8) pp. 911-7). These total extractable fats are analyzed by HPLC or NMR to determine the distribution of lipids among various lipid classes (lipid profile).

Overexpression of SN03 in a host will allow for an increased level of extractable lipids to make, for example, biofuels. The identification of SN03 will allow one skilled in the art to determine the various pathways affected by changes in nitrogen levels that are responsible for the various downstream phenotypes. In addition, the methods described herein will allow for the identification of proteins that are homologous to SN03.

Algae

Oxygenic photosynthetic microalgae and cyanobacteria (for simplicity, algae) represent an extremely diverse, yet highly specialized group of micro-organisms that live in diverse ecological habitats such as freshwater, brackish, marine, and hyper-saline, with a range of temperatures and pH, and unique nutrient availabilities (for example, as described in Falkowski, P. G., and Raven, J. A., Aquatic Photosynthesis, Maiden, M A: Blackwell Science). With over 40,000 species already identified and with many more yet to be identified, algae are classified in multiple major groupings as follows: cyanobacteria (Cyanophyceae), green algae (Chlorophyceae), diatoms (Bacillariophyceae), yellow-green algae (Xanthophyceae), golden algae (Chrysophyeeae), red algae (Rhodophyceae), brown algae (Phaeophyceae), dinoflagellates (Dinophyceae), and 'picoplankton' (Prasinophyceae and Eustigmatophyceae). Several additional divisions and classes of unicellular algae have been described, and details of their structure and biology are available (for example, as described in Van den Hoek et al., 1995). Thousands of species and strains of these algal taxa are currently maintained in culture collections throughout the world (http://www.utex.org; http://ccmp.bigelow.org; http://www.ccap.ac.uk; http://www.marine.csiro.au/microalgae; http://wdcm.nig.ac.jp/hpcc.html). In addition, there are many species of macroalgae, for example, *Cladophora glomerata* and *Fucus vesiculosus*.

The ability of algae to survive or proliferate over a wide range of environmental conditions is, to a large extent, reflected in the tremendous diversity and sometimes unusual pattern of cellular lipids that algae can produce as well as the ability to modify lipid metabolism efficiently in response to changes in environmental conditions (for example, as described in Guschina, I. A. and Harwood, J. L. (2006) Prog. Lipid Res. 45, 160-186; Thompson, G. A, (1996) Biochim. Biophys. Acta, 1302, 17-45; and Wada, H. and Murata, M. (1998) Membrane lipids in cyanobacteria. In Lipids in Photosynthesis: Structure, Function and Genetics (Siegenthaler, P. A. and Murata, N., eds). Dordrecht, The Netherlands: Kluwer Academic Publishers, pp. 65-81). The lipids that algae produce may include, but are not limited to, neutral lipids, polar lipids, wax esters, sterols and hydrocarbons, as well as prenyl derivatives such as tocopherols, carotenoids, terpenes, quinines, and phytylated pyrrole derivatives such as the chlorophylls.

Under optimal conditions of growth, algae synthesize fatty acids principally for esterification into glycerol-based membrane lipids, which constitute about 5-20% of their dry cell weight (DCW). Fatty acids include medium-chain (C10-C14), long-chain (C16-18), and very-long-chain (C20 or more) species and fatty acid derivatives. The major membrane lipids are the glycosylglycerides (e.g. monogalactosyidiacylglycerol, digalactosyldiacylglycerol and sulfoquinovosyldiacylgiycerol), which are enriched in the chloroplast, together with significant amounts of phosphoglycerides (e.g. phosphatidylethanolamine, PE, and phosphatidylgiycerol, PG), which mainly reside in the plasma membrane and many endoplasmic membrane systems (for example, as described in Guckert, J. B. and Cooksey, K. E. (1990) J. Phycol. 26, 72-79; Harwood, J. L. (1998) Membrane lipids in algae. In Lipids in Photosynthesis: Structure, Function and Genetics (Siegenthaler, P. A. and Murata, N., eds). Dordrecht, The Netherlands: Kluwer Academic Publishers, pp. 53-64; Pohl, P. and Zurheide, F. (1979) Fatty acids and lipids of marine algae and the control of their biosynthesis by environmental factors. In Marine Algae in Pharmaceutical Science (Hoppe, H. A., Levring, T, and Tanaka, Y., eds). Berlin: Walter de Gruyter, pp. 473-523; Pohl, P. and Zurheide, F. (1979) Control of fatty acid and lipid formation, in Baltic marine algae by environmental factors. In Advances in the Biochemistry and Physiology of Plant Lipids (Appelqvist, L. A. and Liljenberg, C, eds). Amsterdam: Elsevier, pp. 427-432; and Wada, H, and Murata, N. (1998) Membrane lipids in cyanobacteria. In lipids in Photosynthesis: Structure, Function and Genetics (Siegenthaler, P. A., and Murata, N., eds). Dordrecht, The Netherlands: Kluwer Academic Publishers, pp. 65-81). The major constituents of the membrane glycerolipids are various kinds of fatty acids that are polyunsaturated and derived through aerobic desaturation and chain elongation from the 'precursor' fatty acids palmitic (16:0) and oleic (18:1ω9) acids (for example, as described in Erwin, J. A. (1973) Comparative biochemistry of fatty acids in eukaryotic microorganisms. In Lipids and Biomembranes of Eukaryotic Microorganisms (Erwin, J. A., ed.) New York: Academic Press, pp. 141-143).

Under unfavorable environmental or stress conditions for growth, however, many algae alter their lipid biosynthetic pathways towards the formation and accumulation of neutral lipids (20-50% DCW), mainly in the form of triacylglycerol (TAG). Unlike the glycerolipids found in membranes, TAGs do not perform a structural role but instead serve primarily as a storage form of carbon and energy. However, there is some evidence suggesting that, in algae, the TAG biosynthesis pathway may play a more active role in the stress response, in addition to functioning as a carbon and energy storage under environmental stress conditions. Unlike higher plants where individual classes of lipid may be synthesized and localized in a specific cell, tissue or organ, many of these different types of lipids occur in a single algal cell. After being synthesized, TAGs are deposited in densely packed lipid bodies located in the cytoplasm of the algal cell, although formation and accumulation of lipid bodies also occurs in the inter-thylakoid space of the chloroplast in certain green algae, such as *Dunaliella bardawil* (for example, as described in Ben-Amotz, A., et al. (1989) Plant Physiol. 91, 1040-1043). In the latter case, the chloroplastic lipid bodies are referred to as plastoglobuli. Hydrocarbons are another type of neutral lipid that can be found in algae at quantities generally <5% DCW (for example, as described in Lee, R. F. and Loeblich, A. R. III (1971) Phytochemistry, 10, 593-602). The colonial green alga, *Botryococcus braunii*, has been shown to produce, under adverse environmental conditions, large quantities (up to 80% DCW) of very-long-chain (C23-C40) hydrocarbons, similar to those found in petroleum.

Lipid and Triacylglycerol Content

The majority of photo synthetic micro-organisms routinely used in the laboratory (e.g. *Chlamydomonas reinhardtii*) were selected because of ease of cultivation, or as genetic model systems for studying photosynthesis (for example, as described in Grossman et al., 2007, Curr. Opin. Plant Biol. 10, 190-198; and Merchant et al., 2007, Science, 318, 245-251). These few organisms were not selected for optimal lipid production. Therefore, examination of lipid synthesis and accumulation in diverse organisms has the potential for insights into new mechanisms to enhance lipid production. Over the past few decades, several thousand algae, and cyanobacterial species, have been screened for high lipid content, of which several hundred oleaginous species have been isolated and characterized under laboratory and/or outdoor culture conditions. Oleaginous algae can be found among diverse taxonomic groups, and the total lipid content may vary noticeably among individual species or strains within and between taxonomic groups. Of the strains examined, green algae represent the largest taxonomic group from which oleaginous candidates have been identified. This may not be because green algae naturally contain considerably more lipids than other algal taxa, but rather because many green algae are ubiquitous in diverse natural habitats, can easily be isolated, and generally grow faster than species from other taxonomic groups under laboratory conditions. FIG. 1(a) summarizes the total lipid contents of oleaginous green algae reported in the literature. Each data point represents the total lipid of an individual species or strain grown under optimal culture conditions. Oleaginous green algae show an average total lipid content of 25.5% DCW. The lipid content increases considerably (doubles or triples) when the cells are subjected to unfavorable culture conditions, such as photo-oxidative stress or nutrient starvation. On average, an increase in total lipids to 45.7% DCW was obtained from an oleaginous green algae grown under stress conditions. An effort was made to determine whether green algae at the genus level exhibit different capacities to synthesize and accumulate lipids. Statistical analysis of various oleaginous green algae indicated no significant differences. The intrinsic ability to produce large quantities of lipid and oil is species/strain-specific, rather than genus-specific (for example, as described in Hu et al., 2006, Biodiesel from Algae: Lessons Learned Over the Past 60 Years and Future Perspectives. Juneau, Alaska: Annual Meeting of the Phycological Society of America, July 7-12, pp. 40-41 (Abstract)).

Figure 1B:
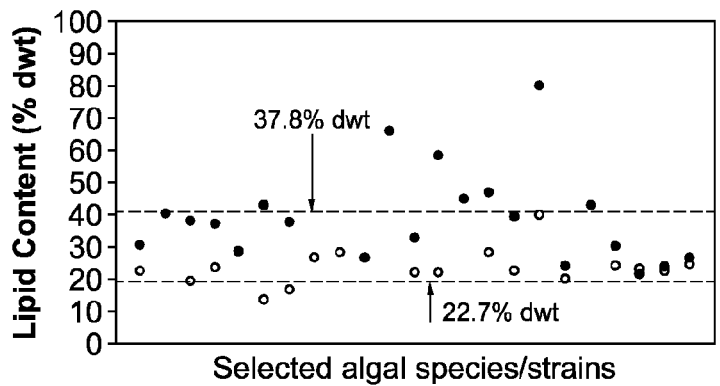

FIG. 1(b) illustrates the lipid content of oleaginous diatoms of freshwater and marine origin grown under normal and stress culture conditions (for example, as described in Hu et al., 2006, Biodiesel from Algae: Lessons Learned Over the Past 60 Years and Future Perspectives. Juneau, Alaska: Annual Meeting of the Phycological Society of America, July 7-12, pp. 40-41 (Abstract)). Statistical analysis indicated that the average lipid content of an oleaginous diatom was 22.7% DCW when maintained under normal growth conditions, whereas a total lipid content of 44.6% DCW was achievable under stress conditions.

Figure 1C:
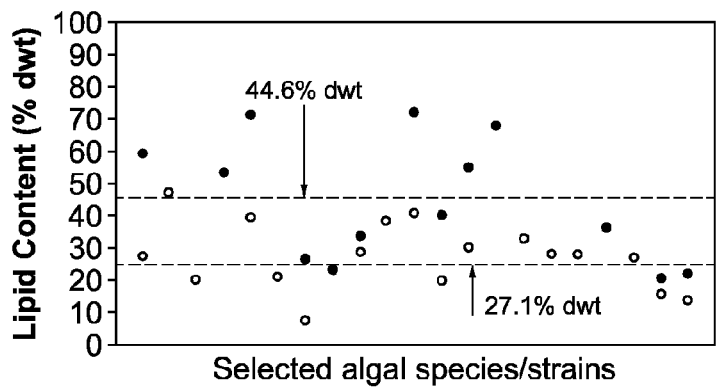

FIG. 1(c) shows the lipid content of oleaginous algae identified as chrysophytes, haptophytes, eustigmatophytes, dinophytes, xanthophytes, or rhodophytes (for example, as described in Hu et al., 2006, Biodiesel from Algae: Lessons Learned Over the Past 60 Years and Future Perspectives. Juneau, Alaska: Annual Meeting of the Phycological Society of America, July 7-12, pp. 40-41 (Abstract)). Similar to oleaginous green algae and diatoms, these species/strains show average total lipid contents of 27.1% and 44.6% DCW under normal and stress culture conditions, respectively.

The increase in total lipids in aging algal cells or cells maintained under various stress conditions consisted primarily of neutral lipids, mainly TAGs. This was due to the shift in lipid metabolism from membrane lipid synthesis to the storage of neutral lipids. De novo biosynthesis and conversion of certain existing membrane polar lipids into triacylglycerols may contribute to the overall increase in TAG. As a result, TAGs may account for as much as 80% of the total lipid content in the cell (for example, as described in Kathen, 1949, Arch. Mikrobiol. 14, 602-634; Klyachko-Gurvich, 1974, Soviet Plant Physiol. 21, 611-618; Suen et al., 1987, J. Phycol. 23, 289-297; Tonon et al., 2002, Phytochemistry 61, 15-24; and Tornabene et al., 1983, Enzyme Microbiol. Technol. 5, 435-440).

Figure 1D:
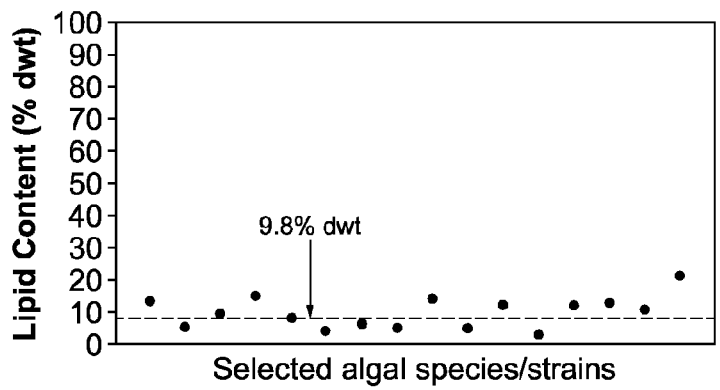

Cyanobacteria have also been subjected to screening for lipid production (for example, as described in Basova, 2005, Int. J. Algae, 7, 33-57: and Cobelas and Lechado, 1989, Grasas y Aceites, 40, 118-145). Unfortunately, considerable amounts of total lipids have not been found in cyanophycean organisms examined in the laboratory (FIG. 1d), and the accumulation of neutral lipid triacylglycerols has not been observed in naturally occurring cyanobacteria.

Fatty Acid Composition

Algae synthesize fatty acids as building blocks for the formation of various types of lipids. The most commonly synthesized fatty acids have chain lengths that range from C16 to C18, similar to those of higher plants (for example, as described in Ohlrogge and Browse, 1995, Plant Cell, 7, 957-970). Fatty acids are either saturated or unsaturated, and unsaturated fatty acids may vary in the number and position of double bonds on the carbon chain, backbone. In general, saturated and mono-unsaturated fatty acids are predominant in most algae examined (for example, as described in Borowitzka, 1988, Fats, oils and hydrocarbons. In Microalgal Biotechnology (Borowitzka, M. A, and Borowitzka, L. J., eds). Cambridge, UK: Cambridge University Press, pp. 257-287). Specifically, the major fatty acids are C16:0 and C16:1 in the Bacillariophyceae, C16:0 and C18:1 in the Chlorophyceae (*Chlamydomonas* sp., *Dunelialla* sp., and *Scenedesmus* sp.), C16:0 and C18:1 in the Euglenophyceae, C16:0, C16:1 and C18:1 in the Chrysophyceae, C16:0 and C20:1 in the Cryptophyceae, C16:0 and C18:1 in the Eustigmatophyceae, C16:0 and C18:1 in the Prasinophyceae, C16:0 in the Dinophyceae, C16:0, C16:1 and C18:1 in the Prymnesiophyceae, C16:0 in the Rhodophyceae, C14:0, C16:0 and C16:1 in the Xanthophyceae, and C16:0, C16:1 and C18:1 in cyanobacteria (for example, as described in Cobelas and Lechado, 1989, Grasas y Aceites, 40, 118-145.

Polyunsaturated fatty acids (PUFAs) contain two or more double bonds. Based on the number of double bonds, individual fatty acids are named dienoic, trienoic, tetraenoic, pentaenoic, and hexaenoic fatty acids. Also, depending on the position of the first double bond from the terminal methyl end (x) of the carbon chain, a fatty acid may be either an x3 PUFA (i.e. the third carbon from the end of the fatty acid) or an x6 PUFAs (i.e. the sixth carbon from the end of the fatty acid). The major PUFAs are C20:5x3 and C22:6x3 in Bacillarilophyceae, C18:2 and C18:3x3 in green algae, C18:2 and C18:3x3 in Euglenophyceae, C20:5, C22:5 and C22:6 in Chrysophyceae, C18:3x3, 18:4 and C20:5 in Cryptophyceae, C20:3 and C20:4x3 in Eustigmatophyceae, C18:3x3 and C20:5 in Prasinophyceae, C18:5x3 and C22:6x3 in Dinophyceae, C18:2, C18:3x3 and C22:6x3 in Prymnesiophyceae, C18:2 and C20:5 in Rhodophyceae, C16:3 and C20:5 in Xanthophyceae, and C16:0, C18:2 and C18:3x3 in cyanobacteria (for example, as described in Basova, 2005, Int. J. Algae, 7, 33-57; and Cobelas and Lechado, 1989, Grasas y Aceites, 40, 118-145).

In contrast to higher plants, greater variation in fatty acid composition is found in algal taxa. Some algae and cyanobacteria possess the ability to synthesize medium-chain fatty acids (e.g. C10, C12 and C14) as predominant species, whereas others produce very-long-chain fatty acids (>C20). For instance, a C10 fatty acid comprising 27-50% of the total fatty acids was found in the filamentous cyanobacterium *Trichodesmium erythraeum* (for example, as described in Parker et al., 1967, Science, 155, 707-708), and a C14 fatty acid makes up nearly 70% of the total fatty acids in the golden alga *Prymnesium parvum* (for example, as described in Lee and Loeblich, 1971, Photochemistry, 10, 593-602). Another distinguishing feature of some algae is the large amounts of very-long-chain PUFAs. For example, in the green alga Parietochloris incise (as described in Bigogno et al., 2002, Phytochemistry, 60, 497-503), the diatom *Phaeodactylum tricornutum* and the dinoflagellate *Cryptheco-dinium cohnii* (as described in De Swaaf et al., 1999, J, Biotechnol. 70, 185-192), the very-long-chain fatty acids arachidonic acid (C20:4x6), eicosapentaenoic acid (C20: 5x3), or docosahexaenoic acid (C22:6x3), are the major fatty acid species accounting for 33.6-42.5%, approximately 30%, and 30-50%, of the total fatty acid content of the three species, respectively.

It should be noted that much of the data provided previously comes from the limited number of species of algae that have been examined to date, and most of the analyses of fatty acid composition from algae have used total lipid extracts rather than examining individual lipid classes. Therefore, these data represent generalities, and deviations should be expected. This may explain why some fatty acids seem to occur almost exclusively in an individual algal taxon. In addition, the fatty acid composition of algae can vary both, quantitatively and qualitatively with their physiological status and culture conditions.

Biosynthesis of Fatty Acids and Triacylglycerols

Lipid metabolism, particularly the biosynthetic pathways of fatty acids and TAG, has been poorly studied in algae in comparison to higher plants. Based upon the sequence homology and some shared biochemical characteristics of a number of genes and/or enzymes isolated from algae and higher plants that are involved in lipid metabolism, it is generally believed that the basic pathways of fatty acid and TAG biosynthesis in algae are directly analogous to those demonstrated in higher plants.

Fatty Acid Biosynthesis

Figure 2:
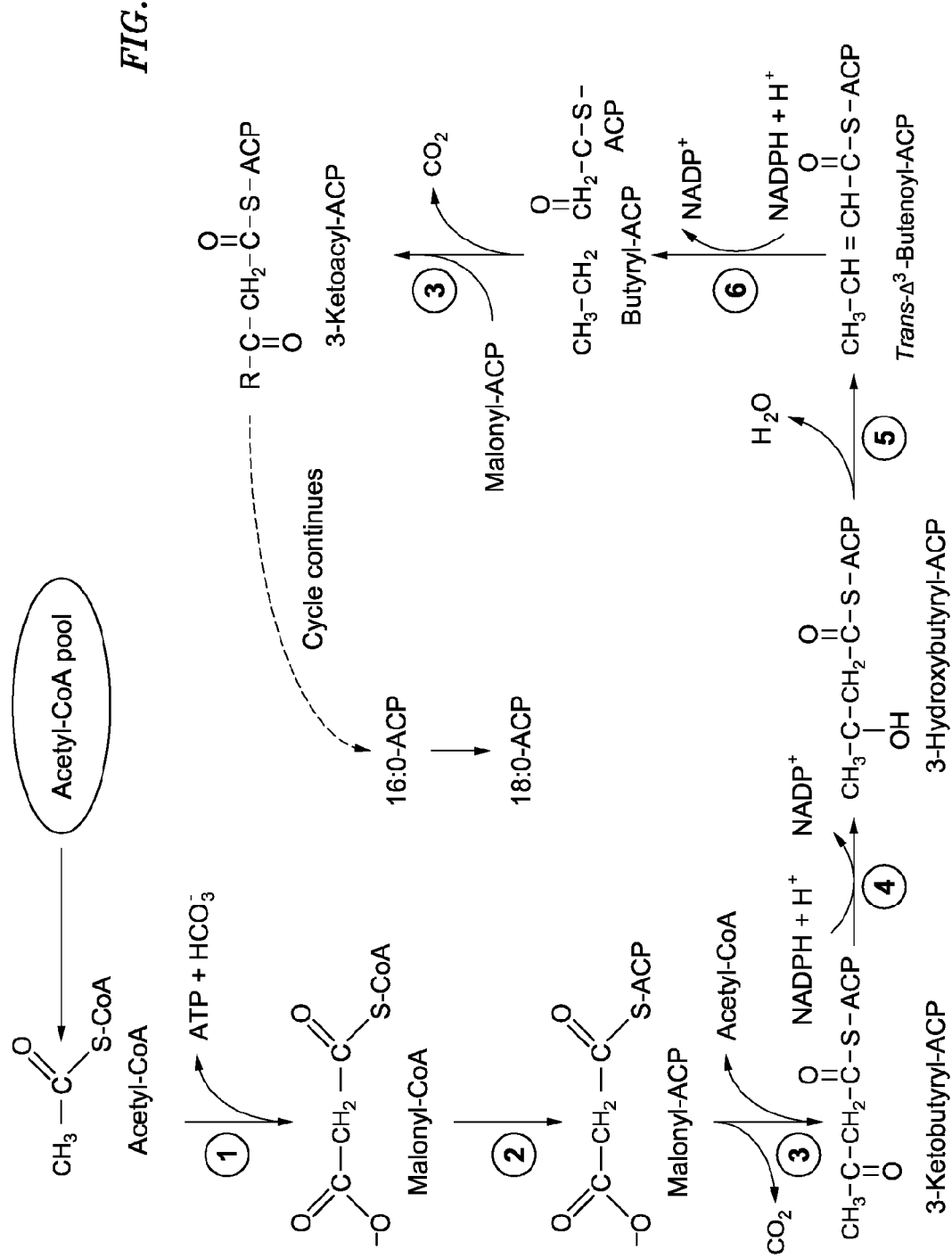
FIG. 2 shows fatty acid de novo synthesis pathway in chloroplasts. Acetyl Co A enters the pathway as a substrate for acetyl CoA carboxylase (Reaction 1) as well as a substrate for the initial condensation reaction (Reaction 3). Reaction 2, which is catalyzed by malonyl CoA:ACP transferase and transfers malonyl from CoA to form malonyl ACP. Malonyl. ACP is the carbon donor for subsequent elongation, reactions. After subsequent condensations, the 3-ketoacyl ACP product is reduced (Reaction 4), dehydrated (Reaction 5) and reduced again (Reaction 6), by 3-ketoacyl ACP reductase, 3-hydroxyacyl ACP dehydrase and enoyl ACP reductase, respectively (adapted and modified from Ohlrogge and Browse, 1995, Plant Cell, 7, 957-970).

In algae, the de novo synthesis of fatty acids occurs primarily in the chloroplast. A generalized scheme for fatty acid biosynthesis is shown in FIG. 2. The pathway produces a 16- or 18-carbon fatty acid or both. These are then used as the precursors for the synthesis of chloroplast and other cellular membranes as well as for the synthesis of neutral storage lipids, mainly TAGs, which can accumulate under adverse environmental or sub-optimal growth conditions.

The committed step in fatty acid synthesis is the conversion of acetyl CoA to malonyl Co A, catalyzed by acetyl CoA carboxylase (ACCase). In the chloroplast, photosynthesis provides an endogenous source of acetyl CoA, and more than one pathway may contribute to maintaining the acetyl CoA pool. In oil seed plants, a major route of carbon flux to fatty acid synthesis may involve cytosolic glycolysis to phosphoenolpyruvate (PEP), which is then preferentially transported from the cytosol to the plastid, where it is converted to pyruvate and consequently to acetyl CoA (for example, as described in Baud et al., 2007, Plant J., 52, 405-419; Ruuska et al., 2002, Plant Cell, 14, 1191-1206; and Schwender and Ohlrogge, 2002, Plant Physiol. 130, 347-361). In green algae, glycolysis and pyruvate kinase (PK), which catalyze the irreversible synthesis of pyruvate from PEP, are present in the chloroplast in addition to the cytosol (for example, as described in Andre et al., 2007, Plant Cell, 19, 2006-2022). Therefore, it is possible that glycolysis-derived pyruvate is the major photosynthate to be converted to acetyl CoA for de novo fatty acid synthesis. An ACCase is generally considered to catalyze the first reaction of the fatty acid biosynthetic pathway—the formation of malonyl CoA from acetyl CoA and $CO_2$. This reaction takes place in two steps and is catalyzed by a single enzyme complex. In the first step, which is ATP-dependent, $CO_2$ (from $HCO_3^-$) is transferred by the biotin carboxylase prosthetic group of ACCase to a nitrogen of a biotin prosthetic group attached to the ε-amino group of a lysine residue. In the second step, catalyzed by carboxyltransferase, the activated $CO_2$ is transferred from biotin to acetyl CoA to form malonyl CoA (for example, as described in Ohlrogge and Browse, 1995, Plant Cell, 7, 957-970).

According to Ohlrogge and Browse (1995, Plant Cell, 7, 957-970), malonyl CoA, the product of the carboxylation reaction, is the central carbon donor for fatty acid synthesis. The malonyl group is transferred from CoA to a protein co-factor on the acyl carrier protein (ACP; FIG. 2). All subsequent reactions of the pathway involve ACP until the finished products are ready for transfer to glycerolipids or export from the chloroplast. The malonyl group of malonyl ACP participates in a series of condensation reactions with acyl ACP (or acetyl CoA) acceptors. The first condensation reaction forms a four-carbon product, and is catalyzed by the condensing enzyme, 3-ketoacyl ACP synthase III (KAS III) (for example, as described in Jaworski et al., 1989, Plant Physiol, 90, 41-44). Another condensing enzyme, KAS I, is responsible for producing varying chain lengths (6-16 carbons). Three additional reactions occur after each, condensation. To form a saturated fatty acid the 3-ketoacyl ACP product is reduced by the enzyme 3-ketoacyl ACP reductase, dehydrated by hydroxyacyl ACP dehydratase and then reduced by the enzyme enoyl ACP reductase (FIG. 2). These four reactions lead to a lengthening of the precursor fatty acid by two carbons. The fatty acid biosynthesis pathway produces saturated 16:0- and 18:0-ACP. To produce an unsaturated fatty acid, a double bond is introduced by the soluble enzyme stearoyl ACP desaturase. The elongation of fatty acids is terminated either when the acyl group is removed from ACP by an acyl-ACP thioesterase that hydrolyzes the acyl ACP and releases free fatty acid, or acyltransferases in the chloroplast transfer the fatty acid directly from ACP to glycerol-3-phosphate or monoacylglycerol-3-phosphate (for example, as described in Ohlrogge and Browse, 1995, Plant Cell, 7, 957-970). The final fatty acid composition of individual algae is determined by the activities of enzymes that use these acyl ACPs at the termination phase of fatty acid synthesis.

ACCases have been purified and kinetically characterized from two unicellular algae, the diatom *Cyclotella* cryptic (for example, as described in Roessler, 1990, Plant Physiol. 92, 73-78) and the prymnesiophyte Isochrysis galbana (for example, as described in Livne and Sukenik, 1990, Plant Cell Physiol. 31, 851-858). Native ACCase isolated from *Cyclotella cryptica* has a molecular mass of approximately 740 kDa, and appears to be composed of four identical biotin-containing subunits. The molecular mass of the native ACCase from I. galbana was estimated at 700 kDa. This suggests that ACCases from algae and the majority of ACCases from higher plants are similar in that they are composed of multiple identical subunits, each of which are multi-functional peptides containing domains responsible for both biotin carboxylation and subsequent carboxyl transfer to acetyl CoA (for example, as described in Roessler, 1990, Plant Physiol. 92, 73-78).

Roessler (1988, Arch. Biochem. Biophys. 267, 521-528) investigated changes in the activities of various lipid and carbohydrate biosynthetic enzymes in the diatom *Cyclotella cryptica* in response to silicon deficiency. The activity of ACCase increased approximately two and four fold after 4 hours and 15 hours of silicon-deficient growth, respectively, suggesting that the higher enzymatic activity may partially result from a covalent modification of the enzyme. As the increase in enzymatic activity can be blocked by the addition of protein synthesis inhibitors, it was suggested that the enhanced ACCase activity could also be the result of an increase in the rate of enzyme synthesis (for example, as described in Roessler, 1988, Arch. Biochem. Biophys. 267, 521-528; and Roessler et al., 1994, Ann. N. Y. Acad. Sci. 721, 250-256).

The gene that encodes ACCase in *Cyclotella cryptica* has been isolated and cloned (for example, as described in Roessler and Ohlrogge, 1993, J. Biol. Chem. 268, 19254-19259). The gene was shown to encode a polypeptide composed of 2089 amino acids, with a molecular mass of 230 kDa. The deduced amino acid sequence exhibited strong similarity to the sequences of animal and yeast ACCases in the biotin carboxylase and carboxyltransferase domains. Less sequence similarity was observed in the biotin carboxyl carrier protein domain, although the highly conserved Met-Lys-Met sequence of the biotin binding site was present. The N-terminus of the predicted ACCase sequence has characteristics of a signal sequence, indicating that the enzyme may be imported into chloroplasts via the endoplasmic reticulum.

Triacylglycerol Biosynthesis

Figure 3:
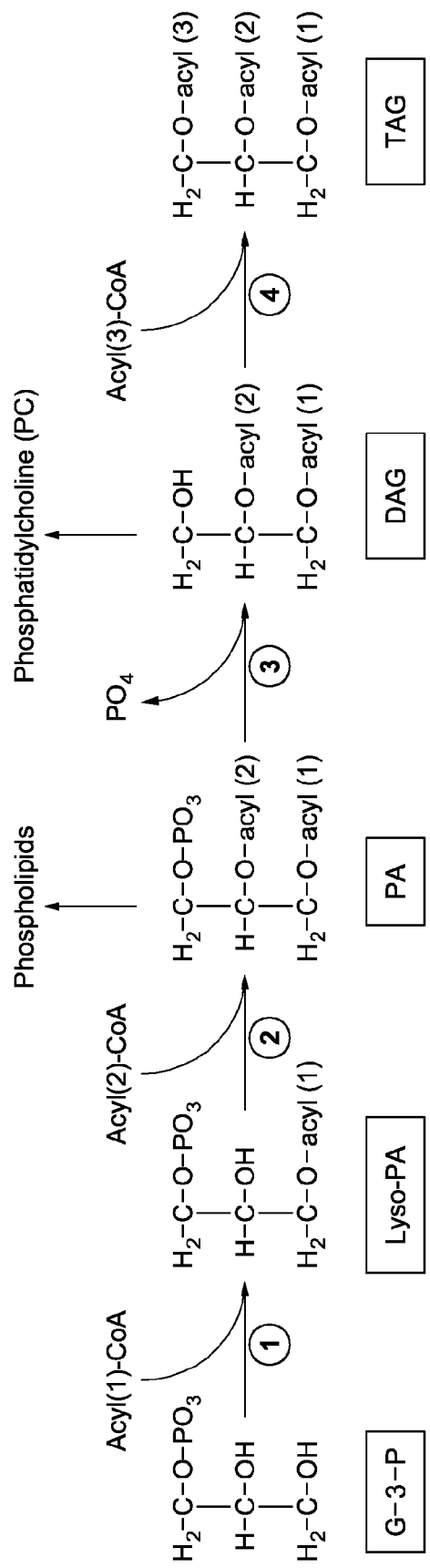
FIG. 3 is a simplified schematic showing the triacylglycerol (TAG) biosynthesis pathway in algae. (1) Cytosolic glycerol-3-phosphate acyl transferase, (2) lyso-phosphatidic acid acyl transferase, (3) phosphatidic acid phosphatase, and (4) diacylglycerol acyl transferase. Adapted from Roessler et al., 1994, Genetic engineering approaches for enhanced production of biodiesel fuel from microalgae. In Enzymatic Conversion of Biomass for Fuels Production (Himmel, M. E., Baker, J. and Overend, R. P., eds). American Chemical Society, pp. 256-270.

Triacylglycerol biosynthesis in algae has been proposed to occur via the direct glycerol pathway (FIG. 3) (for example, as described in Ratledge, 1988, An overview of microbial lipids. In Microbial Lipids, Vol. 1 (Ratledge, C. and Wilkerson, S. G., eds). New York: Academic Press, pp. 3-21). Fatty acids produced in the chloroplast are sequentially transferred from CoA to positions 1 and 2 of glycerol-3-phosphate, resulting in formation of the central metabolite phosphatide acid (PA) (for example, as described in Ohlrogge and Browse, 1995, Plant Cell, 7, 957-970). Dephosphorylation of PA catalyzed by a specific phosphatase releases diacylglycerol (DAG). In the final step of TAG synthesis, a third fatty acid is transferred to the vacant position 3 of DAG, and this reaction is catalyzed by diacylglycerol acyltransferase, an enzymatic reaction that is unique to TAG biosynthesis. PA and DAG can also be used directly as a substrate for synthesis of polar lipids, such as phosphatidylcholine (PC) and galactolipids. The acyltransferases involved in TAG synthesis may exhibit preferences for specific acyl CoA molecules, and thus may play an important role in determining the final acyl composition of TAG. For example, Roessler et al. (1994, Genetic engineering approaches for enhanced production of biodiesel fuel from microalgae. In Enzymatic Conversion of Biomass for Fuels Production (Himmel, M. E., Baker, J. and Overend, R. P., eds). American Chemical Society, pp. 256-270)) reported that, in *Nannochloropsis* cells, the lyso-PA acyltransferase that acylates the second position (sn-2) of the glycerol backbone has a high substrate specificity, whereas glycerol-3-phosphate acyltransferase and DAG acyltransferase are less discriminating. It was also determined that lyso-PC acyltransferase prefers 18:1-CoA over 16:0-CoA.

Although the three sequential acyl transfers from acyl CoA to a glycerol backbone described above are believed to be the main pathway for TAG synthesis, Dahlqvist et al. (2000, Proc. Natl Acad. Sci. USA, 97, 6487-6492) reported an acyl CoA-independent mechanism for TAG synthesis in some plants and yeast. This pathway uses phospholipids as acyl donors and DAG as the acceptor, and the reaction is catalyzed by the enzyme phospholipid:diacylglycerol acyltransferase (PDAT). In an in vitro reaction system, the PDAT enzyme exhibited high substrate specificity for the ricinoleoyl or the vernoloyl group of PC, and it was suggested that PDAT could play an important role in the specific channeling of bilayer-disturbing fatty acids, such as ricinoleic and vernolic acids, from PC into the TAG pool (for example, as described in Dahlqvist et al., 2000, Proc. Natl Acad. Sci. USA, 97, 6487-6492). Under various stress conditions, algae usually undergo rapid degradation of the photosynthetic membrane with concomitant occurrence and accumulation of cytosolic TAG-enriched lipid bodies. If a PDAT orthologue were identified in an algal cell, especially in the chloroplast, then it is conceivable that that orthologue could use PC, PE or even galactolipids derived from the photosynthetic membrane as acyl donors in the synthesis of TAG. As such, the acyl CoA-independent synthesis of TAG could play an important role in the regulation of membrane lipid composition in response to various environmental and growth conditions, not only in plants and yeast but also in algae.

In most of the algal species/strains examined, TAGs are composed primarily of C14-C18 fatty acids that are saturated or mono-unsaturated (for example, as described in Harwood, 1998, Membrane lipids in algae. In Lipids in Photosynthesis: Structure, Function and Genetics (Siegenthaler, P. A. and Murata, N., eds). Dordrecht, The Netherlands: Kluwer Academic Publishers, pp. 53-64; and Roessler, 1990, J. Phycol. 26, 393-399). As exceptions, very-long-chain (>C20) PUFA synthesis and partitioning of such fatty acids into TAGs have been observed in the green alga *Parietochloris incise* (Trebouxiophyceae) (for example, as described in Bigogno et al., 2002, Phytochemistry, 60, 497-503), the freshwater red microalga *Porphyridium cruentum* (for example, as described in Cohen et al., 2000, Biochem. Soc. Trans. 28, 740-743), marine microalgae *Nannochloropsis oculata* (Eustigmatophyceae), *P. tricornutum* and *Thalassiosira pseudonana* (Bacillariophyceae), and the thraustochytrid *Thraustochytrium aureum* (for example, as described in Iida et al., 1996, J. Ferment. Bioeng. 81, 76-78). A strong positional preference of C22:6 in TAG for the sn-1 and sn-3 positions of the glycerol backbone was reported in the marine microalga *Crypthecodinium cohnii* (for example, as described in Kyle et al., 1992, Bioproduction of docoshexaenoic acid (DHA) by microalgae. In Industrial Applications of Single Cell Oils (Kyle, D. J. and Ratledge, C, eds). Champaign, Ill.: American Oil Chemists' Society, pp. 287-300). It has been proposed that very long PUFA-rich TAGs may occur as the result of 'acyl shuttle' between, diacyl glycerol and/or TAG and phospholipid in situations where PUFAs are formed (for example, as described in Kamisaka et al., 1999, Biochim. Biophys. Acta, 1438, 185-198). The biosynthesis of very long PUFAs has been reviewed in detail elsewhere (for example, as described in Certik and Shimizu, 1999, J. Biosci. Bioeng. 87, 1-14; and Guschina and Harwood, 2006, Prog. Lipid Res. 45, 160-186).

Comparison of Lipid Metabolism in Algae and Higher Plants

Although algae generally share similar fatty acid and TAG synthetic pathways with higher plants, there is some evidence that differences in lipid metabolism, do occur. In algae, for example, the complete pathway from, carbon dioxide fixation to TAG synthesis and sequestration takes place within a single cell, whereas the synthesis and accumulation of TAG only occurs in special tissues or organs (e.g. seeds or fruits) of oil crop plants. In addition, very long PUFAs above C18 cannot be synthesized in significant amounts by naturally occurring higher plants, whereas many algae (especially marine species) have the ability to synthesize and accumulate large quantities of very long PUFAs, such as eicosapentaenoic acid (C20:5x3), docosahexaenoic acid (C22:6x3), and arachidonic acid (C20:4x6). Annotation of the genes involved in lipid metabolism in the green alga *C. reinhardtii* has revealed that algal lipid metabolism may be less complex than in *Arabidopsis*, and this is reflected in the presence and/or absence of certain pathways and the apparent sizes of the gene families that represent the various activities (for example, as described in Riekhof et al., 2005, Eukaryotic Cell, 4, 242-252).

Factors Affecting Triacylglycerol Accumulation and Fatty Acid Composition

Although the occurrence and the extent to which TAG is produced appear to be species/strain-specific, and are ultimately controlled by the genetic make-up of individual organisms, oleaginous algae produce only small quantities of TAG under optimal growth or favorable environmental conditions (for example, as described in Hu, 2004, Environmental effects on cell composition. In Handbook of Microalgal Culture (Richmond, A., ed.). Oxford: Blackwell, pp. 83-93). Synthesis and accumulation of large amounts of TAG accompanied by considerable alterations in lipid and fatty acid composition occur in the cell when oleaginous algae are placed under stress conditions imposed by chemical or physical environmental stimuli, either acting individually or in combination. The major chemical stimuli are nutrient starvation, salinity, and growth-medium pH. The major physical stimuli are temperature and light intensity. In addition to chemical and physical factors, growth phase and/or aging of the culture also affects TAG content and fatty acid composition.

Nutrients

Of all the nutrients evaluated, nitrogen limitation is the single most critical nutrient affecting lipid metabolism in algae. A general trend towards accumulation of lipids, particularly TAG, in response to nitrogen deficiency has been observed in numerous species or strains of various algal taxa, as shown in FIG. 1 (for example, as described in Basova, 2005, Int. J. Algae, 7, 33-57; Beijerinck, 1904, Rec. Trav. Bot. Neerl. 1, 28-40; Cobelas and Lechado, 1989, Grasas y Aceites, 40, 118-145; Merzlyak et al., 2007, J. Phycol. 43, 833-843; Roessler, 1990, J. Phycol. 26, 393-399; Shifrin and Chisholm, 1981, J. Phycol. 17, 374-384; Spoehr and Milner, 1949, Plant Physiol. 24, 120-149; and Thompson, 1996, Biochim. Biophys. Acta, 1302, 17-45).

In diatoms, silicon is an equally important nutrient that affects cellular lipid metabolism. For example, silicon-deficient *Cyclotella cryptica* cells have been shown to have higher levels of neutral lipids (primarily TAG) and higher proportions of saturated and mono-unsaturated fatty acids than silicon-replete cells (for example, as described in Roessler, 1988, Arch. Biochem. Biophys. 267, 521-528).

Other types of nutrient deficiency that promote lipid accumulation include phosphate limitation and sulfate limitation. For example, phosphorus limitation results in increased lipid content, mainly TAG, in *Monodus subterraneus* (Eustigmatophyceae) (for example, as described in Khozin-Goldberg and Cohen, 2006, Phytochemistry, 67, 696-701), *P. tricornutum* and *Chaetoceros* sp. (Bacillariophyceae), and *I. galbana* and *Pavlova lutheri* (Prymnesiophyceae), but decreased lipid content in *Nannochloris atomus* (Chlorophyceae) and *Tetraselmis* sp. (Prasiophyceae) (for example, as described in Reitan et al., 1994, J. Phycol. 30, 972-979). Of marine species examined (for example, as described in Reitan et al., 1994, J. Phycol. 30, 972-979), increased phosphorus deprivation was found to result in a higher relative content of 16:0 and 18:1, and a lower relative content of 18:4x3, 20:5x3, and 22:6x3. Studies have also shown that sulfur deprivation enhances the total lipid content in the green algae *Chlorella* sp. (for example, as described in Otsuka, 1961, J. Gen. Appl. Microbiol. 7, 72-77) and *C. reinhardtii* (for example, as described in Sato et al., 2000, Environmental effects on acidic lipids of thylakoid membranes. In Recent Advances in the Biochemistry of Plant Lipids (Harwood, J. L. and Quinn, P. J., eds). London: Portland Press Ltd, pp. 912-914).

Cyanobacteria appear to react to nutrient deficiency differently to eukaryotic algae. Piorreck and Pohl (1984, Phytochemistry, 23, 217-233) investigated the effects of nitrogen deprivation on the lipid metabolism of the cyanobacteria *Anacystis nidulans*, *Microcystis aeruginosa*, *Oscillatoria rubescens* and *Spirulina platensis*, and reported that either lipid content or fatty acid composition of these organisms was changed significantly under nitrogen-deprivation conditions. When changes in fatty acid composition occur in an individual species or strain in response to nutrient deficiency, the C18:2 fatty acid levels decreased, whereas those of both C16:0 and C18:1 fatty acids increased, similar to what occurs in eukaryotic algae (for example, as described in Olson and Ingram, 1975, J. Bacteriol. 124, 373-379). In some cases, nitrogen starvation resulted in reduced synthesis of lipids and fatty acids (for example, as described in Saha et al., 2003, FEMS Microbiol. Ecol. 45, 263-272).

Temperature

Temperature has been found to have a major effect on the fatty acid composition of algae. A general trend towards increasing fatty acid unsaturation with decreasing temperature and increasing saturated fatty acids with increasing temperature has been observed in many algae and cyanobacteria (for example, as described in Lynch and Thompson, 1982, Plant Physiol. 69, 1369-1375; Murata et al., 1975, Plant Physiol. 56, 508-517; Raison, 1986, Alterations in the physical properties and thermal responses of membrane lipids: correlations with acclimation to chilling and high temperature. In Frontiers of Membrane Research in Agriculture (St John, J. B., Berlin, E. and Jackson, P. G., eds) Totowa, N.J.: Rowman and Allanheld, pp. 383-401; Renaud et al., 2002, Aquacolture, 211, 195-214; and Sato and Murata, 1980, Biochim. Biophys. Acta, 619, 353-366). It has been generally speculated that the ability of algae to alter the physical properties and thermal responses of membrane lipids represents a strategy for enhancing physiological acclimatization over a range of temperatures, although the underlying regulatory mechanism is unknown (for example, as discussed in Somerville, 1995, Proc. Natl Acad. Sci. USA, 92, 6215-6218). Temperature also affects the total lipid content in algae. For example, the lipid content in the chrysophytan *Ochromonas danica* (for example, as described in Aaronson, 1973, J. Phycol. 9, 111-113) and the eustigmatophyte *Nannochloropsis salina* (for example, as described in Boussiba et al., 1987, Biomass, 12, 37-47) increases with increasing temperature. In contrast, no significant change in the lipid content was observed in *Chlorella sorokiniana* grown at various temperatures (for example, as described in Patterson, 1970, Lipids, 5, 597-600).

Light Intensity

Algae grown at various light intensities exhibit remarkable changes in their gross chemical composition, pigment content and photo synthetic activity (for example, as described in Falkowski and Owens, 1980, Plant Physiol. 66, 592-595; Post et al., 1985, Mar. Ecol. Prog. Series, 25, 141-149; Richardson et al., 1983, New Phytol. 93, 157-191; and Sukenik et al., 1987, Nature, 327, 704-707). Typically, low light intensity induces the formation of polar lipids, particularly the membrane polar lipids associated with the chloroplast, whereas high light intensity decreases total polar lipid content with a concomitant increase in the amount of neutral storage lipids, mainly TAGs (for example, as described in Brown et al., 1996, J. Phycol. 32, 64-73; Khotimchenko and Yakovleva, 2005, Phytochemistry, 66, 73-79; Napolitano, 1994, J. Phycol. 30, 943-950; Orcutt and Patterson, 1974, Lipids, 9, 1000-1003; Spoehr and Milner, 1949, Plant Physiol. 24, 120-149; and Sukenik et al., 1989, J. Phycol. 25, 686-692).

The degree of fatty acid saturation can also be altered by light intensity. In *Nannochloropsis* sp., for example, the percentage of the major PUFA C20:5x3 remained fairly stable (approximately 35% of the total fatty acids) under light-limited conditions. However, it decreased approximately threefold under light-saturated conditions, concomitant with an increase in the proportion of saturated and mono-unsaturated fatty acids (i.e. C14, C16:0 and C16:1x7) (Fabregas et al., 2004). Based upon the algal species/strains examined (for example, as described in Orcutt and Patterson, 1974, Lipids, 9, 1000-1003; and Sukenik et al., 1993, J. Phycol. 29, 620-626), it appears, with a few exceptions, that low light favors the formation of PUFAs, which in turn are incorporated into membrane structures. On the other hand, high light alters fatty acid synthesis to produce more of the saturated and mono-unsaturated fatty acids that mainly make up neutral lipids.

Growth Phase and Physiological Status

Lipid content and fatty acid composition are also subject to variability during the growth cycle. In many algal species examined, an increase in TAGs is often observed during stationary phase. For example, in the chlorophyte Parietochloris incise, TAGs increased from 43% (total fatty acids) in the logarithmic phase to 77% in the stationary phase (for example, as described in Bigogno et al., 2002, Phytochemistry, 60, 497-503), and in the marine dinoflagellate *Gymnodinium* sp., the proportion of TAGs increased from 8% during the logarithmic growth phase to 30% during the stationary phase (for example, as described in Mansour et al., 2003, Phytochemistry, 63, 145-153). Coincident increases in the relative proportions of both saturated and mono-unsaturated 16:0 and 18:1 fatty acids and decreases in the proportion of PUFAs in total lipid were also associated with growth-phase transition from the logarithmic to the stationary phase. In contrast to these decreases in PUFAs, however, the PUFA arachidonic acid (C20:4x6) is the major constituent of TAG produced in Parietochloris incise cells (for example, as described in Bigogno et al., 2002, Phytochemistry, 60, 497-503), while docosahexaenoic acid (22: 6x3) and eicosapentaenoic acid (20:5x3) are partitioned to TAG in the Eustigmatophyceae *N. oculata*, the diatoms *P. tricornutum* and *T. pseudonana*, and the haptophyte *Pavlova lutheri* (for example, as described in Tonon et al., 2002, Phytochemistry 61, 15-24).

Culture aging or senescence also affects lipid and fatty acid content and composition. The total lipid content of cells increased with age in the green alga *Chlorococcum macrostigma* (for example, as described in Collins and Kalnins, 1969, Phyton, 26, 47-50), and the diatoms *Nitzschia palea* (for example, as described in von Denffer, 1949, Arch. Mikrobiol. 14, 159-202), *Thalassiosira fluviatillis* (for example, as described in Conover, 1975, Mar. Biol. 32, 231-246) and *Coscinodiscus eccentricus* (for example, as described in Pugh, 1971, Mar. Biol. 11, 118-124). An exception to this was reported in the diatom *P. tricornutum*, where culture age had almost no influence on the total fatty acid content, although TAGs were accumulated and the polar lipid content was reduced (for example, as described in Alonso et al., 2000, Phytochemistry, 54, 463-471). Analysis of fatty acid composition in the diatoms *P. tricornutum* and *Chaetoceros muelleri* revealed a marked increase in the levels of saturated and monounsaturated fatty acids (e.g. 16:0, 16:1x7 and 18:1x9), with a concomitant decrease in the levels of PUFAs (e.g. 16:3x4 and 20:5x3) with increasing culture age (for example, as described in Liang et al., 2006, Bot. March, 49, 165-173). Most studies on algal lipid metabolism have been carried out in a batch culture mode. Therefore, the age of a given culture may or may not be associated with nutrient depletion, making it difficult to separate true aging effects from nutrient deficiency-induced effects on lipid metabolism.

Physiological Roles of Triacylglycerol Accumulation

Synthesis of TAG and deposition of TAG into cytosolic lipid bodies may be, with few exceptions, the default pathway in algae under environmental stress conditions. In addition to the obvious physiological role of TAG serving as carbon and energy storage, particularly in aged algal cells or under stress, the TAG synthesis pathway may play more active and diverse roles in the stress response. The de novo TAG synthesis pathway serves as an electron sink under photo-oxidative stress. Under stress, excess electrons that accumulate in the photosynthetic electron transport chain may induce over-production of reactive oxygen species, which may in turn cause inhibition of photosynthesis and damage to membrane lipids, proteins and other macromolecules. The formation of a C18 fatty acid consumes approximately 24 NADPH derived from the electron transport chain, which is twice that required for synthesis of a carbohydrate or protein molecule of the same mass, and thus relaxes the over reduced electron transport chain under high light or other stress conditions. The TAG synthesis pathway is usually coordinated with secondary carotenoid synthesis in algae (for example, as described in Rabbani et al., 1998, Plant Physiol. 116, 1239-1248; and Zhekisheva et al., 2002, J. Phycol. 38, 325-331). The molecules (e.g. b-carotene, lutein or astaxanthin) produced in the carotenoid pathway are esterified with TAG and sequestered into cytosolic lipid bodies. The peripheral distribution of carotenoid-rich lipid bodies serve as a 'sunscreen' to prevent or reduce excess light striking the chloroplast under stress. TAG synthesis may also utilize PC, PE, and galactolipids or toxic fatty acids excluded from the membrane system as acyl donors, thereby serving as a mechanism to detoxify membrane lipids and deposit: them in the form of TAG.

Role of Algal Genomics and Model Systems in Biofuel Production

Because of the potential for photosynthetic micro-organisms to produce 8-24 times more lipids per unit area for biofuel production than the best land plants (for example, as described in Sheehan et al., 1998, A Look Back at: the US Department of Energy's Aquatic Species Program—Biodiesel from Algae, Close Out Report TP-580-24190. Golden, Colo.: National Renewable Energy Laboratory), these microbes are in the forefront as future biodiesel producers. Cyanobacteria, for which over 20 completed genome sequences are available (http://genome.jgi-psf.org/mic_curl.html) (over 30 are in progress), produce some lipids. In addition, the nuclear genomes of eight microalgae, some of which can produce significant quantities of storage lipids, have also been sequenced (http://genome.jgipsf.org/euk_curl.html). These eukaryotes include *C. reinhardtii* (Plant Physiol. (2003) Vol. 131, pp. 401-408), *Volvox carteri* (green alga) (BMC Genomics (2009) 10:132), *Cyanidioschi-* zon merolae (red alga)(DNA Research (2003) 10(2):67-77), *Osteococcus lucimarinus* (Proc Natl Acad Sci U.S.A. (2007) 104, 7705-7710), *Osteococcus tauris* (marine pico-eukaryotes)(Trends in Genetics, Vol. 23, Issue 4 (2007) pp. 151-154), *Aureococcus annophageferrens* (a harmful algal bloom component; http://genome.jgi-psf.org/Auran1/Auran1.info.html; sequence not yet published), *P. tricornutum* (Nature (2008) 456(7219):239-44; and Plant Physiol. (2002) Vol. 129, p. 993-1002), and *T. pseudonana* (diatoms) (Nature (2008) 456 (7219):239-44; and Science (2004) October 1; 306:5693).

*Chlamydomonas reinhardtii* is a single celled chlorophyte. Highly adaptable, these green algae live in many different environments throughout the world. Normally deriving energy from photosynthesis, with an alternative carbon source, *C. reinhardtii* can also thrive in total darkness.

The relative adaptability and quick generation time has made *Chlamydomonas* an important model for biological research. The *C. reinhardtii* genome is described in Science (2007) 318(5848):245-50.

*Volvox carteri* is a multicellular chlorophyte alga, closely related to the single-celled *Chlamydomonas reinhardtii*. *Volvox* normally reproduces as an asexual haploid, but can be induced to undergo sexual differentiation and reproduction. The 48-hour life cycle allows easy laboratory culture and includes an embryogenesis program that features many of the hallmarks of animal and plant development. These features include embryonic axis formation, asymmetric cell division, a gastrulation-like inversion, and differentiation of germ and somatic cells. The ~2000 somatic cells in a *Volvox* spheroid are biflagellate and adapted for motility, while the ~16 large germ cells contained within the spheroid are non-motile and specialized for growth and reproduction. *Volvox* embryogensis generates the coordinated arrangement of somatic flagella and photosensing eye spots needed for the organism's characteristic forward rolling motion. The Volvocales family includes single-celled *Chlamydomonas* (whose genome sequence is available) and *Volvox*, also includes several multicellular or colonial species with intermediate cell numbers and less complex developmental programming.

*Ostreococcus* belongs to the Prasinophyceae, an early-diverging class within the green plant lineage, and is reported as a globally abundant, single-celled alga thriving in the upper (illuminated) water column of the oceans. The most striking feature of *O. lucimarinus* and related species is their minimal cellular organization: a naked, nearly 1-micron cell, lacking flagella, with a single chloroplast and mitochondrion. The *Ostreococcus* genome is described in Proc Natl Acad Sci U.S.A. (2007) 104, 7705-7710.

Three different ecotypes or potential species have been defined, based on their adaptation to light intensity. One (*O. lucimarinus*) is adapted to high light intensities and corresponds to surface-isolated strains. The second (RCC141) has been defined as low-light and includes strains from deeper in the water column. The third (*O. tauri*) corresponds to strains isolated from a coastal lagoon and can be considered light-polyvalent. Comparative analysis of *Ostreococcus* sp will help to understand niche differentiation in unicellular eukaryotes and evolution of genome size in eukaryotes.

*Aureococcus anophagefferens* is a 2-3 um spherical, non-motile pelagophyte which has caused destructive 'brown tide' blooms in northeast and mid-Atlantic US estuaries for two decades. A coastal microalgae species, *A. anophagefferens* is capable of growing to extremely high densities (>10E9 cells L-1) and can enzymatically degrade complex forms of dissolved organic matter as a source of cellular carbon and nitrogen. This species is also known to be well adapted to low light, is associated with annually elevated water temperatures, can rapidly reduce trace metals, and sequesters substantial amounts of carbon during bloom events. The *Aureococcus* is a Harmful Algal Bloom (HAB) species, HABs are blooms of phytoplankton cells resulting in conditions that are unhealthy for humans, animals or ecosystems causing by decrease in light attenuation or oxygen levels, or by production of toxins, HABs may cause marine life poisoning and/or death.

*P. tricornutum* and *T. pseudononan* are both diatoms. Diatoms are eukaryotic, photosynthetic microorganisms found throughout marine and freshwater ecosystems that are responsible for around 20% of global primary productivity. A defining feature of diatoms is their ornately patterned silicified cell wall (known as frustule), which display species-specific nanoscale-structures. These organisms therefore play major roles in global carbon and silicon cycles.

The marine pennate diatom *Phaeodactylum tricornutum* is the second diatom for which a whole genome sequence has been generated. It was chosen primarily because of the superior genetic resources available for this diatom (eg, genetic transformation, 100,000 ESTs), and because it has been used in laboratory-based studies of diatom physiology for several decades. Although not considered to be of great ecological significance, it has been found in several locations around the world, typically in coastal areas with wide fluctuations in salinity. Unlike other diatoms it can exist in different morphotypes, and changes in cell shape can be stimulated by environmental conditions. This feature can be used to explore the molecular basis of cell shape control and morphogenesis. Furthermore the species can grow in the absence of silicon, and the biogenesis of silicified frustules is facultative, thereby providing opportunities for experimental exploration of silicon-based nanofabrication in diatoms. The sequence is 30 mega base pairs and, together with the sequence from the centric diatom *Thalassiosira pseudonana* (34 Mbp; the first diatom whole genome sequence), it provides the basis for comparative genomics studies of diatoms with other eukaryotes and will provide a foundation for interpreting the ecological success of these organisms.

The clone of *P. tricornutum* that was sequenced is CCAP1055/1 and is available from the Culture Collection of Algae and Protozoa (CCAP). This clone represents a monoclonal culture derived from a fusiform cell in May 2003 from strain CCMP632, which was originally isolated in 1956 off Blackpool (U.K.). It has been maintained in culture continuously in F/2 medium. The *Phaeodactylum* genome is described in Nature (2008) 456(7219):239-44.

Extensive genomic, biological and physiological data exist for *C. reinhardtii*, a unicellular, water-oxidizing green alga (for example, as described in Grossman, 2005, Plant Physiol. 137, 410-427; Merchant et al., 2007, Science, 318, 245-251; and Mus et al., 2007, J. Biol. Chem. 282, 25475-25486). For these reasons, *Chlamydomonas* has emerged recently as a model eukaryote microbe for the study of many processes, including photosynthesis, phototaxis, flagellar function, nutrient acquisition, and the biosynthesis and functions of lipids.

The recent availability of the *Chlamydomonas* genome sequence and biochemical studies indicate that this versatile, genetically malleable eukaryote has an extensive network of diverse metabolic pathways that are unprecedented in other eukaryotes for which whole-genome sequence information is available. *Chlamydomonas* is of particular interest to renewable energy efforts because its metabolism can be manipulated by nutrient stress to accumulate various energy-yielding reduced compounds.

The advantage of *C. reinhardtii* as a model for oxygenic photosynthesis derives mainly from its ability to grow either photo-, mixo- or heterotrophically (in the dark and in the presence of acetate) while maintaining an intact, functional photosynthetic apparatus. This property has allowed researchers to study photosynthetic mutations that are lethal in other organisms. Moreover, *C. reinhardtii* spends most of its life cycle as a haploid organism of either mating type + or) (Harris, 1989, The *Chlamydomonas* Sourcebook. A Comprehensive Guide to Biology and Laboratory Use. San Diego, Calif.: Academic Press). Gametogenesis is triggered by environmental stresses, particularly nitrogen deprivation (Sager and Granick, 1954, J. Gen. Physiol. 37, 729-742), and its occurrence can be synchronized by light/dark periods of growth (Kates and Jones, 1964, Biochim. Biophys. Acta, 86, 438-447). During its haploid stage, *C. reinhardtii* can be genetically engineered and single genotypes easily generated. Additionally, different phenotypes can be obtained by crossing two haploid mutants of different mating types carrying different genotypes. Conversely, single-mutant genotypes can be unveiled by back-crossing mutants carrying multiple mutations with the wild-type strain of the opposite mating type.

Figure 4:
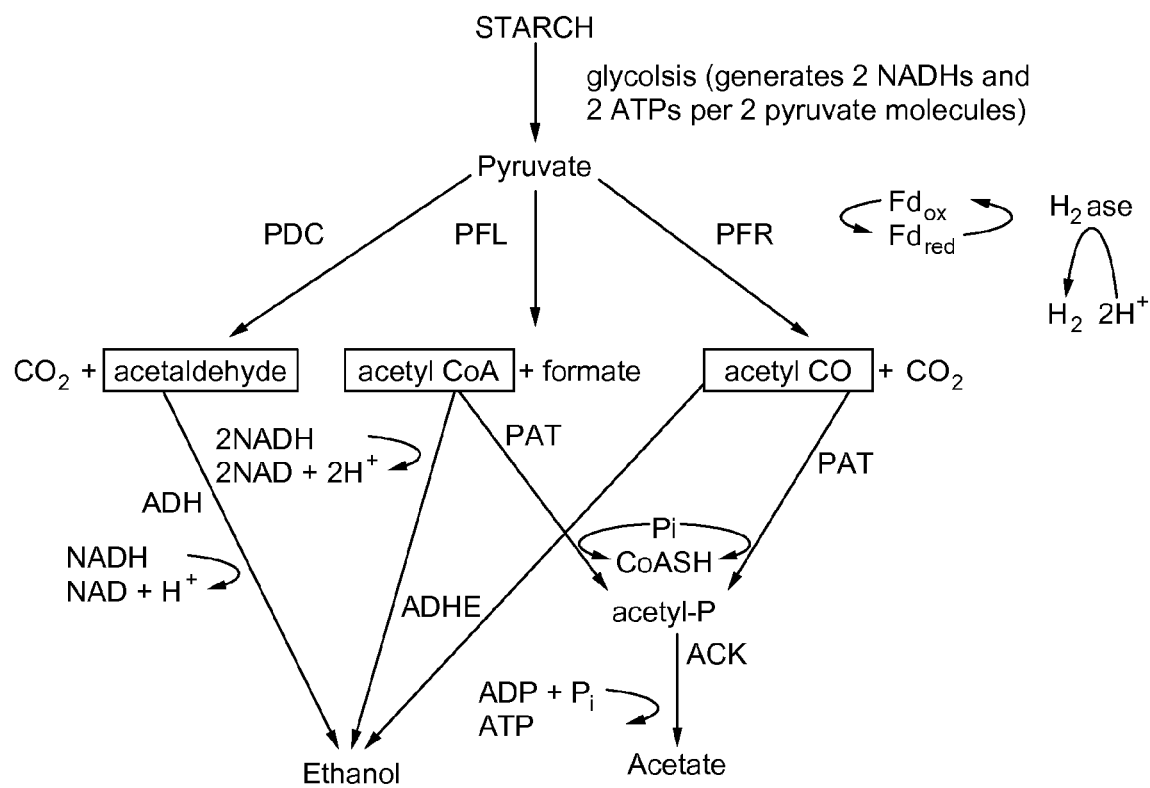
FIG. 4 shows fermentative pathways identified in *Chlamydomonas reinhardtii* following anaerobic incubation (adapted and modified from Mus et al., 2007, J. Biol. Chem. 282, 25475-25486). Under aerobic conditions, pyruvate is metabolized predominantly by the pyruvate dehydrogenase complex to produce NADH and acetyl CoA, the latter of which ties into lipid metabolism (see FIG. 5). ACK, acetate kinase; ADH, alcohol dehydrogenase; ADHE, alcohol aldehyde bifunctional dehydrogenase; H2ase, hydrogenase; PAT, phosphotransacetylase; PDC, pyruvate decarboxylase; PFL, pyruvate formate lyase; PFR, pyruvate ferredoxin oxidoreductase.

*Chlamydomonas reinhardtii* can also be used as a model organism for fermentation, given the number of pathways identified under anaerobic conditions biochemically (for example, as described in Gfeller and Gibbs, 1984, Plant Physiol. 75, 212-238; and Ohta et al., 1987, Plant Physiol. 83, 1022-1026) or by microarray analysis (for example, as described in Mus et al., 2007, J. Biol. Chem. 282, 25475-25486). The results, summarized in FIG. 4, suggest that both the pyruvate formate lyase (PFL) and the pyruvate ferredoxin oxidoreductase (PFR) pathways are functional in *C. reinhardtii* under anaerobiosis, as well as the pyruvate decarboxylase (PDC) pathway. The former two pathways generate acetyl CoA (a precursor for lipid metabolism) and either formate (PFL) or H2 (PFR), and the latter can generate ethanol through the alcohol dehydrogenase (ADH)-catalyzed reduction of acetaldehyde. Finally, acetyl CoA can be further metabolized by *C. reinhardtii* to ethanol, through the alcohol/aldehyde bifunctional dehydrogenase (ADHE) activity, or to acetate, through the sequential activity of two enzymes, phosphotransacetylase (PAT) and acetate kinase (ACK). The last reaction releases ATP. Mus et al. (2007, J. Biol. Chem. 282, 25475-25486) and Hemschemeier and Happe (2005, Chem. Soc. Trans. 33, 39-41) proposed that the unprecedented presence of all these pathways endows *C. reinhardtii* with a higher flexibility to adapt to environmental conditions. Finally, fermentative lactate production has been detected under certain conditions (Kreuzberg, 1984, Physiol, Plant, 61, 87-94).

Figure 5:
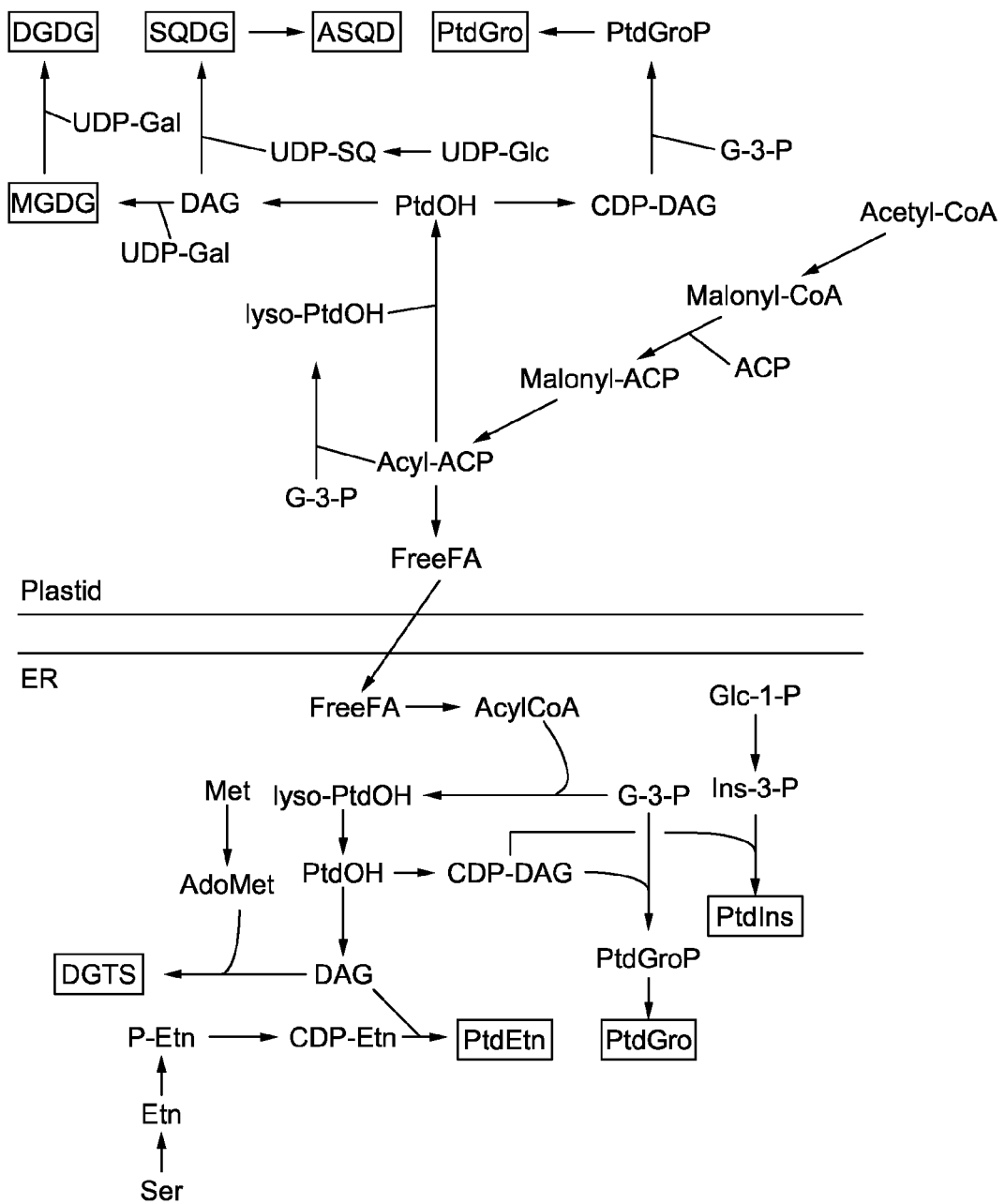
FIG. 5 shows pathways of lipid biosynthesis that are known or hypothesized to occur in *Chlamydomonas*, and their presumed subcellular localizations. Abbreviations: ACP, acyl carrier protein; AdoMet, S-adenosylmethionine; ASQD, 2'-O-acyl sulfoquinovosyldiacylglycerol; CDP, cytidine-5'-diphosphate; CoA, coenzyme A; CTP, cytidine-5'-triphosphate; DAG, diacylglycerol; DGDG, digalactosyldiacylglycerol; DGTS, diacylglyceryl N,N,N-trimethylhomoserine; Etn, ethanolamine; FA, fatty acid; G-3-P, glycerol-3-phosphate; Glc, glucose; Glc-1-P, glucose-1-phosphate; Ins, inositol; Ins-3-P, inositol-3-phosphate; Met, methionine; MGDG, mono-galactosyldiacylglycerol; P-Etn, phosphoethanolamine; PtdEtn, phosphatidylethanolamine; PtdGro, phosphatidylglycerol; PtdGroP, phosphatidylglycerophosphate; PtdIns, phosphatidylinositol; PtdOH, phosphatidic acid; Ser, serine; SQ, sulfoquinovose; SQDG, sulfoquinovosyldiacylglycerol; UDP, uridine-5-diphosphate (as described in Riekhof, W. R., et al., 2005, Eukaryotic Cell, 4, 242-252).
Figure 6:
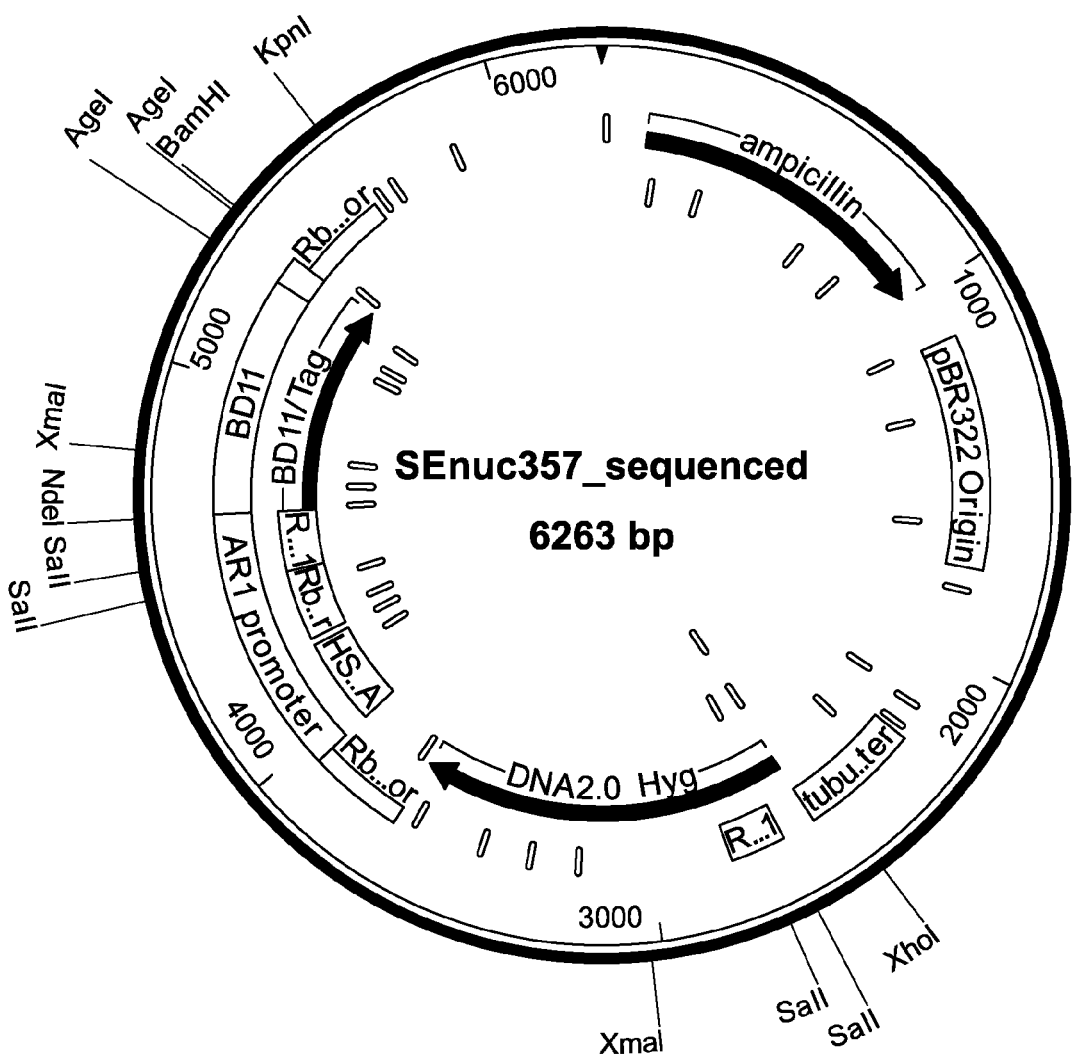
FIG. 6 shows an exemplary expression vector (SEnuc357) that can be used with the embodiments disclosed herein.
Figure 7:
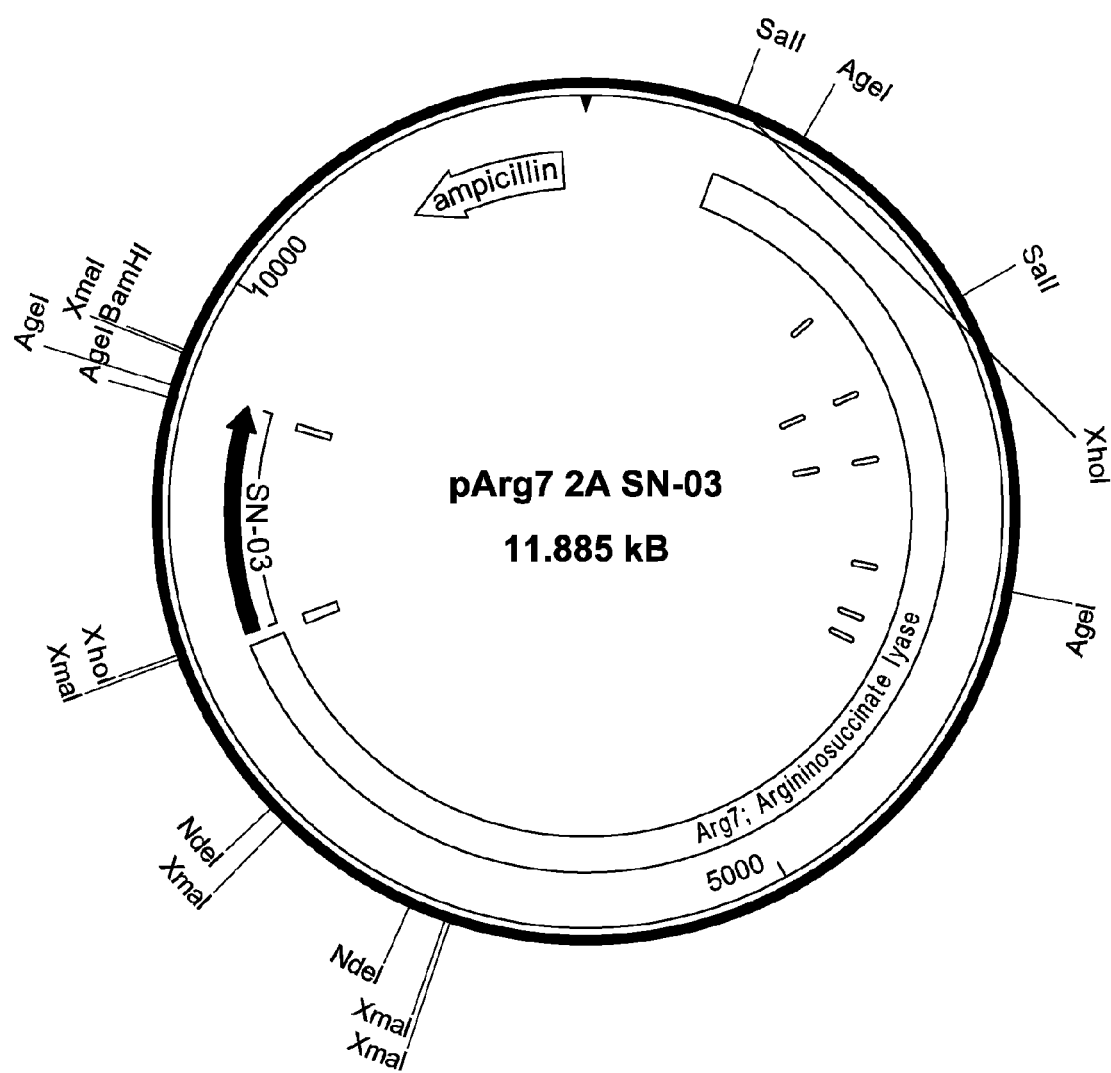
FIG. 7 shows an exemplary expression vector that can be used with the embodiments disclosed herein.

Although pathways for fatty acid biosynthesis are present in *C. reinhardtii* (FIG. 5), they are not known to be over expressed under normal photo-autotrophic or mixotrophic growth (for example, as described in Harris, 1989. The *Chlamydomonas* Sourcebook. A Comprehensive Guide to Biology and Laboratory Use. San Diego, Calif. Academic Press). However, these pathways could be artificially over-expressed in *C. reinhardtii*.

Global expression profiling of *Chlamydomonas* under conditions that produce biofuels (H2 in this case) (for example, as described in Mus et al., 2007, J. Biol. Chem. 282, 25475-25486) has been reported using second-generation microarrays with 10,000 genes of the over 15,000 genes predicted (for example, as described in Eberhard et al., 2006, Curr. Genet. 49, 106-124; and Merchant et al., 2007, Science, 318, 245-251). However, much of the information that was reported involves fermentative metabolism, as discussed above. Little or no research has been conducted to characterize the up- and down regulation of genes associated with lipid metabolism when *Chlamydomonas* is exposed to nutrient stress. N-deprived *C. reinhardtii* will over-accumulate starch and lipids that can be used for formate, alcohol and biodiesel production (for example, as described in Mus et al., 2007, J. Biol. Chem. 282, 25475-25486; and Riekhof et al., 2005, Eukaryotic Cell, 4, 242-252).

Other organisms, for example, those listed in the "Host Cells or Host Organisms" section of the disclosure can be used as a system for the production of useful products, for example, fatty acids, glycerol lipids or biofuels.

Lipid Accumulation by Microalgae.

Under certain growth, conditions, many microalgae can produce lipids that are suitable for conversion to liquid transportation fuels. In the late 1940s, nitrogen limitation was reported to significantly influence microalga lipid storage. Spoehr and Milner (1949, Plant Physiol. 24, 120-149) published detailed information on the effects of environmental conditions on algal composition, and described the effect of varying nitrogen supply on the lipid and chlorophyll content of *Chlorella* and some diatoms. Investigations by Collyer and Fogg (1955, J. Exp. Bot. 6, 256-275) demonstrated that the fatty acid content of most green algae was between 10 and 30% DCW. Werner (1966, Arch. Mikrobiol. 55, 278-308) reported an increase in the cellular lipids of a diatom during silicon starvation. Coombs et al. (1967, Plant Physiol. 42, 1601-1606) repotted that the lipid content of the diatom *Navicula pelliculosa* increased by about 60% during a 14 h silicon starvation period. In addition to nutrition, fatty acid and lipid composition and content were also found to be influenced by a number of other factors such as light (for example, as described in Constantopolous and Bloch, 1967, J. Biol. Chem. 242, 3538-3542; Nichols, 1965, Biochim. Biophys. Acta, 106, 274-279; Pohl and Wagner, 1972, Z. Naturforsch. 27, 53-61; and Rosenberg and Gouaux, 1967, J. Lipid Res. 8, 80-83) and low temperatures (for example, as described in Ackman et al., 1968, J. Fisheries Res. Board Canada, 25, 1603-1620).

Microalgal Physiology and Biochemistry.

Studies on algal physiology under the Aquatic Species Program (ASP) centered on the ability of many species to induce lipid biosynthesis under conditions of nutrient stress (for example, as described in Dempster and Sommerfeld, 1998, J. Phycol. 34, 732-721; and McGinnis et al., 1997, J. Appl. Phycol. 9, 39-24). Focusing on the diatom *Cyclotella cryptica*, biochemical studies indicated that silicon deficiency led to increased activity of the enzyme ACCase, which catalyzes the conversion of acetyl CoA to malonyl CoA, the substrate for fatty acid synthase (Roessler, 1988, Arch. Biochem. Biophys. 267, 521-528). The ACCase enzyme was extensively characterized (Roessler, 1990, Plant Physiol, 92, 73-78). Additional studies focused on the pathway for production of the storage carbohydrate chrysolaminarin, which is hypothesized to compete with the lipid pathway for fixed carbon. UDPglucose pyrophosphorylase (UGPase) and chrysolaminarin synthase activities from *Cyclotella cryptica* were also characterized (for example, as described in Roessler, 1987, J. Phycol. 23, 494-498; and 1988, Arch. Biochem. Biophys. 267, 521-528).

Microalgal Molecular Biology and Genetic Engineering.

In the latter years of the ASP, the research at the National Renewable Research Laboratory focused on the genetic engineering of green algae and diatoms for enhanced lipid production. Genetic transformation of microalgae was a major barrier to overcome. The first successful transformation of a microalga strain with potential for biodiesel production was achieved in 1994, with successful transformation of the diatoms *Cyclotella cryptica* and *Navicula saprophila* (Dunahay et al., 1995, J. Phycol. 31, 1004-1012). The technique utilized particle bombardment and an antibiotic resistance selectable marker under the control of the ACCase promoter and terminator elements. The second major accomplishment was the isolation and characterization of genes from *Cyclotella cryptica* that encoded the ACCase and UGPase enzymes (Jarvis and Roessler, 1999, U.S. Pat. No. 5,928,932; Roessler and Ohlrogge, 1993, J. Biol. Chem., 268, 19254-192.59). Attempts to alter the expression, level of the ACCase and UGPase genes in *Cyclotella cryptica* using this transformation system met with some success, but effects on lipid production were not observed in these preliminary experiments (Sheehan et al., 1998, US Department of Energy's Office of Fuels Development, July 1998. A Look Back at the US Department of Energy's Aquatic Species Program—Biodiesel from Algae, Close Out. Report TP-580-24190. Golden, Colo.: National Renewable Energy Laboratory).

New tag-sequencing methodologies such as 454 (Roche, USA) and Solexa (Illumina, USA), can give an accurate whole-genome picture of expression data, and can be used to provide a quantitative picture of the mRNAs in algal samples.

Procedures for metabolite profiling of *C. reinhardtii* CC-125 cells, which quickly inactivate enzymatic activity, optimize extraction capacity, and are amenable to large sample sizes, were reported by Boiling and Fiehn, (2005, Plant Physiol. 139, 1995-2005). The study explored profiles of Tris-acetate/phosphate-grown cells as well as cells that were deprived of sulfate. Nitrogen-, phosphate- and iron-deprivation profiles were also examined, and each metabolic profile was different. Sulfur depletion leads to the anaerobic conditions required for induction of the hydrogenase enzyme and H2 production (for example, as described in Ghirardi et al., 2007, Annu. Rev. Plant Biol. 58, 71-91; and Hemschemeier et al., 2008, Planta, 227, 397-407). Rapidly sampled cells (cell leakage controls were determined by 14C-labeling techniques) were analyzed by gas chromatography coupled to time-of-flight mass spectrometry, and more than 100 metabolites (e.g. amino acids, carbohydrates, phosphorylated intermediates, nucleotides and organic acids) out of about 800 detected could be identified. The concentrations of a number of phosphorylated glycolysis intermediates increase significantly during sulfur stress (for example, as described in Boiling and Fiehn, 2005, Plant Physiol. 139, 1995-2005), consistent with the upregulation of many genes associated with starch degradation and fermentation observed in anaerobic *Chlamydomonas* cells (for example, as described in Mus et al., 2007, J. Biol. Chem. 282, 25475-25486). Lipid metabolism was not studied.

There are a number of relevant studies of *Chlamydomonas* proteomics, as reviewed by Stauber and Hippler (2004, Plant Physiol, Biochem. 42, 989-1001). However, no proteomics research has yet been reported in algae under biofuel-producing conditions.

Host Cells or Host Organisms

Biomass containing fatty acids and/or glycerol lipids that is useful in the methods and systems described herein can be obtained from host cells or host organisms.

A host cell can contain a polynucleotide encoding a lipid trigger of the present disclosure. In some embodiments, a host cell is part of a multicellular organism. In other embodiments, a host cell is cultured as a unicellular organism.

Host organisms can include any suitable host, for example, a microorganism. Microorganisms which are useful for the methods described herein include, for example, photosynthetic bacteria (e.g., cyanobacteria), non-photosynthetic bacteria (e.g., *E. coli*), yeast (e.g., *Saccharomyces cerevisiae*), and algae (e.g., microalgae such as *Chlamydomonas reinhardtii*).

Examples of host organisms that can be transformed with a polynucleotide of interest (for example, a polynucleotide that encodes for a lipid trigger protein) include vascular and non-vascular organisms. The organism can be prokaryotic or eukaryotic. The organism can be unicellular or multicellular. A host organism is an organism comprising a host cell. In other embodiments, the host organism is photosynthetic. A photosynthetic organism is one that naturally photosynthesizes (e.g., an alga) or that is genetically engineered or otherwise modified to be photosynthetic. In some instances, a photosynthetic organism may be transformed with a construct or vector of the disclosure which renders all or part of the photosynthetic apparatus inoperable.

By way of example, a non-vascular photosynthetic microalga species (for example, *C. reinhardtii, Nannochloropsis oceania, N. salina, D. salina, H. pluvalis, S. dimorphus, D. viridis, Chlorella* sp., and *D. tertiolecta*) can be genetically engineered to produce a polypeptide of interest, for example a lipid trigger protein. Production of the protein in these microalgae can be achieved by engineering the microalgae to express the protein in the algal chloroplast or nucleus.

In other embodiments the host organism is a vascular plant. Non-limiting examples of such plants include various monocots and dicots, including high oil seed plants such as high oil seed *Brassica* (e.g., *Brassica nigra, Brassica napus, Brassica hirta, Brassica rapa, Brassica campestris, Brassica carinata*, and *Brassica juncea*), soybean (*Glycine max*), castor bean (*Ricinus communis*), cotton, safflower (*Carthamus tinctorius*), sunflower (*Helianthus annuus*), flax (*Linum usitatissimum*), corn (*Zea mays*), coconut (*Cocos nucifera*), palm (*Elaeis guineensis*), oil nut trees such as olive (*Olea europaea*), sesame, and peanut (*Arachis hypogaea*), as well as *Arabidopsis*, tobacco, wheat, barley, oats, amaranth, potato, rice, tomato, and legumes (e.g., peas, beans, lentils, alfalfa, etc.).

The host organism or cell can be prokaryotic. Examples of some prokaryotic organisms of the present disclosure include, but are not limited to, cyanobacteria (e.g., *Synechococcus, Synechocystis, Athrospira, Gleocapsa, Oscillatoria*, and, *Pseudoanabaena*). Suitable prokaryotic cells include, but are not limited to, any of a variety of laboratory strains of *Escherichia coli, Lactobacillus* sp., *Salmonella* sp., and *Shigella* sp. (for example, as described in Carrier et al. (1992) J. Immunol. 148:1176-1181; U.S. Pat. No. 6,447, 784; and Sizemore et al. (1995) Science 270:299-302). Examples of *Salmonella* strains which can be employed in the present disclosure include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Pseudomonas pudita, Pseudomonas aeruginosa, Pseudomonas mevalonii, Rhodobacter sphaeroides, Rhodobacter capsulatus, Rhodospirillum rubrum*, and *Rhodococcus* sp.

In some embodiments, the host organism or cell is eukaryotic (e.g. green algae, red algae, brown algae). In some embodiments, the algae is a green algae, for example, a Chlorophycean. The algae can be unicellular or multicellular. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa*, and *Chlamydomonas reinhardtii*. In other embodiments, the host cell is a microalga (e.g., *Chlamydomonas reinhardtii, Dunaliella salina, Haematococcus pluvialis, Nannochloropsis oceania, N. salina, Scenedesmus dimorphus, Chlorella* spp., *D. viridis*, or *D. tertiolecta*).

In some instances the organism is a rhodophyte, chlorophyte, heterokontophyte, tribophyte, glaucophyte, chlorarachniophyte, euglenoid, haptophyte, cryptomonad, dinoflagellum, or phytoplankton.

In some instances a host organism is vascular and photosynthetic. Examples of vascular plants include, but are not limited to, angiosperms, gymnosperms, rhyniophytes, or other tracheophytes.

In some instances a host organism is non-vascular and photosynthetic. As used herein, the term "non-vascular photosynthetic organism," refers to any macroscopic or microscopic organism, including, but not limited to, algae, cyanobacteria and photosynthetic bacteria, which does not have a vascular system such as that found in vascular plants. Examples of non-vascular photosynthetic organisms include bryophtyes, such as marchantiophytes or anthocerotophytes.

In some instances the organism is a cyanobacteria. In some instances, the organism is algae (e.g., macroalgae or microalgae). The algae can be unicellular or multicellular algae. For example, the microalgae *Chlamydomonas reinhardtii* may be transformed with a vector, or a linearized portion thereof, encoding one or more proteins of interest (e.g., a lipid trigger protein).

Methods for algal transformation are described in U.S. Provisional Patent Application No. 60/142,091. The methods of the present disclosure can be carried out using algae, for example, the microalga, *C. reinhardtii*. The use of microalgae to express a polypeptide according to a method of the disclosure provides the advantage that large populations of the microalgae can be grown, including commercially (Cyanotech Corp.; Kailua-Kona Hi.), thus allowing for production and, if desired, isolation of large amounts of a desired product.

The vectors of the present disclosure may be capable of stable or transient transformation of multiple photosynthetic organisms, including, but not limited to, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinofiagellata, pyrmnesiophyta, bacillariophyta, xanthophyta, eustigmatophyta, raphidophyta, phaeophyta, and phytoplankton. Other vectors of the present disclosure are capable of stable or transient transformation of, for example, *C. reinhardtii, N. oceania, N. salina, D. salina, H. pluvalis, S. dimorphus, D. viridis*, or *D. tertiolecta*.

Examples of appropriate hosts, include but are not limited to: bacterial cells, such as *E. coli, Streptomyces, Salmonella typhimurium*; fungal cells, such as yeast; insect cells, such as Drosophila S2 and Spodoptera Sf9; animal cells, such as CHO, COS or Bowes melanoma; adenoviruses; and plant cells. The selection of an appropriate host is deemed to be within the scope of those skilled in the art.

A polynucleotide selected and isolated as described herein is introduced into a suitable host cell. A suitable host cell is any cell which is capable of promoting recombination and/or reductive reassortment. The selected polynucleotides can be, for example, in a vector which includes appropriate control sequences. The host cell can be, for example, a higher eukaryotic cell, such as a mammalian cell, or a lower eukaryotic cell, such as a yeast cell, or the host cell can be a prokaryotic cell, such as a bacterial cell. Introduction of a construct (vector) into the host cell can be effected by, for example, calcium phosphate transfection, DEAE-Dextran mediated transfection, or electroporation.

Recombinant polypeptides can be expressed in plants, allowing for the production of crops of such plants and, therefore, the ability to conveniently produce large amounts of a desired product such as a fatty acid or glycerol lipid. Accordingly, the methods of the disclosure can be practiced using any plant, including, for example, microalga and macroalgae, (such as marine algae and seaweeds), as well as plants that grow in soil.

In one embodiment, the host cell is a plant. The term "plant" is used broadly herein to refer to a eukaryotic organism containing plastids, such as chloroplasts, and includes any such organism at any stage of development or to part of a plant, including a plant cutting, a plant cell, a plant cell culture, a plant organ, a plant seed, and a plantlet. A plant cell is the structural and physiological unit, of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful pails of a plant include harvestable parts and parts useful for propagation of progeny plants. A harvestable part of a plant can be any useful part of a plant, for example, flowers, pollen, seedlings, tubers, leaves, stems, fruit, seeds, and roots. A part of a plant useful for propagation includes, for example, seeds, fruits, cuttings, seedlings, tubers, and rootstocks.

A method of the disclosure can generate a plant containing genomic DNA (for example, a nuclear and/or plastid genomic DNA) that is genetically modified to contain a stably integrated polynucleotide (for example, as described in Hager and Bock, *Appl. Microbiol. Biotechnol.* 54:302-310, 2000). Accordingly, the present disclosure further provides a transgenic plant, e.g. *C. reinhardtii*, which comprises one or more chloroplasts containing a polynucleotide encoding one or more exogenous or endogenous polypeptides, including polypeptides that can allow for secretion of fuel products and/or fuel product precursors (e.g., isoprenoids, fatty acids, lipids, triglycerides). A photosynthetic organism of the present disclosure comprises at least one host cell that is modified to generate, for example, a fuel product or a fuel product precursor.

Some of the host organisms useful in the disclosed embodiments are, for example, are extremophiles, such as hyperthermophiles, psychrophiles, psychrotrophs, halophiles, barophiles and acidophiles. Some of the host organisms which may be used to practice the present disclosure are halophilic (e.g., *Dunaliella salina, D. viridis,* or *D. tertiolecta*). For example, *D. salina* can grow in ocean water and salt lakes (for example, salinity from 30-300 parts per thousand) and high salinity media (e.g., artificial sea water medium, seawater nutrient agar, brackish water medium, and seawater medium). In some embodiments of the disclosure, a host cell expressing a protein of the present disclosure can be grown in a liquid environment which is, for example, 0.1, 0.2, 0.3, 0.4, 0.5, 0.6, 0.7, 0.8, 0.9, 1.0, 3.1, 1.2, 1.3, 3.4, 1.5, 1.6, 1.7, 1.8, 1.9, 2.0, 2.1, 2.2, 2.3, 2.4, 2.5, 2.6, 2.7, 2.8, 2.9, 3.0, 31., 3.2, 3.3, 3.4, 3.5, 3.6, 3.7, 3.8, 3.9, 4.0, 4.1, 4.2, 4.3 molar or higher concentrations of sodium chloride. One of skill in the art will recognize that other salts (sodium salts, calcium salts, potassium salts, or other salts) may also be present in the liquid environments.

Where a halophilic organism is utilized for the present disclosure, it may be transformed with any of the vectors described herein. For example, *D. salina* may be transformed with a vector which is capable of insertion into the chloroplast or nuclear genome and which contains nucleic acids which encode a protein (e.g., a lipid trigger protein). Transformed halophilic organisms may then be grown in high-saline environments (e.g., salt lakes, salt ponds, and high-saline media) to produce the products (e.g., lipids) of interest. Isolation of the products may involve removing a transformed organism from a high-saline environment prior to extracting the product from the organism. In instances where the product is secreted into the surrounding environment, it may be necessary to desalinate the liquid environment prior to any further processing of the product.

The present disclosure further provides compositions comprising a genetically modified host cell. A composition comprises a genetically modified host cell; and will in some embodiments comprise one or snore further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol and dimethylsulfoxide; and nutritional media appropriate to the cell.

A host cell or host organism can be genetically modified, thus becoming a transgenic host cell or transgenic host organism. The plastid of a host cell or host organism can be genetically modified, thus becoming a transgenic plastid.

Culturing of Cells or Organisms

An organism may be grown under conditions which permit photosynthesis, however, this is not a requirement (e.g., a host organism may be grown in the absence of light). In some instances, the host organism may be genetically modified in such a way that its photosynthetic capability is diminished or destroyed. In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, and lactose), complex carbohydrates (e.g., starch and glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

Optimal growth of organisms occurs usually at a temperature of about 20° C. to about 25° C., although some organisms can still grow at a temperature of up to about 35° C. Active growth is typically performed in liquid culture. If the organisms are grown in a liquid medium and are shaken or mixed, the density of the cells can be anywhere from about 1 to $5 \times 10^8$ cells/ml at the stationary phase. For example, the density of the cells at the stationary phase for

*Chlamydomonas* sp. can be about 1 to $5 \times 10^7$ cells/ml; the density of the cells at the stationary phase for *Nannochloropsis* sp. can be about 1 to $5 \times 10^8$ cells/ml; the density of the cells at the stationary phase for *Scenedesmus* sp. can be about 1 to $5 \times 10^8$ cells/ml; and the density of the cells at the stationary phase for *Chlorella* sp. can be about 1 to $5 \times 10^8$ cells/ml. Exemplary cell densities at the stationary phase are as follows: *Chlamydomonas* sp. can be about $1 \times 10^7$ cells/ml; *Nannochloropsis* sp. can be about $1 \times 10^8$ cells/ml; *Scenedesmus* sp. can be about $1 \times 10^7$ cells/ml; and *Chlorella* sp. can be about $1 \times 10^8$ cells/ml. An exemplary growth rate may yield, for example, a two to four fold increase in cells per day, depending on the growth conditions. In addition, doubling times for organisms can be, for example, 5 hours to 30 hours.

The organism can also be grown on solid media, for example, media containing about 1.5% agar, in plates or in slants.

One source of energy is fluorescent light that can be placed, for example, at a distance of about 1 inch to about two feet from the organism. Examples of types of fluorescent lights includes, for example, cool white and daylight. Bubbling with air or $CO_2$ improves the growth rate of the organism. Bubbling with $CO_2$ can be, for example, at 1% to 5% $CO_2$. If the lights are turned on and off at regular intervals (for example, 12:12 or 14:10 hours of light:dark) the cells of some organisms will become synchronized.

Long term storage of organisms can be achieved by streaking them onto plates, sealing the plates with, for example, Parafilm™, and placing them in dim light at about 10° C. to about 18° C. Alternatively, organisms may be grown as streaks or stabs into agar tubes, capped, and stored at about 10° C. to about 18° C. Both methods allow for the storage of the organisms for several months.

For longer storage, the organisms can be grown in liquid culture to mid to late log phase and then supplemented with a penetrating cryoprotective agent like DMSO or MeOH, and stored at less than −130° C. An exemplary range of DMSO concentrations that can be used is 5 to 8%. An exemplary range of MeOH concentrations that can be used is 3 to 9%.

Organisms can be grown on a defined minimal medium (for example, high salt medium (HSM), modified artificial sea water medium (MASM), or F/2 medium) with light as the sole energy source. In other instances, the organism can be grown in a medium (for example, tris acetate phosphate (TAP) medium), and supplemented with an organic carbon source.

Organisms, such as algae, can grow naturally in fresh water or marine water. Culture media for freshwater algae can be, for example, synthetic media, enriched media, soil water media, and solidified media, such as agar. Various culture media have been developed and used for the isolation and cultivation of fresh water algae and are described in Watanabe, M. W. (2005). Freshwater Culture Media. In R. A. Andersen (Ed.), Algal Culturing Techniques (pp. 13-20). Elsevier Academic Press. Culture media for marine algae can be, for example, artificial seawater media or natural seawater media. Guidelines for the preparation of media are described in Harrison, P. J. and Berges, J. A. (2005). Marine Culture Media. In R. A. Andersen (Ed.), Algal Culturing Techniques (pp. 21-33). Elsevier Academic Press.

Organisms may be grown in outdoor open water, such as ponds, the ocean, seas, rivers, waterbeds, marshes, shallow pools, lakes, aqueducts, and reservoirs. When grown in water, the organism can be contained in a halo-like object comprised of lego-like particles. The halo-like object encircles the organism and allows it to retain nutrients from the water beneath while keeping if in open sunlight.

In some instances, organisms can be grown in containers wherein each container comprises one or two organisms, or a plurality of organisms. The containers can be configured to float on water. For example, a container can be filled by a combination of air and water to make the container and the organism(s) in it buoyant. An organism that is adapted to grow in fresh water can thus be grown in salt water (i.e., the ocean) and vice versa. This mechanism allows for automatic death of the organism if there is any damage to the container.

Culturing techniques for algae are well know to one of skill in the art and are described, for example, in Freshwater Culture Media. In R. A. Andersen (Ed.), Algal Culturing Techniques. Elsevier Academic Press.

Because photosynthetic organisms, for example, algae, require sunlight, $CO_2$ and water for growth, they can be cultivated in, for example, open ponds and lakes. However, these open systems are more vulnerable to contamination than a closed system. One challenge with using an open, system is that the organism of interest may not grow as quickly as a potential invader. This becomes a problem when another organism invades the liquid environment in which the organism of interest is growing, and the invading organism has a faster growth rate and takes over the system.

In addition, in open systems there is less control over water temperature, $CO_2$ concentration, and lighting conditions. The growing season, of the organism is largely dependent on location and, aside from tropical areas, is limited to the warmer months of the year. In addition, in an open system, the number of different organisms that can be grown, is limited to those that are able to survive in the chosen, location. An open system, however, is cheaper to set up and/or maintain than a closed system.

Another approach to growing an organism is to use a semi-closed system, such as covering the pond or pool with a structure, for example, a "greenhouse-type" structure. While this can result in a smaller system, it addresses many of the problems associated with an open system. The advantages of a semi-closed system, are that it can allow for a greater number of different organisms to be grown, it can allow for an organism to be dominant over an invading organism by allowing the organism of interest to out compete the invading organism for nutrients required for its growth, and it can extend the growing season for the organism. For example, if the system is heated, the organism can grow year round.

A variation of the pond system is an artificial pond, for example, a raceway pond. In these ponds, the organism, water, and nutrients circulate around a "racetrack." Paddlewheels provide constant motion to the liquid in the racetrack, allowing for the organism to be circulated back to the surface of the liquid at a chosen frequency. Paddlewheels also provide a source of agitation and oxygenate the system. These raceway ponds can be enclosed, for example, in a building or a greenhouse, or can be located outdoors.

Raceway ponds are usually kept shallow because the organism needs to be exposed to sunlight, and sunlight can only penetrate the pond water to a limited depth. The depth of a raceway pond can be, for example, about 4 to about 12 inches. In addition, the volume of liquid that can be contained in a raceway pond can be, for example, about 200 liters to about 600,000 liters.

The raceway ponds can be operated in a continuous manner, with, for example, $CO_2$ and nutrients being constantly fed to the ponds, while water containing the organism is removed at the other end.

If the raceway pond is placed outdoors, there are several different ways to address the invasion of an unwanted organism. For example, the pH or salinity of the liquid in which the desired organism is in can be such that the invading organism either slows down its growth or dies.

Also, chemicals can be added to the liquid, such as bleach, or a pesticide can be added to the liquid, such as glyphosate. In addition, the organism of interest can be genetically modified such that it is better suited to survive in the liquid environment. Any one or more of the above strategies can be used to address the invasion of an unwanted organism.

Alternatively, organisms, such as algae, can be grown in closed structures such as photobioreactors, where the environment is under stricter control than in open systems or semi-closed systems. A photobioreactor is a bioreactor which incorporates some type of light source to provide photonic energy input into the reactor. The term photobioreactor can refer to a system closed to the environment and having no direct exchange of gases and contaminants with, the environment. A photobioreactor can be described as an enclosed, illuminated culture vessel designed for controlled biomass production of phototrophic liquid cell suspension cultures. Examples of photobioreactors include, for example, glass containers, plastic tubes, tanks, plastic sleeves, and bags. Examples of light sources that can be used to provide the energy required to sustain photosynthesis include, for example, fluorescent bulbs, LEDs, and natural sunlight. Because these systems are closed everything that the organism needs to grow (for example, carbon dioxide, nutrients, water, and light) must be introduced into the bioreactor.

Photobioreactors, despite the costs to set up and maintain them, have several advantages over open systems, they can, for example, prevent or minimize contamination, permit axenic organism cultivation of monocultures (a culture consisting of only one species of organism), offer better control over the culture conditions (for example, pH, light, carbon dioxide, and temperature), prevent water evaporation, lower carbon dioxide losses due to out gassing, and permit higher cell concentrations.

On the other hand, certain requirements of photobioreactors, such as cooling, mixing, control of oxygen accumulation and biofouling, make these systems more expensive to build and operate than open systems or semi-closed systems.

Photobioreactors can be set up to be continually harvested (as is with the majority of the larger volume cultivation systems), or harvested one batch at a time (for example, as with polyethlyene bag cultivation). A batch photobioreactor is set up with, for example, nutrients, an organism (for example, algae), and water, and the organism is allowed to grow until the batch is harvested. A continuous photobioreactor can be harvested, for example, either continually, daily, or at fixed time intervals.

High density photobioreactors are described in, for example, Lee, et al., Biotech. Bioengineering 44:1161-1167, 1994. Other types of bioreactors, such as those for sewage and waste water treatments, are described in, Sawayama, et al., Appl. Micro. Biotech., 41:729-731, 1994. Additional examples of photobioreactors are described in, U.S. Appl. Publ. No. 2005/0260553, U.S. Pat. No. 5,958,761, and U.S. Pat. No. 6,083,740. Also, organisms, such as algae may be mass-cultured for the removal of heavy metals (for example, as described in Wilkinson, Biotech. Letters, 11:861-864, 1989), hydrogen (for example, as described in U.S. Patent Application Publication No. 2003/0162273), and pharmaceutical compounds from a water, soil, or other source or sample. Organisms can also be cultured in conventional fermentation bioreactors, which include, but are not limited to, batch, fed-batch, cell recycle, and continuous fermentors. Additional methods of culturing organisms and variations of the methods described herein are known to one of skill in the art.

Organisms can also be grown near ethanol production plants or other facilities or regions (e.g., cities and highways) generating $CO_2$. As such, the methods herein contemplate business methods for selling carbon credits to ethanol plants or other facilities or regions generating $CO_2$ while making fuels or fuel products by growing one or more of the organisms described herein near the ethanol production plant, facility, or region.

The organism of interest, grown in any of the systems described herein, can be, for example, continually harvested, or harvested one batch at a time.

$CO_2$ can be delivered to any of the systems described herein, for example, by bubbling in $CO_2$ from under the surface of the liquid containing the organism. Also, sparges can be used to inject $CO_2$ into the liquid. Spargers are, for example, porous disc or tube assemblies that are also referred to as Bubblers, Carbonators, Aerators, Porous Stones and Diffusers.

Nutrients that can be used in the systems described herein, include, for example, nitrogen (in the form of $NO_3^-$ or $NH_4^+$), phosphorus, and trace metals (Fe, Mg, K, Ca, Co, Cu, Mn, Mo, Zn, V, and B). The nutrients can come, for example, in a solid form or in a liquid form. If the nutrients are in a solid form they can be mixed with, for example, fresh, or salt water prior to being delivered to the liquid containing the organism, or prior to being delivered to a photobioreactor.

Organisms can be grown in cultures, for example large scale cultures, where large scale cultures refers to growth of cultures in volumes of greater than about 6 liters, or greater than about 10 liters, or greater than about 20 liters. Large scale growth can also be growth of cultures in volumes of 50 liters or more, 100 liters or more, or 200 liters or more. Large scale growth can be growth of cultures in, for example, ponds, containers, vessels, or other areas, where the pond, container, vessel, or area that contains the culture is for example, at lease 5 square meters, at least 10 square meters, at least 200 square meters, at least 500 square meters, at least 1,500 square meters, at least 2,500 square meters, in area, or greater.

*Chlamydomonas* sp., *Nannochloropsis* sp., *Scenedesmus* sp., and *Chlorella* sp. are exemplary algae that can be cultured as described herein and can grow under a wide array of conditions. One organism that can be cultured as described herein is a commonly used laboratory species *C. reinhardtii*. Cells of this species are haploid, and can grow on a simple medium of inorganic salts, using photosynthesis to provide energy. This organism can also grow in total darkness if acetate is provided as a carbon source. *C. reinhardtii* can be readily grown at room temperature under standard fluorescent lights. In addition, the cells can be synchronized by placing them on a light-dark cycle. Other methods of culturing *C. reinhardtii* cells are known to one of skill in the art.

Polynucleotides and Polypeptides

Also provided are isolated polynucleotides encoding a protein, for example, a lipid trigger protein described herein. As used herein "isolated polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

The novel proteins of the present disclosure can be made by any method known in the art. The protein may be synthesized using either solid-phase peptide synthesis or by classical solution peptide synthesis also known as liquid-phase peptide synthesis. Using Val-Pro-Pro, Enalapril and Lisinopril as starting templates, several series of peptide analogs such as X-Pro-Pro, X-Ala-Pro, and X-Lys-Pro, wherein X represents any amino acid residue, may be synthesized using solid-phase or liquid-phase peptide synthesis. Methods for carrying out liquid phase synthesis of libraries of peptides and oligonucleotides coupled to a soluble oligomeric support have also been described. Bayer, Ernst and Mutter, Manfred, Nature 237:512-513 (1972); Bayer, Ernst, et al., J. Am. Chem. Soc. 96:7333-7336 (1974); Bonora, Gian Maria, et al., Nucleic Acids Res. 18:3155-3159 (1990). Liquid phase synthetic methods have the advantage over solid phase synthetic methods in that liquid phase synthesis methods do not require a structure present on a first reactant which is suitable for attaching the reactant to the solid phase. Also, liquid phase synthesis methods do not require avoiding chemical conditions which, may cleave the bond between the solid phase and the first reactant (or intermediate product). In addition, reactions in a homogeneous solution may give better yields and more complete reactions than those obtained in heterogeneous solid phase/liquid phase systems such, as those present in solid phase synthesis.

In oligomer-supported liquid phase synthesis the growing product is attached to a large soluble polymeric group. The product, from each step of the synthesis can then be separated from unreacted reactants based on the large difference in size between the relatively large polymer-attached product and the unreacted reactants. This permits reactions to take place in homogeneous solutions, and eliminates tedious purification steps associated with traditional liquid phase synthesis. Oligomer-supported liquid phase synthesis has also been adapted to automatic liquid phase synthesis of peptides. Bayer, Ernst, et al., Peptides: Chemistry, Structure, Biology, 426-432.

For solid-phase peptide synthesis, the procedure entails the sequential assembly of the appropriate amino acids into a peptide of a desired sequence while the end of the growing peptide is linked to an insoluble support. Usually, the carboxyl terminus of the peptide is linked to a polymer from, which it can be liberated upon treatment with a cleavage reagent. In a common method, an amino acid is bound to a resin particle, and the peptide generated in a stepwise manner by successive additions of protected amino acids to produce a chain of amino acids. Modifications of the technique described by Merrifield are commonly used. See, e.g., Merrifield, J. Am. Chem. Soc. 96: 2989-93 (1964). In an automated solid-phase method, peptides are synthesized by loading the carboxy-terminal amino acid onto an organic linker (e.g., PAM, 4-oxymethylphenylacetamidomethyl), which is covalently attached to an insoluble polystyrene resin cross-linked with divinyl benzene. The terminal amine may be protected by blocking with t-butyloxycarbonyl. Hydroxyl- and carboxyl-groups are commonly protected by blocking with O-benzyl groups. Synthesis is accomplished in an automated peptide synthesizer, such as that available from Applied Biosystems (Foster City, Calif.). Following synthesis, the product may be removed from the resin. The blocking groups are removed by using hydrofluoric acid or trifluoromethyl sulfonic acid according to established methods. A routine synthesis may produce 0.5 mmole of peptide resin. Following cleavage and purification, a yield of approximately 6 0 to 70% is typically produced. Purification of the product peptides is accomplished by, for example, crystallizing the peptide from an organic solvent such as methyl-butyl ether, then dissolving in distilled water, and using dialysis (if the molecular weight of the subject peptide is greater than about 500 daltons) or reverse high pressure liquid chromatography (e.g., using a $C^{18}$ column with 0.1% trifluoroacetic acid and acetonitrile as solvents) if the molecular weight of the peptide is less than 500 daltons. Purified peptide may be lyophilized and stored in a dry state until use. Analysis of the resulting peptides may be accomplished using the common methods of analytical high pressure liquid chromatography (HPLC) and electrospray mass spectrometry (ES-MS).

In other cases, a protein, for example, a lipid trigger protein, is produced by recombinant methods. For production of any of the proteins described herein, host cells transformed with an expression vector containing the polynucleotide encoding such a protein can be used. The host cell can be a higher eukaryotic cell, such as a mammalian cell, or a lower eukaryotic cell such as a yeast or algal cell, or the host can be a prokaryotic cell such as a bacterial cell. Introduction of the expression vector into the host cell can be accomplished by a variety of methods including calcium phosphate transfection, DEAE-dextran mediated transfection, polybrene, protoplast fusion, liposomes, direct microinjection into the nuclei, scrape loading, biolistic transformation and electroporation. Large scale production of proteins from recombinant organisms is a well established process practiced on a commercial scale and well within the capabilities of one skilled in the art.

The polynucleotide sequence can comprise at least one mutation comprising one or more nucleotide additions, deletions or substitutions. The at least one mutation can be in a coding region, can result in one or more amino acid additions, deletions or substitutions in a protein encoded by the coding region, can be in a regulatory region, can be in a 5' UTR, can be in a 3' UTR, and/or can be in a promoter.

It should be recognized that the present disclosure is not limited to transgenic cells, organisms, and plastids containing a protein or proteins as disclosed herein, but also encompasses such cells, organisms, and plastids transformed with additional nucleotide sequences encoding enzymes involved in fatty acid synthesis. Thus, some embodiments involve the introduction of one or more sequences encoding proteins involved in fatty acid synthesis in addition to a protein disclosed herein. For example, several enzymes in a fatty acid production pathway may be linked, either directly or indirectly, such that products produced by one enzyme in the pathway, once produced, are in close proximity to the next enzyme in the pathway. These additional sequences may be contained in a single vector either operatively linked to a single promoter or linked to multiple promoters, e.g. one promoter for each sequence. Alternatively, the additional coding sequences may be contained in a plurality of additional vectors. When a plurality of vectors are used, they can be introduced into the host cell or organism simultaneously or sequentially.

Additional embodiments provide a plastid, and in particular a chloroplast, transformed with a polynucleotide encoding a protein of the present disclosure. The protein may be introduced into the genome of the plastid using any of the methods described herein or otherwise known in the art. The plastid may be contained in the organism in which it naturally occurs. Alternatively, the plastid may be an isolated plastid, that is, a plastid that has been removed from the cell in which it normally occurs. Methods for the isolation of plastids are known in the art and can be found, for example, in Maliga et al., *Methods in Plant Molecular Biology*, Cold Spring Harbor Laboratory Press, 1995; Gupta and Singh, *J. Biosci.*, 21:819 (3996); and Camara et al., *Plant Physiol.*, 73:94 (1983). The isolated plastid transformed with a protein of the present disclosure can be introduced into a host cell. The host cell can be one that naturally contains the plastid or one in which the plastid is not naturally found.

Also within the scope of the present disclosure are artificial plastid genomes, for example chloroplast genomes, that contain nucleotide sequences encoding any one or more of the proteins of the present disclosure. Methods for the assembly of artificial plastid genomes can be found in co-pending U.S. patent application Ser. No. 12/287,230 filed Oct. 6, 2008, published as U.S. Publication No. 2009/0123977 on May 14, 2009, and U.S. patent application Ser. No. 12/384,893 filed Apr. 8, 2009, published as U.S. Publication No. 2009/0269816 on Oct. 29, 2009, each of which is incorporated by reference in its entirety.

Introduction of Polynucleotide into a Host Organism or Cell

To generate a genetically modified host cell, a polynucleotide, or a polynucleotide cloned into a vector, is introduced stably or transiently into a host cell, using established techniques, including, but not limited to, electroporation, calcium phosphate precipitation, DEAE-dextran mediated transfection, and liposome-mediated transfection. For transformation, a polynucleotide of the present disclosure will generally further include a selectable marker, e.g., any of several well-known selectable markers such as neomycin resistance, ampicillin resistance, tetracycline resistance, chloramphenicol resistance, and kanamycin resistance.

A polynucleotide or recombinant nucleic acid molecule described herein, can be introduced into a cell (e.g., alga cell) using any method known in the art. A polynucleotide can be introduced into a cell by a variety of methods, which are well known in the art and selected, in part, based on the particular host cell. For example, the polynucleotide can be introduced into a cell using a direct gene transfer method such, as electroporation or microprojectile mediated (Holistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus, *Ann. Rev. Plant. Physiol. Plant Mol. Biol.* 42:205-225, 1991).

As discussed above, microprojectile mediated transformation can be used to introduce a polynucleotide into a cell (for example, as described in Klein et al., *Nature* 327:70-73, 1987).

This method utilizes microprojectiles such as gold or tungsten, which are coated with the desired polynucleotide by precipitation with calcium chloride, spermidine or polyethylene glycol. The microprojectile particles are accelerated at high speed into a cell using a device such as the BIOLISTIC PD-1000 particle gun (BioRad; Hercules Calif.). Methods for the transformation using biolistic methods are well known in the art (for example, as described in Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (for example, as described in Duan et al., *Nature Biotech.* 14:494-498, 1996; and Shimamoto, *Curr. Opin. Biotech.* 5:158-362, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

The basic techniques used for transformation and expression in photosynthetic microorganisms are similar to those commonly used for *E. coli, Saccharomyces cerevisiae* and other species. Transformation methods customized for a photosynthetic microorganisms, e.g., the chloroplast of a strain of algae, are known in the art. These methods have been described in a number of texts for standard molecular biological manipulation (see Packer & Glaser, 1988, "Cyanobacteria", Meth. Enzymol, Vol. 167; Weissbach & Weissbach, 1988, "Methods for plant molecular biology," Academic Press, New York, Sambrook, Fritsch & Maniatis, 1989, "Molecular Cloning: A laboratory manual," 2nd edition Cold Spring Harbor Laboratory Press, Cold Spring Harbor, N.Y.; and Clark M S, 1997, Plant Molecular Biology, Springer, N.Y.). These methods include, for example, biolistic devices (See, for example, Sanford, Trends In Biotech. (1988) 6: 299-302, U.S. Pat. No. 4,945,050; electroporation (Fromm et al., Proc. Nat'l. Acad. Sci. (USA) (1985) 82: 5824-5828); use of a laser beam, electroporation, microinjection or any other method capable of introducing DNA into a host cell.

Plastid transformation is a routine and well known method for introducing a polynucleotide into a plant: cell chloroplast (see U.S. Pat. Nos. 5,451,513, 5,545,817, and 5,545,818; WO 95/16783; McBride et al., *Proc. Natl. Acad. Sci.*, USA 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation. (Svab et al., *Proc. Natl. Acad. Sci.*, USA 87:8526-8530, 1990), and can result in stable homoplasmic transformants, at a frequency of approximately one per 100 bombardments of target leaves.

A further refinement in chloroplast transformation/expression technology that facilitates control over the timing and tissue pattern, of expression of introduced DNA coding sequences in plant plastid genomes has been described in PCT International Publication WO 95/36783 and U.S. Pat. No. 5,576,398. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promotes specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs.

Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase.

When nuclear transformation is utilized, the protein can be modified for plastid targeting by employing plant cell nuclear transformation constructs wherein DNA coding sequences of interest are fused to any of the available transit peptide sequences capable of facilitating transport of the encoded enzymes into plant plastids, and driving expression by employing an appropriate promoter. Targeting of the protein can be achieved by fusing DNA encoding plastid, e.g., chloroplast, leucoplast, amyloplast, etc., transit peptide sequences to the 5' end of DNAs encoding the enzymes. The sequences that encode a transit peptide region can be obtained, for example, from plant nuclear-encoded plastid proteins, such as the small subunit (SSU) of ribulose bisphosphate carboxylase, EPSP synthase, plant fatty acid biosynthesis related genes including fatty acyl-ACP thioesterases, acyl carrier protein (ACP), stearoyl-ACP desaturase, p-ketoacyl-ACP synthase and acyl-ACP thioesterase, or LHCPII genes, etc. Plastid transit peptide sequences can also be obtained from nucleic acid sequences encoding carotenoid biosynthetic enzymes, such as GGPP synthase, phytoene synthase, and phytoene desaturase. Other transit peptide sequences are disclosed in Von Heijne et al. (1991) *Plant Mol. Biol. Rep.* 9: 104; Clark et al. (1989) *J. Biol. Chem.* 264: 17544; della-Cioppa et al. (1987) *Plant Physiol.* 84: 965; Romer et al. (1993) *Biochem. Biophys. Res. Commun.* 196: 1434; and Shah et al. (1986) *Science* 233: 478. Another transit peptide sequence is that of the intact ACCase from *Chlamydomonas* (genbank EDO96563, amino acids 1-33). The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present disclosure are not critical as long as delivery into a plastid is obtained. Proteolytic processing within the plastid then produces the mature enzyme. This technique has proven successful with enzymes involved in polyhydroxyalkanoate biosynthesis (Nawrath et al. (1994) *Proc. Natl. Acad. Sci. USA* 91: 12760), and neomycin phosphotransferase II (NPT-II) and CP4 EPSPS (Padgette et al. (1995) *Crop Sci.* 35: 1451), for example.

Of interest are transit peptide sequences derived from enzymes known to be imported into the leucoplasts of seeds. Examples of enzymes containing useful transit peptides include those related to lipid biosynthesis (e.g., subunits of the plastid-targeted dicot acetyl-CoA carboxylase, biotin carboxylase, biotin carboxyl carrier protein, α-carboxytransferase, and plastid-targeted monocot multifunctional acetyl-CoA carboxylase (Mw, 220,000); plastidic subunits of the fatty acid synthase complex (e.g., acyl carrier protein (ACP), malonyl-ACP synthase, KASI, KASIL and KASIII); steroyl-ACP desaturase; thioesterases (specific for short, medium, and Song chain acyl ACP); plastid-targeted acyl transferases (e.g., glycerol-3-phosphate and acyl transferase); enzymes involved in the biosynthesis of aspartate family amino acids; phytoene synthase; gibberellic acid biosynthesis (e.g., ent-kaurene synthases 1 and 2); and carotenoid biosynthesis (e.g., lycopene synthase).

In some embodiments, an alga is transformed with a nucleic acid which encodes a protein of interest, for example, a lipid trigger protein.

In one embodiment, a transformation may introduce a nucleic acid into a plastid of the host alga (e.g., chloroplast). In another embodiment, a transformation may introduce a nucleic acid into the nuclear genome of the host alga. In still another embodiment, a transformation may introduce nucleic acids into both the nuclear genome and into a plastid.

Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PGR); however, any other appropriate technique known in the art may be utilized. Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Transporter and/or product screening may be performed by any method known in the art, for example ATP turnover assay, substrate transport assay, HPLC or gas chromatography.

The expression of the protein or enzyme can be accomplished by inserting a polynucleotide sequence (gene) encoding the protein or enzyme into the chloroplast or nuclear genome of a microalgae. The modified strain of microalgae can be made homoplasmic to ensure that the polynucleotide will be stably maintained in the chloroplast genome of all descendents. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given, locus of interest.

Vectors

Construct, vector and plasmid are used interchangeably throughout the disclosure. Nucleic acids encoding the proteins described herein, can be contained in vectors, including cloning and expression vectors. A cloning vector is a self-replicating DNA molecule that serves to transfer a DNA segment into a host cell. Three common types of cloning vectors are bacterial plasmids, phages, and other viruses. An expression vector is a cloning vector designed so that a coding sequence inserted at a particular site will be transcribed and translated into a protein. Both cloning and expression vectors can contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences.

In some embodiments, a polynucleotide of the present disclosure is cloned or inserted into an expression vector using cloning techniques know to one of skill in the art. The nucleotide sequences may be inserted into a vector by a variety of methods. In the most common method the sequences are inserted into an appropriate restriction endonuclease site(s) using procedures commonly known to those skilled in the art and detailed in, for example, Sambrook et al., Molecular Cloning, A Laboratory Manual, 2nd Ed., Cold Spring Harbor Press, (1989) and Ausubel et al., Short Protocols in Molecular Biology, 2nd Ed., John Wiley & Sons (1992).

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, and herpes simplex virus), PI-based artificial chromosomes, yeast plasmids, yeast artificial chromosomes, and any other vectors specific for specific hosts of interest (such as *E. coli* and yeast). Thus, for example, a polynucleotide encoding a lipid trigger protein, can be inserted into any one of a variety of expression vectors that are capable of expressing the protein. Such vectors can include, for example, chromosomal, nonchromosomal and synthetic DNA sequences.

Suitable expression vectors include chromosomal, non-chromosomal and synthetic DNA sequences, for example, SV 40 derivatives; bacterial plasmids; phage DNA; baculovirus; yeast plasmids; vectors derived from combinations of plasmids and phage DNA; and viral DNA such as vaccinia, adenovirus, fowl pox virus, and pseudorabies. In addition, any other vector that is replicable and viable in the host may be used. For example, vectors such as Ble2A, Arg7/2A, and SEnuc357 can be used for the expression of a protein.

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, pET21a-d(+) vectors (Novagen), and pSVLSV40 (Pharmacia). However, any other plasmid or other vector may be used so long as it is compatible with the host cell.

The expression vector, or a linearized portion thereof, can encode one or more exogenous or endogenous nucleotide sequences. Examples of exogenous nucleotide sequences that can be transformed into a host include genes from bacteria, fungi, plants, photosynthetic bacteria or other algae. Examples of other types of nucleotide sequences that can be transformed into a host, include, but are not limited to, lipid trigger genes, transporter genes, isoprenoid producing genes, genes which encode for proteins which, produce isoprenoids with two phosphates (e.g., GPP synthase and/or FPP synthase), genes which encode for proteins which produce fatty acids, lipids, or triglycerides, for example, ACCases, endogenous promoters, and 5' UTRs from the psbA, atpA, or rbcL genes. In some instances, an exogenous sequence is flanked by two homologous sequences.

Homologous sequences are, for example, those that have at least 50%, at least 60%, at least 70%, at least 80%, at least 90%, at least 95%, at least 98%, or at least 99% sequence identity to a reference amino acid sequence or nucleotide sequence, for example, the amino acid sequence or nucleotide sequence that is found in the host cell from which the protein is naturally obtained from or derived from.

A nucleotide sequence can also be homologous to a codon-optimized gene sequence. For example, a nucleotide sequence can have, for example, at least 50%, at least 60%, at least 70%, at least 80%, at least 90%, at least 95%, at least 98%, or at least 99% nucleic acid sequence identity to the codon-optimized gene sequence.

The first and second homologous sequences enable recombination of the exogenous or endogenous sequence into the genome of the host organism. The first and second homologous sequences can be at least 100, at least 200, at least 300, at least 400, at least 500, or at least 1500 nucleotides in length.

In some embodiments, about 0.5 to about 1.5 kb flanking nucleotide sequences of chloroplast genomic DNA may be used. In other embodiments about 0.5 to about 1.5 kb flanking nucleotide sequences of nuclear genomic DNA may be used, or about 2.0 to about 5.0 kb may be used.

In some embodiments, the vector may comprise nucleotide sequences that are codon-biased for expression in the organism being transformed. In another embodiment, a gene of interest, for example, a lipid trigger gene, may comprise nucleotide sequences that are codon-biased for expression in the organism being transformed. In addition, the nucleotide sequence of a tag may be codon-biased or codon-optimized for expression in the organism being transformed.

A polynucleotide sequence may comprise nucleotide sequences that are codon biased for expression in the organism being transformed. The skilled artisan is well aware of the "codon-bias" exhibited by a specific host cell in usage of nucleotide codons to specify a given amino acid. Without being bound by theory, by using a host cell's preferred codons, the rate of translation may be greater. Therefore, when synthesizing a gene for improved expression in a host cell, it may be desirable to design the gene such that its frequency of codon usage approaches the frequency of preferred codon usage of the host cell. In some organisms, codon bias differs between the nuclear genome and organelle genomes, thus, codon optimization or biasing may be performed for the target genome (e.g., nuclear codon biased or chloroplast codon biased). In some embodiments, codon biasing occurs before mutagenesis to generate a polypeptide. In other embodiments, codon biasing occurs after mutagenesis to generate a polynucleotide. In yet other embodiments, codon biasing occurs before mutagenesis as well as after mutagenesis. Codon bias is described in detail herein.

In some embodiments, a vector comprises a polynucleotide operably linked to one or more control elements, such as a promoter and/or a transcription terminator. A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion, of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual*, $2^{nd}$ Ed., Cold Spring Harbor Press, (1989) and Ausubel et al., *Short Protocols in Molecular Biology*, $2^{nd}$ Ed., John Wiley & Sons (1992).

A vector in some embodiments provides for amplification of the copy number of a polynucleotide. A vector can be, for example, an expression vector that provides for expression of a lipid trigger protein in a host cell, e.g., a prokaryotic host cell or a eukaryotic host cell.

A polynucleotide or polynucleotides can be contained in a vector or vectors. For example, where a second (or more) nucleic acid molecule is desired, the second nucleic acid molecule can be contained in a vector, which can, but need not be, the same vector as that containing the first nucleic acid molecule. The vector can be any vector useful for introducing a polynucleotide into a genome and can include a nucleotide sequence of genomic DNA (e.g., nuclear or plastid) that is sufficient to undergo homologous recombination with genomic DNA, for example, a nucleotide sequence comprising about 400 to about 1500 or more substantially contiguous nucleotides of genomic DNA.

A regulatory or control element, as the term is used herein, broadly refers to a nucleotide sequence that regulates the transcription or translation of a polynucleotide or the localization of a polypeptide to which if is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, and an IRES. A regulatory element can include a promoter and transcriptional and translational stop signals. Elements may be provided with linkers for the purpose of introducing specific restriction sites facilitating ligation of the control sequences with the coding region of a nucleotide sequence encoding a polypeptide. Additionally, a sequence comprising a cell compartmentalization signal (i.e., a sequence that targets a polypeptide to the cytosol, nucleus, chloroplast membrane or cell membrane) can be attached to the polynucleotide encoding a protein of interest. Such signals are well known in the art and have been widely reported (see, e.g., U.S. Pat. No. 5,776,689).

In a vector, a nucleotide sequence of interest is operably linked to a promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control.

Promoters useful for the present disclosure may come from any source (e.g., viral, bacterial, fungal, protist, and animal). The promoters contemplated herein can be specific to photosynthetic organisms, non-vascular photosynthetic organisms, and vascular photosynthetic organisms (e.g., algae, flowering plants). In some instances, the nucleic acids above are inserted into a vector that comprises a promoter of a photosynthetic organism, e.g., algae. The promoter can be a constitutive promoter or an inducible promoter. A promoter typically includes necessary nucleic acid sequences near the start site of transcription, (e.g., a TATA element).

Common promoters used in expression, vectors include, but are not limited to, LTR or SV40 promoter, the E. coli lac or trp promoters, and the phage lambda PL promoter. Non-limiting examples of promoters are endogenous promoters such as the psbA and atpA promoter. Other promoters known to control the expression of genes in prokaryotic or eukaryotic cells can be used and are known to those skilled in the art. Expression vectors may also contain, a ribosome binding site for translation initiation, and a transcription terminator. The vector may also contain sequences useful for the amplification, of gene expression.

A "constitutive" promoter is, for example, a promoter that is active under most environmental and developmental conditions. Constitutive promoters can, for example, maintain a relatively constant level of transcription.

An "inducible" promoter is a promoter that is active under controllable environmental or developmental conditions. For example, inducible promoters are promoters that initiate increased levels of transcription from DNA under their control in response to some change in the environment, e.g. the presence or absence of a nutrient or a change in temperature.

Examples of inducible promoters/regulatory elements include, for example, a nitrate-inducible promoter (for example, as described in Bock et al, Plant Mol. Biol. 17:9 (1991)), or a light-inducible promoter, (for example, as described in Feinbaum et al, Mol Gen. Genet. 226:449 (1991); and Lam and Chua, Science 248:471 (1990)), or a heat responsive promoter (for example, as described in Muller et al., Gene 111: 165-73 (1992)).

In many embodiments, a polynucleotide of the present disclosure includes a nucleotide sequence encoding a protein or enzyme of the present disclosure, where the nucleotide sequence encoding the polypeptide is operably linked to an inducible promoter. Inducible promoters are well known in the art. Suitable inducible promoters include, but are not limited to, the pL of bacteriophage λ; Placo; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (for example, as described in Guzman et al. (1995) J. Bacteriol. 177:4121-4130); a xylose-inducible promoter, e.g., Pxyl (for example, as described in Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; and a heat-inducible promoter, e.g., heat inducible lambda $P_L$ promoter and a promoter controlled by a heat-sensitive repressor (e.g., C1857-repressed lambda-based expression vectors; for example, as described in Hoffmann et al. (1999) FEMS Microbiol Lett. 177(2):327-34).

In many embodiments, a polynucleotide of the present disclosure includes a nucleotide sequence encoding a protein or enzyme of the present disclosure, where the nucleotide sequence encoding the polypeptide is operably linked to a constitutive promoter. Suitable constitutive promoters for use in prokaryotic cells are known in the art and include, but are not limited to, a sigma70 promoter, and a consensus sigma70 promoter.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter; an araBAD promoter; in vivo regulated promoters, such as an ssaG promoter or a related promoter (for example, as described in U.S. Patent Publication No. 20040131637), a pagC promoter (for example, as described in Pulkkinen and Miller, J. Bacteriol., 1991: 173(1): 86-93; and Alpuche-Aranda et al., PNAS, 1992; 89(21): 10079-83), a nirB promoter (for example, as described in Harborne et al. (1992) Mol. Micro. 6:2805-2813; Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (for example, GenBank Accession Nos. AX798980, AX798961, and AX798183); a stationary phase promoter, e.g., a dps promoter, an spv promoter; a promoter derived from the pathogenicity island SPI-2 (for example, as described in WO96/17951); an actA promoter (for example, as described in Shetron-Rama et al. (2002) Infect Immun. 70:1087-1096); an rpsM promoter (for example, as described in Valdivia and Falkow (1996). Mol. Microbiol. 22:367-378); a tet promoter (for example, as described in Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); and an SP6 promoter (for example, as described in Melton et al. (1984) Nucl. Acids Res. 12:7035-7056).

In yeast, a number of vectors containing constitutive or inducible promoters may be used. For a review of such vectors see, Current Protocols in Molecular Biology, Vol. 2, 1988, Ed. Ausubel, et at, Greene Publish, Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (for example, as described in Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

Non-limiting examples of suitable eukaryotic promoters include CM V immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A vector utilized in the practice of the disclosure also can contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, and sequences that encode a selectable marker. As such, the vector can contain, for example, one or more cloning sites such as a multiple cloning site, which can, but need not, be positioned such that a exogenous or endogenous polynucleotide can be inserted into the vector and operatively linked to a desired element.

The vector also can contain a prokaryote origin of replication (ori), for example, an *E. coli* ori or a cosmid ori, thus allowing passage of the vector into a prokaryote host cell, as well as into a plant chloroplast. Various bacterial and viral origins of replication are well known to those skilled in the art and include, but are not limited to the pBR322 plasmid origin, the 2u plasmid origin, and the SV40, polyoma, adenovirus, VSV, and BPV viral origins.

A regulatory or control element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, an IRES. Additionally, an element can be a cell compartmentalization signal (i.e., a sequence that targets a polypeptide to the cytosol, nucleus, chloroplast membrane or cell membrane). In some aspects of the present disclosure, a cell compartmentalization signal (e.g., a cell membrane targeting sequence) may be ligated to a gene and/or transcript, such that translation of the gene occurs in the chloroplast. In other aspects, a cell compartmentalization signal may be ligated to a gene such that, following translation of the gene, the protein is transported to the cell membrane. Cell compartmentalization signals are well known in the art and have been widely reported (see, e.g., U.S. Pat. No. 5,776,689).

A vector, or a linearized portion thereof, may include a nucleotide sequence encoding a reporter polypeptide or other selectable marker. The term "reporter" or "selectable marker" refers to a polynucleotide (or encoded polypeptide) that confers a detectable phenotype.

A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (for example, as described in Giacomin, *Plant Sci.* 116:59-72, 1996; Scikantha, *J. Bacterial.* 178:121, 1996; Gerdes, *FEBS Lett.* 389:44-47, 1996; and Jefferson, *EMBO J.* 6:3901-3907, 1997, fl-glucuronidase).

A selectable marker (or selectable gene) generally is a molecule that, when present or expressed in a cell, provides a selective advantage (or disadvantage) to the cell containing the marker, for example, the ability to grow in the presence of an agent that otherwise would kill the cell. The selection gene can encode for a protein necessary for the survival or growth of the host cell transformed with the vector.

A selectable marker can provide a means to obtain, for example, prokaryotic cells, eukaryotic cells, and/or plant cells that express the marker and, therefore, can be useful as a component of a vector of the disclosure. The selection gene or marker can encode for a protein necessary for the survival or growth of the host cell transformed with the vector. One class of selectable markers are native or modified genes which restore a biological or physiological function to a host cell (e.g., restores photosynthetic capability or restores a metabolic pathway). Other examples of selectable markers include, but are not limited to, those that confer antimetabolite resistance, for example, dihydrofolate reductase, which confers resistance to methotrexate (for example, as described in Reiss, *Plant Physiol.* (*Life Sci. Adv.*) 13:343-149, 1994); neomycin phosphotransferase, which confers resistance to the aminoglycosides neomycin, kanamycin and paromycin (for example, as described in Herrera-Estrella, *EMBO J.* 2:987-995, 1983), hygro, which confers resistance to hygromycin (for example, as described in Marsh, *Gene* 32:481-485, 1984), trpB, which allows cells to utilize indole in place of tryptophan; hisD, which allows cells to utilize histinol in place of histidine (for example, as described in Hartman, *Proc. Natl. Acad. Sci., USA* 85:8047, 1988); mannose-6-phosphate isomerase which allows cells to utilize mannose (for example, as described in PCT Publication Application No. WO 94/20627); ornithine decarboxylase, which confers resistance to the ornithine decarboxylase inhibitor, 2-(difluoromethyl)-DL-ornithine (DFMO; for example, as described in McConlogue, 1987, In: Current Communications in Molecular Biology, Cold Spring Harbor Laboratory ed.); and deaminase horn *Aspergillus terreus*, which confers resistance to Blasticidin S (for example, as described in Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (for example, as described in White et al., *Nucl. Acids Res.* 18:1062, 1990; and Spencer et al., *Theor. Appl. Genet.* 79:625-631, 1990), a mutant EPSPV-synthase, which confers glyphosate resistance (for example, as described in Hinchee et al., *BioTechnology* 91:915-922, 1998), a mutant acetolactate synthase, which confers imidazoline or sulfonylurea resistance (for example, as described in Lee et al., *EMBO J.* 7:1241-1248, 1988), a mutant psbA, which confers resistance to atrazine (for example, as described in Smeda et al., *Plant Physiol.* 103:911-917, 1993), or a mutant protoporphyrinogen oxidase (for example, as described in U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells; tetramycin or ampicillin resistance for prokaryotes such as *E. coli* and bleomycin, gentamycin, glyphosate, hygromycin, kanamycin, methotrexate, phleomycin, phosphinothricin, spectinomycin, streptomycin, streptomycin, sulfonamide and sulfonylurea resistance in plants (for example, as described in Maliga et al., Methods in Plant Molecular Biology, Cold Spring Harbor Laboratory Press, 1995, page 39). The selection marker can have its own promoter or its expression can be driven by a promoter driving the expression of a polypeptide of interest The promoter driving expression of the selection marker can be a constitutive or an inducible promoter.

Reporter genes greatly enhance the ability to monitor gene expression in a number of biological organisms. Reporter genes have been successfully used in chloroplasts of higher plants, and high levels of recombinant protein expression have been reported. In addition, reporter genes have been used in the chloroplast of *C. reinhardtii*. In chloroplasts of higher plants, β-glucuronidase (uidA, for example, as described in Staub and Maliga, *EMBO J.* 12:601-606, 1993), neomycin phosphotransferase (nptII, for example, as described in Carrer et al., *Mol. Gen. Genet.* 241:49-56, 1993), adenosyl-3-adenyltransferase (aadA, for example, as described in Svab and Maliga, *Proc. Natl. Acad. Sci.*, USA 90:913-917, 1993), and the *Aequorea victoria* GFP (for example, as described in Sidorov et al., *Plant J.* 19:209-216, 1999) have been used as reporter genes (for example, as described in Heifetz, *Biochemie* 82:655-666, 2000). Each of these genes has attributes that make them useful reporters of chloroplast gene expression, such as ease of analysis, sensitivity, or the ability to examine expression in situ. Based upon these studies, other exogenous proteins have been expressed in the chloroplasts of higher plants such as *Bacillus thuringiensis* Cry toxins, conferring resistance to insect herbivores (for example, as described in Kota et al., *Proc. Natl. Acad. Sci.*, USA 96:1840-3845, 1999), or human somatotropin (for example, as described in Staub et al., *Nat. Biotechnol.* 18:333-338, 2000), a potential biopharmaceutical. Several reporter genes have been expressed in the chloroplast of the eukaryotic green alga, *C. reinhardtii*, including aadA (for example, as described in Goldschmidt-Clermont, *Nucl. Acids Res.* 19:4083-4089 1991; and Zerges and Rochaix, *Mol. Cell Biol.* 14:5268-5277, 1994), uidA (for example, as described in Sakamoto et al., *Proc. Natl. Acad. Sci.*, USA 90:477-501, 1993; and Ishikura et al., *J. Biosci. Bioeng.* 87:307-314 1999), *Renilla luciferase* (for example, as described in Minko et al., *Mol. Gen. Genet.* 262:421-425, 1999) and the amino glycoside phosphotransferase from *Acinetobacter baumanii*, aphA6 (for example, as described in Bateman and Purton, *Mol. Gen. Genet* 263:404-410, 2000).

In one embodiment the protein described herein is modified by the addition of an N-terminal strep-tag epitope to aid in the detection of protein expression. In another embodiment, the protein described herein is modified at the C-terminus by the addition of a Flag-tag epitope to aid in the detection of protein expression, and to facilitate protein purification.

Affinity tags can be appended to proteins so that they can be purified from their crude biological source using an affinity technique. These include, for example, chitin binding protein (CBP), maltose binding protein (MBP), and glutathione-S-transferase (GST). The poly(His) tag is a widely-used protein tag; it binds to metal matrices. Some affinity Sags have a dual role as a solubilization, agent, such as MBP, and GST. Chromatography tags are used to alter chromatographic properties of the protein to afford different resolution across a particular separation technique. Often, these consist of polyanionic amino acids, such as FLAG-tag. Epitope Sags are short peptide sequences which are chosen because high-affinity antibodies can be reliably produced in many different species. These are usually derived from viral genes, which explain their high immunoreactivity. Epitope tags include, but are not limited to, V5-tag, c-myc-tag, and HA-tag. These tags are particularly useful for western blotting and immunoprecipitation experiments, although they also find use in antibody purification.

Fluorescence tags are used to give visual readout on a protein, GFP and its variants are the most commonly used fluorescence tags. More advanced applications of GFP include using it as a folding reporter (fluorescent if folded, colorless if not).

In one embodiment, the proteins described herein can be fused at the amino-terminus to the carboxy-terminus of a highly expressed protein (fusion partner). These fusion partners may enhance the expression of the gene. Engineered processing sites, for example, protease, proteolytic, or tryptic processing or cleavage sites, can be used to liberate the protein from the fusion partner, allowing for the purification of the intended protein. Examples of fusion partners that can be fused to the gene are a sequence encoding the mammary-associated serum amyloid (M-SAA) protein, a sequence encoding the large and/or small subunit of ribulose bisphosphate carboxylase, a sequence encoding the glutathione S-transferase (GST) gene, a sequence encoding a thioredoxin (TRX) protein, a sequence encoding a maltose-binding protein (MBP), a sequence encoding any one or more of *E. coli* proteins NusA, NusB, NusG, or NusE, a sequence encoding a ubiqutin (Ub) protein, a sequence encoding a small ubiquitin-related modifier (SUMO) protein, a sequence encoding a cholera toxin B subunit (CTB) protein, a sequence of consecutive histidine residues linked to the 3'end of a sequence encoding the MBP-encoding malE gene, the promoter and leader sequence of a galactokinase gene, and the leader sequence of the ampicillinase gene.

In some instances, the vectors of the present disclosure will contain elements such as an *E. coli* or *S. cerevisiae* origin of replication. Such features, combined with appropriate selectable markers, allows for the vector to be "shuttled" between the target host cell and a bacterial and/or yeast cell. The ability to passage a shuttle vector of the disclosure in a secondary host may allow for more convenient manipulation of the features of the vector. For example, a reaction mixture containing the vector and inserted polynucleotide(s) of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. A shuttle vector then can be introduced into plant cell chloroplasts, wherein a polypeptide of interest can be expressed and, if desired, isolated according to a method of the disclosure.

Knowledge of the chloroplast or nuclear genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, *J. Mol. Biol.* 312:425-438, 2001; Staub and Maliga, *Plant Cell* 4:39-45, 1992; and Kavanagh et al., *Genetics* 152:1111-1122, 1999, each, of which is incorporated herein by reference). The entire chloroplast genome of *C. reinhardtii* is available to the public on the world wide web, at the URL "biology.duke.edu/chlamy_genome/-chloro.html" (see "view complete genome as text, file" link and "maps of the chloroplast genome" link; J. Maul, J. W. Lilly, and D. B. Stern, unpublished results; revised Jan. 28, 2002; to be published as GenBank Acc. No. AF396929; and Maul, J. E. et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast.

In this respect, the website containing the *C. reinhardtii* chloroplast genome sequence also provides maps showing coding and non-coding regions of the chloroplast genome, thus facilitating selection of a sequence useful for constructing a vector (also described in Maul, J. E., et al. (2002) The Plant Cell, Vol. 14 (2659-2679)). For example, the chloroplast vector, p322, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chloro140.html").

In addition, the entire nuclear genome of *C. reinhardtii* is described in Merchant, S. S., et al., Science (2007), 318 (5848):245-250, thus facilitating one of skill in the art to select a sequence or sequences useful for constructing a vector.

For expression of the polypeptide in a host, an expression cassette or vector may be employed. The expression vector will comprise a transcriptional and translational initiation region, which may be inducible or constitutive, where the coding region is operably linked under the transcriptional control of the transcriptional initiation region, and a transcriptional and translational termination region. These control regions may be native to the gene, or may be derived from an exogenous source. Expression vectors generally have convenient restriction sites located near the promoter sequence to provide for the insertion of nucleic acid sequences encoding exogenous or endogenous proteins. A selectable marker operative in the expression host may be present.

The nucleotide sequences may be inserted into a vector by a variety of methods. In the most common method the sequences are inserted into an appropriate restriction endonuclease site(s) using procedures commonly known to those skilled in the art and detailed in, for example, Sambrook et al., *Molecular Cloning, A Laboratory Manual,* 2$^{nd}$ Ed., Cold Spring Harbor Press, (1989) and Ausubel et al., *Short Protocols in Molecular Biology,* 2$^{nd}$ Ed., John Wiley & Sons (1992).

The description herein provides that host cells may be transformed with vectors. One of skill in the art will recognize that such transformation includes transformation with circular vectors, linearized vectors, linearized portions of a vector, or any combination of the above.

Thus, a host cell comprising a vector may contain the entire vector in the cell (in either circular or linear form), or may contain a linearized portion of a vector of the present disclosure.

Codon Optimization

As discussed above, one or snore codons of an encoding polynucleotide can be "biased" or "optimized" to reflect. The codon usage of the host organism. For example, one or more codons of an encoding polynucleotide can be "biased" or "optimized" to reflect chloroplast codon usage (Table B) or nuclear codon usage (Table C). Most amino acids are encoded by two or snore different, (degenerate) codons, and it is well recognized that various organisms utilize certain codons in preference to others, "Biased" or codon "optimized" can be used interchangeably throughout the specification. Codon bias can be variously skewed in different plants, including, for example, in alga as compared to tobacco. Generally, the codon bias selected reflects codon usage of the plant (or organelle therein) which is being transformed with the nucleic acids of the present disclosure.

A polynucleotide that is biased for a particular codon usage can be synthesized de novo, or can be genetically modified using routine recombinant DNA techniques, for example, by a site directed mutagenesis method, to change one or more codons such that they are biased for chloroplast codon usage.

Such preferential codon usage, which is utilized in chloroplasts, is referred to herein as "chloroplast codon usage." Table B (below) shows the chloroplast codon usage for *C. reinhardtii* (see U.S. Patent Application Publication No.: 2004/0014174, published Jan. 22, 2004).

TABLE B

Chloroplast Codon Usage in *Chlamydomonas reinhardtii*

| | | | |
|---|---|---|---|
| UUU 34.1*(348**) | UCU 19.4(198) | UAU 23.7(242) | UGU 8.5(87) |
| UUC 14.2(145) | UCC 4.9(50) | UAC 10.4(106) | UGC 2.6(27) |
| UUA 72.8(742) | UCA 20.4(208) | UAA 2.7(28) | UGA 0.1(1) |
| UUG 5.6(57) | UCG 502(53) | UAG 0.7(7) | UGG 13.7(140) |
| CUU 14.8(151) | CCU 14.9(152) | CAU 11.1(113) | CGU 25.5(260) |
| CUC 1.0(10) | CCC 5.4(55) | CAC 8.4(86) | CGC 5.1(52) |
| CUA 6.8(69) | CCA 19.3(197) | CAA 34.8(355) | CGA 3.8(39) |
| CUG 7.2(73) | CCG 3.0(31) | CAG 5.4(55) | CGG 0.5(5) |
| AUU 44.6(455) | ACU 23.3(237) | AAU 44.0(449) | AGU 16.9(172) |
| AUC 9.7(99) | ACC 7.8(80) | AAC 19.7(201) | AGC 6.7(68) |
| AUA 8.2(84) | ACA 29.3(299) | AAA 61.5(627) | AGA 5.0(51) |
| AUG 23.3(238) | ACG 4.2(43) | AAG 11.0(112) | AGG 1.5(15) |
| GUU 27.5(280) | GCU 30.6(312) | GAU 23.8(243) | GGU 40.0(408) |

TABLE B-continued

Chloroplast Codon Usage in *Chlamydomonas reinhardtii*

| GUC 4.6(47) | GCC 11.1(113) | GAC 11.6(118) | GGC 8.7(89) |
| GUA 26.4(269) | GCA 19.9(203) | GAA 40.3(411) | GGA 9.6(98) |
| GUG 7.1(72) | GCG 4.3(44) | GAG 6.9(70) | GGG 4.3(44) |

*Frequency of codon usage per 1,000 codons,
**Number of times observed in 36 chloroplast coding sequences (10,193 codons).

The *C. reinhardtii* chloroplast genome shows a high AT content, and noted codon bias (for example, as described in Franklin. S., et al., (2002) *Plant J* 30:733-744; Mayfield S. P. and Schultz J. (2004) *Plant J* 37:449-458). To achieve protein expression, a gene of interest can be first converted to match the codon usage of *C. reinhardtii* by synthesizing the gene in a codon-bias optimized for the *C. reinhardtii* chloroplast (Table B). A codon bias threshold of greater than 10% of codons normally used for that amino acid can be chosen and the genes can be assembled via overlapping oligonucleotides.

Codon optimization for *C. reinhardtii* chloroplast expression can be performed using software specifically designed for polymerase cycling assembly (PCA)-based de-novo gene synthesis. This program generates gene sequences by the simultaneous optimization of multiple parameters: normalization of the codon distribution to that of the *C. reinhardtii* chloroplast (data obtained from http://www.kazusa.or.jp/codon (Nakamura Y., et al. (2000) *Nucleic Acids Res* 28:292)); uniformity of physical properties of the output oligonucleotides (GC content, melting temperature, length); and avoidance of unfavorable mRNA structures. A gene can be assembled by PCA using sense and antisense oligonucleotides (for example, as described in Minshull J., et al. (2004) *Methods* 32:416-427).

The coding sequence of a gene can be ordered in *C. reinhardtii* chloroplast codon bias from, for example, DNA2.0 (www.dna20.com; DNA2.0 Headquarter, 1430 O'Brien Drive, Suite E, Menlo Park, Calif. 94025, USA).

CAI values can be determined with the CAI calculator (http://genomes.urv.cat/CAIcal/ Puigbo, P., et al., (2008) CAIcal: a combined assess codon usage adaptation. Biology Direct, 3:38) using the *C. reinhardtii* chloroplast codon usage table (http://www.kazusa.or.jp/codon/cgi-bin/showcodon.cgi?species=3055.chloroplast; for example, Table B). CAI values range from 0 to 1, with 1 being if a gene always uses the most frequently used codon of a reference set (Puigbo P., et al. (2008) *BMC Bioinformatics* 9:65).

The chloroplast codon bias can, but need not, be selected based on a particular organism in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect chloroplast codon usage, or can be the de novo synthesis of polynucleotide sequence such that the change (bias) is introduced as a consequence of the synthesis procedure.

In addition to utilizing chloroplast codon bias as a means to provide efficient translation of a polypeptide, if will be recognized that an alternative means for obtaining efficient translation of a polypeptide in a chloroplast is to re-engineer the chloroplast genome (e.g., a *C. reinhardtii* chloroplast genome) for the expression of tRNAs not otherwise expressed in the chloroplast genome. Such an engineered algae expressing one or more exogenous tRNA molecules provides the advantage that it would obviate a requirement to modify every polynucleotide of interest that is to be introduced info and expressed from a chloroplast genome; instead, algae such as *C. reinhardtii* that comprise a genetically modified chloroplast genome can be provided and utilized for efficient translation of a polypeptide according to any method of the disclosure. Correlations between tRNA abundance and codon usage in highly expressed genes is well known (for example, as described in Franklin et al., Plant J. 30:733-744, 2002; Dong et al., J. Mol. Biol. 260:649-663, 1996; Duret, Trends Genet. 16:287-289, 2000; Goldman et al., J. Mol. Biol. 245:467-473, 1995; and Komar et. al., Biol. Chem. 379:1295-1300, 1998). In *E. coli*, for example, re-engineering of strains to express underutilized tRNAs resulted in enhanced expression of genes which utilize these codons (see Novy et al., in Novations 12:1-3, 2001). Utilizing endogenous tRNA genes, site directed mutagenesis can be used to make a synthetic tRNA gene, which can be introduced into chloroplasts to complement rare or unused tRNA genes in a chloroplast genome, such as a *C. reinhardtii* chloroplast genome.

Generally, the chloroplast codon bias selected for purposes of the present disclosure, including, for example, in preparing a synthetic polynucleotide as disclosed herein reflects chloroplast codon usage of a plant chloroplast, and includes a codon bias that, with respect to the third position of a codon, is skewed towards A/T, for example, where the third position has greater than, about 66% AT bias, or greater than about 70% AT bias. In one embodiment, the chloroplast codon usage is biased to reflect alga chloroplast codon usage, for example, *C. reinhardtii*, which has about 74.6% AT bias in the third codon position. An exemplary preferred codon usage in the chloroplasts of algae has been described in US 2004/0014174.

Table C exemplifies codons that are preferentially used in algal nuclear genes. The nuclear codon bias can, but need not, be selected based on a particular organism in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect nuclear codon usage, or can be the de novo synthesis of polynucleotide sequence such that the change (bias) is introduced as a consequence of the synthesis procedure.

In addition to utilizing nuclear codon bias as a means to provide efficient translation of a polypeptide, it will be recognized that an alternative means for obtaining efficient translation of a polypeptide in a nucleus is to re-engineer the nuclear genome (e.g., a *C. reinhardtii* nuclear genome) for the expression of tRNAs not otherwise expressed in the nuclear genome. Such an engineered algae expressing one or more exogenous tRNA molecules provides the advantage that it would obviate a requirement to modify every polynucleotide of interest that is to be introduced into and expressed from a nuclear genome; instead, algae such as *C. reinhardtii* that comprise a genetically modified nuclear genome can be provided and utilized for efficient translation of a polypeptide according to any method of the disclosure. Correlations between tRNA abundance and codon usage in highly expressed genes is well known (for example, as described in Franklin et al., Plant J. 30:733-744, 2002; Dong et al., J. Mol. Biol. 260:649-663, 3996; Duret, Trends Genet. 16:287-289, 2000; Goldman et. Al., J. Mol. Biol. 245:467-473, 1995; and Komar et. Al., Biol. Chem. 379:1295-1300, 1998). In *E. coli*, for example, re-engineering of strains to express underutilized tRNAs resulted in enhanced expression of genes which utilize these codons (see Novy et al., in Novations 12:1-3, 2001). Utilizing endogenous tRNA genes, site directed mutagenesis can be used to make a synthetic tRNA gene, which can be introduced into the nucleus to complement rare or unused tRNA genes in a nuclear genome, such as a *C. reinhardtii* nuclear genome.

Generally, the nuclear codon bias selected for purposes of the present disclosure, including, for example, in preparing a synthetic polynucleotide as disclosed herein, can reflect nuclear codon usage of an algal nucleus and includes a codon bias that results in the coding sequence containing greater than 60% G/C content.

restriction, site is created, the next best choice according to the regular *Chlamydomonas* chloroplast usage table that eliminates the restriction site is selected.

TABLE D

| Amino acid | Codon utilized |
|---|---|
| F | TTC |
| L | TTA |
| I | ATC |
| V | GTA |
| S | TCA |
| P | CCA |
| T | ACA |
| A | GCA |
| Y | TAC |
| H | CAC |
| Q | CAA |
| N | AAC |
| K | AAA |
| D | GAC |
| E | GAA |
| C | TGC |
| R | CGT |
| G | GGC |
| W | TGG |
| M | ATG |
| STOP | TAA |

TABLE C fields: [triplet] [frequency: per thousand] ([number])
Coding GC 66.30% 1$^{st}$ letter GC 64.80% 2$^{nd}$ letter
GC 47.90% 3$^{rd}$ letter GC 86.21%
Nuclear Codon Usage in *Chlamydomonas reinhardtii*

| | | | |
|---|---|---|---|
| UUU 5.0 (2110) | UCU 4.7 (1992) | UAU 2.6 (1085) | UGU 1.4 (601) |
| UUC 27.1 (11411) | UCC 16.1 (6782) | UAC 22.8 (9579) | UGC 13.1 (5498) |
| UUA 0.6 (247) | UCA 3.2 (1348) | UAA 1.0 (441) | UGA 0.5 (227) |
| UUG 4.0 (1673) | UCG 16.1 (6763) | UAG 0.4 (183) | UGG 13.2 (5559) |
| CUU 4.4 (1869) | CCU 8.1 (3416) | CAU 2.2 (919) | CGU 4.9 (2071) |
| CUC 13.0 (5480) | CCC 29.5 (12409) | CAC 17.2 (7252) | CGC 34.9 (14676) |
| CUA 2.6 (1086) | CCA 5.1 (2124) | CAA 4.2 (1780) | CGA 2.0 (841) |
| CUG 65.2 (27420) | CCG 20.7 (8684) | CAG 36.3 (15283) | CGG 11.2 (4711) |
| AUU 8.0 (3360) | ACU 5.2 (2171) | AAU 2.8 (1157) | AGU 2.6 (1089) |
| AUC 26.6 (11200) | ACC 27.7 (11663) | AAC 28.5 (11977) | AGC 22.8 (9590) |
| AUA 1.1 (443) | ACA 4.1 (1713) | AAA 2.4 (1028) | AGA 0.7 (287) |
| 0AUG 25.7 (10796) | ACG 15.9 (6684) | AAG 43.3 (18212) | AGG 2.7 (1150) |
| GUU 5.1 (2158) | GCU 16.7 (7030) | GAU 6.7 (2805) | GGU 9.5 (3984) |
| GUC 15.4 (6496) | GCC 54.6 (22960) | GAC 41.7 (17519) | GGC 62.0 (26064) |
| GUA 2.0 (857) | GCA 10.6 (4467) | GAA 2.8 (1172) | GGA 5.0 (2084) |
| GUG 46.5 (19558) | GCG 44.4 (18688) | GAG 53.5 (22486) | GGG 9.7 (4087) |

Table D lists the codon selected at each position for backtranslating the protein to a DNA sequence for synthesis. The selected codon is the sequence recognized by the tRNA encoded in the *Chlamydomonas* chloroplast genome when present; the stop codon (TAA) is the codon most frequently present in the chloroplast encoded genes. If an undesired Percent Sequence Identity One example of an algorithm that is suitable for determining percent sequence identity or sequence similarity between nucleic acid or polypeptide sequences is the BLAST algorithm, which is described, e.g., in Altschul et al., *J. Mol. Biol.* 215:403-410 (1990). Software for performing BLAST analysis is publicly available through the National Center for Biotechnology Information. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (as described, for example, in Henikoff & Henikoff (1989) *Proc. Natl. Acad. Sci. USA*, 89:10915). In addition to calculating percent sequence identity, the BLAST algorithm also can perform a statistical analysis of the similarity between two sequences (for example, as described in Karlin & Altschul, *Proc. Nat'l. Acad. Sci. USA*, 90:5873-5787 (1993)). One measure of similarity provided by the BLAST algorithm is she smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

Fatty Acids and Glycerol Lipids

The present disclosure describes host cells capable of making polypeptides that contribute to the production, accumulation, and/or secretion of fatty acids, glycerol lipids, or oils, by transforming host cells (e.g., alga cells such as *C. reinhardtii, D. salina, H. pluvalis*, and cyanobacterial cells) with nucleic acids encoding one or more different proteins or enzymes. Examples of such enzymes include acetyl-CoA carboxylase, ketoreductase, thioesterase, malonyltransferase, dehydratase, acyl-CoA ligase, ketoacylsynthase, enoylreductase, and desaturase. The enzymes can be, for example, catabolic or biodegrading enzymes.

In some instances, the host cell will naturally produce the fatty acid, glycerol lipid, triglyceride, or oil of interest. Therefore, transformation of the host cell with a polynucleotide encoding a protein, for example a lipid trigger, will allow for the increased activity of the protein and/or increased production, accumulation, and/or secretion of a molecule of interest (e.g., a lipid) in the cell.

A change in the production, accumulation, and/or secretion of a desired product, for example, fatty acids, glycerol lipids, or oils, by a transformed host cell can include, for example, a change in the total oil content over that normally present in the cell, or a change in the type of oil that is normally present in the cell.

A change in the production, accumulation, and/or secretion of a desired product, for example, fatty acids, glycerol lipids, or oils, by a transformed host cell can include, for example, a change in the total lipid content over that normally present in the cell, or a change in the type of lipids that are normally present in the cell.

Increased malonyl CoA production is required for increased fatty acid biosynthesis. Increased fatty acid biosynthesis is required for increased accumulation of fatty acid based lipids. An increase in fatty acid based lipids can be measured by methyl tert-buryl ether (MTBE) extraction.

Some host cells may be transformed with multiple genes encoding one or more enzymes. For example, a single transformed cell may contain exogenous nucleic acids encoding enzymes that make up an entire glycerolipid synthesis pathway. One example of a pathway might include genes encoding an acetyl CoA carboxylase, a malonyltransferase, a ketoacylsynthase, and a thioesterase. Cells transformed with an entire pathway and/or enzymes extracted from those cells, can synthesize, for example, complete fatty acids or intermediates of the fatty acid synthesis pathway. Constructs may contain, for example, multiple copies of the same gene, multiple genes encoding the same enzyme from different organisms, and/or multiple genes with one or more mutations in the coding sequence(s).

The enzyme(s) produced by the modified cells may result in the production of fatty acids, glycerol lipids, triglycerides, or oils that may be collected from the cells and/or the surrounding environment (e.g., bioreactor or growth medium). In some embodiments, the collection of the fatty acids, glycerol lipids, triglycerides, or oils is performed after the product is secreted from the cell via a cell membrane transporter.

Examples of candidate *Chlamydomonas* genes encoding enzymes of glycerolipid metabolism that can be used in the described embodiments are described in The *Chlamydomonas* Sourcebook Second Edition, Organellar and Metabolic Processes, Vol. 2, pp. 41-68, David B. Stem (Ed.), (2009), Elsevier Academic Press.

For example, enzymes involved in plastid, mitochondrial, and cytosolic pathways, along with plastidic and cytosolic isoforms of fatty acid desaturases, and triglyceride synthesis enzymes are described (and their accession numbers provided). An exemplary chart of some of the genes described is provided below:

| | | |
|---|---|---|
| Acyl-ACP thioesterase | FAT1 | EDP08596 |
| Long-chain acyl-CoA synthetase | LCS1 | EDO96800 |
| CDP-DAG: Inositol phosphotransferase | PIS1 | EDP06395 |
| Acyl-CoA: Diacylglycerol acyltransferase | DGA1 | EDO96893 |
| Phospholipid: Diacylglycerol acyltransferase | LRO1 (LCA1) | EDP07444 |

Examples of the types of fatty acids and/or glycerol lipids that a host cell or organism can produce, are described below.

Lipids are abroad group of naturally occurring molecules which includes fats, waxes, sterols, fat-soluble vitamins (such as vitamins A, D, E and K), monoglycerides, diglycerides, phospholipids, and others. The main biological functions of lipids include energy storage, as structural components of cell membranes, and as important signaling molecules.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from, two distinct types of biochemical subunits or "building blocks": ketoacyl and isoprene groups. Lipids may be divided into eight categories: fatty acyls, glycerolipids, glycerophospholipids, sphingolipids, saccharolipids and polyketides (derived from condensation of ketoacyl subunits); and sterol lipids and prenol lipids (derived from condensation of isoprene subunits). For this disclosure, saccharolipids will not be discussed.

Fats are a subgroup of lipids called triglycerides. Lipids also encompass molecules such as fatty acids and their derivatives (including tri-, di-, and monoglycerides and phospholipids), as well as other sterol-containing metabolites such as cholesterol. Humans and other mammals use various biosynthetic pathways to both break down and synthesize lipids.

Fatty Acyls

Fatty acyls, a generic term for describing fatty acids, their conjugates and derivatives, are a diverse group of molecules synthesized by chain-elongation of an acetyl-CoA primer with malonyl-CoA or methylmalonyl-CoA groups in a process called fatty acid synthesis. A fatty acid is any of the aliphatic monocarboxylic acids that can be liberated by hydrolysis from naturally occurring fats and oils. They are made of a hydrocarbon chain that terminates with a carboxylic acid group; this arrangement confers the molecule with a polar, hydrophilic end, and a nonpolar, hydrophobic end that is insoluble in water. The fatty acid structure is one of the most fundamental categories of biological lipids, and is commonly used as a building block of more structurally complex lipids. The carbon chain, typically between four to 24 carbons long, may be saturated or unsaturated, and may be attached to functional groups containing oxygen, halogens, nitrogen and sulfur; branched fatty acids and hydroxyl fatty acids also occur, and very-long chain acids of over 30 carbons are found in waxes. Where a double bond exists, there is the possibility of either a cis or trans geometric isomerism, which significantly affects the molecule's molecular configuration. Cis-double bonds cause the fatty acid chain to bend, an effect that is more pronounced the more double bonds there are in a chain. This in turn plays an important role in the structure and function of cell membranes. Most naturally occurring fatty acids are of the cis configuration, although the trans form does exist in some natural and partially hydrogenated fats and oils.

Examples of biologically important fatty acids are the eicosanoids, derived primarily from arachidonic acid and eicosapentaenoic acid, which include prostaglandins, leukotrienes, and thromboxanes. Other major lipid classes in the fatty acid category are the fatty esters and fatty amides. Fatty esters include important biochemical intermediates such as wax esters, fatty acid thioester coenzyme A derivatives, fatty acid thioester ACP derivatives and fatty acid carnitines. The fatty amides include N-acyl ethanolamines.

Glycerolipids

Glycerolipids are composed mainly of mono-, di- and tri-substituted glycerols, the most well-known being the fatty acid esters of glycerol (triacylglycerols), also known as triglycerides. In these compounds, the three hydroxyl groups of glycerol are each esterified, usually by different fatty acids. Because they function as a food store, these lipids comprise the bulk of storage fat in animal tissues. The hydrolysis of the ester bonds of triacylglycerols and the release of glycerol and fatty acids from adipose tissue is called fat mobilization.

Additional subclasses of glycerolipids are represented by glycosylglycerols, which are characterized by the presence of one or more sugar residues attached to glycerol via a glycosidic linkage. An example of a structure in this category is the digalactosyldiacylglycerols found in plant membranes.

Exemplary *Chlamydomonas* glycerolipids include: DGDG, digalactosyldiacylglycerol; DGTS, diacylglyceryl-N,N,N-trimethylhomoserine; MGDG, monogalactosyldiacylglycerol; PtdEtn, phosphatidylethanolamine; PtdGro, phosphatidylglycerol; PtdIns, phosphatidylinositol; SQDG, sulfoquinovosyldiacylglycerol; and TAG, triacylglycerol.

Glycerophospholipids

Glycerophospholipids are any derivative of glycerophosphoric acid that, contains at least one O-acyl, O-alkyl, or O-alkenyl group attached to the glycerol residue. The common glycerophospholipids are named as derivatives of phosphatidic acid (phosphatidyl choline, phosphatidyl serine, and phosphatidyl ethanolamine).

Glycerophospholipids, also referred to as phospholipids, are ubiquitous in nature and are key components of the lipid bilayer of cells, as well as being involved in metabolism and cell signaling. Glycerophospholipids may be subdivided into distinct classes, based on the nature of the polar headgroup at the sn-3 position of the glycerol backbone in eukaryotes and eubacteria, or the sn-1 position in the case of archaebacteria.

Examples of glycerophospholipids found in biological membranes are phosphatidylcholine (also known as PC, GPCho or lecithin), phosphatidylethanolamine (PE or GPEtn) and phosphatidylserine (PS or GPSer). In addition to serving as a primary component of cellular membranes and binding sites for intra- and intercellular proteins, some glycerophospholipids in eukaryotic cells, such as phosphatidylinositols and phosphatidic acids are either precursors of, or are themselves, membrane-derived second messengers. Typically, one or both of these hydroxyl groups are acylated with long-chain fatty acids, but there are also alkyl-linked and 1Z-alkenyl-linked (plasmalogen) glycerophospholipids, as well as dialkylether variants in archaebacteria.

Sphingolipids

Sphingolipids are any of class of lipids containing the long-chain amino diol, sphingosine, or a closely related base (i.e. a sphingoid). A fatty acid is bound in an amide linkage to the amino group and the terminal hydroxyl may be linked to a number of residues such as a phosphate ester or a carbohydrate. The predominant base in animals is sphingosine while in plants it is phytosphingosine.

The main classes are: (1) phosphosphigolipids (also known as sphingophospholipids), of which the main representative is sphingomyelin; and (2) glycosphingolipids, which contain at least one monosaccharide and a sphingoid, and include the cerebrosides and gangliosides.

Sphingolipids play an important structural role in cell membranes and may be involved in the regulation of protein kinase C.

As mentioned above, sphingolipids are a complex family of compounds that share a common structural feature, a sphingoid base backbone, and are synthesized de novo from the amino acid serine and a long-chain fatty acyl CoA, that are then converted into ceramides, phosphosphingolipids, glycosphingolipids and other compounds. The major sphingoid base of mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms.

The major phosphosphingolipids of mammals are sphingomyelins (ceramide phosphocholines), whereas insects contain mainly ceramide phosphoethanolamines, and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol Lipids

Sterol lipids, such as cholesterol and its derivatives, are an important component of membrane lipids, along with. The glycerophospholipids and sphingomyelins. The steroids, all derived from the same fused four-ring core structure, have different biological roles as hormones and signaling molecules. The eighteen-carbon. (C18) steroids include the estrogen family whereas the C19 steroids comprise the androgens such as testosterone and androsterone. The C21 subclass includes the progestogens as well as the glucocorticoids and mineralocorticoids. The secosteroids, comprising various forms of vitamin D, are characterized by cleavage of the B ring of the core structure. Other examples of sterols are the bile acids and their conjugates, which in mammals are oxidized derivatives of cholesterol and are synthesized in the liver. The plant equivalents are the phytosterols, such, as β-sitosterol, stigmasterol, and brassicasterol; the latter compound is also used as a biomarker for algal growth. The predominant sterol in fungal cell membranes is ergosterol.

Prenol Lipids

Prenol lipids are synthesized from, the 5-carbon precursors isopentenyl diphosphate and dimethylallyl diphosphate that are produced mainly via the mevalonic acid (MVA) pathway. The simple isoprenoids (for example, linear alcohols and diphosphates) are formed by the successive addition of C5 units, and are classified according to the number of these terpene units. Structures containing greater than 40 carbons are known as polyterpenes. Carotenoids are important simple isoprenoids that function as antioxidants and as precursors of vitamin A. Another biologically important class of molecules is exemplified by the quinones and hydroquinones, which contain an isoprenoid tail attached to a quinonoid core of non-isoprenoid origin. Prokaryotes synthesize polyprenols (called bactoprenols) in which the terminal isoprenoid unit attached to oxygen remains unsaturated, whereas in animal polyprenols (dolichols) the terminal isoprenoid is reduced.

Polyketides

Polyketides or sometimes acetogenin are any of a diverse group of natural products synthesized via linear poly-β-ketones, which are themselves formed by repetitive head-to-tail addition of acetyl (or substituted acetyl) units indirectly derived from acetate (or a substituted acetate) by a mechanism similar to that for fatty-acid biosynthesis but without the intermediate reductive steps. In many case, acetyl-CoA functions as the starter unit and malonyl-CoA as the extending unit. Various molecules other than acetyl-CoA may be used as starter, often with methoylmalonyl-CoA as the extending unit. The poly-β-ketones so formed may undergo a variety of further types of reactions, which include alkylation, cyclization, glycosylation, oxidation, and reduction. The classes of product formed—and their corresponding starter substances—comprise inter alia: coniine (of hemlock) and orsellinate (of lichens)—acetyl-CoA; flavanoids and stilbenes—cinnamoyl-CoA; tetracyclines—amide of malonyl-CoA; urushiols (of poison ivy)—palmitoleoyl-CoA; and erythonolides—propionyl-CoA and methyl-malonyl-CoA as extender.

Polyketides comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, and/or other processes. Many commonly used anti-microbial, anti-parasitic, and anti-cancer agents are polyketides or polyketide derivatives, such as erythromycins, tetracyclines, avermectins, and antitumor epothilones.

The following examples are intended to provide illustrations of the application of the present disclosure. The following examples are not intended to completely define or otherwise limit the scope of the disclosure.

One of skill in the art will appreciate that many other methods known in the art may be substituted in lieu of the ones specifically described or referenced herein.

EXAMPLES

Example 1

Nitrogen, Starvation Phenotypes in Wild Type Algae

Figure 8A:
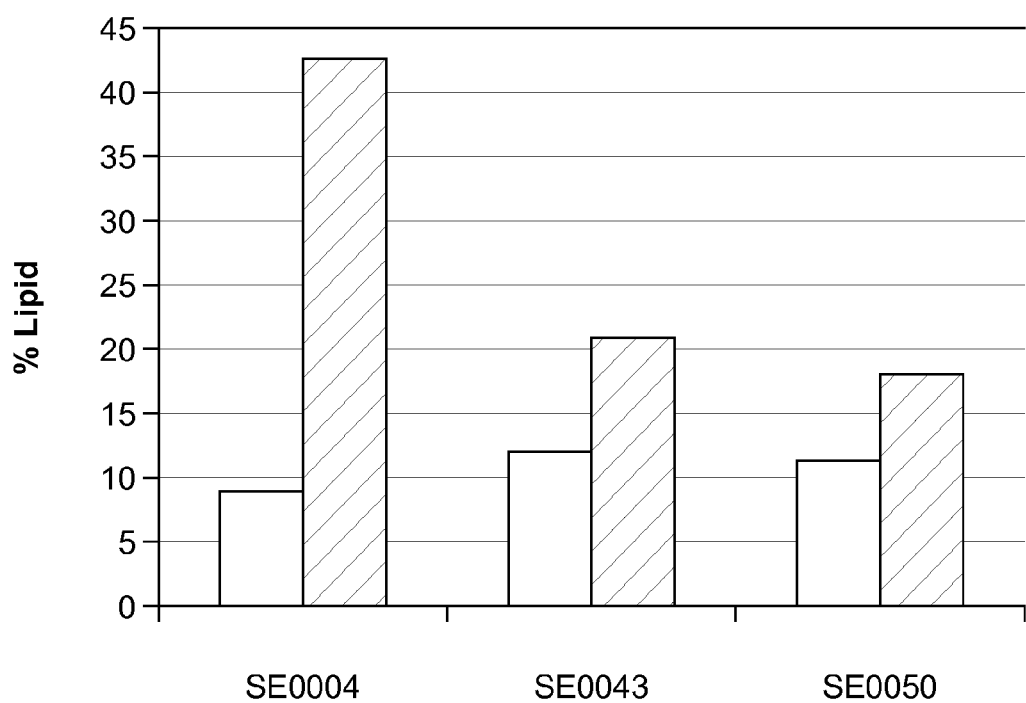
FIGS. 8A, 8B, 8C, and 8D show typical nitrogen stress phenotypes.
Figure 8B:
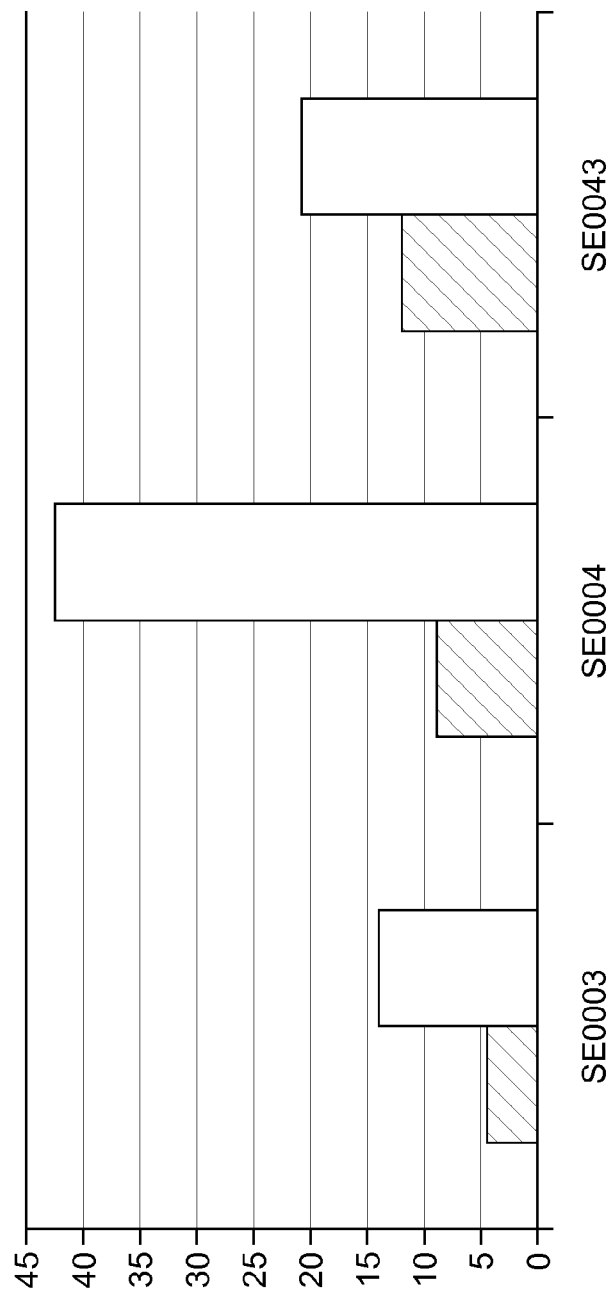
Figure 8C:
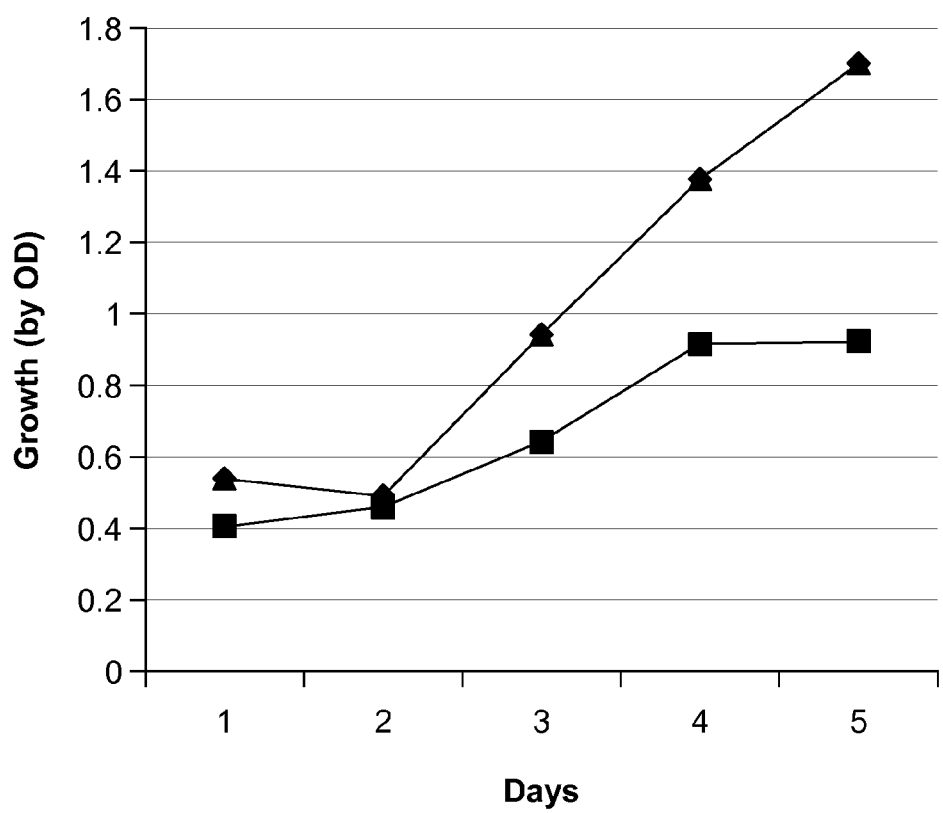
Figure 8D:
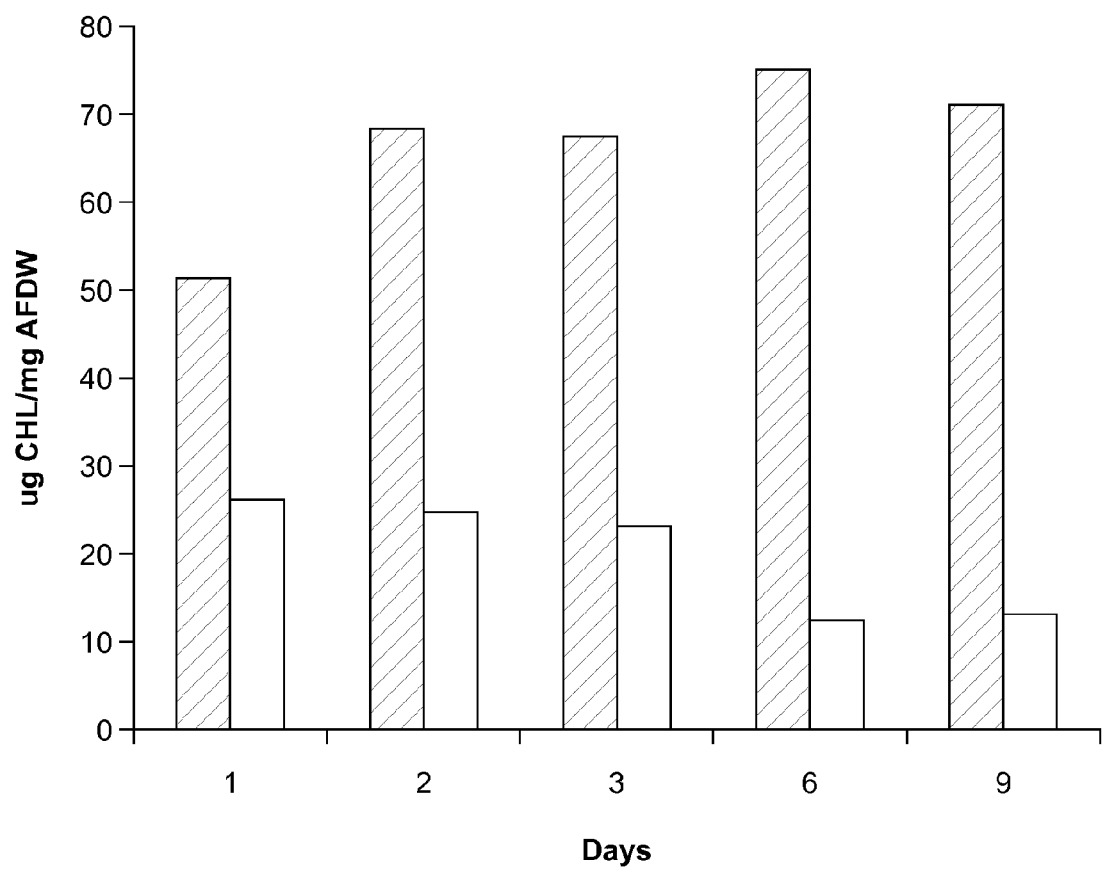
Figure 41A:
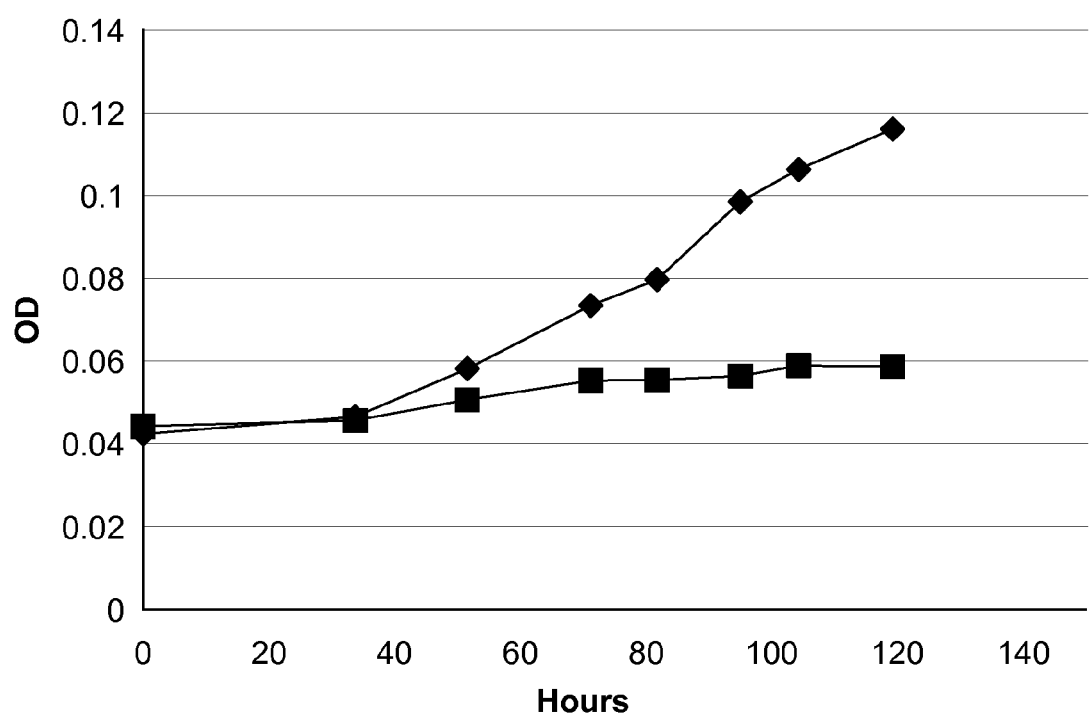
FIG. 41A shows growth of wild-type *Nannochloropsis salina* in modified artificial sea water media (MASM) media in the presence and absence of nitrogen. The diamonds represent growth in the presence of nitrogen and squares represent growth in the absence of nitrogen.
Figure 41B:
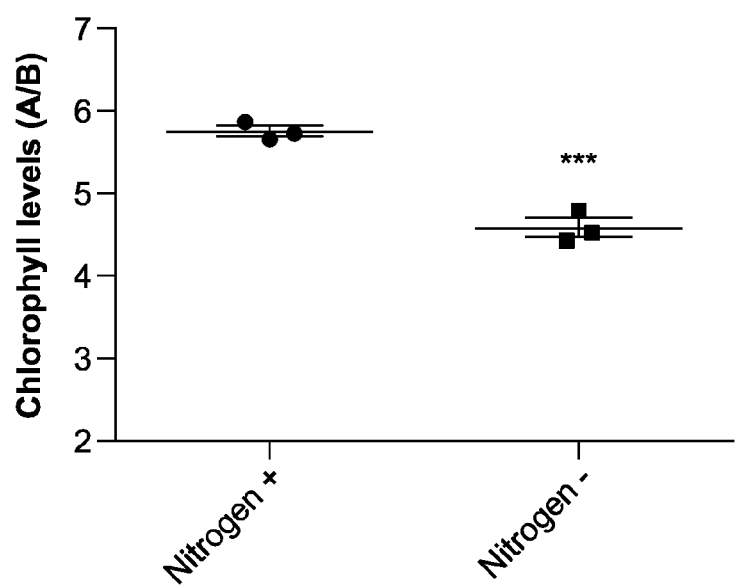
FIG. 41B shows chlorophyll levels of wild-type *Nannochloropsis salina* in modified artificial sea water media (MASM) media in the presence and absence of nitrogen.
Figure 41C:
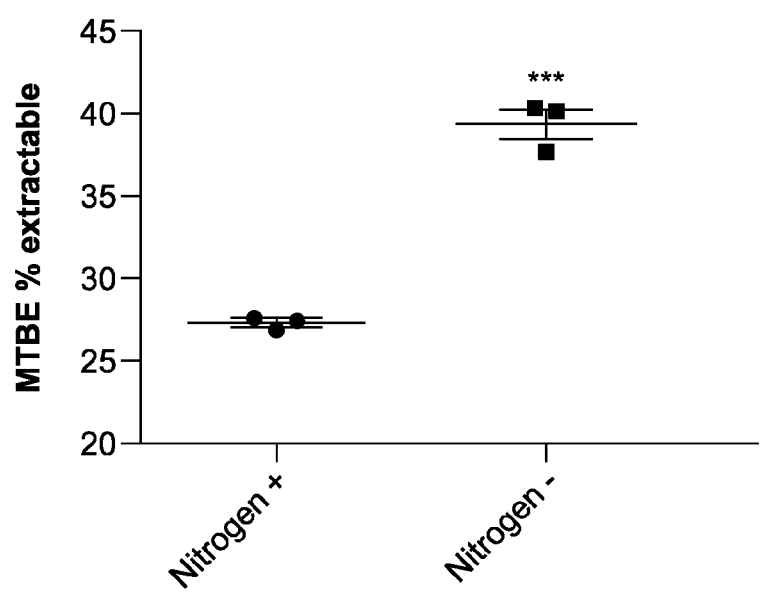
FIG. 41C shows MTBE extraction of wild-type *Nannochloropsis salina* in MASM media in the presence and absence of nitrogen.
Figure 41D:
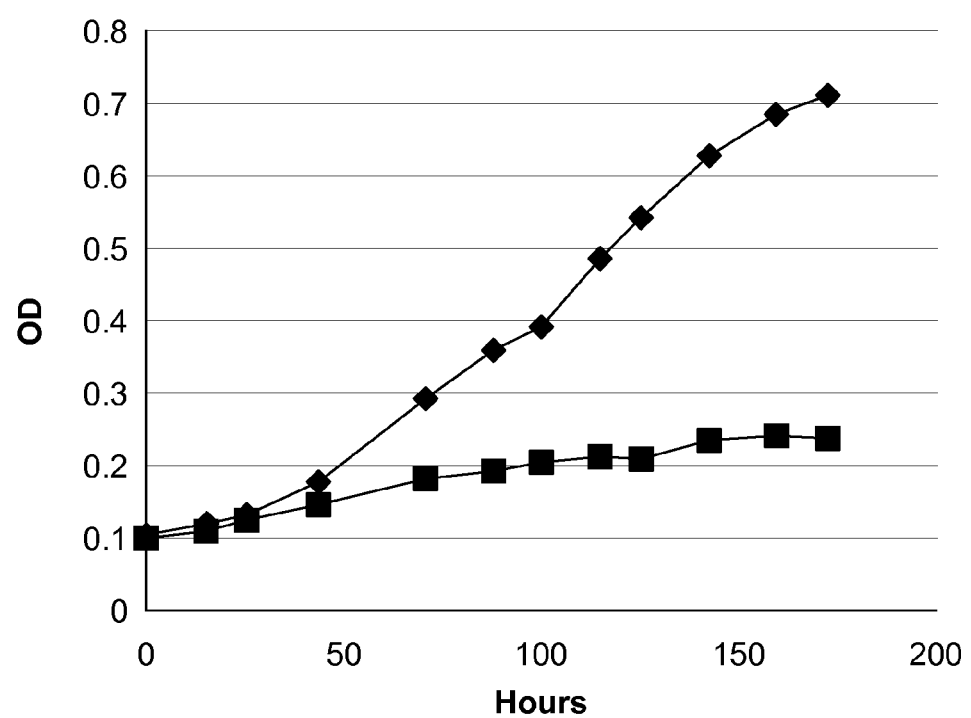
FIG. 41D shows growth of wild-type *Scenedesmus dimorphus* in HSM media in the presence and absence of nitrogen. The diamonds represent growth in the presence of nitrogen and squares represent growth in the absence of nitrogen.
Figure 41E:
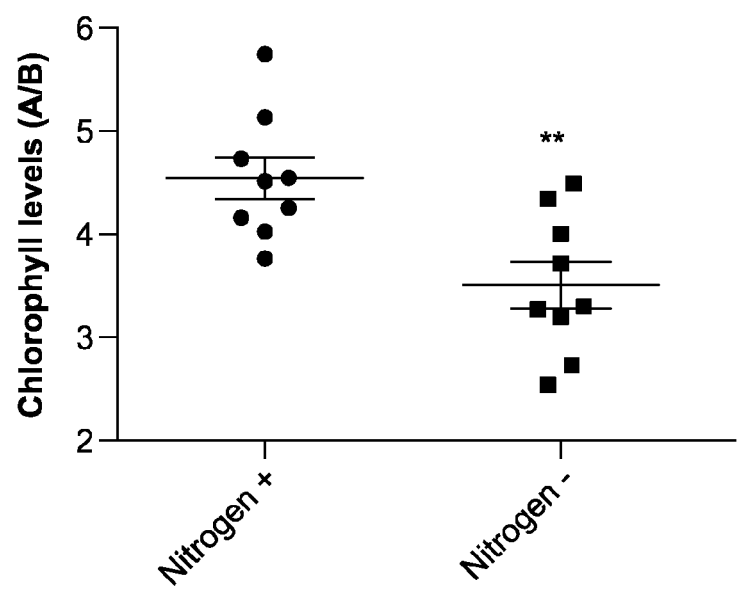
FIG. 41E shows chlorophyll levels of wild-type *Scenedesmus dimorphus* in HSM media in the presence and absence of nitrogen.

Nitrogen starvation in many wild type algae species (for example, *Dunaliella salina, Scenedesmus dimorphus, Dunaliella viridis, Chlamydomonas reinhardtii* and *Nannochloropsis salina*) is known to cause several phenotypes, among them an increase in total lipids (FIGS. 8A and 8B, FIG. 41C), reduced growth (FIG. 8C, FIGS. 41A and 41D), and a breakdown of chlorophyll (FIG. 8D and FIGS. 41B and 41E). It would be desirable to separate these phenotypic pathways at the molecular level. For example, it would be desirable to obtain an increased lipid phenotype that does not have decreased growth and the breakdown of algal components.

FIG. 8A shows gravimatric fats analyses (hexane extractables). The left hand column of each group of two is percent lipids by hexane extractable (% DW) after growth in minimal media containing 7.5 mM $NH_4Cl$, and the right hand column of each group of two is percent lipids by hexane extractable (% DW) after growth in minimal media in the absence of nitrogen. Three different strains are identified: SE0004 (*Scenedesmus dimorphus*), SE0043 (*Dunaliella viridis*) and SE0050 (*Chlamydomas reinhardtii*). These strains represent three different orders of the Class Chlorophyceae.

FIG. 8B shows gravimatric fats analyses (hexane extractables). The left hand column of each group of two is percent lipids by hexane extractable (% DW) after growth in minimal media containing 7.5 mM $NH_4Cl$, and the right hand column of each group of two is percent lipids by hexane extractable (% DW) after growth in minimal media in the absence of nitrogen. Three different strains are identified: SE0003 (*Dunaliella salina*), SE0004 (*Scenedesmus dimorphus*) and SE0043 (*Dunaliella viridis*). These strains represent three different orders of the Class Chlorophyceae.

FIG. 41C shows extractable lipid in algae grown under nitrogen stress. Wild type *Nannochloropsis salina* was grown in MASM containing 11.8 mM $NaNO_3$, 0.5 mM $NH_4Cl$ and 16 ppt NaCl in a 5% carbon dioxide in an air environment under constant light to early log phase. 2-3 L of the culture was centrifuged at 3000 to 5000×g for 5-10 minutes and one half of the culture was washed with 300-500 mL MASM, the other half with 300-500 mL MASM containing no nitrogen. After re-centrifigation, the two cultures were resuspended in a volume of media (MASM or MASM containing no nitrogen) equivalent to the starting culture volume. After two days, samples were collected and centrifuged. The cells were analyzed for total gravimetric lipids by methanol/methyl-tert-butyl ether extraction according to a modified Bligh Dyer method (as described in Matyash V., et al. (2008) journal of Lipid Research 49:1137-1146). The percent extractable is shown on the y axis and the sample in the presence and absence of nitrogen are indicated on the x axis.

FIG. 8C shows algal growth under nitrogen stress. *Chlamydomonas reinhardtii* wild type was grown in 50-100 mL HSM containing 7.5 mM $NH_4Cl$ in a 5% carbon dioxide in an air environment under constant light to early log phase.

The culture was centrifuged at 3000 to 5000×g for 5-10 minutes and one half of the culture was washed with 20-50 mL of HSM, the other half with 20-50 mL HSM containing no nitrogen. After re-centrifigation, the two cultures were resuspended in a volume of media (HSM or HSM containing no nitrogen) equivalent to the starting culture volume. This point was recorded as day 0. Optical density (OD) as 750 nm was taken each day over a time course of 5 days and is shown on the y axis. The x-axis represents the time course of nitrogen starvation over 5 days. The triangle represents growth in the presence of nitrogen and the square represents growth in the absence of nitrogen.

FIG. 41A shows growth of *Nannochloropsis salina* under nitrogen stress. Wild type *Nannochloropsis salina* was grown in 50-100 ml. of MASM containing 11.8 mM NaNO3, 0.5 mM NH$_4$Cl and 16 ppt NaCl in a 5% carbon dioxide in an air environment under constant light. To early log phase. The culture was centrifuged at 3000 to 5000×g for 5-10 minutes and one half of the culture was washed with 20-50 mL of MASM, the other half with 20-50 mL of MASM containing no nitrogen. After re-centrifigation, the two cultures were resuspended in a volume of media (MASM or MASM containing no nitrogen) equivalent to the starting culture volume. This point was recorded as time 0, Optical density (OD) as 750 nm was taken each day over a time course of 120 hours and is shown on the y axis. The x-axis represents the time course of nitrogen starvation over 5 days. The diamond represents growth in the presence of nitrogen and the square represents growth in the absence of nitrogen.

FIG. 41D shows growth of *Scenedesmus dimorphus* under nitrogen stress. Wild type *Scenedesmus dimorphus* was grown in 50-100 mL of HSM containing 7.5 mM NH$_4$Cl in a 5% carbon dioxide in an air environment under constant light to early log phase. The culture was centrifuged at 3000 to 5000×g for 5-10 minutes and one half of the culture was washed with 30-50 mL of HSM, the other half with 20-50 mL of HSM containing no nitrogen. After re-centrifigation, the two cultures were resuspended in a volume of media (HSM or HSM containing no nitrogen) equivalent to the starting culture volume. This point was recorded as time 0. Optical density (OD) as 750 nm was taken 1-2 times a day over a time course of 180 hours and is shown on the y axis. The x-axis represents the time course of nitrogen starvation over 7.5 days. The diamond represents growth in the presence of nitrogen and the square represents growth in the absence of nitrogen.

FIG. 8D shows chlorophyll (μg chlorophyll/mg ash free dry weight (AFDW)) under nitrogen stress. *Chlamydomonas reinhardtii* wild type was grown in 50-100 mL HSM containing 7.5 mM NH4Cl in a 5% carbon dioxide in an air environment under constant light to early log phase. The culture was centrifuged at 3000 to 5000×g for 5-10 minutes and one half of the culture was washed with 20-50 mL HSM, the other half with 20-50 mL HSM containing no nitrogen. After re-centrifigation, the two cultures were resuspended in a volume of media (HSM or HSM containing no nitrogen) equivalent to the starting culture volume. This point was recorded as day 0. Samples were collected and centrifuged. Cells were extracted in methanol and chlorophyll levels were determined spectroscopically as described in (LICHTENTHALER. Chlorophylls and Carotenoids: Pigments of Photosynthetic Biomembranes. Meth Enzymol (1987) vol. 148 pp. 350-382). Optical density (OD) of the culture at 750 nm was used to normalize to cell density and to approximate AFDW. Measurements were taken over a time course of 9 days. The left hand column of each group of two is chlorophyll content in the presence of nitrogen and the right hand column of each group of two is chlorophyll content in the absence of nitrogen.

FIG. 41B shows chlorophyll levels under nitrogen stress. Wild type *Nannochloropsis salina* was grown in 50-100 mL of MASM containing 11.8 mM NaNO3, 0.5 mM NH$_4$Cl and 16 ppt NaCl in a 5% carbon dioxide in an air environment under constant light to early log phase. The culture was centrifuged at 3000 to 5000×g for 5-10 minutes and one half of the culture was washed with 20-50 mL MASM, the other half with 20-50 mL MASM containing no nitrogen. After re-centrifigation, the two cultures were resuspended in a volume of media (MASM or MASM containing no nitrogen) equivalent to the starting culture volume. After two days, samples were collected and centrifuged. Cells were extracted in methanol and chlorophyll levels we determined spectroscopicaily as described in (LICHTENTHALER. Chlorophylls and Carotenoids: Pigments of Photosynthetic Biomembranes. Meth. Enzymol. (1987) vol. 148 pp. 350-382). Calculations of chlorophyll A and chlorophyll B were added and optical density (OD) of the culture at 750 nm was used to normalize to cell density. This value is plotted on the y axis and the sample in the presence and absence of nitrogen are indicated on the x axis.

FIG. 41E shows chlorophyll levels under nitrogen stress. Wild type *Scenedesmus dimorphus* was grown in 50-100 mL of HSM containing 7.5 mM NH$_4$Cl in a 5% carbon dioxide in an air environment under constant light to early log phase. The culture was centrifuged at 3000 to 5000×g for 5-10 minutes and one half of the culture was washed with 20-50 mL HSM, the other half with 20-50 ml. HSM containing no nitrogen. After re-centrifigation, the two cultures were resuspended in a volume of media (HSM or HSM containing no nitrogen) equivalent to the starting culture volume. After two days, samples were collected and centrifuged. Cells were extracted in methanol and chlorophyll levels we determined spectroscopically as described in (LICHTENTHALER. Chlorophylls and Carotenoids: Pigments of Photosynthetic Biomembranes. Meth Enzymol (1987) vol. 148 pp. 350-382). Calculations of chlorophyll A and chlorophyll B were added and optical density (OD) of the culture at 750 nm was used to normalize to cell density. This value is plotted on the y axis and the sample in the presence and absence of nitrogen are indicated on the x axis.

Example 2

Timing of the Stress Response in Wild Type *Chlamydomonas reinhardtii* at the Biochemical and Molecular Level In this example, the timing of the biochemical and molecular responses of wild type *Chlamydomonas reinhardtii* was investigated. Wild-type *Chlamydomonas reinhardtii* cells were grown in 5-10 L of HSM media in a 5% carbon dioxide in an air environment under constant light, until cells reached early log phase. The culture was centrifuged at 3000 to 5000×g for 5-10 minutes and one half of the culture was washed with 500-1000 mL HSM, the other half with 500-1000 mL HSM containing no nitrogen. After re-centrifigation, the two cultures were resuspended in a volume of media (HSM or HSM containing no nitrogen) equivalent to the starting culture volume. At the time points listed in Table 2, 0.5-2 L of the cells were harvested by centrifugation and analyzed for total gravimetric lipids by the Bligh Dyer method (as described in BLIGH and DYER. A rapid method of total lipid extraction and purification. Can J Biochem Physiol (1959) vol. 37 (8) pp. 911-7). The percent extractables was calculated using the ash free dry weight of the sample.

Figure 9:
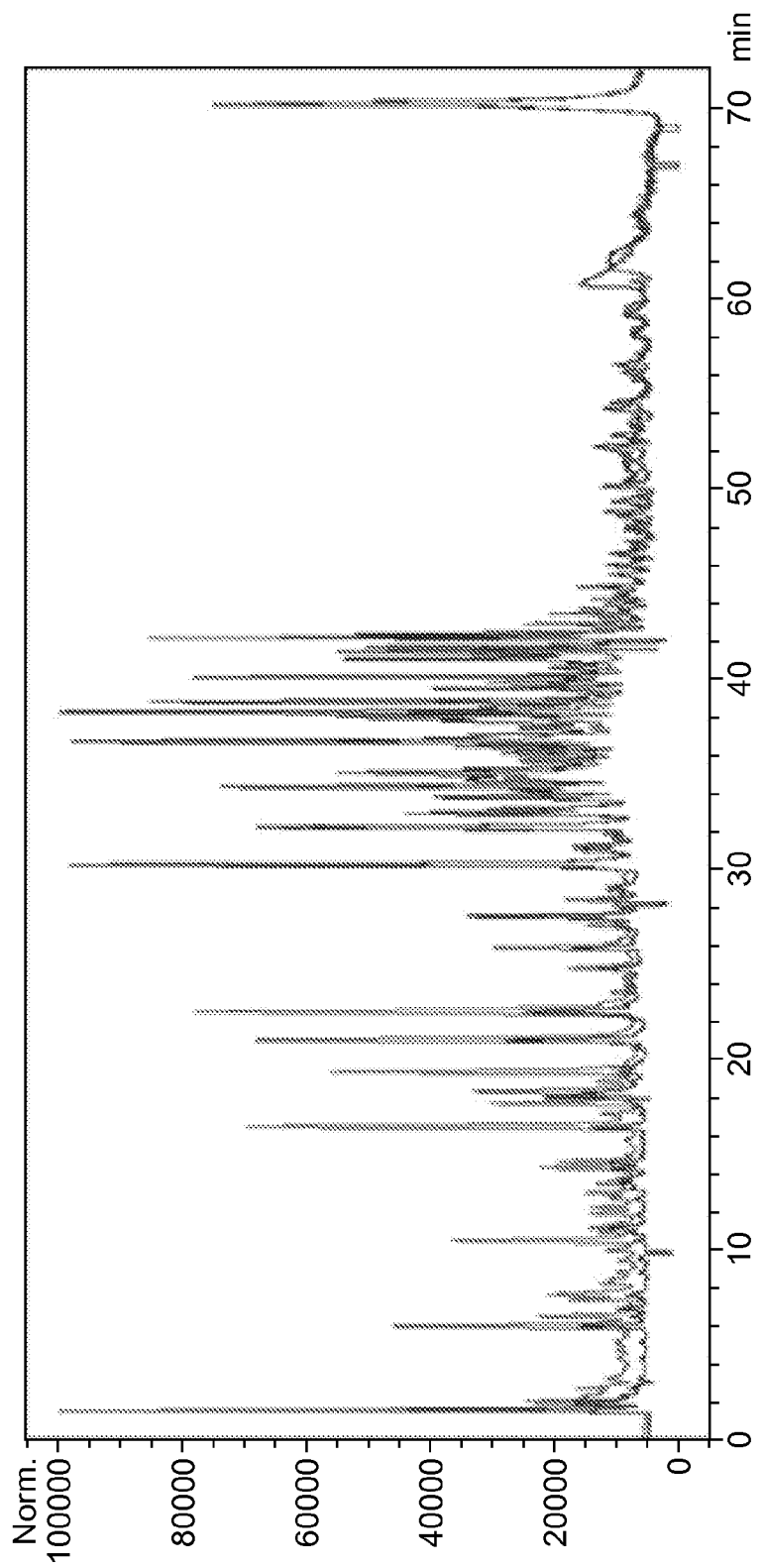
FIG. 9 shows total fat analysis via HPLC-CAD in the presence and absence of nitrogen (24 hour time point). No significant difference was observed in the two spectra after 24 hours in the absence of nitrogen.
Figure 10:
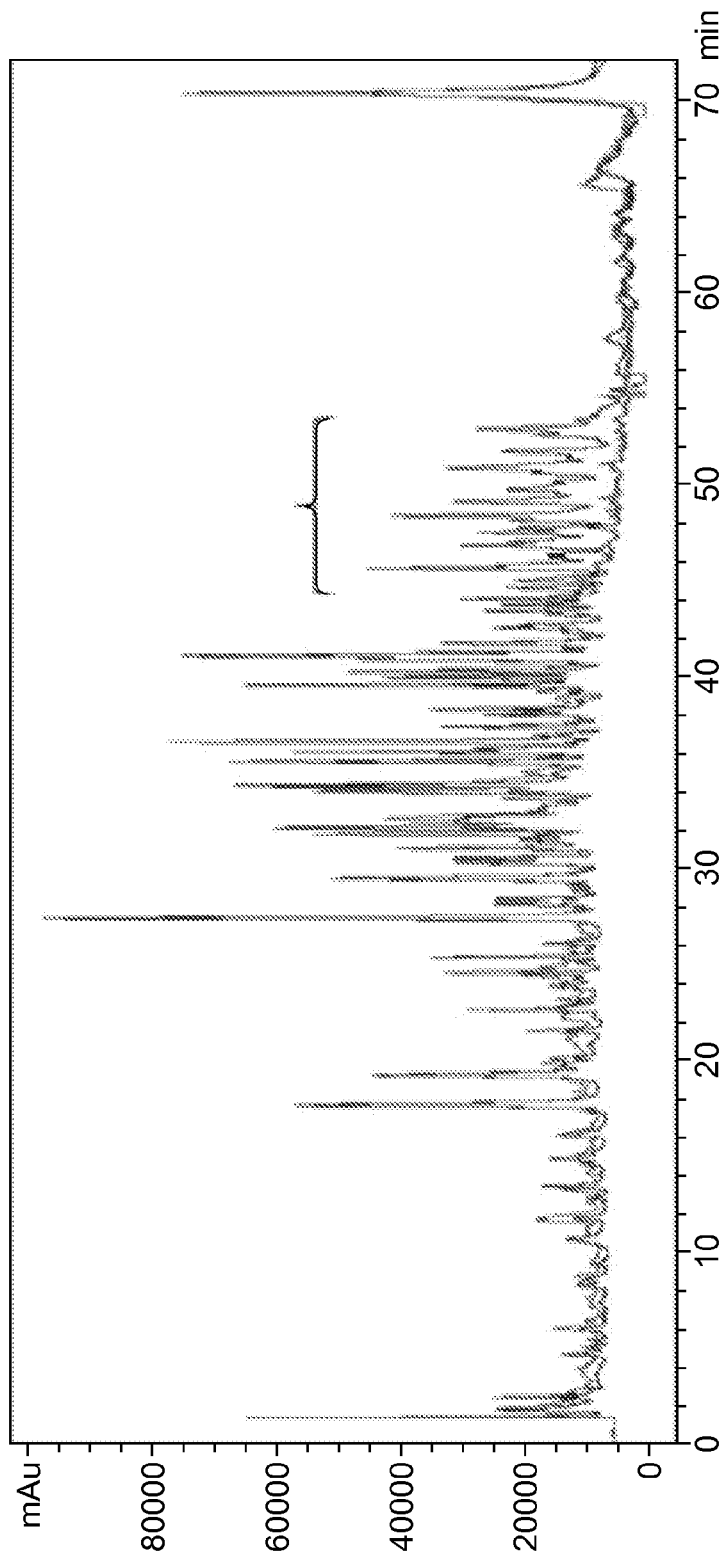
FIG. 10 shows total fat analysis via HPLC-CAD in the presence and absence of nitrogen (48 hour time point). There is an increase in neutral lipid (*) peaks (44 to 54 minute retention time) after 48 hours in the absence of nitrogen.

Bligh-Dyer extracted oils from SE0050 were run on reverse-phase HPLC on a C18 column. Mobile phase A was MeOH/water/HOAc (750:250:4). Mobile phase B was CAN/MeOH/THF/HOAc (500:375:125:4) with a gradient between A and B over 72 minutes and flow rate of 0.8 mL/min. Defection was via a Charged Aerosol Detector (CAD). Differences in the lipid phenotype of SE0050 were observed at 24 and 48 hours after nitrogen starvation. This assay is a qualitative assay for total lipid profile in nitrogen replete and nitrogen starved conditions. The y-axis is the CAD signal which represents abundance and the x axis is HPLC column retention time (in minutes). As shown in FIG. 9, some minor differences (in the lipid profile) are seen at the 24 hour time point. In contrast, a major shift: (as shown in FIG. 10) is seen 48 hours after the removal of nitrogen from the HSM media. TAGs are detected between 44 and 54 minutes retention time, demonstrating that there is a large increase in TAGs by 48 hours of nitrogen starvation. These differences indicate that the lipid phenotype is seen (in this strain under this starvation regime) between 24 and 48 hours after nitrogen starvation.

Figure 26:
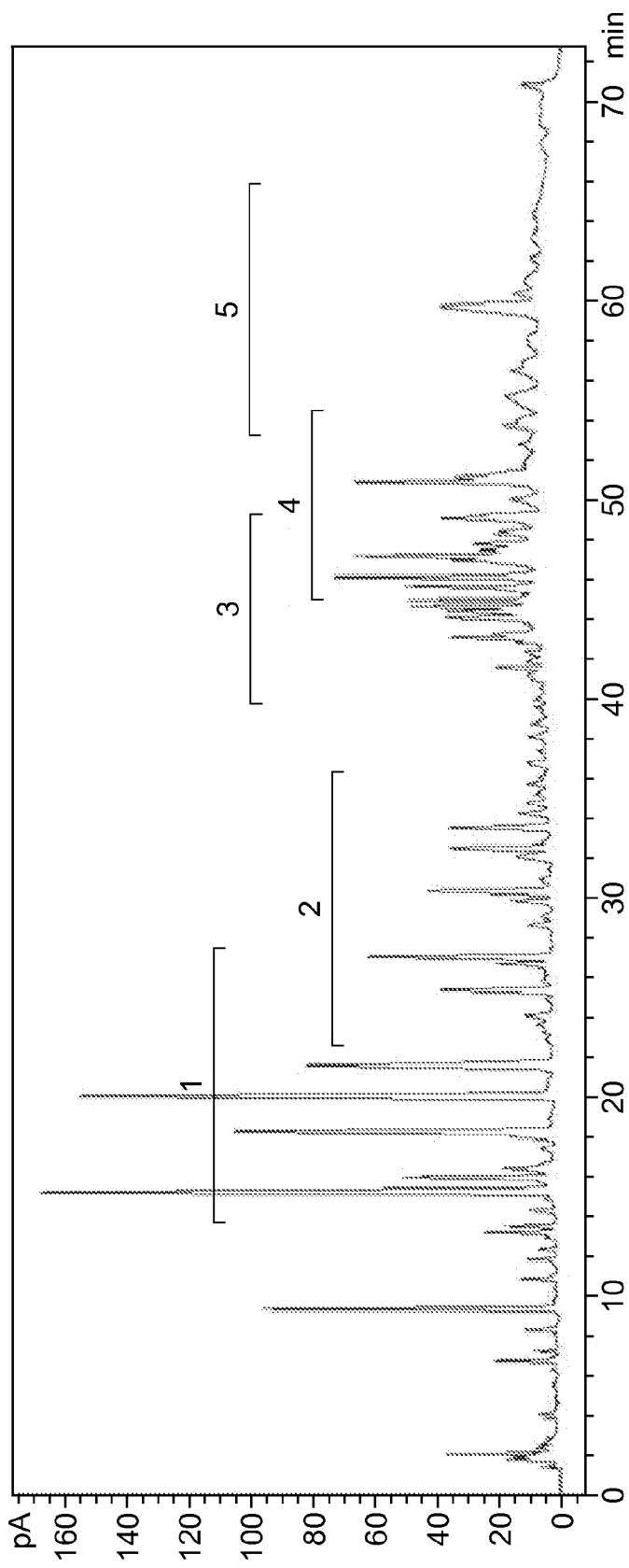
FIG. 26 shows a reference trace for hexane extracted total lipid for *Chlamydomonas reinhardtii* using HPLC and a charged Aerosol detector (CAD).

FIG. 26 shows a reference trace for an algal hexane extract on HPLC/CAD as produced by the CAD vendor (ESA—A Dionex Company). This reference was used to interpret the data in FIGS. 9 and 10. 1=free fatty acids; 2=fatty alcohols, 3=phospholipids, 4=diacylglycerides; and 5=triacylglycerides.

Figure 11:
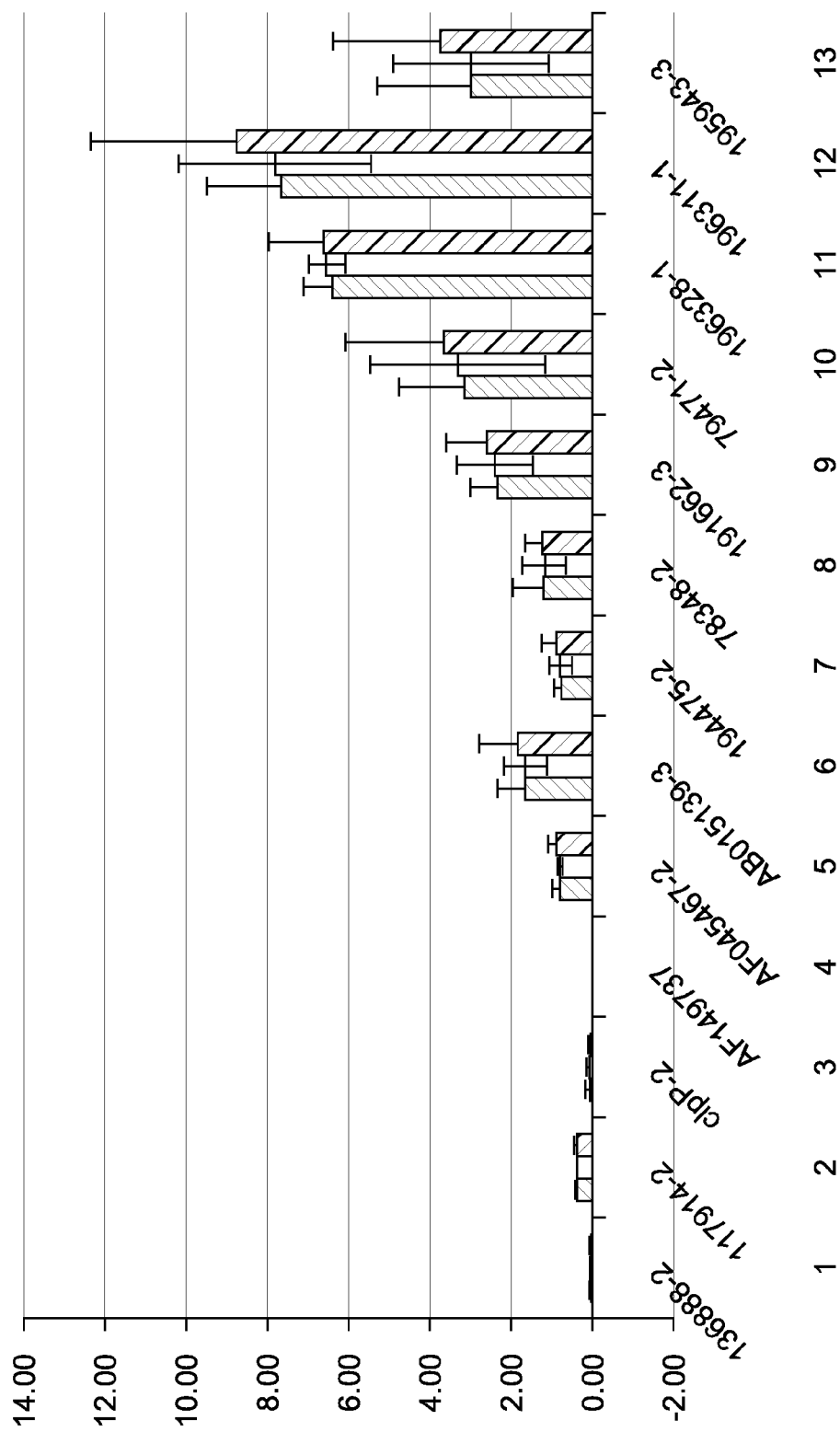
FIG. 11 shows up regulation of genes by qPCR in *Chlamydomonas reinhardtii* grown in TAP (Tris-acetate-phosphate) in the absence of nitrogen (24 hour time point).

A range finding experiment was performed at the molecular level using qPCR on nitrogen replete and nitrogen starved samples (24 hour time point shown in FIG. 11). This experiment was conducted in order to find the molecular cues involved in the nitrogen starvation, phenotypes. Target genes (listed along the X-axis and in Table 1) were selected based on expectations derived from the literature or pathways involved in nitrogen response. Wild-type *Chlamydomonas reinhardtii* cells were grown in 5-10 L of HSM media in a 5% carbon dioxide in an air environment under constant light, until cells reached early log phase. The culture was centrifuged at 3000 to 5000×g for 5-10 minutes and one half of the culture was washed with 500-1000 mL HSM, the other half with 500-1000 ml, HSM containing no nitrogen. After re-centrifugation, the two cultures were resuspended in a volume of media (HSM or HSM containing no nitrogen) equivalent to the starting culture volume. At the time points listed in Table 2, 50-100 mL of the cells were harvested by centrifugation and RNA was purified from the cultures. 0.25-1.0 ug of RNA was combined with 0.25 ug human brain RNA (Biochain, Hayward, Calif.) as normalization control and used for iScript cDNA synthesis (Bio-Rad, USA) and standard qPCR using iQ SybrGreen (Bio-Rad, USA) detection. Significant upregulation (as shown by fold upregulation on the Y-axis) of 5 genes is seen within 24 hours of nitrogen starvation (as shown in FIG. 11). Triplicate qPCR reactions were run versus three human brain control genes (control gene in left hand column is PGAM1 (UniGene Hs.632918), middle column is BASP1 (UniGene Hs.201641), and right hand column is SLC25A14 (UniGene Hs.194686)).

Figure 12:
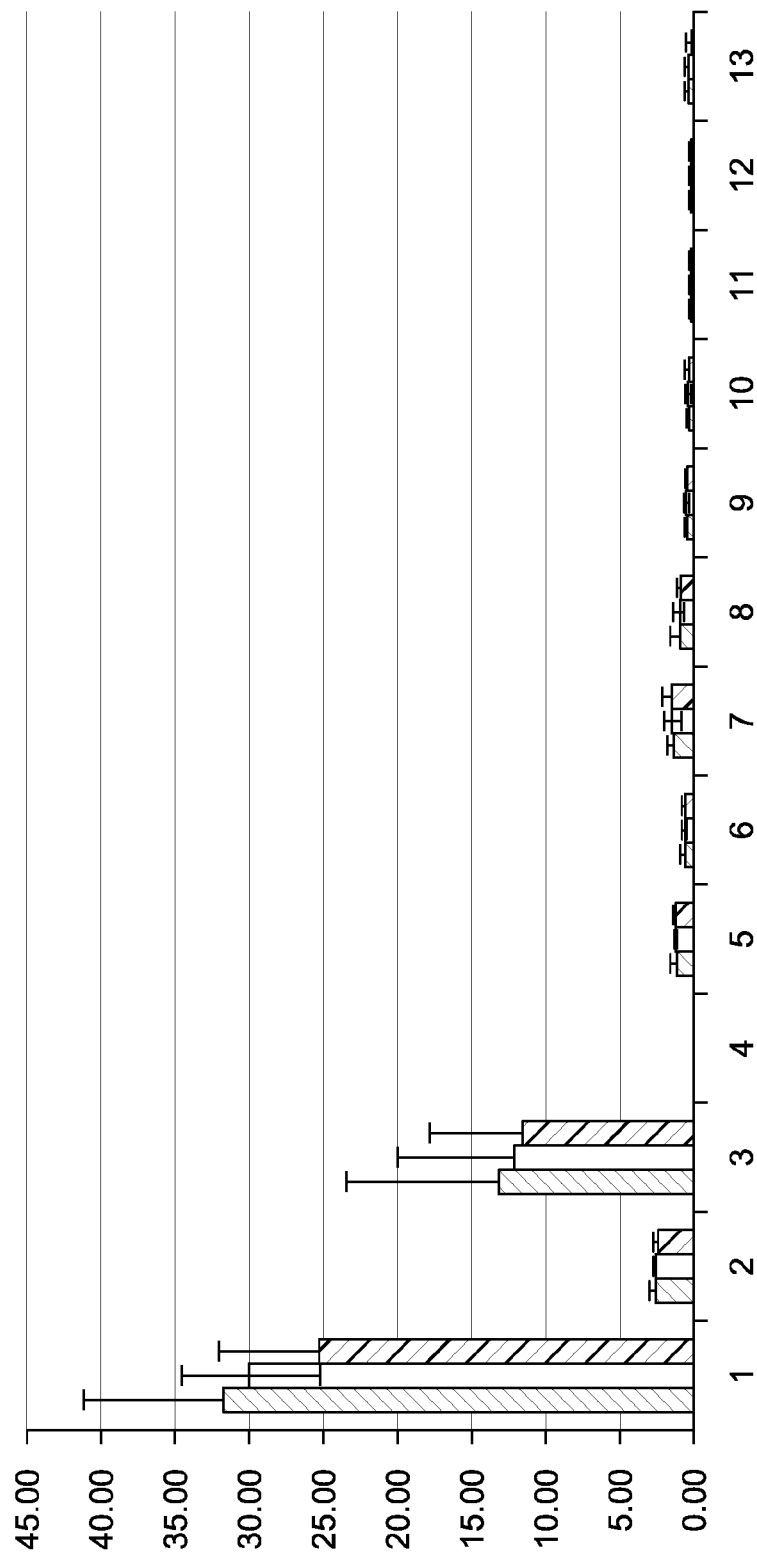
FIG. 12 shows down regulation of genes by qPCR in *Chlamydomonas reinhardtii* grown in TAP in the absence of nitrogen (24 hour time point).

FIG. 12 shows gene expression changes (fold down regulation) in the same set of genes in Table 1 after 24 hours of nitrogen starvation. FIG. 12 contains the same data as FIG. 11, with FIG. 12 showing up regulation and FIG. 11 showing down regulation. Significant downregulation (as shown by fold downregulation on the Y-axis) of 3 genes is seen within 24 hours of nitrogen starvation. Similar changes (up and down regulation) were also seen at the 6 hour time point. Triplicate qPCR reactions were run versus three control genes (control gene in left hand column is PGAM1 (UniGene Hs.632918), middle column is BASP1 (UniGene Hs.201641), and right hand column is SLC25A14 (UniGene Hs.194686)). These results indicate that molecular changes (as shown by qPCR in FIGS. 11 and 12) occur early and are seen prior to the lipid changes seen at 48 hours (as shown in FIGS. 9 and 10)

A key for the target genes used in the qPCR data shown in FIGS. 11 and 12 is provided below in Table 1, The below-listed genes are known *Chlamydomonas reinhardtii* genes. The first column indicates the fold up or down regulation at 24 hours. The second column indicates the fold up or down regulated at 48 hours. In the first and second columns, down regulation is indicated by (−) following the number and up regulation is indicated by (+) following the number.

These experiments show that the lipid accumulation and profile changes induced by nitrogen starvation begin primarily between 24 and 48 hours. The molecular changes (i.e. RNA expression) that are associated with nitrogen starvation begin earlier, with RNA expression level changes as early as 6 hours after nitrogen starvation.

TABLE 1

| 24 H | 48 H | # on x-axis | Gene |
|---|---|---|---|
| 29.0 (−) | 19.1 (−) | (1) 136888-2 | Glutamate synthase, NADH-dependent |
|  |  | (2) 117914-2 | Heat shock transcription factor 1 |
| 12.3 (−) | 2.5 (−) | (3) clpP-2 | L28803.1|CRECLPP *Chlamydomonas reinhardtii* chloroplast Clp protease (clpP) gene |
| 4000 (−) | 4000 (−) | (4) AF149737 | *Chlamydomonas reinhardtii* nitrite transporter NAR1 |
|  |  | (5) AF045467-2 | *Chlamydomonas reinhardtii* Ac115p (AC115) nuclear gene encoding chloroplast protein |
| 1.7 (+) | 8.9 (+) | (6) AB015139-3 | *Chlamydomonas reinhardtii* mRNA for chlorophyll a oxygenase |
| 0.8 (+) | 25.0 (+) | (7) 194475-2 | Porphobilinogen deaminase |
|  |  | (8) 78348-2 | beta subunit of mitochondrial ATP synthase |
|  |  | (9) 191662-3 | soluble starch synthase III |
| 3.4 (+) | 2.6 (+) | (10) 79471-2 | 2-oxoglutarate dehydrogenase, E1 subunit |
| 6.5 (+) | 9.5 (+) | (11) 196328-1 | malate synthase |
| 8.1 (+) | 7.5 (+) | (12) 196311-1 | Acetyl CoA synthetase |
| 3.3 (+) | 5.9 (+) | (13) 195943-3 | Uroporphyrinogen-III synthase |

Example 3

RNA-Seq Transcriptomic Method

In this example, an exemplary method used to identify the gene encoding SN03 is described. The method described herein can be used to identify other proteins, polypeptides, or transcription factors, for example, those involved in the regulation or control of different nitrogen deficient phenotypes found in an organism, for example, an alga. Such nitrogen deficient phenotypes include, for example, increased lipid production and/or accumulation, breakdown of photosystem, decreased growth, and mating induction.

Figure 13:
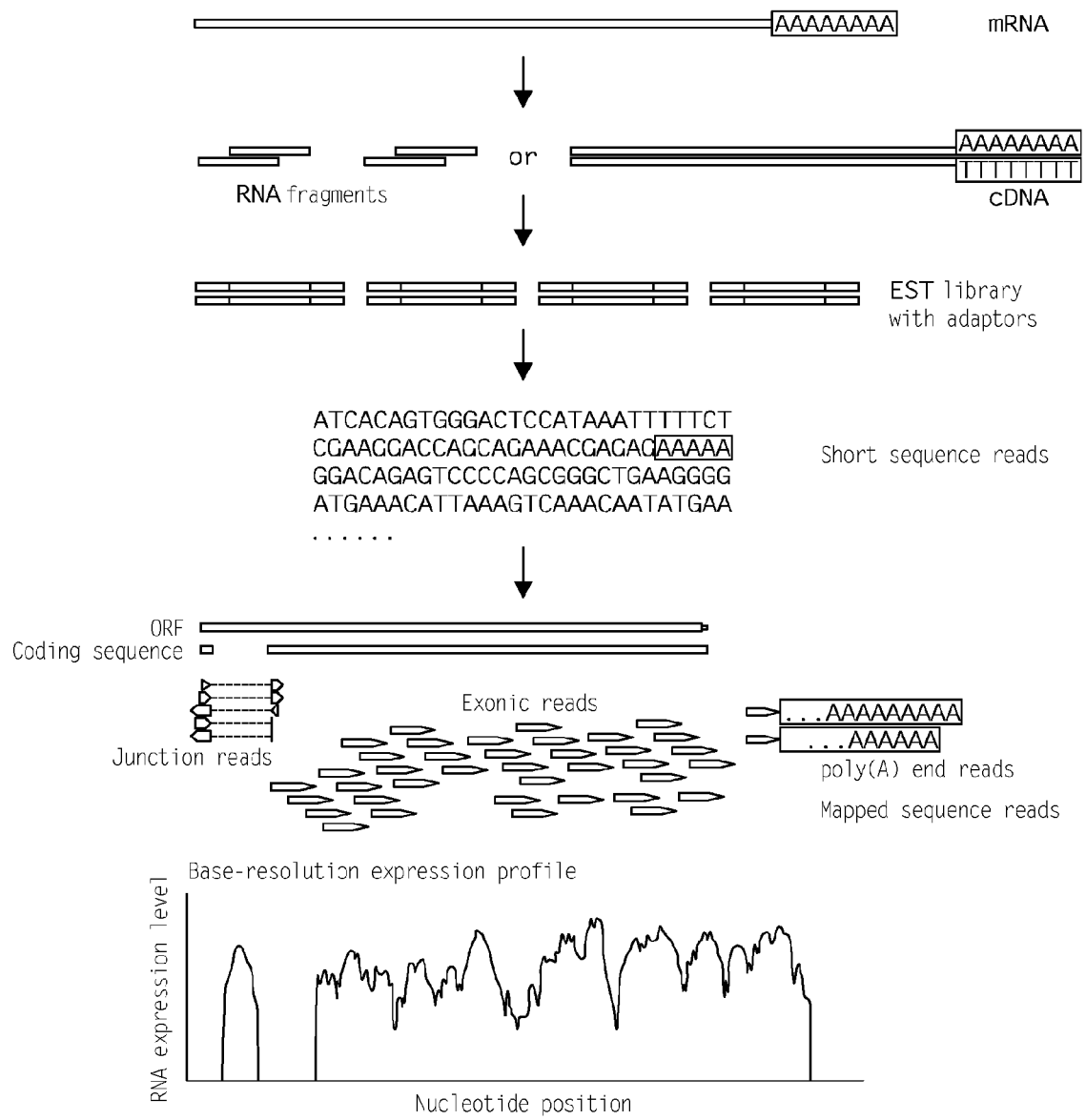
FIG. 13 describes the RNA-Seq transcriptomic method. An example of a short sequence read that can be obtained from the described method is "ATCACAGTGGGACTC-CATAAATTTTTCTCGAAGGACCAGCAGAAACGA-GAGAAAAAGGACAGAGTCCCCAGCGGGCT-GAAGGGGATGAAACATTAAAGTCAAACAATATGA A" (SEQ ID NO: 62).

In order to identify genes/proteins involved in the nitrogen starvation induced lipid phenotype, the RNA-Seq transcriptomic method (FIG. 13; Wang, et al., Nat. Rev. Genet. (2009) vol. 10 (1) pp. 57-63) was used to determine expression levels of all genes in algae grown under six different conditions (listed in Table 2). These conditions were established based on the range finding experiments described in FIGS. 9, 10, 11 and 12. The RNA-Seq transcriptomic method is described below.

Briefly, mRNAs are first converted into a library of cDNA fragments through either RNA fragmentation or DNA fragmentation (see FIG. 13). Sequencing adaptors are subsequently added to each cDNA fragment (EST library with adapters) and a short sequence read is obtained from each cDNA fragment using high-throughput sequencing technology (Solexa). The resulting sequence reads are aligned with the reference transcriptome, and can be classified as three types: exonic reads, junction reads and poly(A) end-reads. These alignments are used to generate an expression profile for each gene, as illustrated at the bottom of FIG. 13; a yeast ORF with one intron is shown.

SE0050 RNA from six different conditions (exponential growth: +nitrogen; exponential growth: 6 hours –nitrogen; exponential, growth: 24 hours –nitrogen; exponential growth: 48 hours –nitrogen; stationary phase: +nitrogen; and stationary phase: –nitrogen (approximately 11 days)) was prepared. Wild-type *Chlamydomonas reinhardtii* cells were grown in 5-10 L of HSM media in a 5% carbon dioxide in an air environment under constant light, until cells reached early log phase. The culture was centrifuged at 3000 to 5000×g for 5-10 minutes and one half of the culture was washed with 500-1000 mL HSM, the other half with 500-1000 ml, HSM containing no nitrogen. After re-centrifigation, the two cultures were resuspended in a volume of media (HSM or HSM containing no nitrogen) equivalent to the starting culture volume. At the time points listed in Table 2, 50-100 mL of the cells were harvested by centrifugation and RNA was purified from the cultures. This RNA was sequenced using standard Solexa methodologies (Sequensys, Inc, La Jolla, Calif.) for use in the RNA-Seq analysis method. Between 3.8 million to 17.8 million 36-mer reads were generated per sample (see Table 2).

This RNA-Seq transcriptomic data was mapped against version 3.0 of the Department of Energy (DOE) Joint Genome Institute's (JGI) *Chlamydomonas reinhardtii* genome using Arraystar software (DNASTAR, USA). The set of genes used for the mapping included 16,824 annotated nuclear genes. JGI's functional annotations (version 3.0) were also used and imported into the Arraystar software. Most of these annotations are based on prediction algorithms and do not have supporting experimental evidence. A small fraction have supporting experimental evidence. Approximately 7,500 have functional annotations of some kind. The JGI functional annotations used included KOG (clusters of orthologous genes), EC (Enzyme Commission numeric assignments), and GO (Gene Ontology).

SE0050 Solexa data mapped to version 3.0 transcripts. 4-18 million reads were generated for each sample and mapped to the genome, representing over 2GBases of data–2 billion+nucleotides. Presented below in Table 2 are the total number of Solexa 36 bp reads generated for each of the six RNA samples. Also shown for each sample are the number of those reads that successfully mapped to the *Chlamydomonas reinhardtii* v3.0 transcriptome (total reads with mer hits) and the percentage of total hits mapped to the transcriptome.

TABLE 2

| Exp +N |
| --- |
| Total Sample reads: 10,071,444 |
| Total reads with mer hits: 6,468,875 |
| Percentage mapped: 64.2 |
| Stationary +N |
| Total Sample reads: 3,871,450 |
| Total reads with mer hits: 2,523,731 |
| Percentage mapped: 65.2 |
| 6 H –N |
| Total Sample reads: 7,606,940 |
| Total reads with mer hits: 4,965,650 |
| Percentage mapped: 65.3 |
| 24 H –N |
| Total Sample reads: 7,709,562 |
| Total reads with mer hits: 5,021,348 |
| Percentage mapped: 65.1 |
| 48 H –N |
| Total Sample reads: 10,644,517 |
| Total reads with mer hits: 6,691,219 |
| Percentage mapped: 62.9 |
| Stationary –N |
| Total Sample reads: 17,799,413 |
| Total reads with mer hits: 8,761,230 |
| Percentage mapped: 49.2 |

Figure 14:
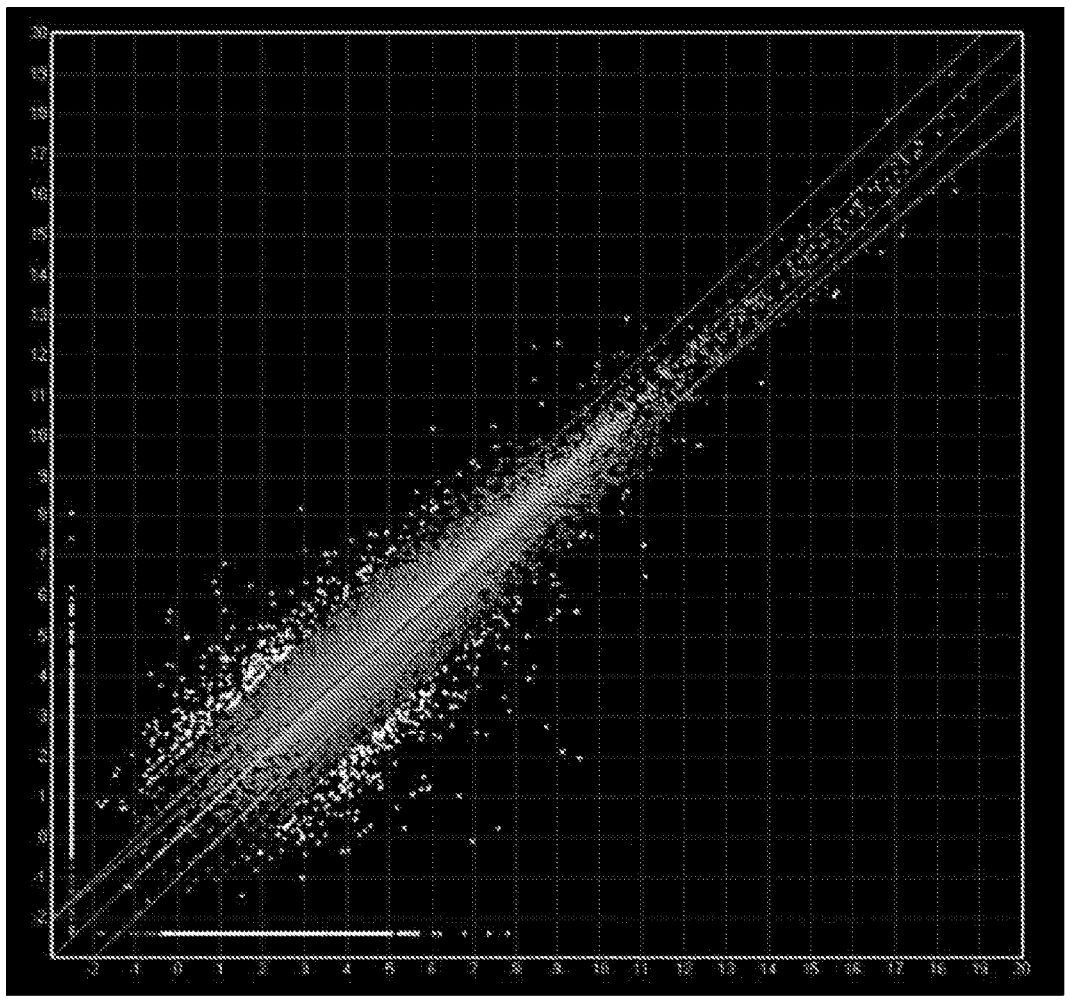
FIG. 14 shows all *Chlamydomonas reinhardtii* genes and their expression levels at a six hour time point generated by the method described in FIG. 13 in the presence and absence of nitrogen. White dots represent genes that are up or down regulated at least four fold at the six hour time point.

The transcriptomic data was then analyzed by looking at changes in expression levels between the six samples and across the time course of nitrogen starvation. FIG. 14 shows a plot, of all 16,000+ genes in SE0050 with expression levels from a different sample on each axis. Shown here are Exponential growth+Nitrogen (x-axis) versus Exponential growth 6H –Nitrogen (y-axis). Genes with no change in expression level are on the diagonal. The white data points represent at least 4-fold change in expression, those above the diagonal are upregulated after 6 hours of nitrogen starvation and those below the diagonal are down regulated after 6 hours of nitrogen starvation. These plots can be generated for any pair wise comparison of the six sequenced samples. These expression profiles were used in selecting target genes.

Figure 15:
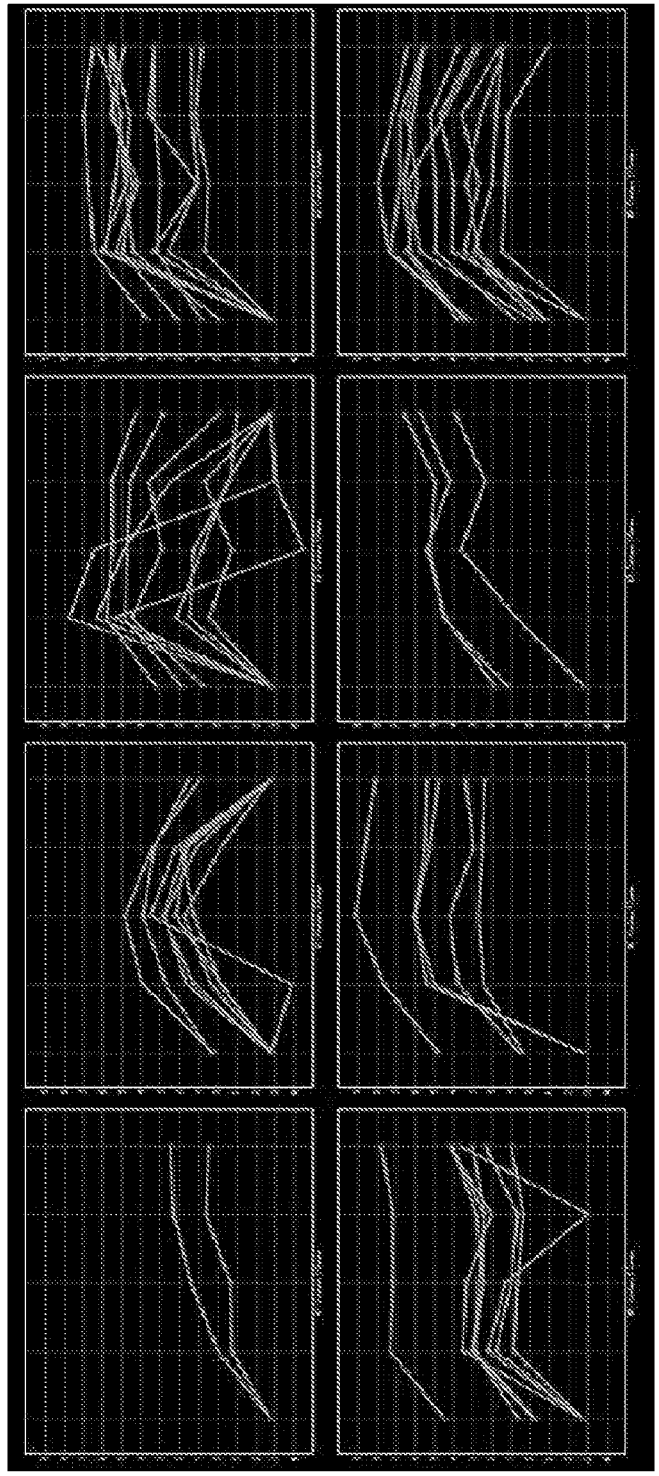
FIG. 15 shows gene expression levels across a time course of nitrogen starvation (as described in Table 2). Each line represents a different gene.

Example of time course of expression (as mentioned above regarding FIG. 14). FIG. 15 shows how the dynamics of gene expression during nitrogen starvation (6H, 24H, 48H, stationary) were used to further refine the target gene list. Each line represents one gene, with the y axis in each case being the level of expression and the x axis representing the 6 samples sequenced. The eight graphs represent genes that have similar expression patterns across the conditions represented by the 6 samples. These patterns and groupings can be used to further refine target gene lists.

Figure 16:
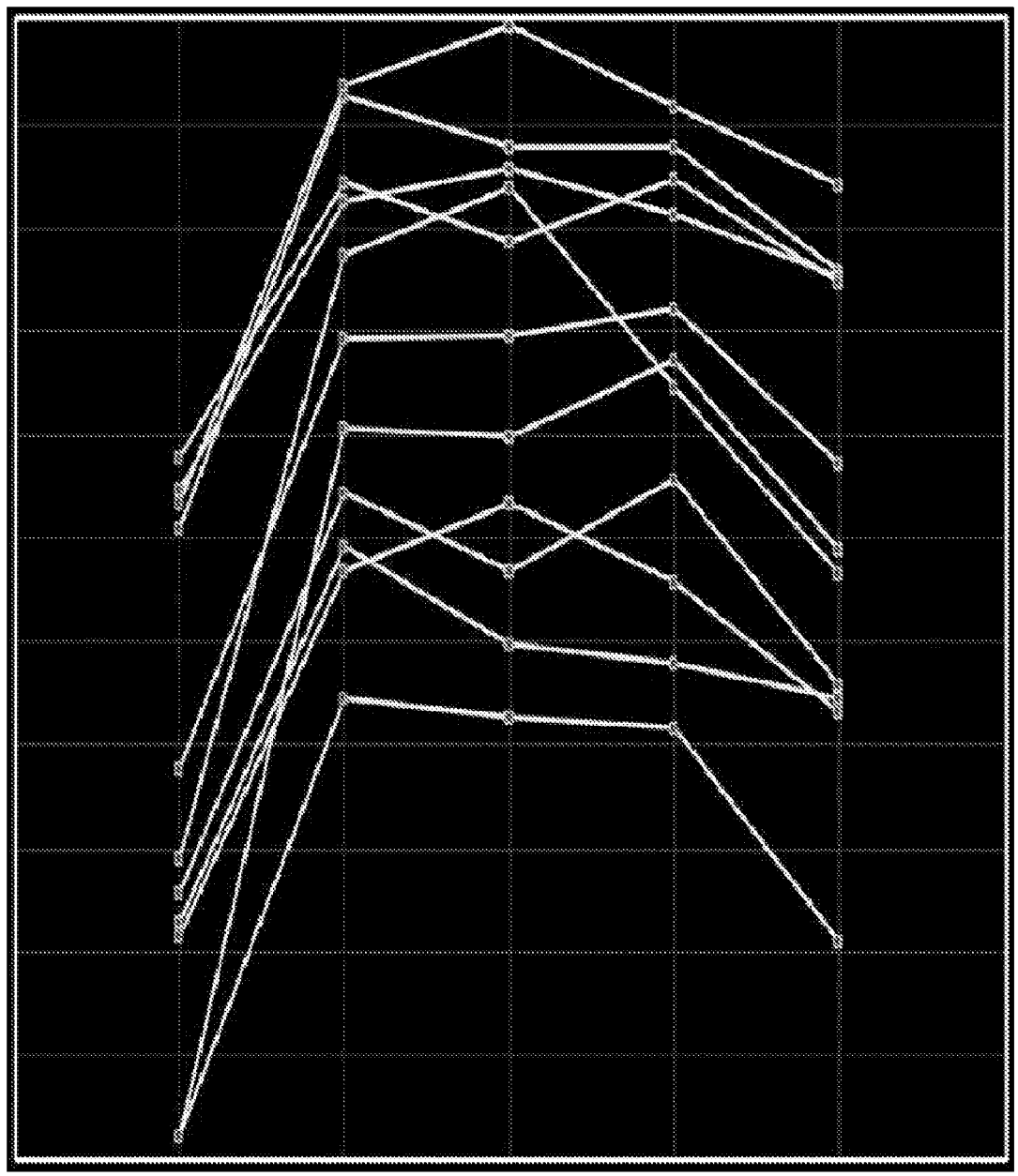
FIG. 16 shows the expression levels of the 14 target genes that were selected. Gene expression levels are across a time course of nitrogen starvation (as described in Table 2). Each line represents a different gene.
Figure 17:
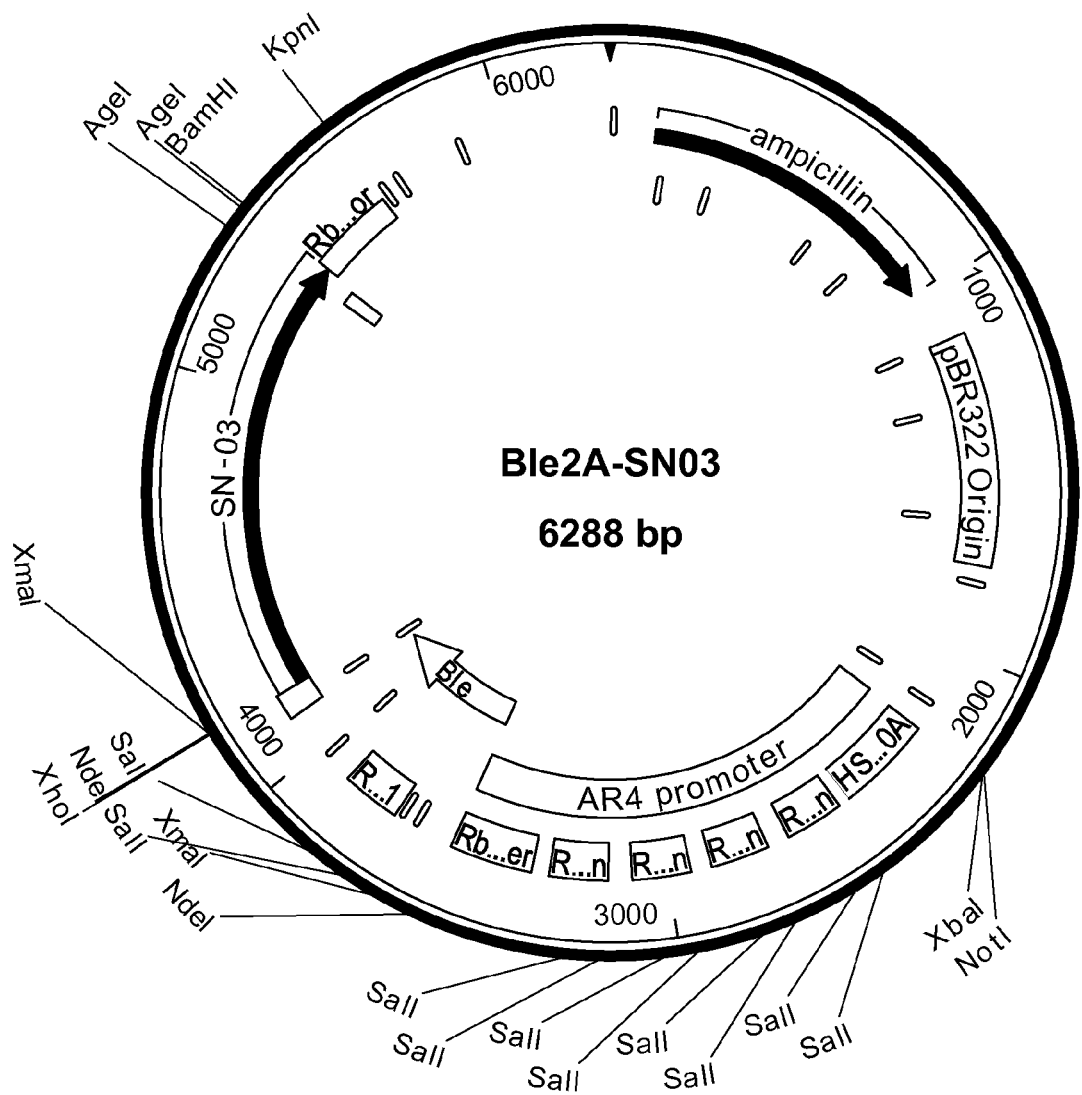
FIG. 17 shows a cloning vector used for cloning SN (stress-nitrogen) targets into algae.

FIG. 16 shows the expression pattern for 14 genes that had expression patterns indicating that the genes were turned on quickly after nitrogen starvation and stayed on. The 14 genes represent the lower right hand box of FIG. 15. This set of 14 was selected because the functional annotations from JGI indicated that these genes were expected to be involved in transcription and/or gene regulation. Genes that potentially control the nitrogen starvation response and are expected to be regulatory genes were selected as targets. The completeness of the JGI gene annotation at the molecular level also determines the usability of potential targets. For example, many of the annotated genes do not have start and/or stop codons, and therefore the complete open reading frame (ORF) is unknown. The initial 14 targets were limited to 5 due to poor annotation. 3 of the 14 did not have start codons, 3 did not have stop codons, 2 had neither start nor stop codons, and 1 had an inappropriate stop codon. The five selected targets were full length ORFs with start and stop codons.

Example 4

Cloning of Target Genes into Ble2A

Figure 34:
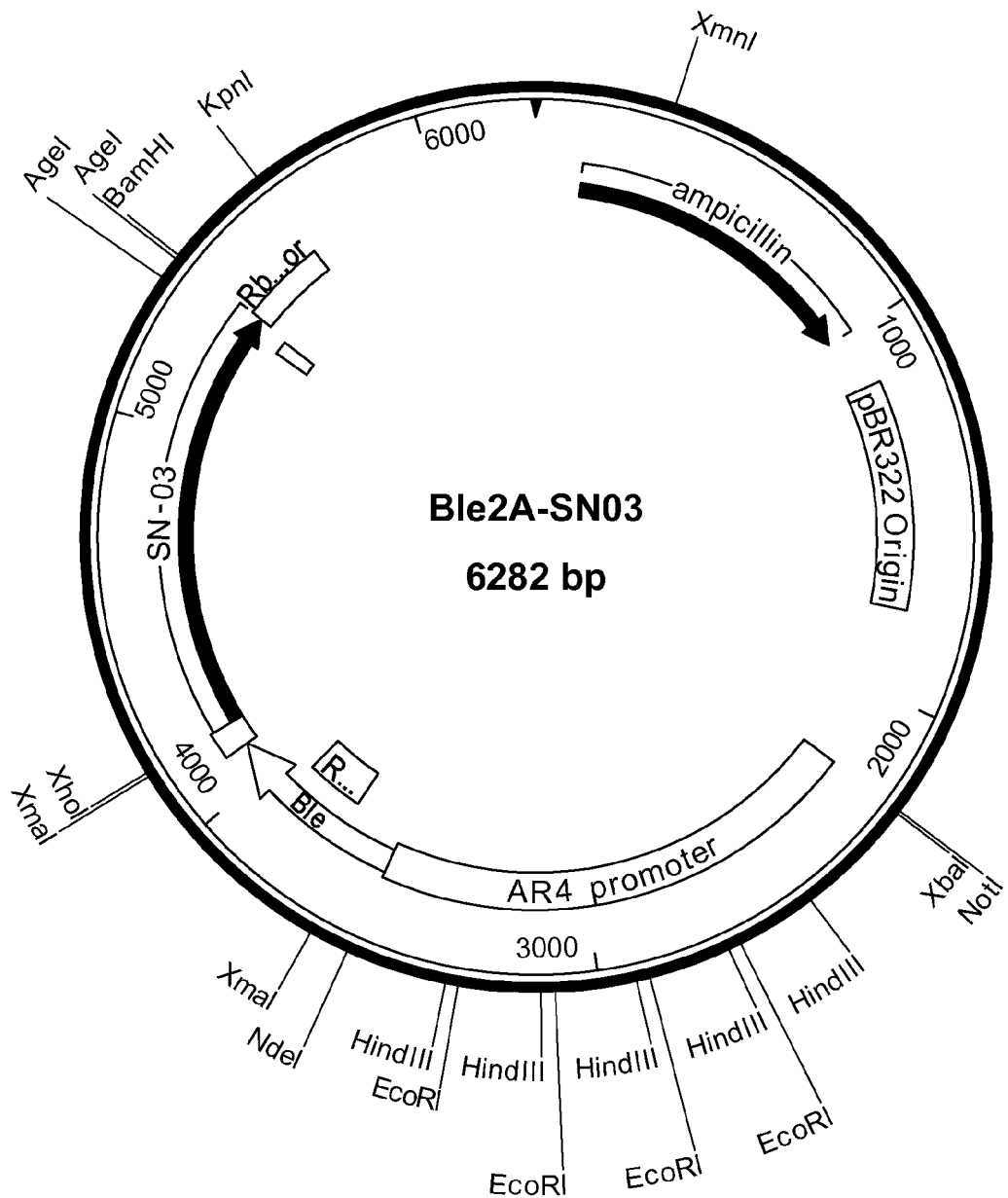
FIG. 34 shows a cloning vector (Ble2A-SN03) used for cloning SN (stress-nitrogen) targets into algae. The vector used the AR4 promoter to drive a bleomycin resistance gene and the SN gene. It has an ampicillin resistance cassette for growth in bacteria.
Figure 35:
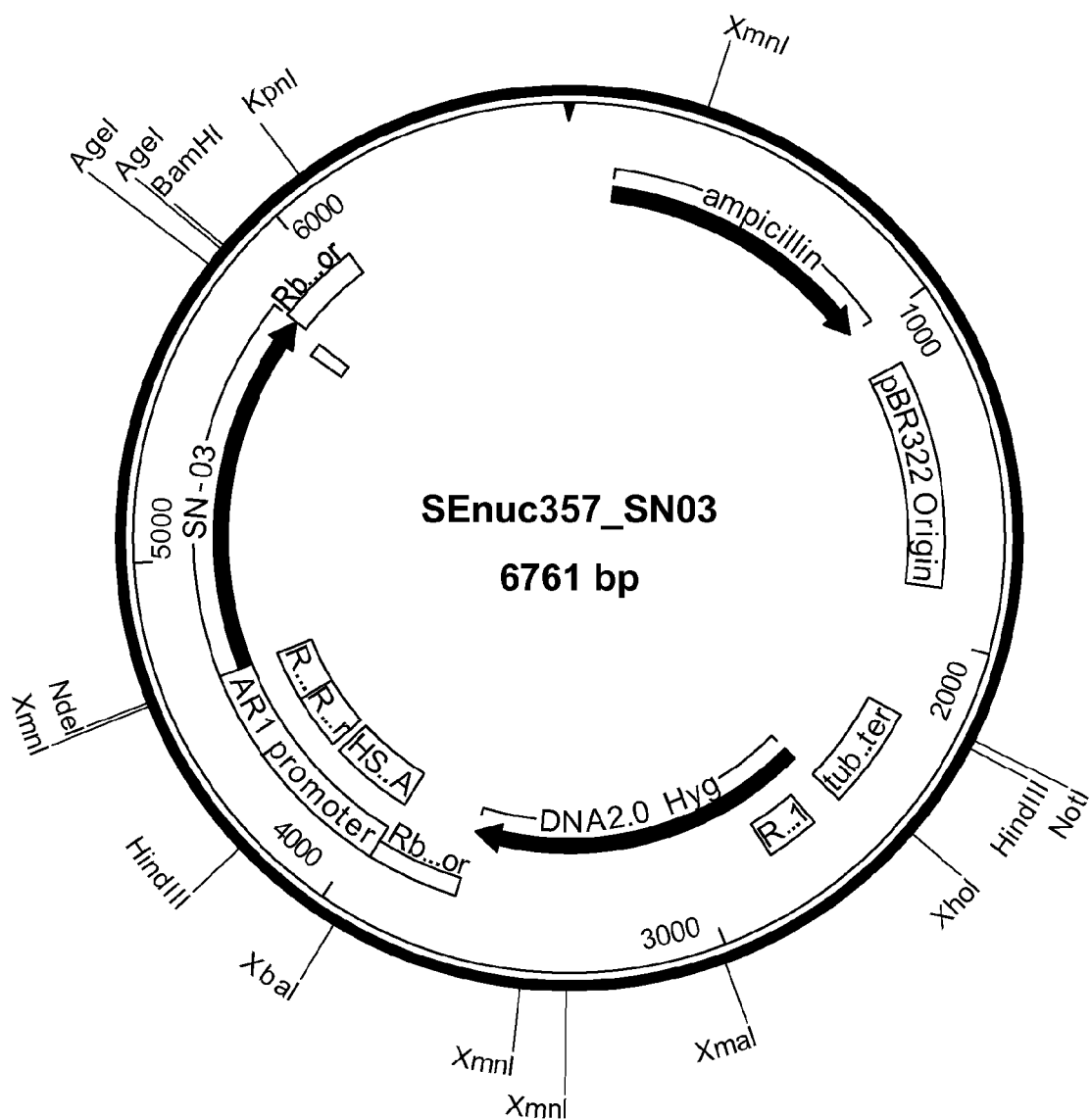
FIG. 35 shows an exemplary expression vector (SEnuc357_SN03) that can be used with the embodiments disclosed herein.

The ORFs for the first five stress response targets (described in the table below) were each codon optimized using *Chlamydomonas reinhardtii* codon usage tables and synthesized. The DNA constructs for the five targets were individually cloned into nuclear overexpression vector Ble2A (as shown in FIG. 34) and transformed into SE0050. This construct produces one RNA with a nucleotide sequence encoding a selection protein (Ble) and a nucleotide sequence encoding a protein of interest (any one of SN01 to SN05). The expression of the two proteins are linked by the viral peptide 2A (for example, as described in Donnelly et al., J Gen Virol (2001) vol. 82 (Pt 5) pp. 1013-25). This protein sequence facilitates expression of two polypeptides from a single mRNA. The first five targets are described below in Table 3.

TABLE 3

| SN01 | Translation initiation factor 4F, ribosome/mRNA-bridging subunit (eIF-4G) JGI Chlre v3 protein ID # 179214 |
| SN02 | HMG box-containing protein JGI Chlre v3 protein ID # 151215 |
| SN03 | CREB binding protein/P300 and related TAZ Zn-finger proteins JGI Chlre v3 protein ID # 147817 |
| SN04 | Transcription factor CHX10 and related HOX domain proteins JGI Chlre v3 protein ID # 141971 |
| SN05 | KOG: Zn finger; BLAST: fatty-acid synthase complex protein JGI Chlre v3 protein ID #168511 |

Transforming DNA, the Ble2A-SN03 plasmid shown, in FIG. 34, was created by using pBluescript II SK(−) (Agilent Technologies, Calif.) as a vector backbone. The segment labeled "AR4 Promoter" indicates a fused promoter region beginning with the *C. reinhardtii* Hsp70A promoter, *C. reinhardtii* rbcS2 promoter, and the four copies of the first intron from the *C. reinhardtii* rbcS2 gene (Sizova et al. Gene, 277:221-229 (2001)). The gene encoding bleomycin binding protein was fused to the 2A region of foot-and-mouth, disease virus and the SN ORF with a FLAG-MAT tag cloned in with XhoI and BamHI. This was followed by the *Chlamydomonas reinhardtii* rbcS2 terminator.

Transformation DNA was prepared by digesting the Ble2A-SN vector with the restriction enzyme KpnI, XbaI or PsiI followed by heat, inactivation of the enzyme. For these experiments, all transformations were carried out on *C. reinhardtii* cc1690 (mt+). Cells were grown and transformed via electroporation. Cells were grown to mid-log phase (approximately 2-6×$10^6$ cells/ml) in TAP media. Cells were spun down at between 2000×g and 5000×g for 5 min. The supernatant was removed and the cells were resuspended in TAP media+40 mM sucrose. 250-1000 ng (in 1-5 μL $H_2O$) of transformation DNA was mixed with 250 uL of 3×$10^8$ cells/mL on ice and transferred to 0.4 cm electroporation cuvettes. Electroporation was performed with the capacitance set at 25 uF, the voltage at 800 V to deliver 2000 V/cm resulting in a time constant of approximately 10-14 ms. Following electroporation, the cuvette was returned to room temperature for 5-20 min. For each transformation, cells were transferred to 10 ml of TAP media+40 mM sucrose and allowed to recover at room temperature for 12-16 hours with continuous shaking. Cells were then harvested by centrifugation at between 2000×g and 5000×g, the supernatant was discarded, and the pellet was resuspended in 0.5 ml TAP media+40 mM sucrose. The resuspended cells were then plated on solid TAP media+20 μg/mL zeocin. As a result, overexpression lines for SN01 to SN05 were created.

Example 5

Lipid Dye/Flow Cytometry Analysis on SN01 to SN05

Approximately 300 to 400 independent clones of SN01 to SN05/Ble2A were grown to mid-log phase in 1-10 mL TAP and pooled. The pool of transgenic clones was then combined with an equivalent amount of wild-type SE0050 grown to mid-log phase in TAP (ratio of pooled population to wild-type was 1:1). This mixed population was sorted for single colonies by FACS onto permissive media (TAP) and selective media (TAP+20 ug/mL zeocin). The same number of cells (approximately 500) was sorted onto each media. The population was then stained with lipid dyes (LipidTox Green and Bodipy), and high lipid containing lines were selected by FACS analyses. The main population after staining showed high levels of staining after one dye, while the selected population after staining showed high levels of staining using both dyes. These populations were also sorted onto both permissive and selective media (approximately 500 per population per media). The total number of colonies on each media for each population was counted and the percentage of total cells (permissive) that contained an SN transgene (selective) was calculated. The main population unstained contained 49% transgenic cells, consistent with the initial 1:1 pooling of transgenic and wild type. After sorting for high lipid staining cells, 64.5% of the cells are transgenic, indicating that some fraction of the pooled SN transgenic lines have higher lipid dye staining than the rest of the pooled population. The results are shown in Table 4.

TABLE 4

|  | # on TAP/Ble | # on TAP | % |
|---|---|---|---|
| Main population unstained | 250 | 510 | 49.0 |
| Main population stained | 248 | 543 | 45.7 |
| Selected population stained | 256 | 397 | 64.5 |

The fact that the percentage of transgenics in the selected population goes up (to 64.5%) relative to the main unstained (49%) indicates that one or more of the transgenic lines containing genes SN01-05 have higher fluorescence with the lipid dyes—and presumably more lipid.

SE0050 SN-FACS-results. In order to determine which transgenic lines were responsible for the increased lipid dye staining, the SN gene from individual clones from the FACS experiment were PGR amplified from genomic DNA and sequenced to determine the distribution of SN01 to SN05 in the starting population relative to the selected population. Individual clones were grown on solid TAP+agar plates then a small amount of biomass was placed into standard PCR reactions using primers specific for vector regions so that the SN ORF is amplified. The resulting PGR product was then sequenced. This analysis showed that the starting population comprised only partially gene positive clones. SN04 and SN05 were not well represented in the starting population and therefore likely did not contribute to the final result. The results of the initial screening of the starting transgenic lines (prior to pooling) are shown in Table 5.

TABLE 5

|  | # screened | #gene positive | % |
| --- | --- | --- | --- |
| SN01 | 96 | 63 | 66 |
| SN02 | 96 | 5 | 5 |
| SN03 | 24 | 12 | 50 |
| SN04 | 12 | 2 | 17 |
| SN05 | 26 | 1 | 4 |

The number of clones that were sequenced in each FACS sorted population is shown in Table 6. The SN ORF from individual clones from the selective plates were PCR amplified from genomic DNA and the SN gene was sequenced. The number of clones containing each of the SN01, SN02 and SN03 genes is indicated in Table 6, SN04 and SN05 were not detected. The lines in the table represent the three sorted populations: main unstained (MU); main stained (MS); and stained and selected for high fluorescence (SEL).
* A large proportion of the lines containing SN02 (particularly in the MS population) did not contain a complete gene and can be considered false positives.

TABLE 6

|  | SN01 | SN02* | SN03 |
| --- | --- | --- | --- |
| MU | 52 | 9 | 7 |
| MS | 62 | 29 | 7 |
| SEL | 57 | 7 | 37 |

Figure 18:
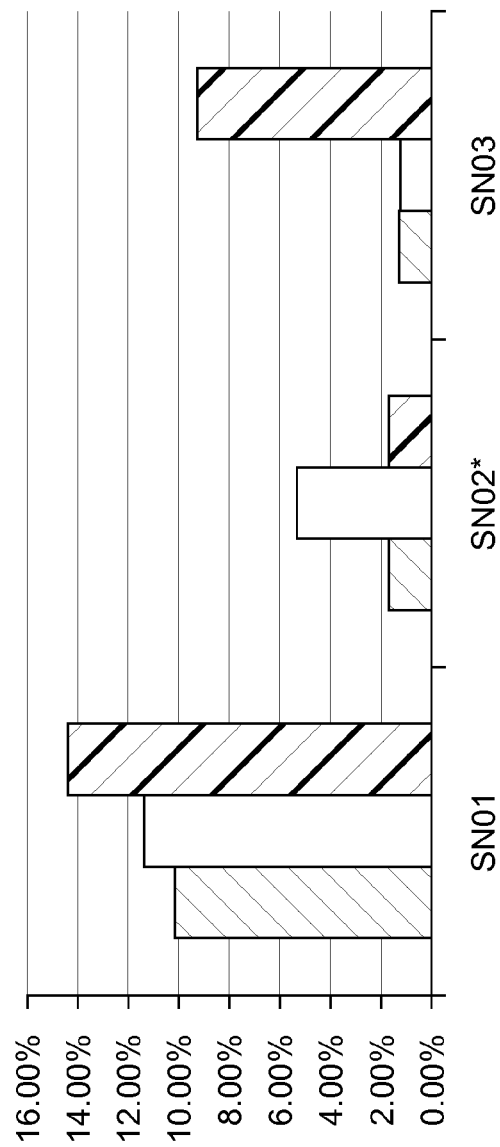
FIG. 18 describes the distribution of *Chlamydomonas reinhardtii* strains overexpressing SN01, SN02, and SN03 after FACS enrichment for high-lipid dye staining.

SN03 went from less than 2% in the main unstained population to almost 10% of the stained and selected population (as shown in FIG. 18), indicating that transgenic lines over expressing SN03 have higher lipid dye fluorescence and higher lipid content. MU is the left hand column in each set of three columns, MS is the middle column in each set of three columns, and SEL is the right hand column in each set of three columns.

Figure 42A:
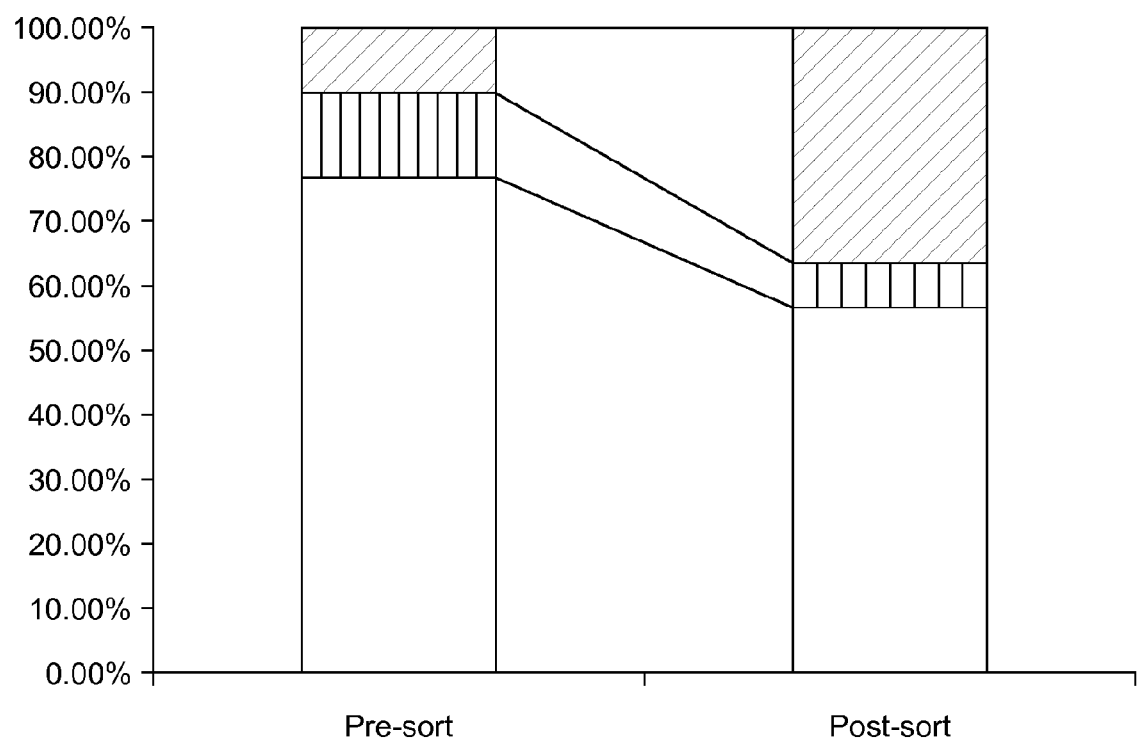
FIG. 42A shows the distribution of *Chlamydomonas reinhardtii* strains overexpressing SN01, SN02, and SN03 after FACS enrichment for high-lipid dye staining. The solid portion of each bar represents the percentage of lines overexpressing SN03; the striped portion of each bar represents the percentage of lines overexpressing SN02, and the unfilled portion of each bar represents the percentage of lines overexpressing SN01.

FIG. 42A shows the distribution of SN01, SN02 and SN03 in the MU, main unstained population (indicated on x axis as Pre-sort) and the SEL, selected population (indicated on the x axis as Post-sort). The percentage of sequences representing each of the SN01-SN03 is shown on the y axis, with SN01 as the white box, SN02 as the striped box, and SN03 as the black box. This demonstrates the increase in SN03 from 10% of the sequences in the Pre-sort population to 37% of the sequences in the Post-sort population.

Figure 19A:
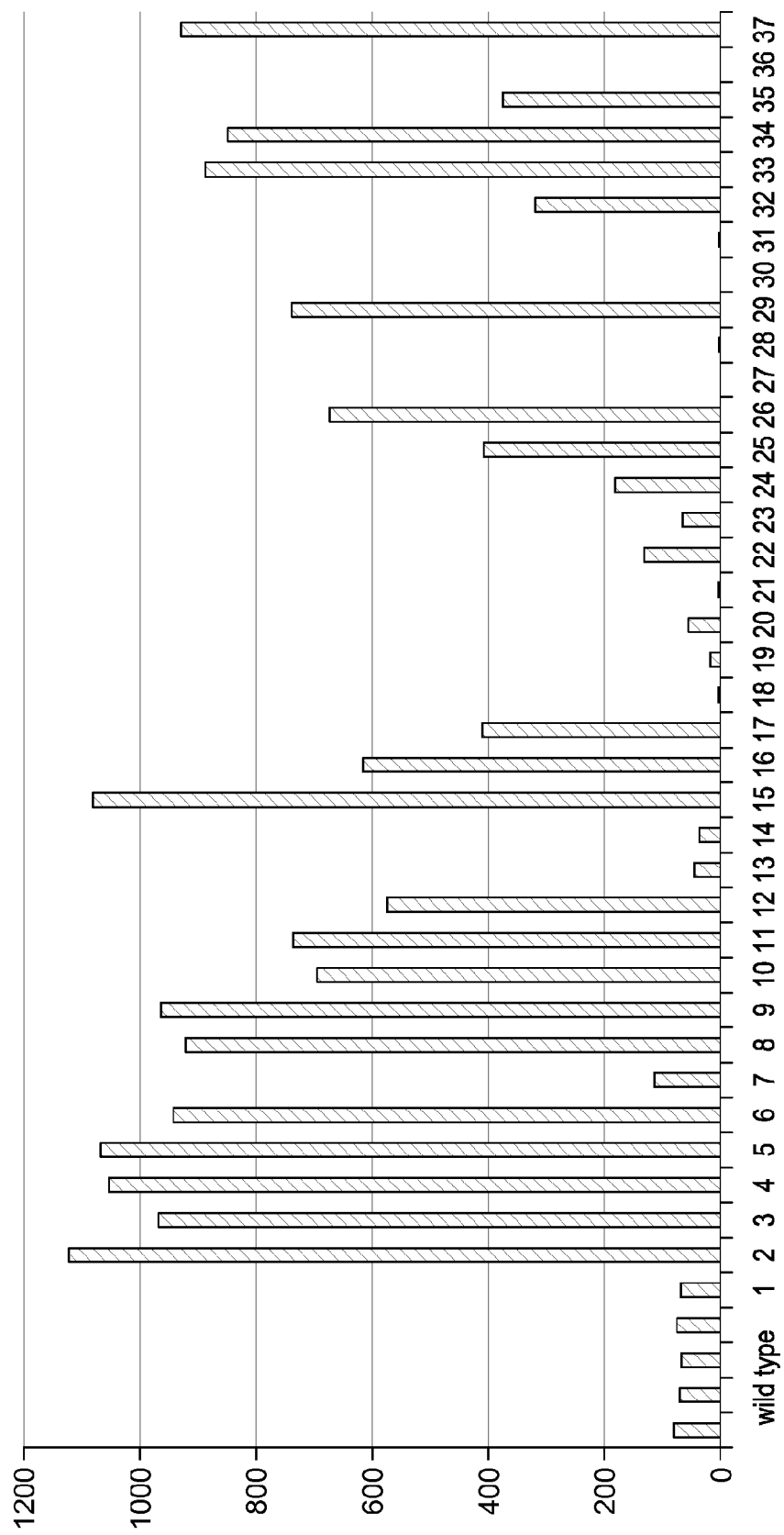
FIGS. 19A, 19B, 19C, and 19D show flow cytometry (Guava) results for SN03 strains identified from the FACS experiment of FIG. 18.
Figure 19B:
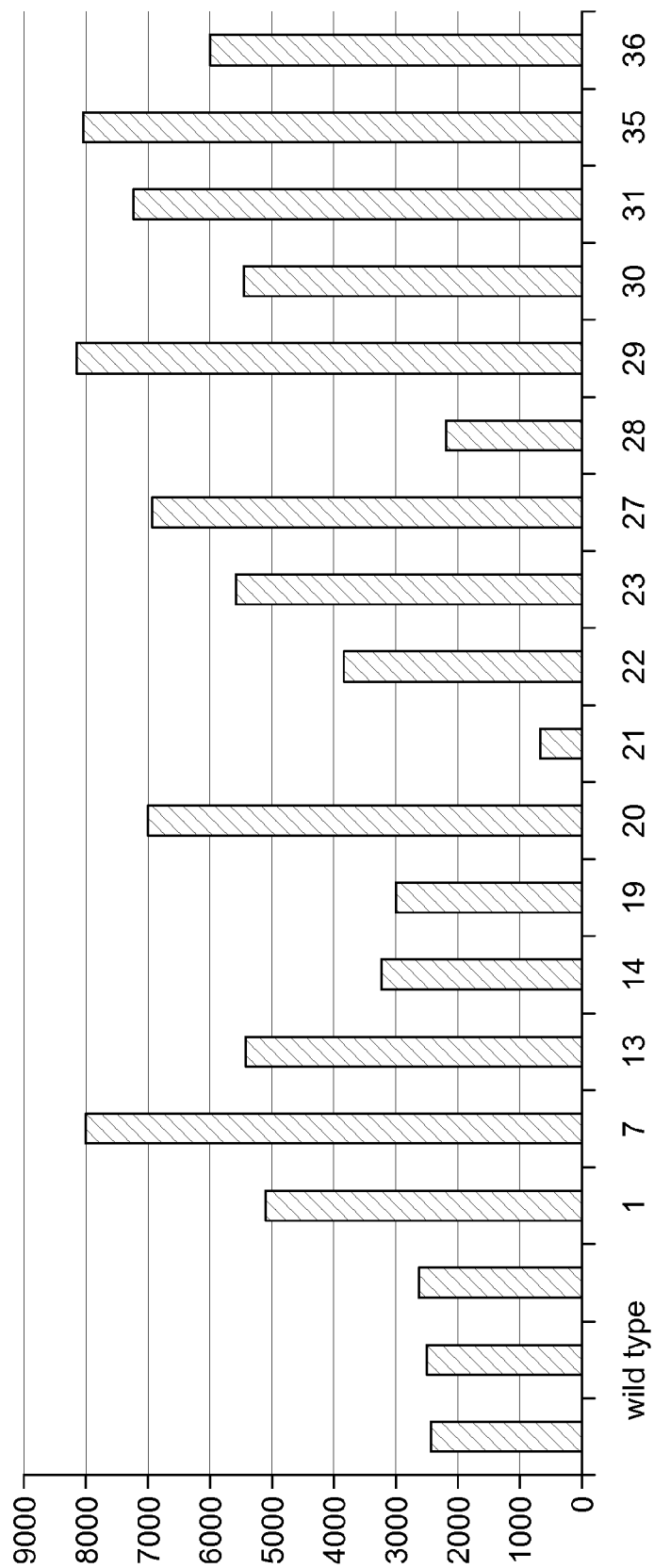
Figure 19C:
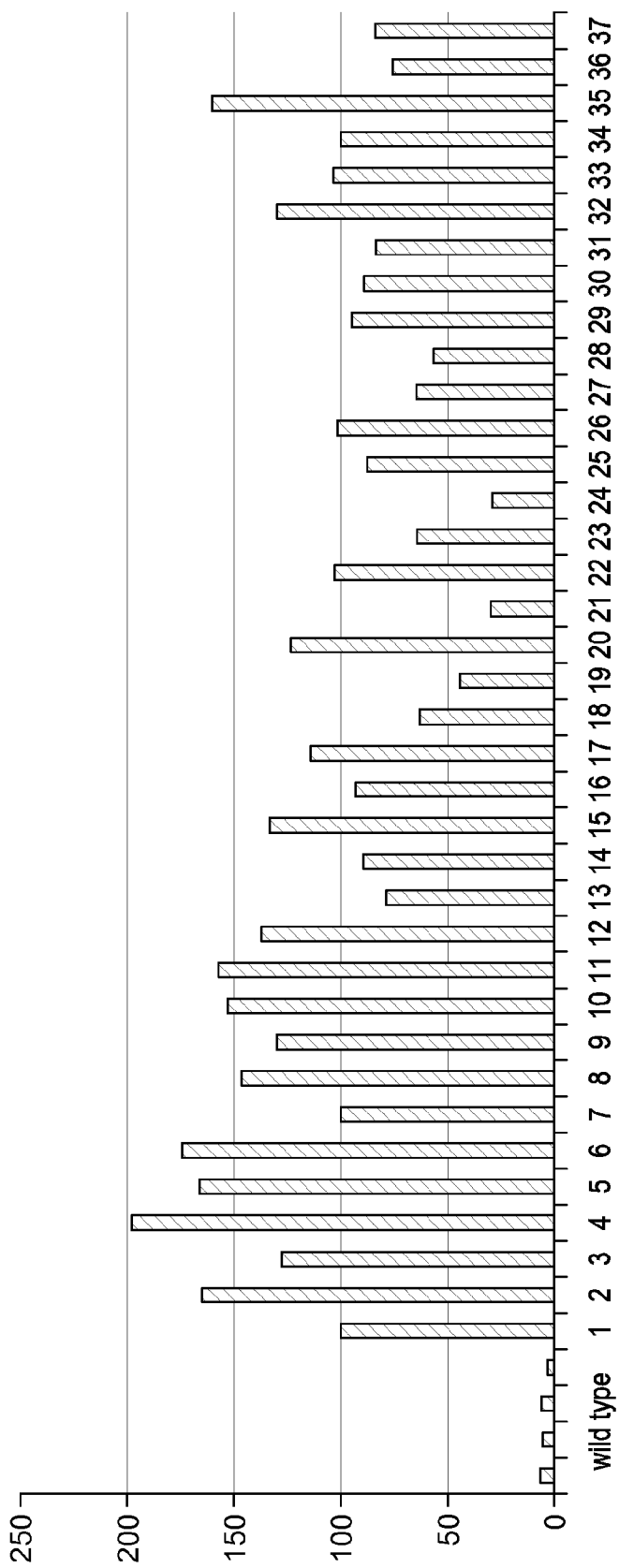
Figure 19D:
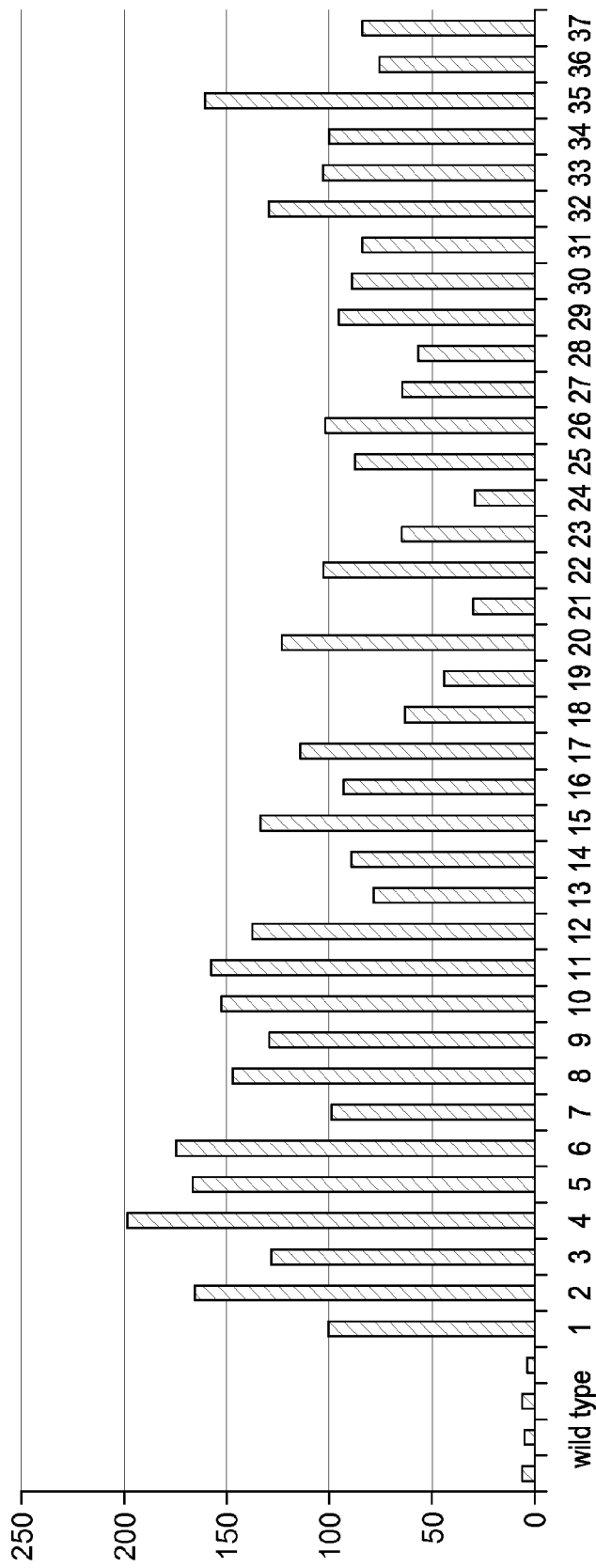

The 37 individual SN03 colonies were re-screened by flow cytometry (Guava) using three lipid dyes. Cells were grown in 1-5 mL of TAP to mid-log phase, then diluted into media containing the lipid dyes before analysis on the flow cytometer (Guava). Overall, the SN03 lines show higher lipid dye staining than wild type (wt 1-4 are biological replicates of wild type), again suggesting that they have more lipid. FIG. 19A shows Bodipy staining, FIG. 19B shows a repeated Bodipy staining; FIG. 19C shows Lipid-TOX staining; and FIG. 19D shows Nile Red staining. The x-axis represents individual strains, whether wild type or the 37 SN03 overexpressing lines (named SN03-1 to SN03-37) while the y-axis represents relative fluorescence units.

Figure 42B:
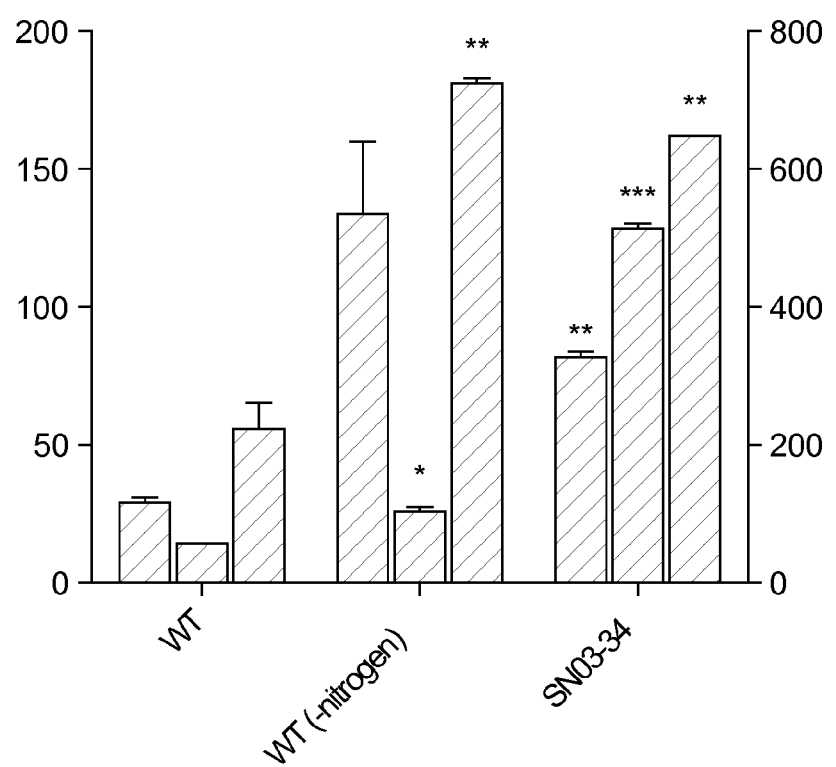
FIG. 42B shows flow cytometry (Guava) results for wild-type *Chlamydomonas reinhardtii* in the presence and absence of nitrogen and an SN03 overexpressing strain. The left hand column of each set is Nile Red; the middle column of each set is LipidTOX green; and the right hand column of each set is Bodipy.

FIG. 42B shows the lipid content as determined by lipid dyes and flow cytometry (Guava) in wild type *Chlamydomonas reinhardtii* grown in the presence and absence of nitrogen and an SN03 overexpression line. Wild-type *Chlamydomonas reinhardtii* cells were grown in 10-100 ml, of TAP media containing 7.5 mM $NH_4Cl$ in an air environment under constant light, until cells reached early log phase. The culture was centrifuged at 3000 to 5000×g for 5-10 minutes and one half of the culture was washed with 5-100 mL TAP, the other half with 5-100 mL TAP containing no nitrogen. After re-centrifigation, the two cultures were resuspended in a volume equivalent to the starting culture volume. Additionally, one SN03 overexpression line was grown in 10-100 mL of TAP media containing 7.5 mM $NH_4Cl$ in an air environment under constant light, until cells reached early log phase. After 2-3 days of nitrogen starvation for the wild type culture, the cultures were diluted into media containing lipid dye before analysis on the flow cytometer (Guava). Three dyes were used independently. In FIG. 42B, the x axis indicates the sample for each set of three dyes represented by the columns. In each set of three columns, the left column represents Nile Red, the middle column represents Lipid-TOX Green and the right column represents Bodipy. The left y axis shows relative fluorescence units (RFU) for Nile Red and LipidTOX Green (NR, LT), while the right y axis shows RFU for Bodipy. The SN03 overexpression line shows lipid staining higher than wild type in the presence of nitrogen and comparable to wild type in the absence of nitrogen.

Figure 42C:
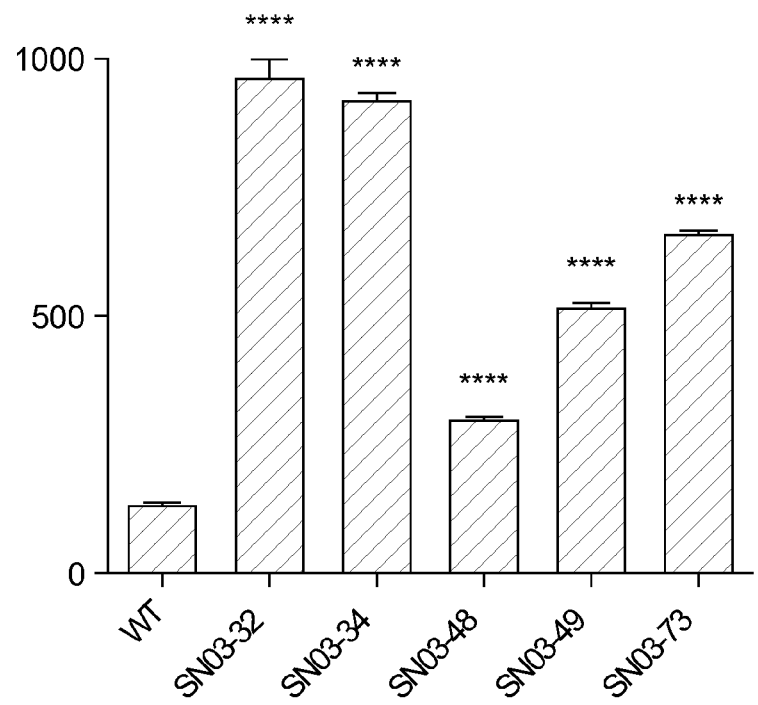
FIG. 42C shows flow cytometry (Guava) results using Bodipy for wild-type *Chlamydomonas reinhardtii* and several SN03 overexpressing strains.

FIG. 42C shows the lipid content of several independent SN03 overexpression lines. Wild type *Chlamydomonas reinhardtii* and five SN03 overexpression line were grown in 10-100 mL of TAP media containing 7.5 mM $NH_4Cl$ in an air environment under constant light, until cells reached early log phase. The cultures were diluted into media containing Bodipy before analysis on the flow cytometer (Guava). The x axis indicates wild type (wt) or the SN03 overexpression line, while the y axis indicates relative fluorescence units (RFU). All five SN03 overexpression lines show lipid staining higher than wild type.

Example 5

Identification of Insertion Sites for SN03 Vector

FIG. 43 shows that two SN03 overexpression lines have SN03 vector insertions in different chromosomes of *Chlamydomonas reinhardtii*. Genomic DNA from two independent SN03 overexpression lines was isolated. Thirty five cycles of primer extension using a biotinylated primer (SEQ ID NO: 42) specific to the SN03 ORF and Phusion DNA Polymerase (NEB) produced DNA products that were then purified with Streptavidin magnetic beads. DNA was eluted from the beads by boiling for 10 minutes, then 1.0-2.5 ug of this DNA was dT tailed with Terminal Transferase (NEB). Nested PCR was performed using standard protocols and a polyA primer with a nested primer (SEQ ID NO: 43) specific for the SN03 ORF. PCR products were TOPO cloned (Invitrogen) and sequenced.

In addition, FIG. 43 shows the junction between the transforming vector (as described in FIG. 34) and the *Chlamydomonas reinhardtii* genomic sequence. For overexpression line SN03-34, the vector is inserted into chromosome 12 at position 2137908. For overexpression line SN03-73, the vector is inserted into chromosome 9 at position 419725. The three horizontal arrows represent the SN03 ORF (open box arrow), the rbcs2 terminator (line arrow pointing right) and a portion of the vector adjacent to the terminator (line arrow pointing left). The open box represents the genomic sequence, with an arrow pointing to the integration site. The nucleotide sequence below each diagram represents a portion of the vector sequence (non-underlined) and a portion of the genomic sequence (underlined). The integration sites in different chromosomes demonstrates that the transformed SN03 overexpression lines are independent and are not inserted into the same genomic region, and the phenotypes observed are not due to disruption of a common gene rather than overexpression of SN03.

Example 6

Phenotypic Analysis of SN03 Overexpression Lines

Seven of the SN03 transgenic lines along with the wild-type cells (FIG. 20A) were grown in TAP media in an air environment under constant light, until cells reached late log phase. Separately, three of the SN03 transgenic lines along with a transgenic line that does not contain an SN gene (gene neg), one SN01 transgenic line and wild type (FIG. 20B) were grown in HSM media in a 5% carbon dioxide in an air environment under constant light, until cells reached late log phase. 1-2 L of cells were harvested by centrifugation and analyzed for total gravimetric lipids by methanol/methyl-tert-butyl ether extraction according to a modified Bligh Dyer method (as described in Matyash V., et al. (2008) Journal of Lipid Research 49:1137-1146).

Specifically, biomass was pelleted and excess water removed. After the addition of methanol, samples were vortexed vigorously to lyse cells. MTBE was added and samples were vortexed again for an extended period of time (approximately 1 hr). Addition of water to samples after vortexing gave a ratio of 4:1.2:1; MTBE:MeOH:water respectively. Samples were centrifuged to aid in phase separation. The organic layer was removed and the process repeated a second time. Samples were extracted a third time adding only MTBE; the samples were vortexed, centrifuged, and phase separated as described above. The organic layers were combined, dried with magnesium sulfate, filtered and concentrated into tared vials. The percent extractables was calculated using the ash free dry weight of the sample.

Figure 20A:
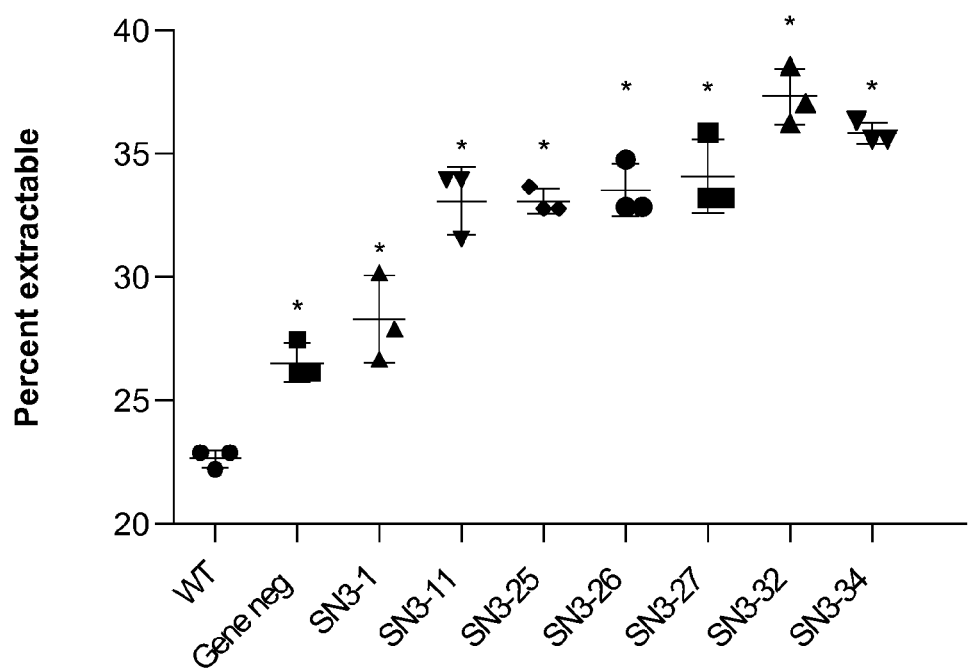
FIGS. 20A and 20B show *Chlamydomonas reinhardtii* strains overexpressing SN03 grown on TAP or high salt media (HSM) and then MTBE extracted for lipid content.
Figure 20B:
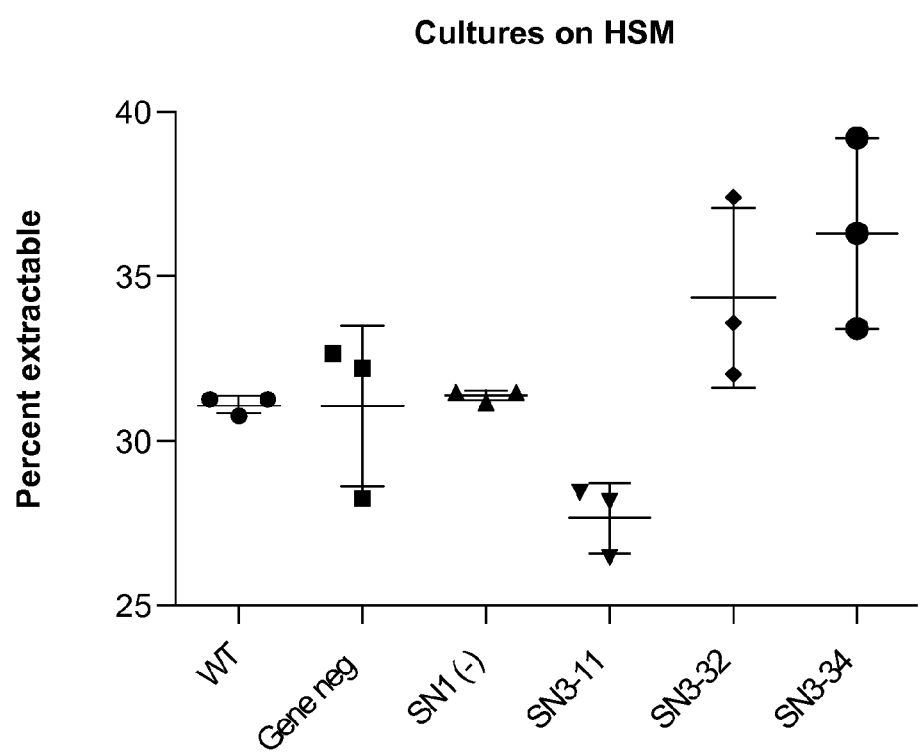

FIGS. 20A and B show data points with error bars at mean +/− standard deviation. The y-axis represents percent extractables and the x-axis represents the strains as described above. The samples were different at p<0.05 from wild type marked with star. SN03 lines have significantly more lipid than the wild type line.

Figure 45A:
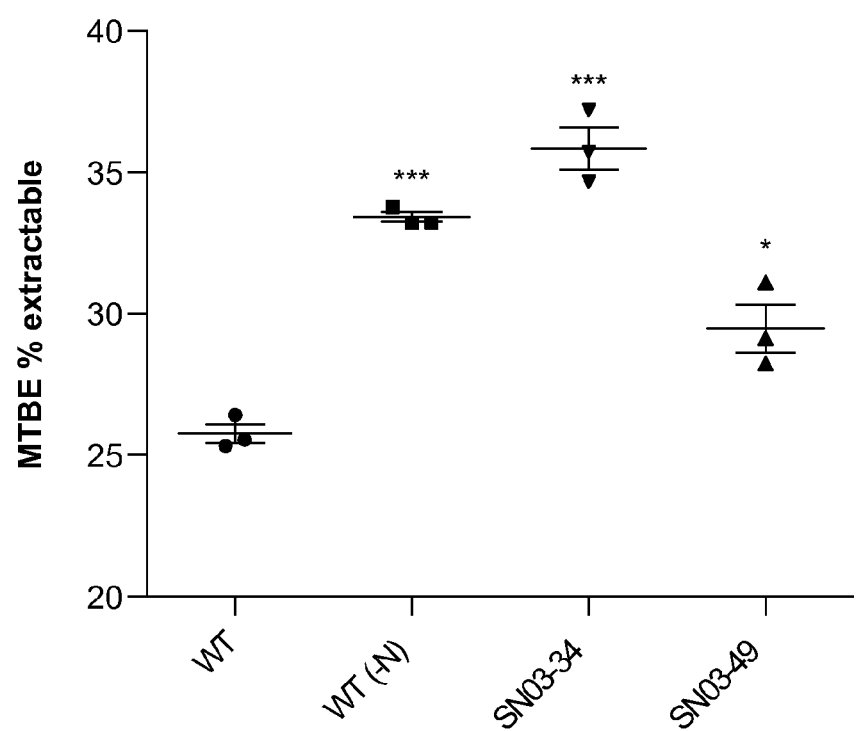
FIG. 45A shows wild-type *Chlamydomonas reinhardtii* in the presence and absence of nitrogen and *Chlamydomonas reinhardtii* strains overexpressing SN03 MTBE extracted for lipid content.

FIG. 45A is an additional example showing that SN03 overexpression lines accumulate more lipids than wild type. Wild-type *Chlamydomonas reinhardtii* cells were grown in 1-2 L of TAP media containing 7.5 mM $NH_4Cl$ in an air environment, under constant, light, until cells reached early log phase. The culture was centrifuged at 3000 to 5000×g for 5-10 minutes and one half of the culture was washed with 100-500 mL TAP, the other half with 100-500 mL TAP containing no nitrogen. After re-centrifigation. The two cultures were resuspended in a volume equivalent. To the starting culture volume. Additionally, two SN03 overexpression lines were grown in 1-2 L of TAP media containing 7.5 mM $NH_4Cl$ in an air environment under constant, light, until cells reached early log phase. After 2-3 days of nitrogen starvation for the wild type culture, cells were harvested by centrifugation and analyzed for total gravimetric lipids by methanol/methyl-tert-butyl ether extraction according to a modified Bligh Dyer method (as described in Matyash V., et al. (2008) Journal of Lipid Research 49:1137-1146). FIG. 45A shows data points with error bars at mean +/− standard deviation. The y-axis represents percent extractables and the x-axis represents the strains as described above. The samples were different at p <0.05 from wild type marked with star. SN03 lines have significantly more lipid than the wild type line and levels comparable to wild type in the absence of nitrogen.

Figure 21:
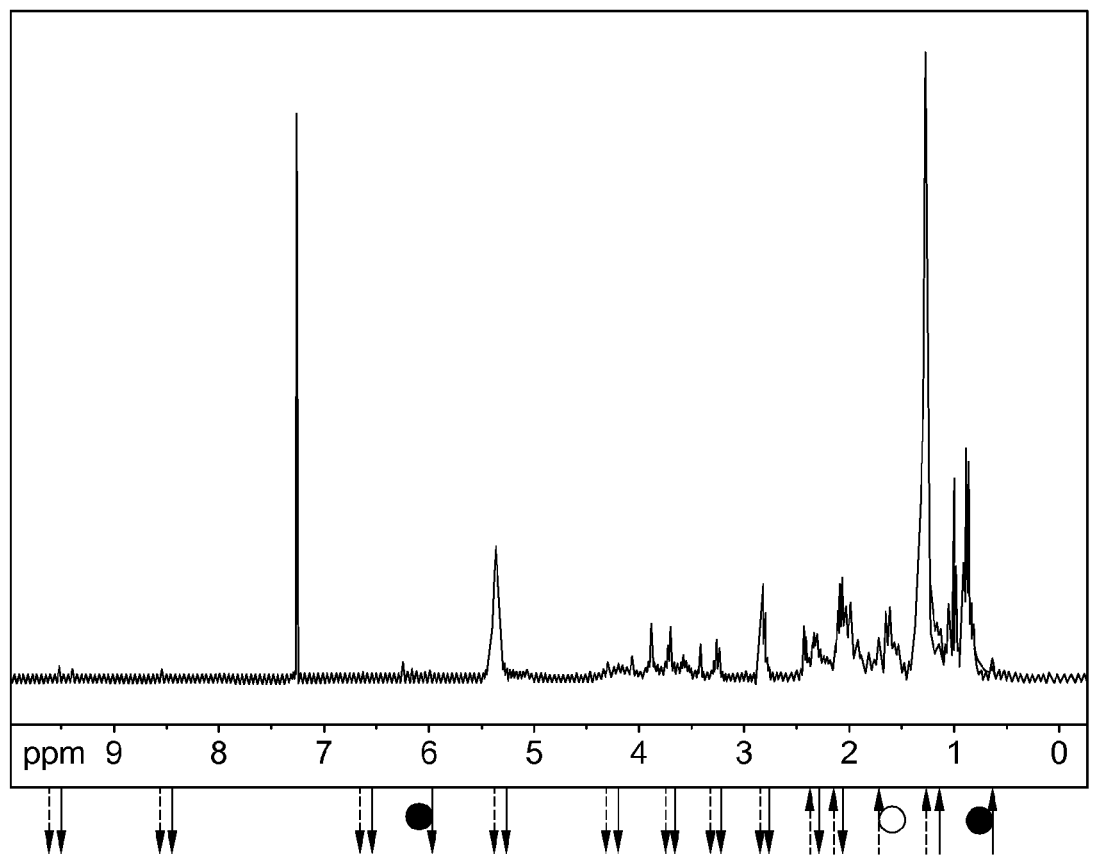
FIG. 21 shows 1D 1H NMR of the MTBE extracted oil from wild type *Chlamydomonas reinhardtii* grown in the presence and absence of nitrogen and a *Chlamydomonas reinhardtii* strain overexpressing SN03 (SN03-34).

FIG. 21 is a comparison of 1-D 1H NMR spectra of MTBE:MeOH extracts (wild-type, SN3 gene positive, and nitrogen starved) taken from the samples described in FIG. 20a. Samples were dissolved in $CDCl_3$ prior to collection of NMR spectra.

Comparison of ID proton NMR spectra of MTBE:methanol extracts of nitrogen replete wild type, SN3-34, and nitrogen starved wild type cultures. Peaks with differences in relative integrals marked with arrows. Direction of change of integral area from nitrogen replete wild type to SN3-34 is shown by the left arrow for each peak. Direction of change of integral area from nitrogen replete wild type to nitrogen starved wild type is shown by the right arrow for each peak. For most peaks, the direction of change in peak area (relative increase or decrease in component concentration) is the same for wild type undergoing nitrogen stress and SN3-34 overexpression.

These figures show that the SN03 lipid profile is similar to the profile of oil from nitrogen starved cultures, while both are different as compared to oil from wild type cultures. This shows that the nitrogen stress response has been turned on by over expressing SN03.

For most peaks, the direction of change in peak area is the same for cells expressing SN3 or for cells undergoing nitrogen stress.

Figure 22A:
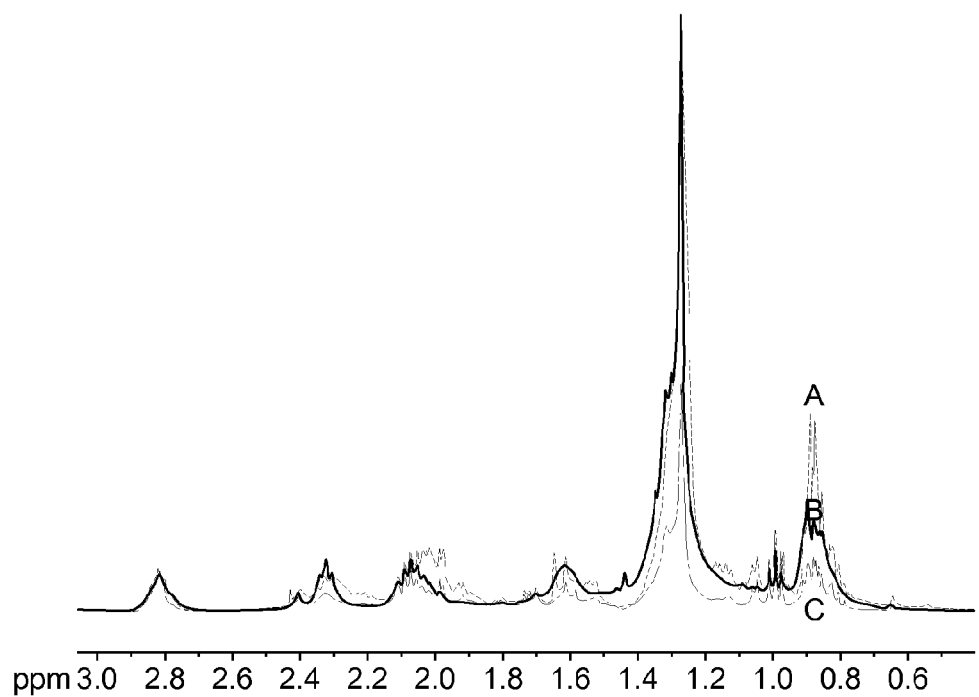
FIGS. 22A and B shows close up of peaks from the experiment described in FIG. 21.
Figure 22B:
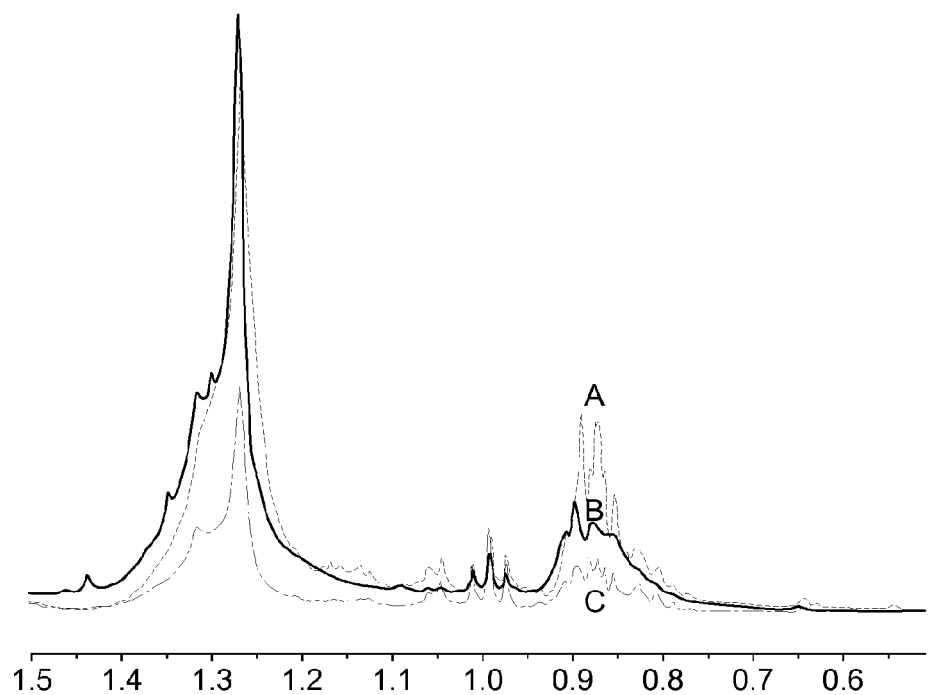

FIGS. 22A and B are close ups of the NMR peaks from FIG. 21. The SN03 and starved oil samples are similar and both are distinct from wild type oil. Again the SN03 lines mimic the stress response. Saturated methylene peaks appear at 1.27 ppm and terminal methyl peaks appear at 0.88 ppm. Starved wild type and SN03-34 spectra are similar to each other (relative to unstarved wild type). Normalized to peak at 2.8 ppm, wild type starved (B), wild type replete (C), and SN 3-34 replete (A). Comparison of nitrogen replete wild type, nitrogen starved wild-type, and SN03-34 MTBE: Methanol extract proton NMR spectra in $CDCl_3$. The SN3-34 spectrum (A) and wild-type starved (B) are similar at most peak positions, while wild-type replete (C) is different.

Figure 27:
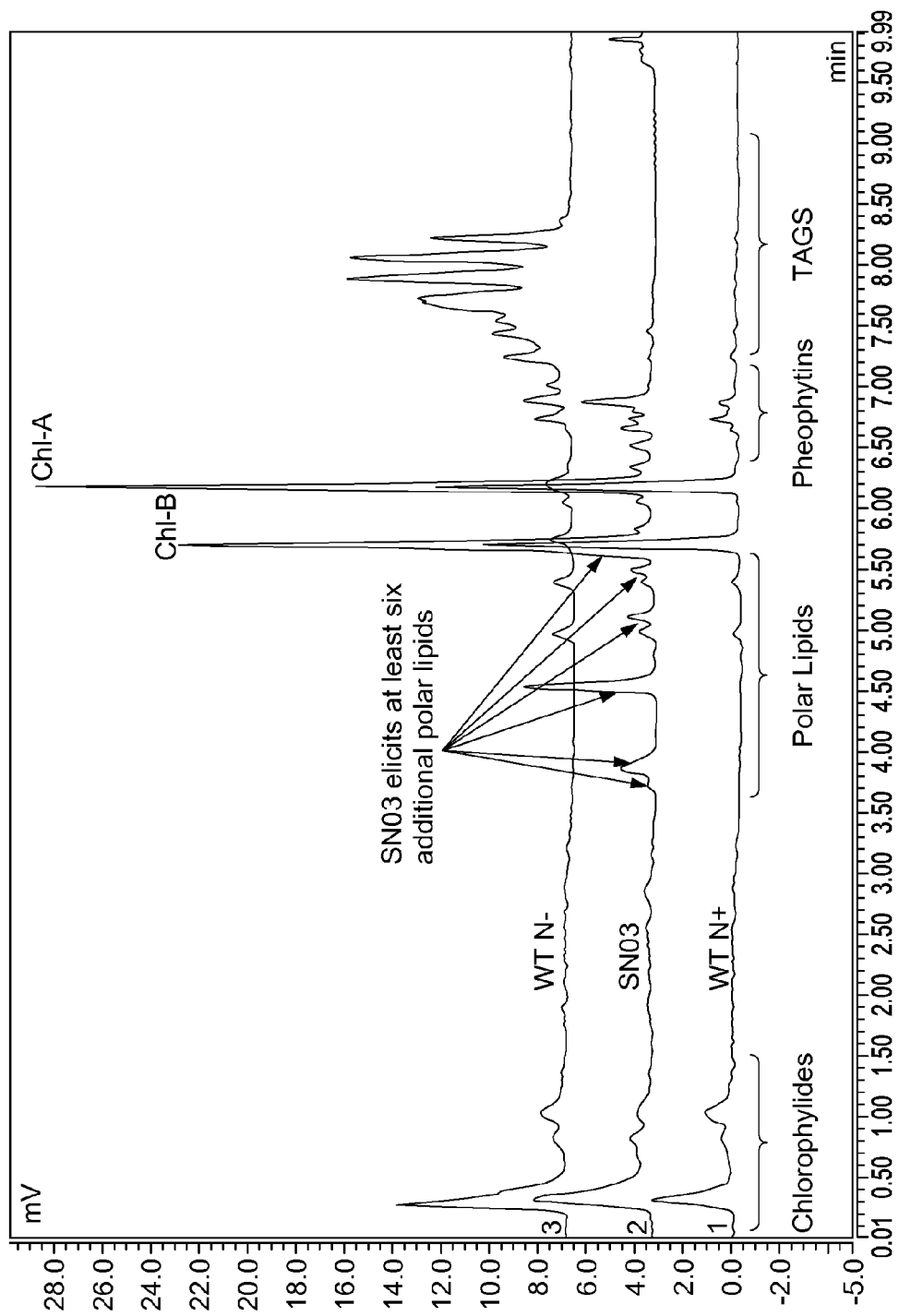
FIG. 27 shows HPLC data from MTBE extracted oil from *Chlamydomonas reinhardtii* strains overexpressing SN03 and MTBE extracted oil from wild type *Chlamydomonas reinhardtii* grown in the presence and absence of nitrogen.
Figure 28:
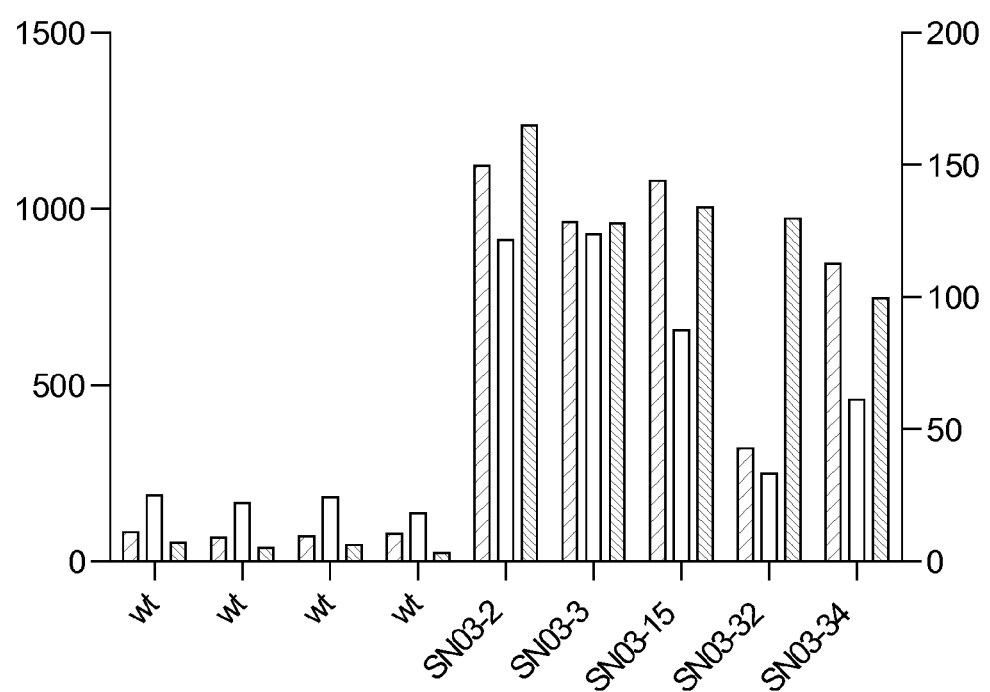
FIG. 28 shows Flow cytometry results of *Chlamydomonas reinhardtii* strains overexpressing SN03 confirming a high lipid phenotype using several different lipid dyes. The left hand column of each group represents staining with Bodipy. The middle column of each group represents staining with Nile Red. The right hand column of each group represents staining with LipidTOX Green. Wild type is *Chlamydomonas reinhardtii* replicates and SN03-2, -3, -15, -32, and -34 represent the various SN03 strains.
Figure 29:
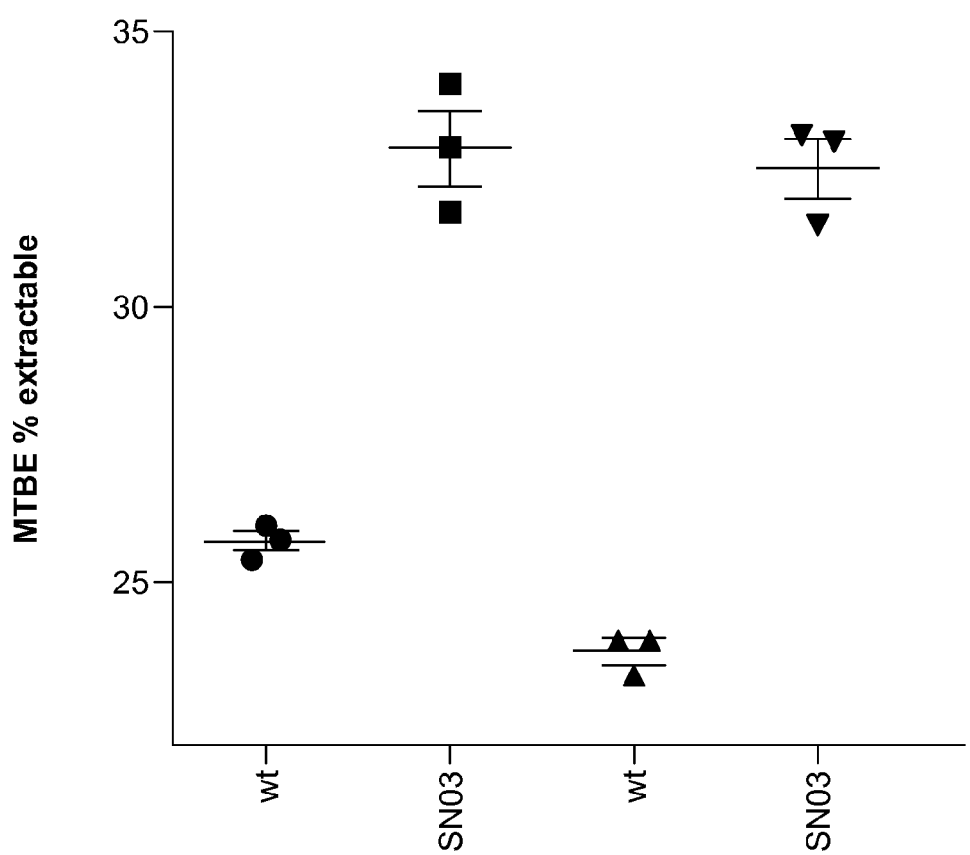
FIG. 29 shows *Chlamydomonas reinhardtii* strains overexpressing SN03 grown on TAP and MTBE extracted for lipid content.
Figure 30:
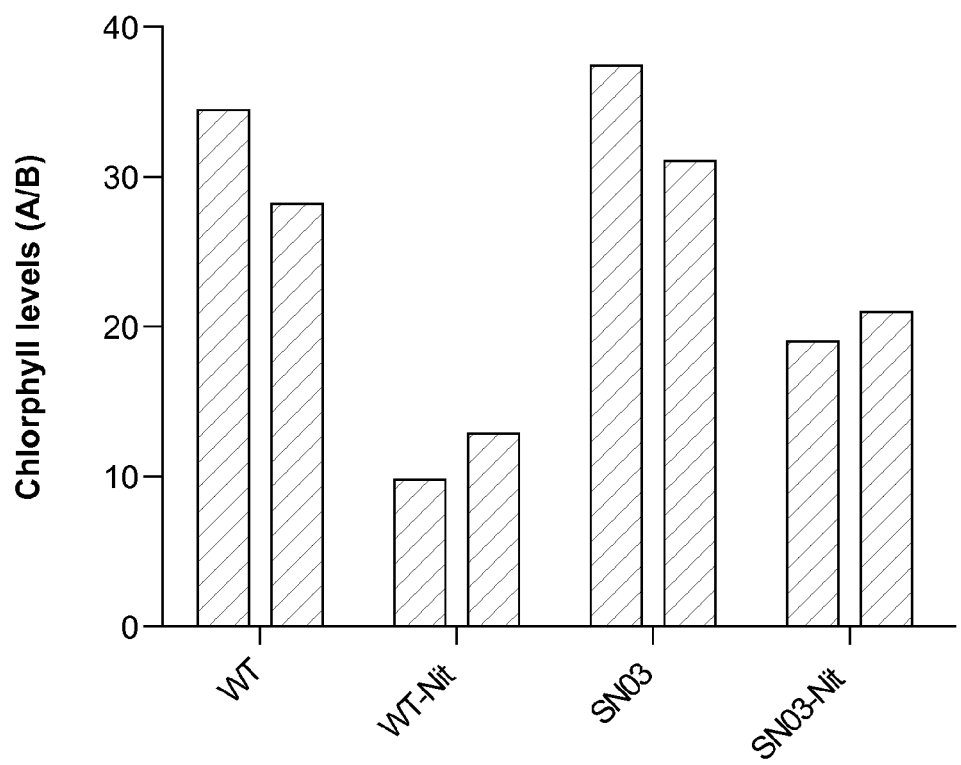
FIG. 30 shows chlorophyll levels in *Chlamydomonas reinhardtii* wild type and *Chlamydomonas reinhardtii* strains overexpressing SN03 in the presence and absence of nitrogen.
Figure 31:
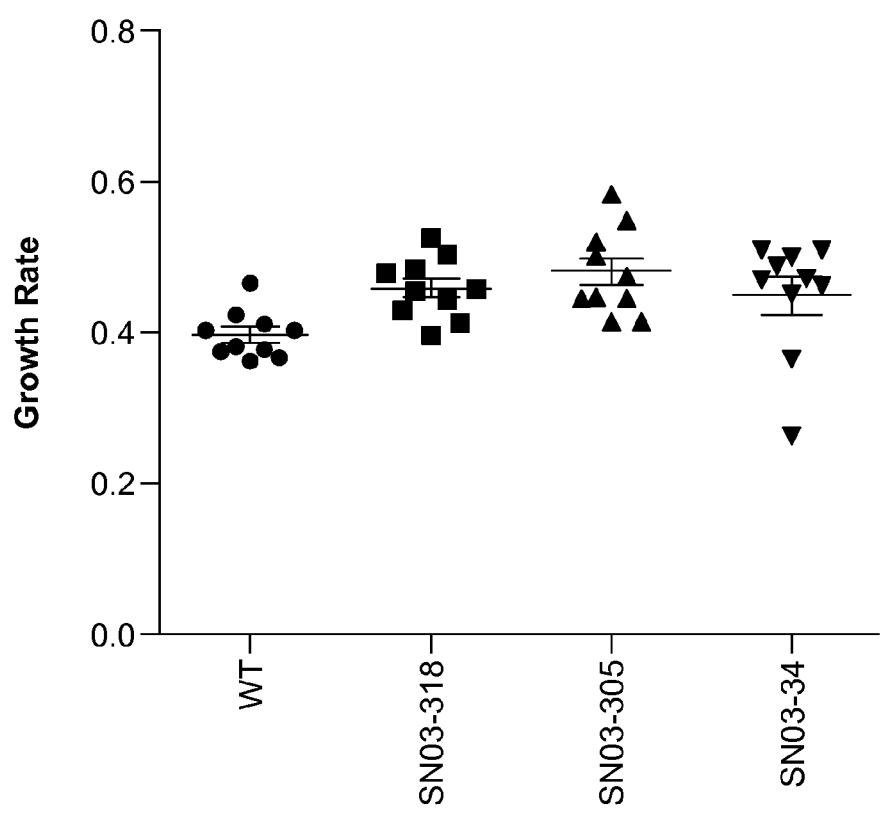
FIG. 31 shows growth rates of *Chlamydomonas reinhardtii* wild type and *Chlamydomonas reinhardtii* strains overexpressing SN03.

FIG. 27 is HPLC data showing the differences seen between MTBE extracted oil from an SN03 overexpression line and from *Chlamydomonas reinhardtii* wild type grown in the presence or absence of nitrogen. MTBE extracted oils were run on reverse-phase HPLC on a C18 column. Mobile phase was Acetonitrile/water/THF run over 10 minutes and flow rate of 0.9 mL/min. Detection was via an Evaporative Light Scattering Detector (ELSD). The three chromatograms are labeled with sample names for wild type grown in the presence of nitrogen (WT N+), an SN03 overexpression line (SN03), and wild type grown in the absence of nitrogen (WT N−). Groups of peaks representing classes of molecules are labeled at the bottom of the traces (Chlorphylides, Polar Lipids, Pheophytins and TAGs) and the chlorophyll-A (Chl-A) and chlorophyll B (Chl-B) peaks are labeled at top. The y-axis is the ELSD signal representing abundance and the x axis is HPLC column retention time (in minutes).

Figure 23A:
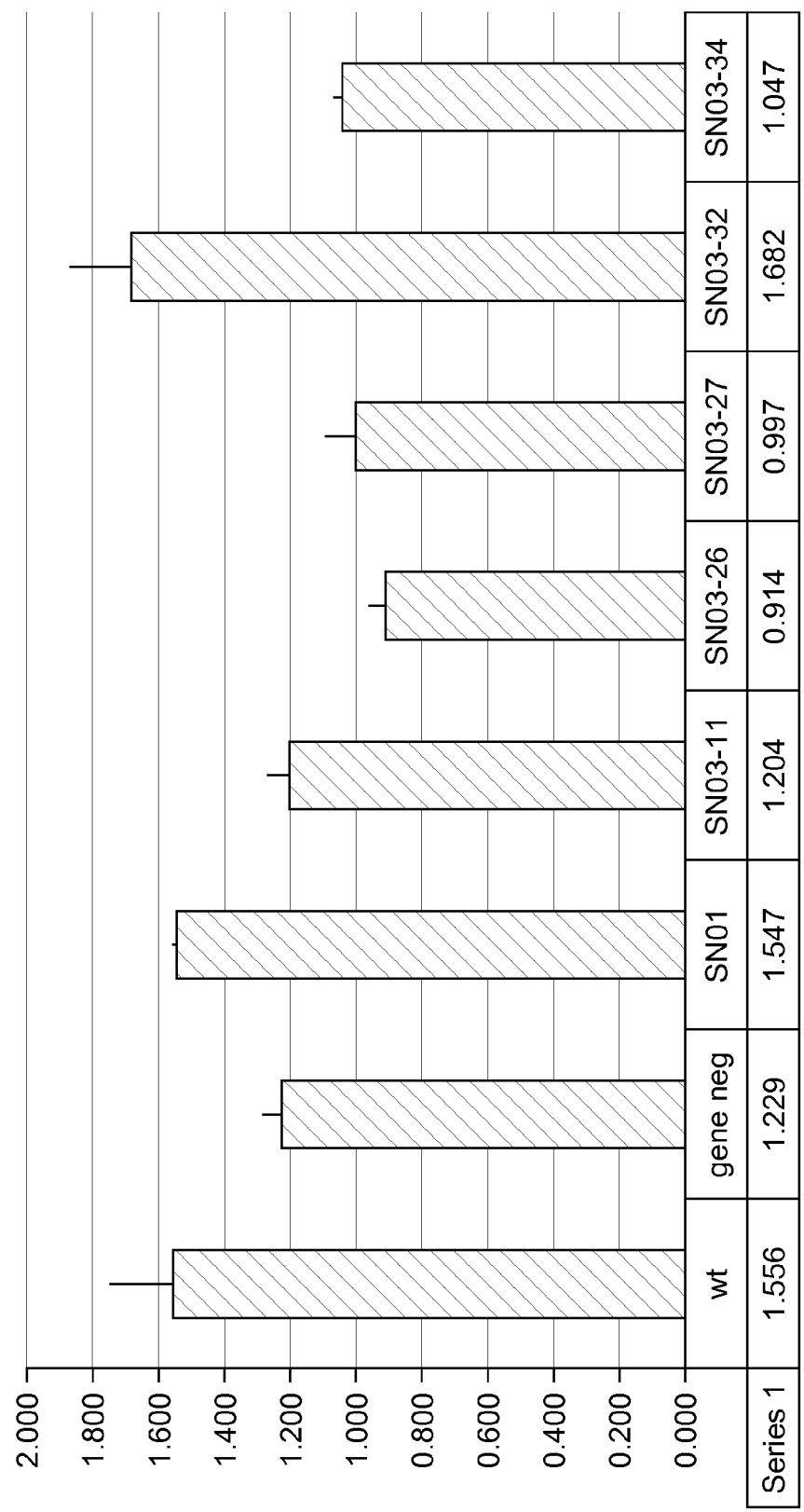
FIGS. 23A, 23B, and 23C show the growth rates of *Chlamydomonas reinhardtii* strains overexpressing SN03. Gene negative is a control *Chlamydomonas reinhardtii* transgenic line in which the SN03 open reading frame was truncated. Wild type is *Chlamydomonas reinhardtii*.
Figure 23B:
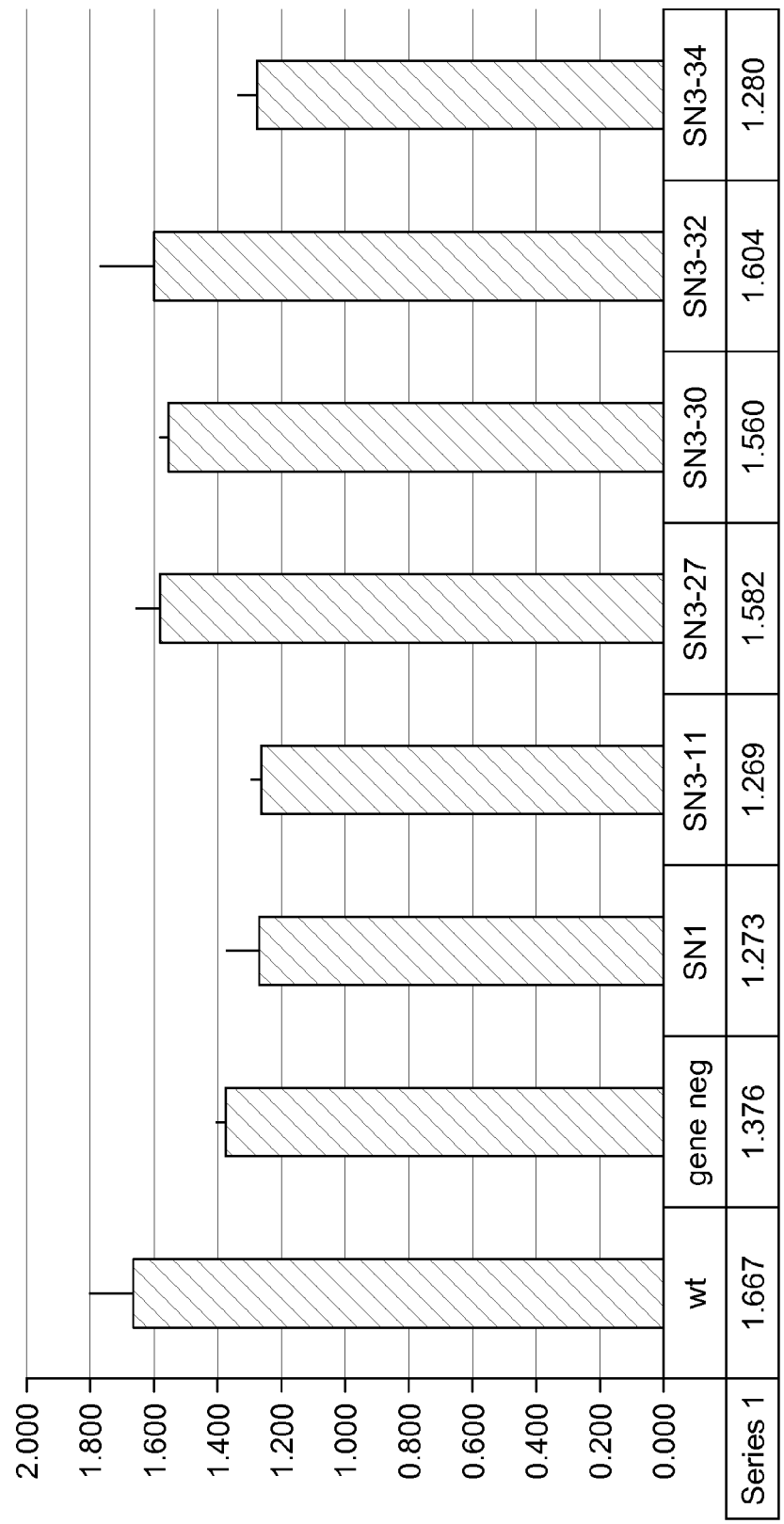
Figure 23C:
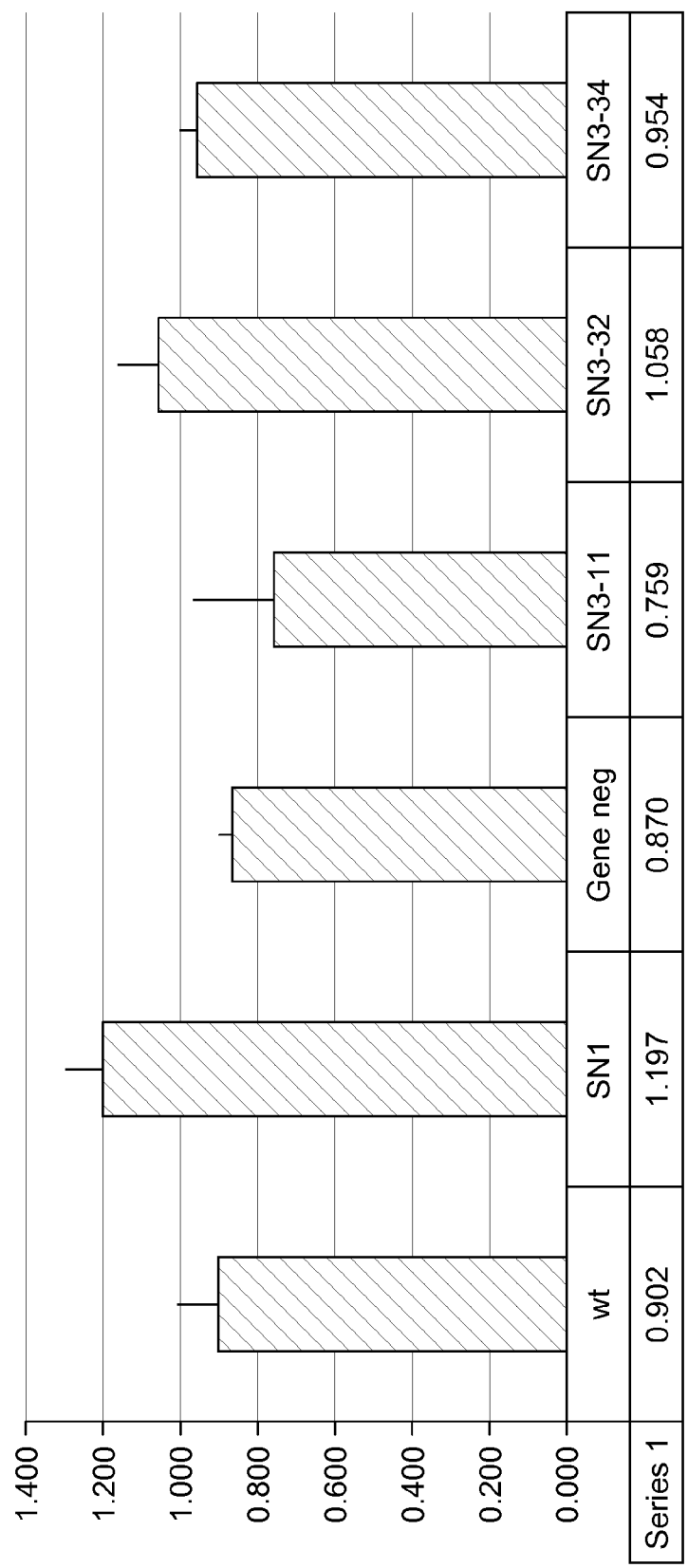

Growth rates in three SN03 over expression lines do not show notable differences relative to wild type, whether grown in TAP or HSM media. FIGS. 23A and B show growth rates of five different. SN03 over expression lines grown in TAP media in an air environment under constant light as compared to a transgenic line that does not contain an SN gene (gene neg), one SN01 transgenic line and wild type. FIG. 23C shows the growth rate of three SN03 over expression lines grown in HSM media in a 5% carbon dioxide in air environment, under constant light as compared to a transgenic line that does not contain an SN gene (gene neg), one SN01 transgenic line and wild type. Triplicates were grown for 4 to 5 days in 5 ml tubes on a rotating shaker. Optical density at 750 nm was taken 1-2 times a day and the growth rate was calculated as the slope of the linear portion of the growth curve based on the natural logarithm of the measured OD. This growth rate is shown on the y axis. The x axis represents the different lines used.

Figure 45B:
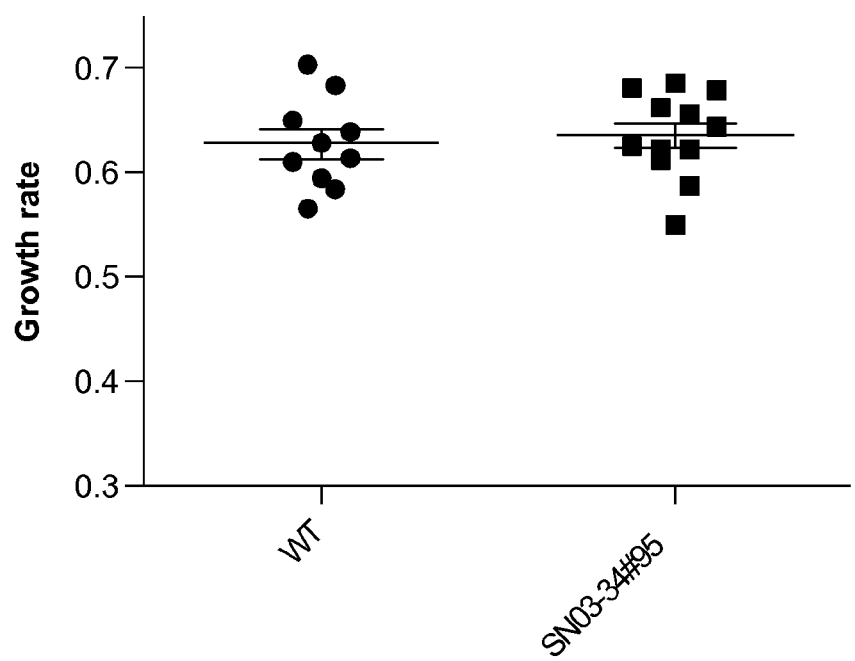
FIG. 45B shows the growth rates of wild-type *Chlamydomonas reinhardtii* and a *Chlamydomonas reinhardtii* strain overexpressing SN03 in HSM.

FIG. 45B is an additional example showing that growth rates in SN03 overexpression lines are comparable to wild type. Wild type *Chlamydomonas reinhardtii* and one SN03 over expression line were grown in 10-100 mL HSM media in a 5% carbon dioxide in air environment under constant light to mid log phase. Cells were diluted 1:100 info 12 to 24 wells of a 96-well plate containing 200 uL of HSM. The cells were grown in a 5% carbon dioxide in air environment under constant light to mid log phase. Optical density at 750 nm was taken 1-2 times a day and the growth rate was calculated as the slope of the linear portion of the growth curve based on the natural logarithm of the measured OD. This growth rate is shown on the y axis. The x axis represents the different strains used.

Figure 45C:
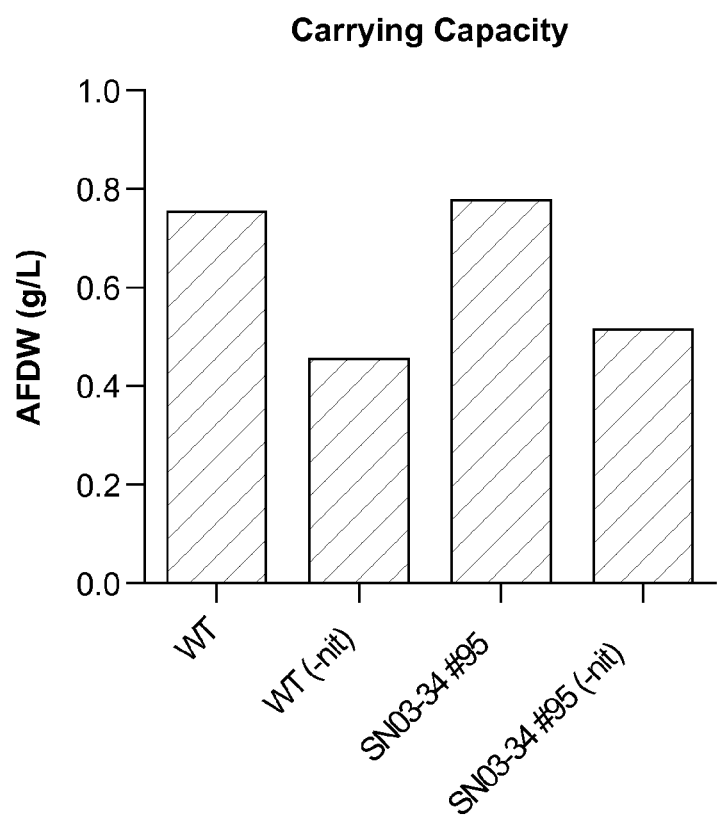
FIG. 45C shows the carrying capacity of wild-type *Chlamydomonas reinhardtii* grown in the presence and absence of nitrogen and an SN03 overexpression line grown in the presence and absence of nitrogen.

FIG. 45C shows that the carrying capacity of an SN03 overexpression line is similar to wild type. Wild-type *Chlamydomonas reinhardtii* cells and an SN03 overexpression line were grown in 0.5-2.0 L of HSM media in a 5% carbon dioxide in an air environment under constant light, until cells reached early log phase. The culture was centrifuged at 3000 to 5000×g for 5-10 minutes and one half of the culture was washed with 100-500 mL HSM, the other half with 100-500 mL HSM containing no nitrogen. After re-centrifigation, the two cultures were resuspended in a volume of media (HSM or HSM containing no nitrogen) equivalent to the starting culture volume. Cells were then grown in a 5% carbon dioxide in an air environment under constant light, until cells reached early stationary phase. 15 mL of culture was harvested by centrifugation and ash-free dry weight (AFDW) was determined. The AFDW in g/L is shown on the y-axis and the x-axis represents the lines used. Carrying capacity of the SN03 line is similar to wild type in the presence of nitrogen, and is reduced for both wild type and the SN03 overexpression line when grown in the absence of nitrogen.

Figure 45D:
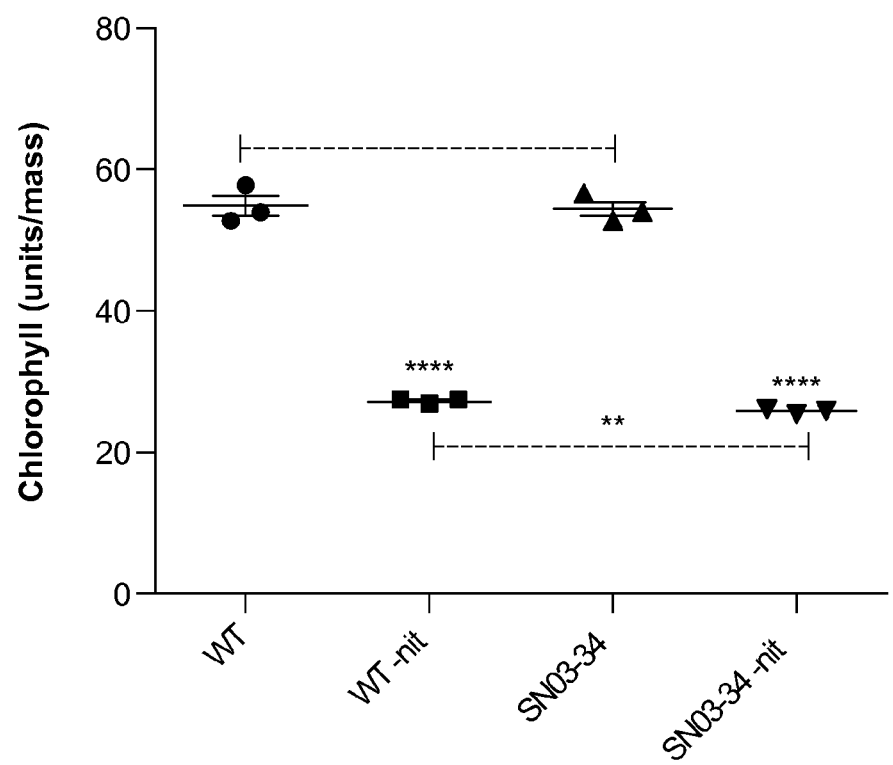
FIG. 45D shows the chlorophyll levels of wild-type *Chlamydomonas reinhardtii* grown in the presence and absence of nitrogen and an SN03 overexpression line grown in the presence and absence of nitrogen.

FIG. 45D shows that total chlorophyll levels are comparable in wild type and an SN03 overexpression line, and that both wild type and the SN03 overexpression line have decreased chlorophyll when grown in the absence of nitrogen. Wild-type *Chlamydomonas reinhardtii* cells and an SN03 overexpression line were grown in 50-500 mL of HSM media in a 5% carbon dioxide in an air environment under constant light, until cells reached early log phase. The culture was centrifuged at 3000 to 5000×g for 5-10 minutes and one half of the culture was washed with 10-100 mL HSM, the other half with 10-100 mL HSM containing no nitrogen. After re-centrifigation, the two cultures were resuspended in a volume of media (HSM or HSM containing no nitrogen) equivalent to the starting culture volume. Cells were then grown in a 5% carbon dioxide in an air environment under constant light, for an additional two days. 1-2 mL of culture was harvested by centrifugation. Cells were extracted in methanol and chlorophyll levels were determined spectroscopically as described in (LICHTENTHALER. Chlorophylls and Carotenoids: Pigments of Photosynthetic Biomembranes. Meth Enzymol (1987) vol. 148 pp. 350-382). Optical density (OD) of the culture at 750 nm was used to normalize to cell density. Chlorophyll levels are shown on the y axis and the x-axis represents the lines used.

Figure 24:
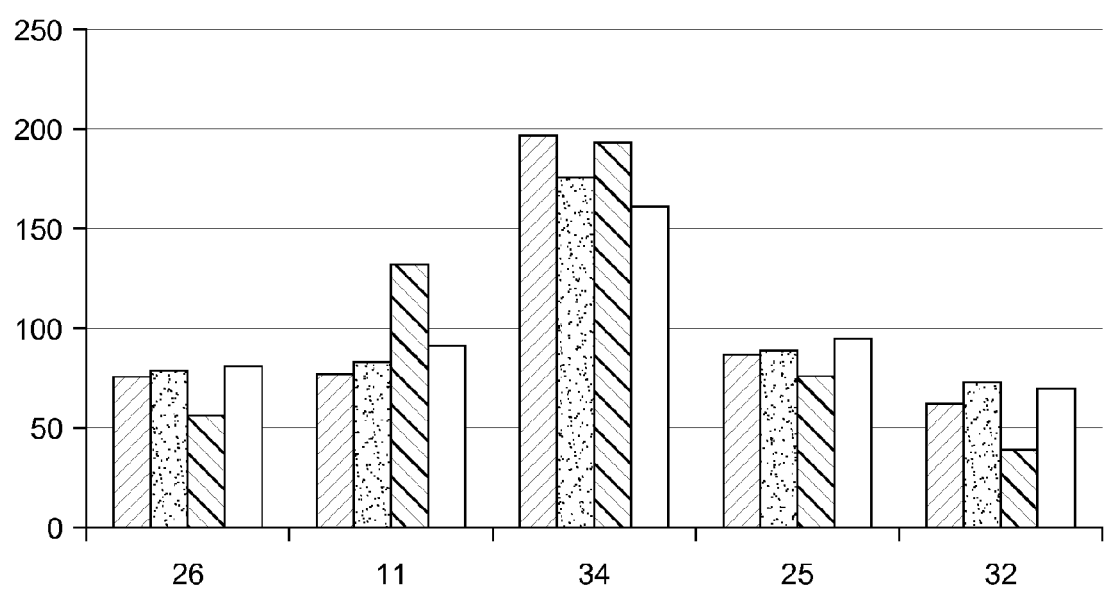
FIG. 24 shows SN03 RNA levels by qPCR in *Chlamydomonas reinhardtii* strains overexpressing SN03.

FIG. 24 shows that RNA is transcribed from the SN03 transgene. Wild-type *Chlamydomonas reinhardtii* cells as well as 5 SN03 overexpression lines were grown in 100-500 ml, of TAP media in an air environment under constant light, until cells reached early log phase. Total RNA was prepared from wild type and 5 SN03 overexpression lines. 0.25-1.0 ug of RNA was used for iScript cDNA synthesis (BioRad, USA) and standard qPCR using iQ SybrGreen (BioRad, USA) detection was performed. Relative RNA levels were determined by qPCR using primers that amplify the SN03 transgene (four separate primer sets: SN03-1,2,3,4, represented by the four columns of each set in FIG. 24 (SEQ ID NOs: 24-31). Standard qPCR using SybrGreen detection was performed using *Chlamydomonas reinhardtii* ribosomal protein L11 for normalization between samples. Primers specific for the L11 RNA are SEQ ID NOs: 22 and 23. RNA levels on the y axis are relative to the average SN03 expression (levels in each of the five lines are normalized to an average of 100). The transgene was codon optimized for nuclear expression in *Chlamydomonas reinhardtii* so the endogenous gene was not detected. There is some variation amongst the different transgenic lines, but overall the absolute level of expression is high across the board (based on subjective assessment of Ct value in qPCR). The x-axis represents the SN03 overexpression strains (i.e. 26=SN03−26, 11=SN03−11, etc).

Figure 44A:
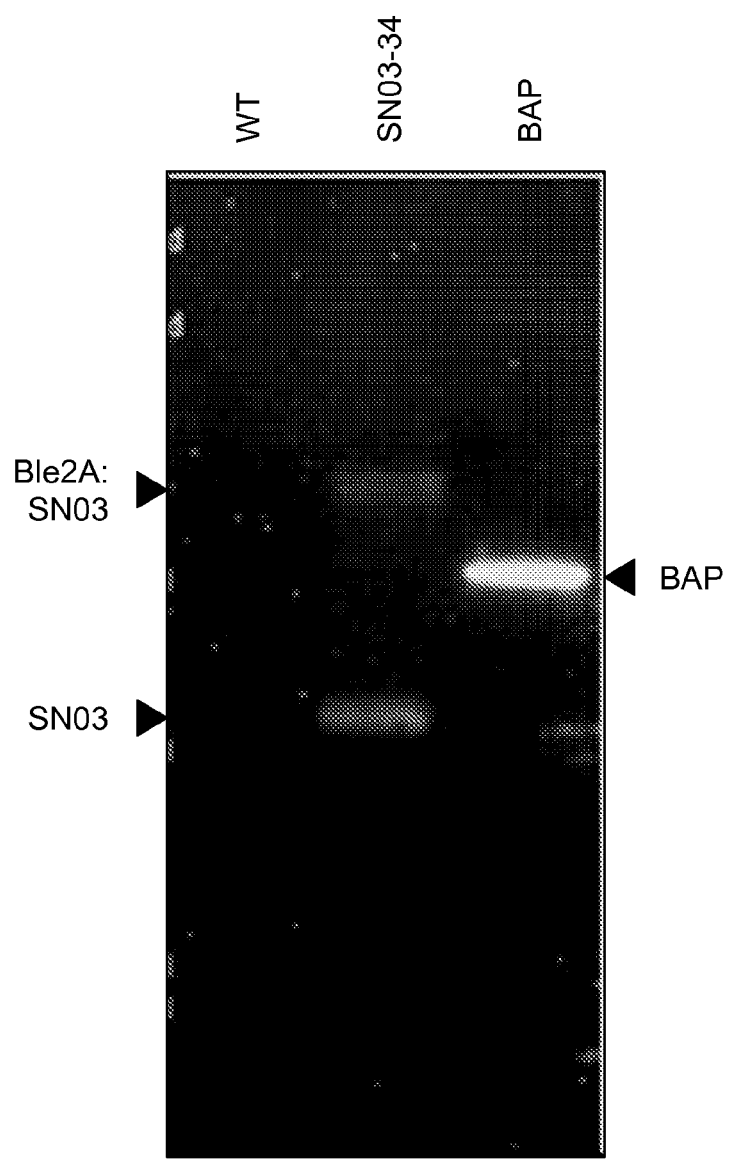
FIG. 44A shows SN03 protein expression levels in a *Chlamydomonas reinhardtii* SN03 overexpressing strain. Bacterial alkaline phosphatase (BAP) was used as a positive control.
Figure 44B:
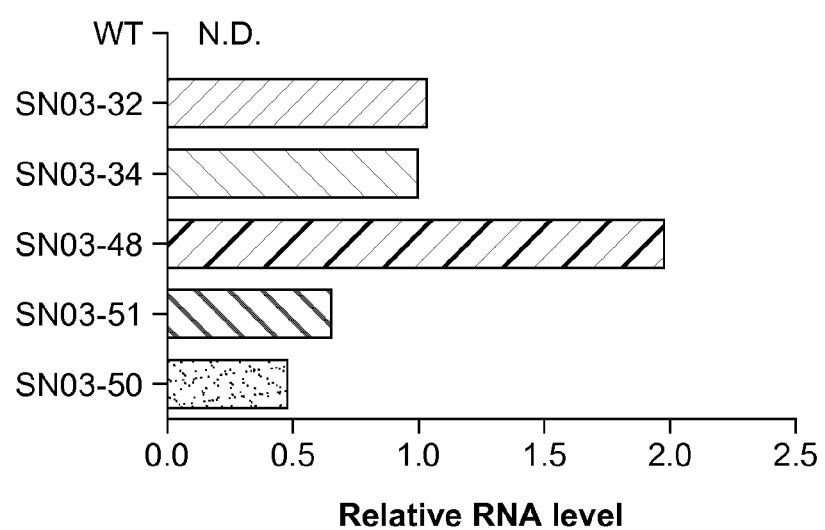
FIG. 44B shows SN03 RNA levels by qPCR in *Chlamydomonas reinhardtii* strains overexpressing SN03. Expression of SN03 RNA in wild-type *Chlamydomonas reinhardtii* was not detected (N.D.).

FIG. 44B is an additional example showing that RNA is transcribed from the SN03 transgene. Wild-type *Chlamydomonas reinhardtii* cells as well as 5 SN03 overexpression lines were grown in 100-500 mL of TAP media in an air environment under constant light, until cells reached early log phase. Total RNA was prepared from wild type and 5 SN03 overexpression lines. 0.25-1.0 ug of RNA was used for iScript cDNA synthesis (BioRad, USA) and standard qPCR using iQ SybrGreen (BioRad, USA) defection was performed. Relative RNA levels were determined by qPCR using primers that amplify the SN03 transgene. Standard qPCR using SybrGreen detection was performed using *Chlamydomonas reinhardtii* ribosomal protein L11 for normalization between samples. RNA levels on the x axis are relative to the expression of an average SN03 line (levels in each of the five lines are normalized to the level in line SN03-34 which was set to 1.0). The transgene was codon optimized for nuclear expression in *Chlamydomonas reinhardtii* so the endogenous gene was not detected. There is some variation amongst the different transgenic lines, but overall the absolute level of expression is high across the board (based on subjective assessment of Ct value in qPCR). The y-axis represents the SN03 overexpression strains.

Figure 25:
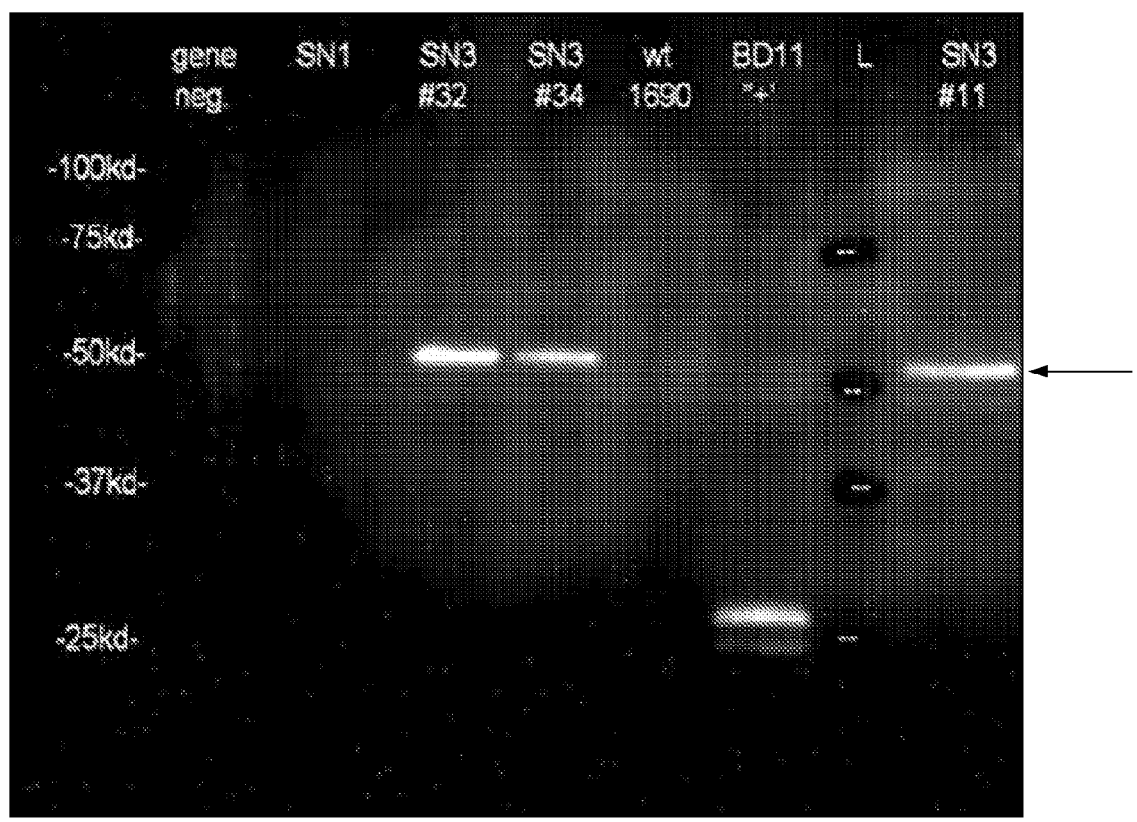
FIG. 25 shows SN03 protein expression levels in *Chlamydomonas reinhardtii* strains overexpressing SN03.

FIG. 25 shows that the SN03 protein (42 kDa) is detected in SN03 overexpression lines. Three of the SN03 transgenic lines along with a transgenic line that does not contain an SN gene (gene neg), one SN01 transgenic line and wild type were grown in 50-200 mL of TAP, centrifuged at 3000 to 5000×g for 5-10 minutes and prepared for Western immunoblotting. The SN03 protein has a FLAG-MAT Sag attached. A strain overexpressing BD11 (xylanase) with a FLAG-MAT tag attached was used as a positive control. An antibody against FLAG was used to detect the tagged proteins after the samples were pulled down with a nickel column, run on 8DS-PAGE and transferred to a nylon membrane. SN3 #32, SN3 #34, and SN3 #11show a band at the correct size for the SN03 protein. The BD11 positive control is detected as well.

FIG. 44A is an additional example showing that the SN03 protein (42 kDa) is detected in an SN03 overexpression line. One SN03 overexpression line along with wild type was grown, in 50-200 mL of TAP, centrifuged at 3000 to 5000×g for 5-10 minutes and prepared for Western immunoblotting. The SN03 protein has a FLAG-MAT tag attached. A bacterial alkaline phosphatase protein (BAP) with a FLAG-MAT tag attached was used as a positive control. An antibody against FLAG was used to detect the tagged proteins after the samples were pulled down with a nickel column, run on SDS-PAGE and transferred to a nylon membrane. The SN03-34 line shows two bands. The upper band is a fusion of bleomycin binding protein with SN03 protein connected by the 2A peptide. The lower band is the SN03 protein alone. The presence of the 2A mediated fusion protein has been described previously (Donnelly et al. Analysis of the aphthovirus 2A/2B polyprotein 'cleavage' mechanism indicates not a proteolytic reaction, but a novel translational effect: a putative ribosomal 'skip'. J Gen Virol (2001) vol. 82 (Pt 5) pp. 1013-25). The BAP positive control is detected as well.

Example 7

Formation of Lipid Bodies in SN03 Overexpression Lines

Figure 50:
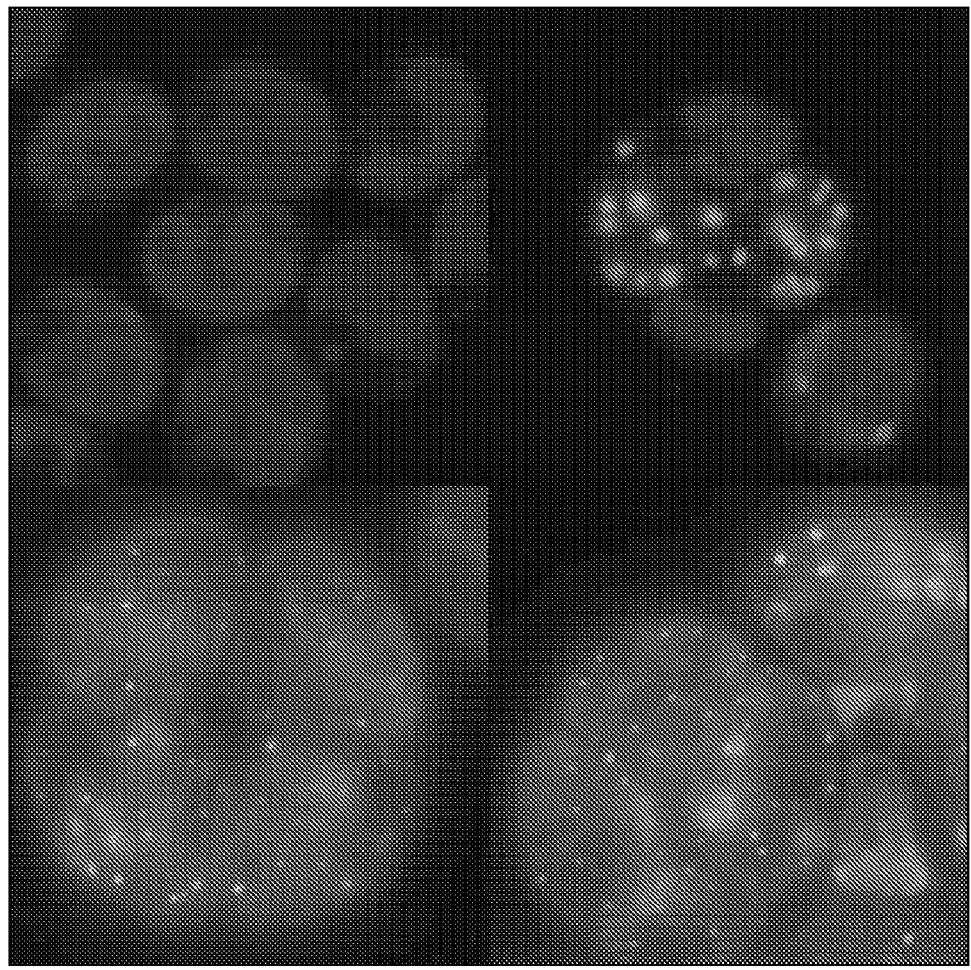
FIG. 50 shows the presence of lipid bodies in wild type *Chlamydomonas reinhardtii* in the absence of nitrogen, and in an SN03 overexpression line. Top left panel is wild type *Chlamydomonas reinhardtii* in the presence of nitrogen. Top right panel is wild type *Chlamydomonas reinhardtii* in the absence of nitrogen. Bottom panels are two images of an SN03 overexpression line. The dye used was Nile Red.

In this example, lipid body formation was investigated in *Chlamydomonas reinhardtii* overexpressing SN03. Wild-type *Chlamydomonas reinhardtii* cells were grown in 50-500 mL of TAP media in an air environment under constant light, until cells reached early log phase. The culture was centrifuged at 3000 to 5000×g for 5-10 minutes and one half of the culture was washed with 10-100 mL TAP, the other half with 10-100 mL TAP containing no nitrogen. After re-centrifugation, the two cultures were resuspended in a volume of media (TAP or TAP containing no nitrogen) equivalent to the starting culture volume. Cells were then grown in an air environment under constant light for an additional three days. Additionally, an SN03 overexpression line was grown in 50-500 mL of TAP media in an air environment under constant light, until cells reached early log phase. An aliquot of cells was stained with Nile Red and the cells were visualized with a fluorescent microscope with appropriate filters. FIG. 50 shows images from these cultures, with wild type in the presence of nitrogen in the upper left, wild type in the absence of nitrogen in the upper right, and two images of an SN03 overexpression line in the lower panels. Lipid bodies are seen as highly fluorescing dots within the wild type cells grown in the absence of nitrogen. These lipid bodies are not visible in wild type cells grown in the presence of nitrogen. Lipid bodies are also visible in the SN03 overexpression line.

Example 8

Characterization of SN03 Protein Sequence

The protein sequence of SN03 is shown in SEQ ID NO: 6. The version 3.0 annotation indicates a KOG (eukaryotic clusters of orthologous groups) annotation of CREB binding protein/P300 and related TAZ Zn-finger proteins, KOG ID: KOG1778, KOG Class: Transcription. A BLAST search (blastp against nr (non-redundant) database with default parameters) reveals percent sequence similarity to an arrestin domain protein. Additional searches against KOG suggest a Serine/threonine protein phosphatase 2A, regulatory subunit. In SEQ ID NO: 6 the sequence ARHAHLQQDAS-EQAPAHVLVVV (SEQ ID NO: 61) is a putative partial Zn-finger. The putative Zn finger domain is missing one of the four canonical His/Cys residues. In addition, amino acids 39-47 are a poly-Q region, suggesting a role in transcriptional regulation.

Mutations can be made to the SN03 sequence by mutating the histidine residues that make tip the putative Zn finger to an amino acid that cannot coordinate zinc, for example, threonine. These mutations could be made to each of the three histidines individually, in pairwise combinations, or to all three at once (for example, SEQ ID NOs: 16, 17 and 18). These mutated sequences can then be used in a transformation vector, for example, the vector shown in FIG. 37, and transformed into algae. The lipid accumulation phenotype of these transformed lines can then be analyzed in order to understand the role of this putative zinc finger in SN03 function.

Example 9

Identification of Homologous Protein(s) in Other Strains of Algae

As nitrogen starvation induces lipid increases in many species of algae, we expect, that, the SN03 protein is a conserved mechanism for inducing this increase in lipid and are therefore identifying homologous proteins in other algae strains. We are using bioinformatics tools such as BLAST to query the published genome and transcriptome sequences of algae and other organisms. We are also searching the published functional annotations of algae and other organisms for annotations similar to those for SN03. Candidate sequences are aligned using Clustal W to determine identity and similarity to SN03. These sequences will be expressed in SE0050 and, where applicable, in the species from which they are derived, to determine their effect on lipid accumulation.

Example 10

Transcriptomics Using Additional Algae Species Under Nitrogen Starved Conditions We are applying the approaches described in EXAMPLE 3 for SE0050 (*Chlamydomonas reinhardtii*) to the algae

*Scenedesmus dimorphus* (SE0004). We have generated a reference transcriptome by sequencing a normalized cDNA library using 454 technology. The library was generated from 10 different algae cultures all grown under varying treatments in order to maximize representation of all transcripts in the organism. We have sequenced RNA using Solexa technology from a set of SE0004 samples grown under five nitrogen starvation and replete conditions (1:nitrogen replete, exponential growth; 2:nitrogen replete; stationary growth; 3: nitrogen starvation, 6H; 4: nitrogen starvation, 24H; 5: nitrogen starvation, 48H). We have mapped this RNA-Seq data against the SE0004 reference transcriptome and are now identifying genes involved in the nitrogen starvation pathways, including the lipid increase pathway. These genes will be over expressed and/or knocked down in SE0050 and SE0004 to determine their effect on lipid accumulation.

Table 7 shows the details of the SE0004 reference transcriptome. Under the heading RAW is listed the number of 454 sequencing reads, their average length and the total amount of sequence generated. Under the Assembled heading is listed the number of sequence contigs, their average length and the total nucleotide bases represented by the assembled reference transcriptome.

TABLE 7

|  | RAW | | | Assembled | | |
| --- | --- | --- | --- | --- | --- | --- |
|  | # reads | average length | total bases | # contigs | average length | total bases |
| SE0004 Reference | 1,295,297 | 330 base pairs | 427.6 mega bases | 17,672 | 753 base pairs | 13.3 mega bases |

Example 11

Expression of a Set of Nitrogen Starvation Induced Genes in Other Algae Species

We are identifying genes from SE0004 that show an upregulated expression pattern under nitrogen starvation, as identified by RNA-Seq transcriptomics. These genes are being cloned into expression vectors specific for SE0004, which are then transformed into SE0004 algae. We are using SE0050 expression vectors (Ble2A, SEnuc357, and Arg7/2A) to over express in SE0050 (*Chlamydomonas*), genes from SE0004 identified as upregulated under nitrogen, starvation. We are using SE0004 vectors to over express SN03 from SE0050 in SE0004 strains.

Example 12

RNA Transcriptomics of SN03 Transgenic Lines

Nitrogen starvation results in gene expression changes in *Chlamydomonas*, some subset of which, is responsible for the increased lipid phenotype observed. SN03, as a putative transcription factor is upregulated upon nitrogen, starvation, and is likely involved in controlling some of the gene expression changes. Over expression of SN03 resulted in the increased lipid phenotype. Therefore, we are investigating the corresponding gene expression levels in transgenic cell lines over expressing SN03. We expect that the genes whose expression is modified by over expression of the SN03 transgene will be a subset of the genes affected by nitrogen starvation. This data will help us understand what downstream, pathways the SN03 protein is acting upon to produce more lipid.

Three *Chlamydomonas reinhardtii* lines overexpressing SN03 were grown in 0.5-2 L of HSM media in a 5% carbon dioxide in an air environment under constant light, until cells reached early log phase. 50-100 mL of the cells were harvested by centrifugation at 3000 to 5000×g for 5-10 minutes and RNA was purified from the cultures. This RNA was sequenced using standard Solexa methodologies (Sequensys, Inc, La Jolla, Calif.) for use in the RNA-Seq analysis method. Sequences were mapped to the JGI *Chlamydomonas reinhardtii* version 3.0 or version 4.0 transcriptome using Arraystar software (DNASTAR, USA). Presented below in Table 8 is the total number of Solexa 36 bp reads generated for each of the three RNA samples. Also shown for each sample are the number of those reads that successfully mapped to the *Chlamydomonas reinhardtii* transcriptome (total reads with mer hits) and the percentage of total hits mapped to the transcriptome.

TABLE 8

SN03-41

Total Sample reads: 17,308,430
Total reads with mer hits: 13,204,180
Percentage mapped: 76.3

TABLE 8-continued

SN03-48

Total Sample reads: 14,256,269
Total reads with mer hits: 10,669,978
Percentage mapped: 74.8

SN03-34

Total Sample reads: 11,885,067
Total reads with mer hits: 8,637,432
Percentage mapped: 72.7

Figure 36:
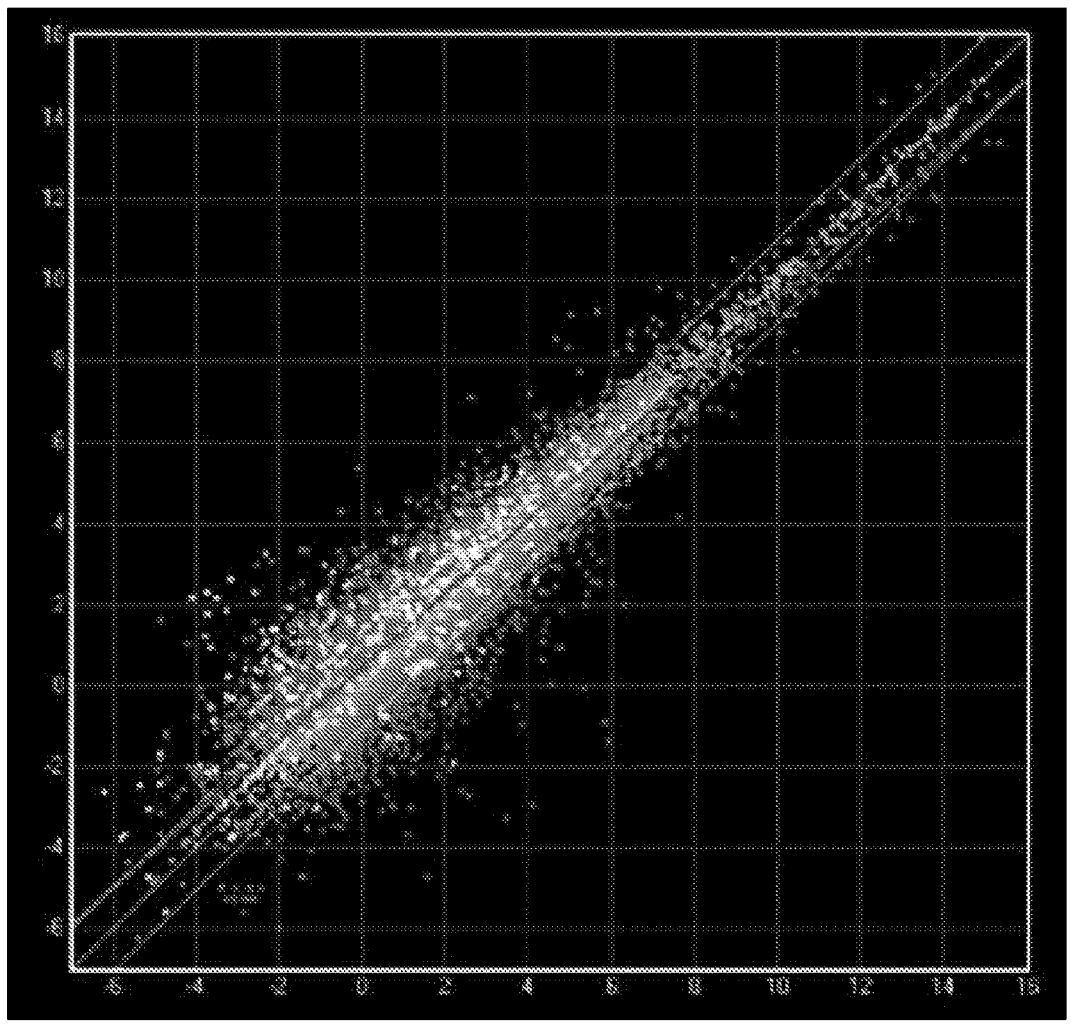
FIG. 36 shows all *Chlamydomonas reinhardtii* genes and their expression levels at a six hour time point generated by the method described in FIG. 13 in the presence and absence of nitrogen. White dots represent genes that are up regulated four fold or greater in a *Chlamydomonas reinhardtii* strain overexpressing SN03.

FIG. 36 shows a plot of all 16,000+ genes in SE0050 with expression levels from a different sample on each axis. Shown here are Exponential growth +Nitrogen (x-axis) versus Exponential growth 6H-Nitrogen (y-axis). Genes with no change in expression level are on the diagonal; those above the diagonal are upregulated after 6 hours of nitrogen starvation and those below the diagonal are down regulated after 6 hours of nitrogen starvation. The white data points represent at least 4-fold increase in expression in one SN03 overexpression line relative to wild type. Many of the genes that are upregulated in the SN03 overexpression line are also upregulated after 6 hours of nitrogen starvation (shown by the white dots above the diagonal). However, there are some genes that are up regulated in the SN03 overexpression line while also down regulated after 6 hours of nitrogen starvation (shown by white dots below the diagonal).

Figure 37:
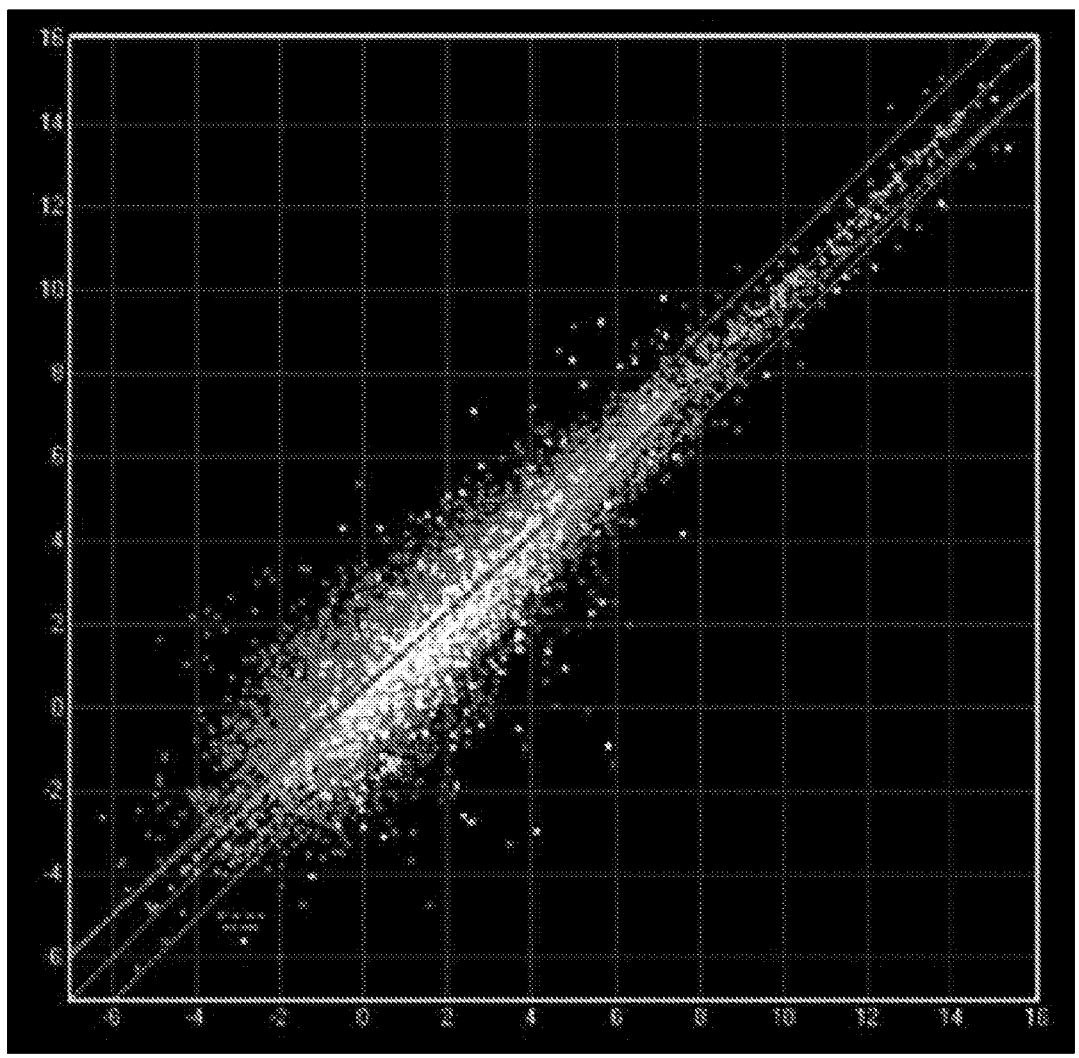
FIG. 37 shows all *Chlamydomonas reinhardtii* genes and their expression levels at a six hour time point generated by the method described in FIG. 13 in the presence and absence of nitrogen. White dots represent genes that are down regulated four fold or greater in a *Chlamydomonas reinhardtii* strain overexpressing SN03.

FIG. 37 shows a plot of all 16,000+ genes in SE0050 with expression levels from a different sample on each axis. Shown here are Exponential growth +Nitrogen (x-axis) versus Exponential growth 6H −Nitrogen (y-axis). Genes with no change in expression level are on the diagonal; those above the diagonal are upregulated after 6 hours of nitrogen starvation and those below the diagonal are down regulated after 6 hours of nitrogen starvation. The white data points represent at least 4-fold decrease in expression in one SN03 overexpression line relative to wild type. Many of the genes that are down regulated in the SN03 overexpression line are also down regulated after 6 hours of nitrogen starvation (shown by the white dots below the diagonal). However, there are some genes that are down regulated in the SN03 overexpression line while also up regulated after 6 hours of nitrogen starvation (shown by white dots above the diagonal).

Figure 38:
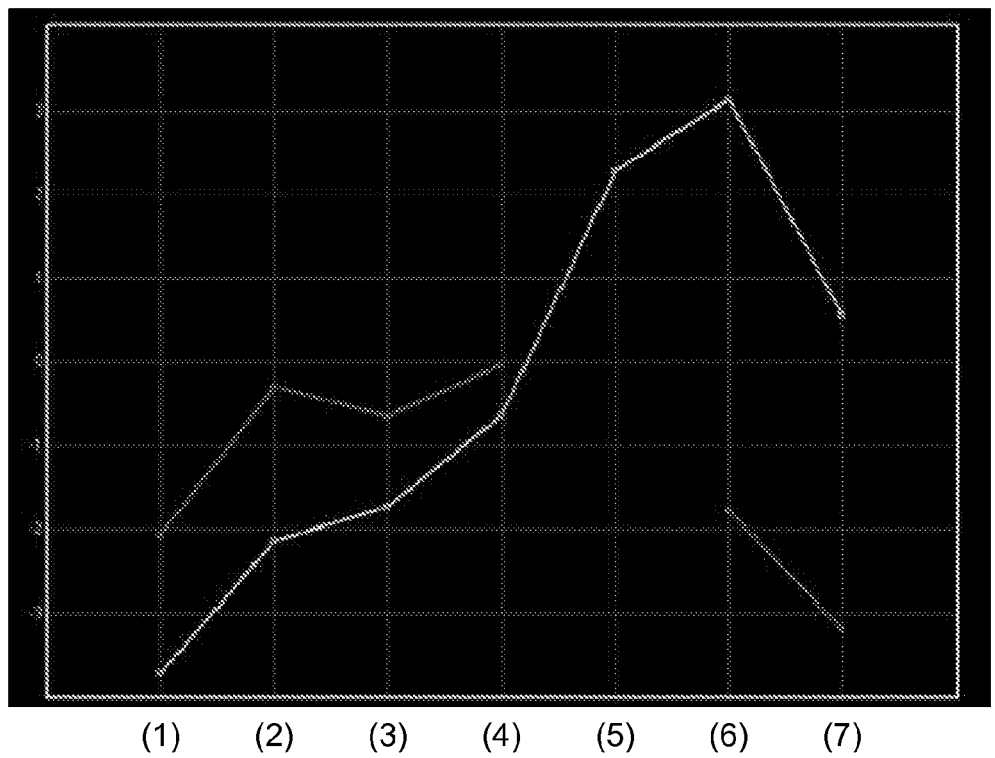
FIG. 38 shows expression levels of endogenous and transgenic SN03 RNA in wild type *Chlamydomonas reinhardtii* over a time course of nitrogen starvation and expression levels of endogenous and transgenic SN03 RNA in SN03 overexpressing strains. Transgenic (Ble) SN03 is represented by the continuous line and endogenous SN03 is represented by the broken line.

FIG. 38 shows RNA levels for the endogenous SN03 transcript and the transgenic SN03 transcript. Expression level (shown on y axis in log 2 scale) was determined by the DNASTAR Arraystar software from the RNA-Seq data on a time course of nitrogen starved wild type *Chlamydomonas reinhardtii* and three SN03 overexpression lines (strains and conditions indicated on x axis). Because the endogenous and transgenic SN03 sequences are similar but not identical (due to codon optimization), the Arraystar software cannot assign reads to the transcripts with 100% accuracy. The transgenic SN03 transcript is not present in the wild type samples as shown by the low expression levels indicated for the wild type samples and the high levels in the SN03 overexpression lines. Induction of endogenous SN03 expression upon nitrogen starvation is demonstrated here in the nitrogen starved wild type samples.

Figure 39:
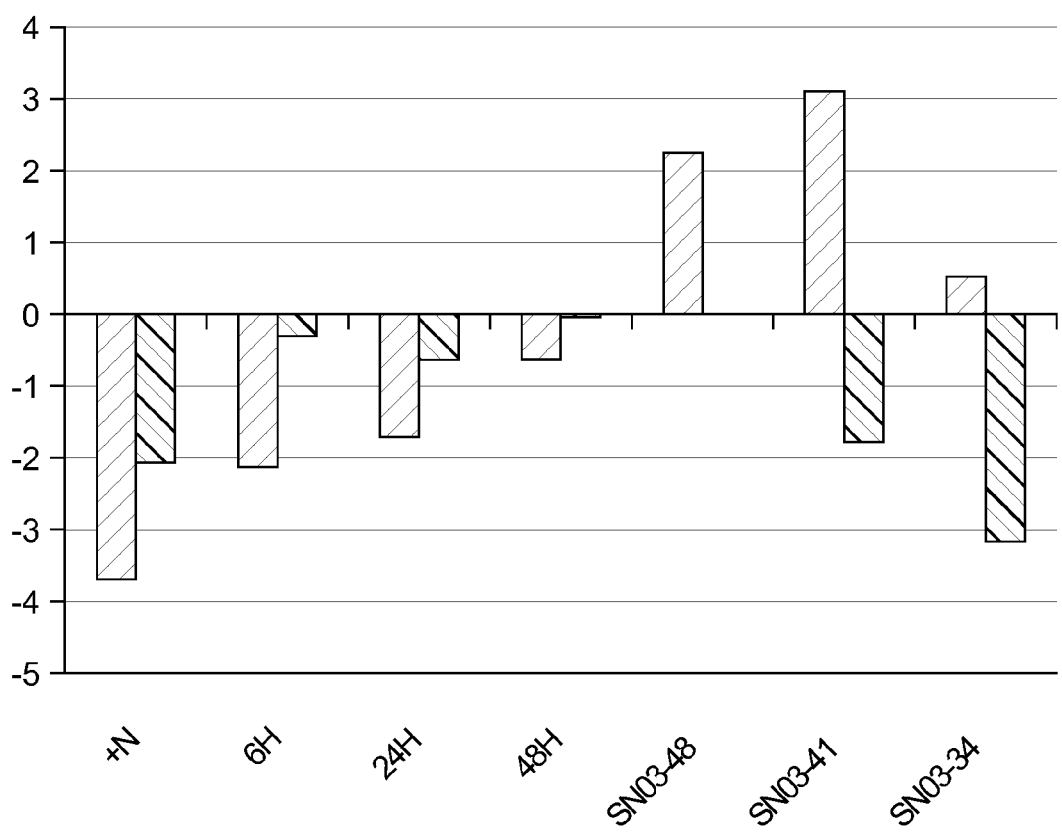
FIG. 39 shows expression levels of endogenous and transgenic SN03 RNA in wild type *Chlamydomonas reinhardtii* over a time course of nitrogen starvation and expression levels of endogenous and transgenic SN03 RNA in SN03 overexpressing strains. The left hand column of each pair represents Transgenic (Ble) SN03 and the right hand column of each pair represents endogenous SN03.

FIG. 39 shows RNA levels for the endogenous SN03 transcript and the transgenic SN03 transcript, as in FIG. 38. The y axis shows the RNA expression level (log 2 scale) and each set of two columns represents the strains and conditions used. The left column in each set is the expression level of the transgenic SN03 RNA and the right column in each set is the expression level of the endogenous SN03 RNA. The transgenic SN03 transcript is not present in the wild type samples as shown by the low expression levels indicated for the wild type samples and the high levels in the SN03 overexpression lines. Induction of endogenous SN03 expression upon nitrogen starvation is demonstrated here in the nitrogen starved wild type samples.

This RNA-Seq data is used to identify candidate gene lists for further understanding the impact of SN03 overexpression and for additional target gene identification. Solexa sequenced RNA from a nitrogen starved time course of wild type *Chlamydomonas reinhardtii* and from three SN03 overexpression lines was mapped to the JGI *Chlamydomonas reinhardtii* transcriptome using DNASTAR Arraystar.

Using Arraystar software, sets of genes with relevant expression patterns were identified, 235 genes were identified that were at least 4 fold up regulated in one or more nitrogen starvation sample as well as at least 4 fold up regulated in at least one SN03 overexpression strain, 191 genes were identified that were at least 4 fold down regulated in one or more nitrogen starvation sample as well as at least 4 fold down regulated in at least one SN03 overexpression strain. 134 genes were identified that were at least 4 fold up regulated in one or more nitrogen starvation sample as well as at least 4 fold down regulated in at least one SN03 overexpression strain. 38 genes were identified that were at least 4 fold down regulated in one or more nitrogen starvation sample as well as at least 4 fold up regulated in at least one SN03 overexpression strain.

Figure 40:
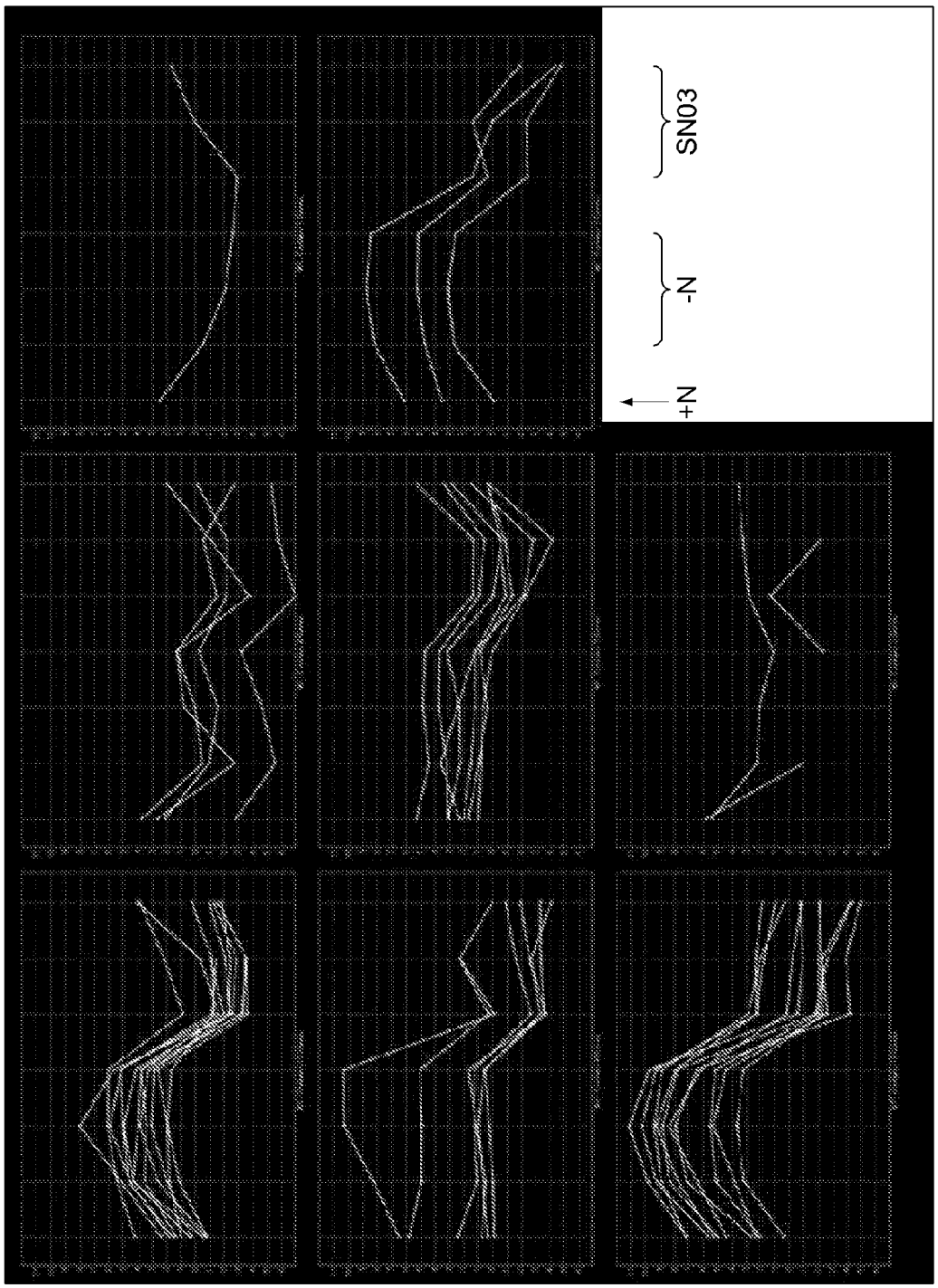
FIG. 40 shows gene expression levels in wild type *Chlamydomonas reinhardtii* over a time course of nitrogen starvation and gene expression levels in SN03 overexpressing strains. Each line represents a different gene. The genes shown are upregulated in nitrogen starvation and down regulated in SN03 overexpressing strains.

An additional way to analyze the RNA-Seq data is shown in FIG. 40. This figure shows the dynamics of gene expression, during nitrogen starvation (Exponential +nitrogen and 6H, 24H, 48H −nitrogen) and in three SN03 overexpression strains. Each Sine represents one gene, with the y axis in each case being the level of expression and the x axis representing the 7 sequenced samples. The eight graphs represent genes that have similar expression patterns across the conditions represented by the 7 samples. Most of the graphs here represent sets of genes that are upregulated by nitrogen starvation but that are not upregulated by SN03 overexpression.

As examples of the genes that can be identified by this approach, at least five genes with a KOG functional annotation of Histone protein (either Histone H2B or Histone H3 and H4) are up and/or down regulated by both nitrogen starvation and SN03 overexpression. These are examples of expression patterns derived from SN03 overexpression lines that can be used to understand the nitrogen starvation pathways. These genes and their expression patterns are as follows: JGI protein ID 97703: 9 fold up in nitrogen starvation, 82 fold up in SN03 overexpression line; JGI protein ID 170323: 89 fold up in nitrogen starvation, 40 fold up in SN03 overexpression line; JGI protein ID 115268: 5 fold down in nitrogen starvation, 45 fold down in SN03 overexpression line; JGI protein ID 167094: 79 fold down in nitrogen starvation, 22 fold down in SN03 overexpression line; and JGI protein ID 100008: 4 fold up in nitrogen starvation, 9 fold down in SN03 overexpression line.

Example 13

Use of SN03 DNA, RNA or Protein to Identify Interacting Molecules or Other Genes Involved in the Nitrogen Starvation Pathways This example describes a method to use the DNA or RNA encoding SN03 or the SN03 protein to identify other DNAs, RNAs or proteins and/or their corresponding genes that are involved in the nitrogen starvation pathways, whose knowledge and use can lead to manipulations of the lipid accumulation and profile in algae.

One method would be to use the SN03 protein expressed in vitro or from cell culture to probe high density DNA microarrays, as in (Berger et al. Compact, universal DNA microarrays to comprehensively determine transcription-factor binding site specificities. Nature Biotechnology (2006) vol. 24 (11) pp. 1429-35). This could be used to identify DNA binding sites that could then be mapped to the genome to indicate genes whose transcription is controlled by the SN03 protein. These genes could then be used to understand and modify the phenotypes caused by nitrogen starvation.

Another method would be to use the SN03 protein in a two-hybrid assay, as in (for example, as described in Miller and Stagljar. Using the yeast two-hybrid system to identify interacting proteins. Methods Mol Biol (2004) vol. 261 pp. 247-62). The SN03 protein can be used in this yeast system to identify other algal proteins that bind to the SN03 protein. The genes for these proteins could then be used to understand and modify the phenotypes caused by nitrogen starvation.

Example 14

Overexpression of SN03 in Other Algae Species

This example describes a method to overexpress SN03 in other algae species in order to change the lipid accumulation and/or lipid profile in another algal species. The SN03 ORF can be cloned into a transformation vector, for example, as described in FIGS. 6, 7, 18, 34 and 35 and the protein expressed in other algal species. Alternatively, a transformation vector with nucleotide sequence elements (for example, promoter, terminator, UTR) specific to the host algae species can be used with the SN03 ORF. This alternate vector can be transformed into algae species such as *Dunaliella* sp. *Scenedesmus* sp. or *Nannochloropsis* sp. Overexpression of SN03 in these species can be used to produce a lipid accumulation and/or lipid profile phenotype.

Example 15

Identification and Characterization of the Endogenous SN03 RNA from *Chlamydomonas reinhardtii*

In this example, the endogenously expressed version of SN03 was obtained from wild type *Chlamydomonas reinhardtii*. This sequence was then used to create *Chlamydomonas reinhardtii* lines overexpressing the endogenous SN03 protein. RNA from *Chlamydomonas reinhardtii* wild-type strain CC-1690 21 gr mt+ was used to produce cDNA via reverse transcription, using primers (SEQ ID NOs: 32 and 33) specific for the JGI annotated SN03 3' untranslated region. Standard PGR protocols were followed using multiple sets of primers designed against the 5' and 3' untranslated regions of the JGI annotated SN03 RNA sequence SEQ ID NOs:34-37. PCR products representing the endogenous SN03 ORF with portions of the 5" and 3' UTR were cloned using a TOPO-TA kit (Invitrogen). Individual clones were isolated and sequenced. Sequences were aligned and a consensus for the ORF of the endogenous SN03 was obtained (SEQ ID NO: 8).

FIG. 49 shows a ClustalW alignment of the protein sequence of SN03 as determined by the JGI *Chlamydomonas reinhardtii* genome version 3.0 (listed as JGI SN03) SEQ ID NO: 6 and the protein sequence of the cloned and sequenced endogenous SN03 (listed as Endo SN03) SEQ ID NO: 14. The additional amino acids present in the endogenous SN03 sequence that, are not present, in the JGI SN03 are indicated in the figure by dashes in the JGI SN03 sequence.

Two transformation vectors were constructed. In the first, the ORF for the endogenous SN03 was codon optimized (SN03C, SEQ ID NO: 12) using a *Chlamydomonas reinhardtii* codon usage table (Table A). This sequence was synthesized with an XhoI site in place of the ATG and an AgeI site in place of the stop codon. A nucleotide sequence encoding a FLAG-MAT tag protein sequence, flanked by an AgeI site on the 5'end of the tag and an XmaI site on the 3" end of the tag, was cloned 3" of the ORF, with a stop codon 3' of the tag sequence and XmaI/AgeI site, resulting in the sequence of SEQ ID NO: 13. In the second, standard PCR was used to place an XhoI site in place of the ATG and a AgeI site in place of the stop codon of the endogenous sequence. A nucleotide sequence encoding a FLAG-MAT tag protein sequence, flanked by an AgeI site on the 5'end of the tag and an XmaI site on the 3' end of the tag, was cloned 3' of the ORF, with a stop codon 3' of the tag sequence and XmaI/AgeI site (SN03E, SEQ ID NO: 10). These two DNA constructs for the endogenous SN03 and the codon optimized endogenous SN03 were individually cloned into nuclear overexpression vector Ble2A (as shown in FIG. 34). These two vectors were individually transformed into SE0050 and overexpression lines were isolated.

Transformation DNA was prepared by digesting the Ble2A-SN vector with the restriction enzyme KpnI, XbaI or PsiI followed by heat inactivation of the enzyme. For these experiments, all transformations were carried out on *C. reinhardtii* cc1690 (mt+). Cells were grown and transformed via electroporation. Cells were grown to mid-log phase (approximately $2-6\times10^6$ cells/ml) in TAP media. Cells were spun down at between 2000×g and 5000×g for 5 min. The supernatant was removed and the cells were resuspended in TAP media+40 mM sucrose. 250-1000 ng (in 1-5 μL $H_2O$ of transformation DNA was mixed with 250 μL of $3\times10^8$ cells/mL on ice and transferred to 0.4 cm electroporation cuvettes. Electroporation was performed with the capacitance set at 25 uF, the voltage at 800 V to deliver 2000 V/cm resulting in a time constant of approximately 10-14 ms. Following electroporation, the cuvette was returned to room temperature for 5-20 min. For each transformation, cells were transferred to 10 ml of TAP media+40 mM sucrose and allowed to recover at room temperature for 12-16 hours with continuous shaking. Cells were then harvested by centrifugation at between 2000×g and 5000×g, the supernatant was discarded, and the pellet was resuspended in 0.5 ml TAP media+40 mM sucrose. The resuspended cells were then plated on solid TAP media+20 μg/mL zeocin. As a result, overexpression lines for SN03C and SN03E were created.

Figure 32:
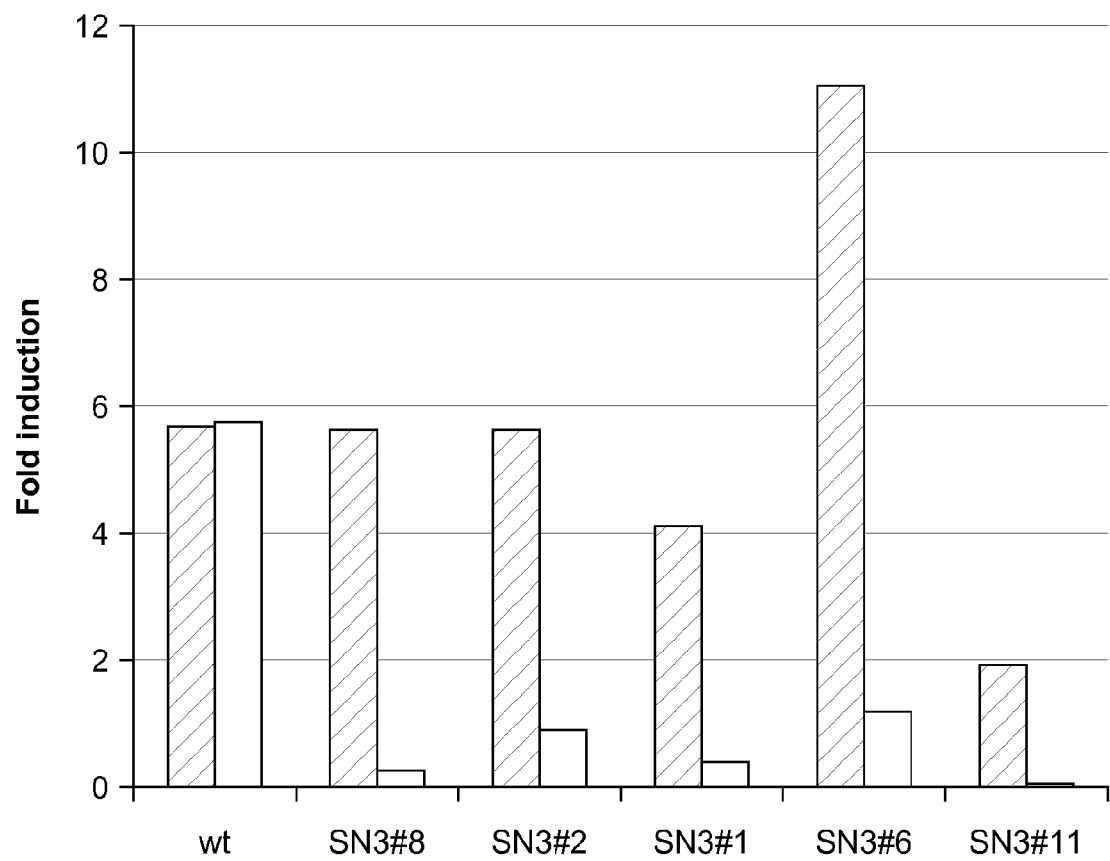
FIG. 32 shows induction of endogenous SN03 and stress-induced protein kinase (PK) upon nitrogen starvation in *Chlamydomonas reinhardtii* wild type and *Chlamydomonas reinhardtii* expressing a miRNA specific to SN03 (knock-down). The left hand column of each group represents a stressed induced PK and the right hand column of each group represents endogenous SN03 (147817). The x-axis represents the various knock-down lines.
Figure 33:
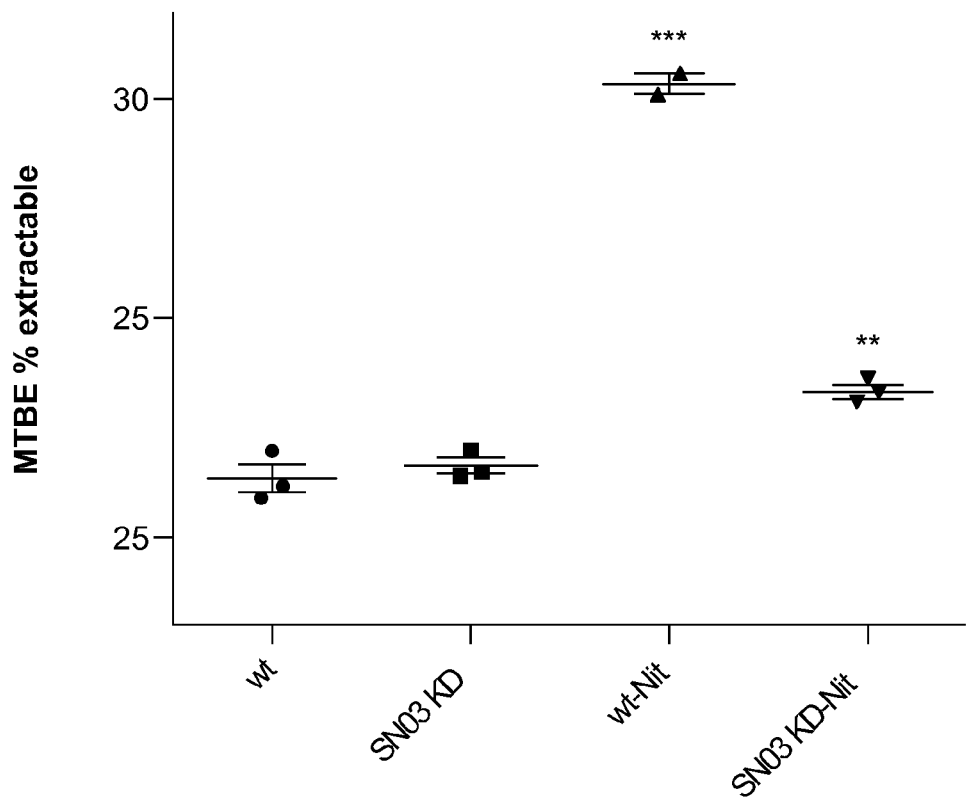
FIG. 33 shows MTBE extraction, of wild type *Chlamydomonas reinhardtii* and a *Chlamydomonas reinhardtii* strain expressing a miRNA specific to SN03 (knock-down). The two strains are grown, in the presence and absence of nitrogen. The knock-down strain demonstrates that SN03 is necessary for lipid accumulation upon nitrogen starvation.
Figure 47A:
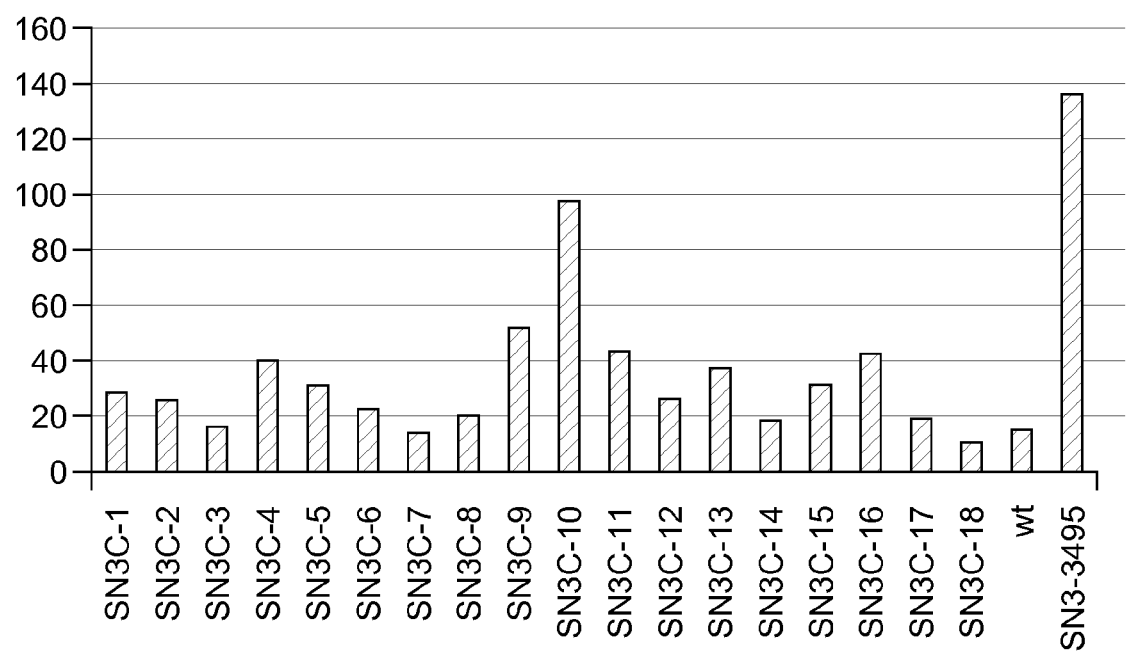
FIG. 47A shows flow cytometry (Guava) results using Nile Red for wild-type *Chlamydomonas reinhardtii* and several SN03 overexpressing strains. "C" represents the codon-optimized endogenous SN03 sequence (SEQ ID NO: 13) from *Chlamydomonas reinhardtii* with a nucleotide sequence coding for a FLAG-MAT tag at the 3' end.
Figure 47B:
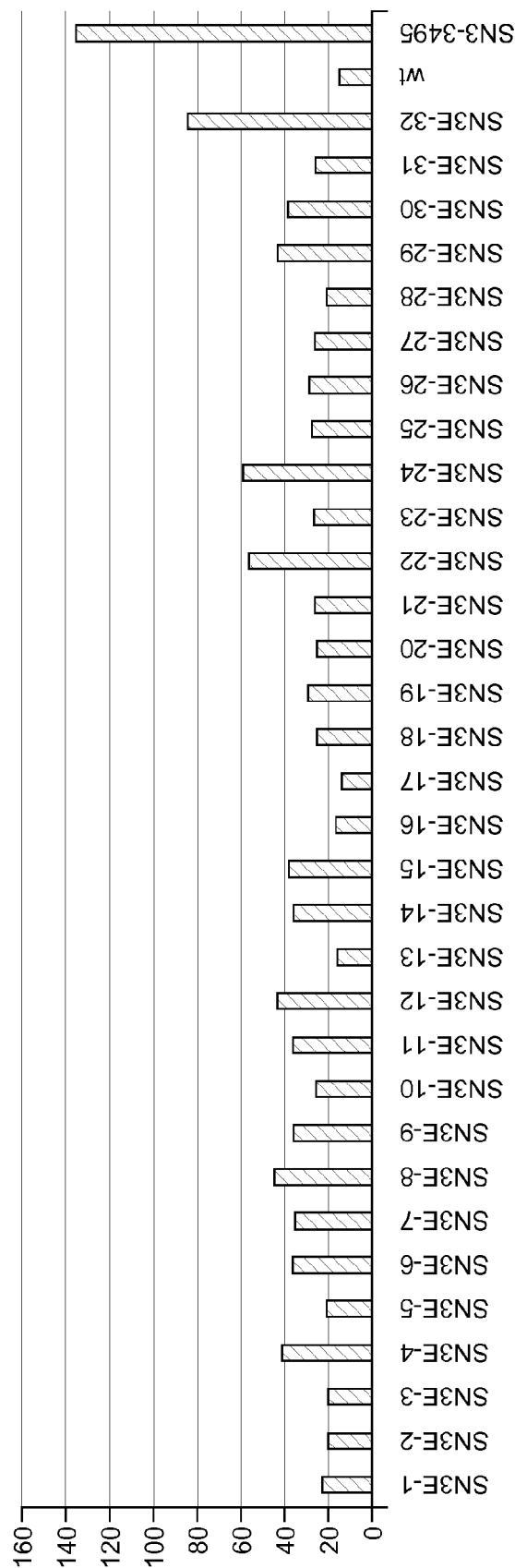
FIG. 47B shows flow cytometry (Guava) results using Nile Red for wild-type *Chlamydomonas reinhardtii* and several SN03 overexpressing strains. "E" represents the endogenous SN03 sequence (SEQ ID NO: 10) from *Chlamydomonas reinhardtii* with a nucleotide sequence coding for a FLAG-MAT tag at the 3' end.

FIGS. 47A and 47B show the higher lipid content, of lines overexpressing the endogenous SN03. Individual transformed lines were grown to mid log phase in 1-10 mL of TAP, stained with. Nile Red and analyzed by flow cytometry (Guava). In FIG. 47A, 18 lines overexpressing the codon optimized endogenous SN03 are represented along the x-axis. The amount of lipid staining in relative fluorescence units (RFU) is shown on the y axis. Wild type *Chlamydomonas reinhardtii* and one line overexpressing the original SN03 (SN03-34) are shown as controls. In FIG. 47B, 32 lines overexpressing the endogenous SN03 are represented along the x-axis. The amount of lipid staining in relative fluorescence units (RFU) is shown on the y axis. Wild type *Chlamydomonas reinhardtii* and one line overexpressing the original SN03 (SN03-34) are shown as controls. As compared to wild type *Chlamydomonas reinhardtii*, overexpression of the both the endogenous SN03 and the codon optimized endogenous SN03 leads to higher lipid content, as seen by Nile Red lipid staining.

Figure 48:
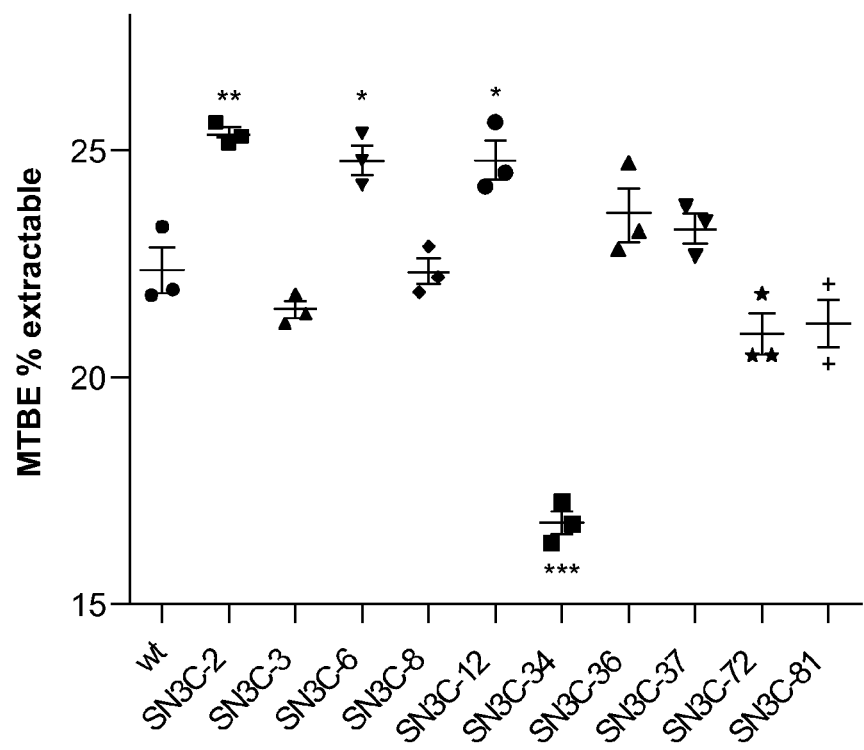
FIG. 48 shows wild-type *Chlamydomonas reinhardtii* and *Chlamydomonas reinhardtii* strains overexpressing SN03 MTBE extracted for lipid content "C" represents the codon-optimized endogenous SN03 sequence (SEQ ID NO: 13)) from *Chlamydomonas reinhardtii* with a nucleotide sequence coding for a FLAG-MAT tag at the 3' end.

FIG. 48 shows increased total extractable lipid in lines overexpressing the codon optimized endogenous SN03. Ten of the lines overexpressing the codon optimized endogenous SN03 along with wild-type cells were grown in 1-2 L of TAP media in an air environment under constant light, until cells reached late log phase. The cells were harvested by centrifugation and analyzed for total gravimetric lipids by methanol/methyl-tert-butyl ether extraction according to a modified Bligh Dyer method (as described in Matyash V., et al. (2008) Journal of Lipid Research 49:1137-1146). The percent extractable lipid is shown on the y axis and the strains are indicated on the x-axis. At least three lines overexpressing the codon optimized endogenous SN03 show increased lipid relative to wild type (indicated by * $P<0.05$ and ** $P<0.01$).

Example 16

Creation of Lines for Knockdown of Endogenous SN03

In this example, microRNA (miRNA) technology is used to knock down the levels of endogenous SN03 RNA. Expression of a transcript may be suppressed by expressing inverted repeat transgenes or artificial miRNAs (Rohr, J., et al., *Plant J,* 40, 611-621 (2004); Molnar et al., *Nature,* 447:1126-1130 (2007); Molnar et al., *Plant J,* 58:3 65-174 (2009)).

The artificial miRNA expression vector was constructed as follows. The modified expression vector, SENuc391 (FIG. 51), was created by using pBluescript II SK(-) (Agilent Technologies, CA) as a vector backbone. The segment labeled "Aph 7"" was the hygromycin resistance gene from *Streptomyces hygroscopicus*. The first intron from the *Chlamydomonas reinhardtii* rbcS2 gene was cloned into Aph 7" in order to increase expression levels and consequentially, the number of transformants (Berthold et al *Protist* 153:401-412 (2002)). Aph 7" was preceded by the *Chlamydomonas reinhardtii* β2-tubulin promoter and was followed by the *Chlamydomonas reinhardtii* rbcS2 terminator. The hygromycin resistance cassette was cloned into the NotI and XbaI sites of pBluescript II SK(-). Subsequently, the segment labeled "Hybrid Promoter" indicates a fused promoter region beginning with the *C. reinhardtii* Hsp70A promoter, *C. reinhardtii* rbcS2 promoter, and the first intron from the *C. reinhardtii* rbcS2 gene (Sizova et al *Gene,* 277:221-229 (2001)). The "Hybrid Promoter" was PCR amplified using overlapping primers while introducing restriction sites to both the 5' (XbaI) and 3' (NdeI, BamHI, KpnI) ends. This PCR-generated fragment was cloned into the XbaI and KpnI sites of the hygromycin resistance cassette-containing pBluescript II SK(-). The segment labeled "Aph VIII" was the paromomycin resistance gene flanked by the promoter and terminator of the *C. reinhardtii* psaD gene. The cassette was blunt end ligated into the digested KpnI site treated with Klenow.

The generation of the precursor scaffold was performed similarly as previously described (Molnar et al., *Plant J,* 58:165-174 (2009)). The 5' arm of the precursor scaffold was amplified from *C. reinhardtii* genomic DNA by two primers Arm Primer 1 (SEQ ID NO: 44) and Arm Primer 2 (SEQ ID NO: 45). The 3' arm of the precursor scaffold was amplified by the two primers Arm Primer 3 (SEQ ID NO: 46) and Arm Primer 4 (SEQ ID NO: 47). The two resulting PCR fragments were gel purified and fused together in a PCR reaction using the primers Arm Primer 1 (SEQ ID NO: 44) and Arm Primer 4 (SEQ ID NO: 47) resulting in a 259 bp fusion product. The PCR fragment was gel-purified, digested with AseI and BamHI, and ligated into the NdeI and BamHI sites of SEnuc391.

The transcript IDs of SN03 was submitted to the Web MicroRNA Designer (Ossowski et al., *Plant J,* 53:674-690; WMD3, http://wmd3.weigelworld.org/). The predicted miRNAs (SEQ ID NOs: 38-41) were converted to full stem-loop sequences, including the endogenous cre-MIR1157 spacer, and the corresponding miRNA*, using the WMD3 Oligo function with "pChlamiRNA2 and 3" selected as the vector. The resulting sequences were modified by adding flanking BglII sites, as well as adding sequence complementary to the 5' end of the anti sense strand of the BD11 (SEQ ID NO: 48) sequence to the 3' end. The modified sequences were synthesized. In order to clone the miRNA stem-loop sequences into SENuc391, a complementary strand was first added by PCR amplification in the presence of BD11, each ultramer, and a primer (SEQ ID NO: 49) in a 2-cycle Phusion PCR reaction following the manufacturer's instructions (Finnzymes). The resulting double-stranded DNA fragments were cloned into the BglII site of SENuc391. The resulting plasmid was sequenced for the appropriate orientation.

Preparation of the transformation DNA involves a restriction digest with the enzymes PsiI to linearize the DNA. All transformations were carried out on *C. reinhardtii* cc1690 (mt+). Cells were grown and transformed via electroporation. Cells were grown to mid-log phase (approximately $2-6 \times 10^6$ cells/ml) in TAP media. Cells were spun down gently (between 2000 and $5000 \times g$) for 5 min. The supernatant was removed and the cells were resuspended in TAP media+40 mM sucrose. 1 µg (in 1-5 µL $H_2O$) of transformation DNA was mixed with 250 µL of $3 \times 10^8$ cells/mL on ice and transferred to 0.4 cm electroporation cuvettes. Electroporation was performed with the capacitance set at 25 uF, the voltage at 800 V to deliver 2000 V/cm resulting in a time constant of approximately 10-14 ms. Following electroporation, the cuvette was returned to room temperature for 5-20 min. Cells were transferred to 10 ml of TAP media+40 mM sucrose and allowed to recover at room temperature for 12-16 hours with continuous shaking. Cells were then harvested by centrifugation for 5 min at between $2000 \times g$ and $5000 \times g$, the supernatant was discarded, and the pellet was resuspended in 0.5 ml TAP media+40 mM sucrose. The resuspended cells were then plated on solid TAP media+10 µg/mL hygromycin and +10 µg/mL paromomycin.

Example 17

Characterization of SN03 Knockdown Lines

Figure 46A:
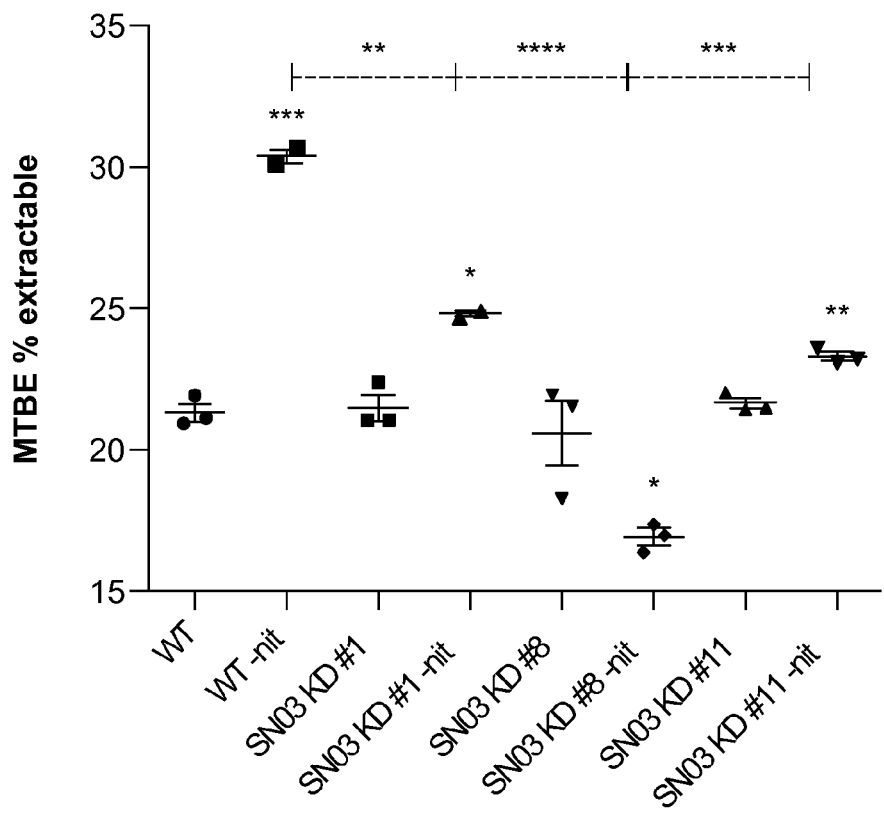
FIG. 46A shows MTBE extraction of wild type *Chlamydomonas reinhardtii* and three SN03 knockdown lines in the presence and absence of nitrogen.

First, lipid content in SN03 knockdown lines in the presence and absence of nitrogen was analyzed. Wild-type *Chlamydomonas reinhardtii* cells and three lines expressing the SN03 miRNA knockdown were grown in 1-2 L of TAP media containing 7.5 mM $NH_4Cl$ in an air environment under constant light, until cells reached early log phase. The culture was centrifuged at 3000 to $5000 \times g$ for 5-10 minutes and one half of the culture was washed with 100-500 mL TAP, the other half with 100-500 mL TAP containing no nitrogen. After re-centrifigation, the cultures were resuspended in a volume equivalent to the starting culture volume. After 2-3 days of nitrogen starvation, cells were harvested by centrifugation and analyzed for total gravimetric lipids by methanol/methyl-tert-butyl ether extraction according to a modified Bligh Dyer method (as described in Matyash V., et al. (2008) Journal of Lipid Research 49: 1137-1146). FIG. 46A shows data points with error bars at mean +/- standard deviation. The y-axis represents percent extractables and the x-axis represents the strains as described above. The stars (*-****) above each sample labeled "-nit" indicates a comparison wish the partner sample that was grown in the presence of nitrogen. The stars (*-****) above the bar at top indicates a comparison of each sample labeled with "-nit" to the wild type sample grown in the absence of nitrogen. (* $P<0.05$,  $P<0.01$, * $P<0.001$, **** $P<0.0001$ (unpaired t-test)). This data shows that in the SN03 knockdown lines, starvation does not produce the same level of lipid increase as in the wild type strain, indicating that the SN03 RNA and protein are necessary for the complete level of lipid induction seen in wild type upon nitrogen starvation.

Figure 46B:
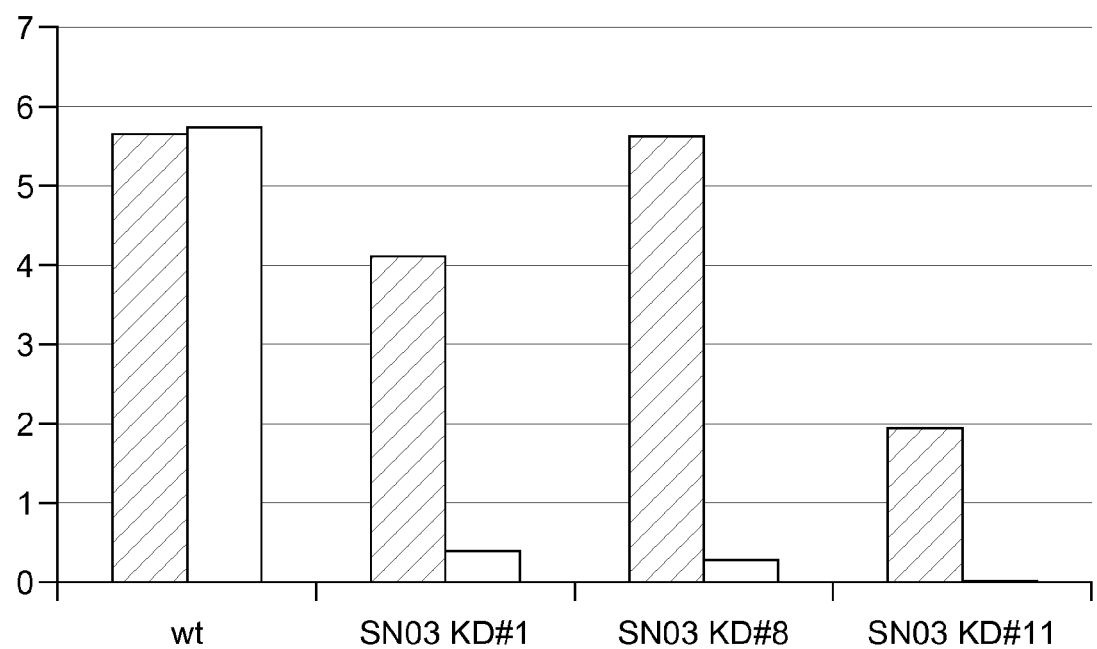
FIG. 46B shows upregulation of SN03 RNA and a stress induced protein kinase RNA by qPCR in wild type *Chlamydomonas reinhardtii* and three SN03 knockdown lines upon nitrogen starvation.
Figure 51:
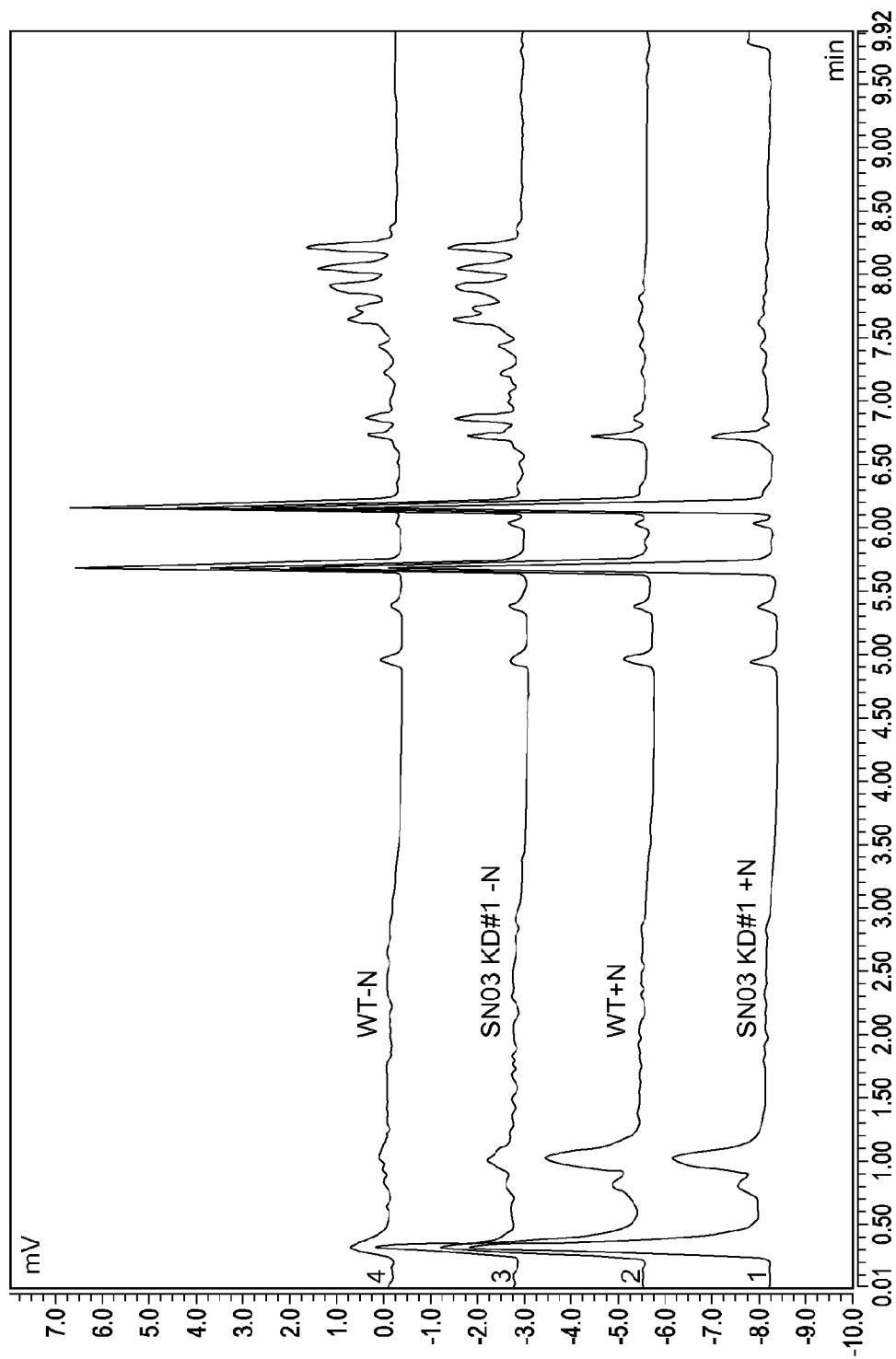
FIG. 51 shows HPLC analyses of wild type and SN03 knock-down line in the presence and absence of nitrogen.
Figure 52:
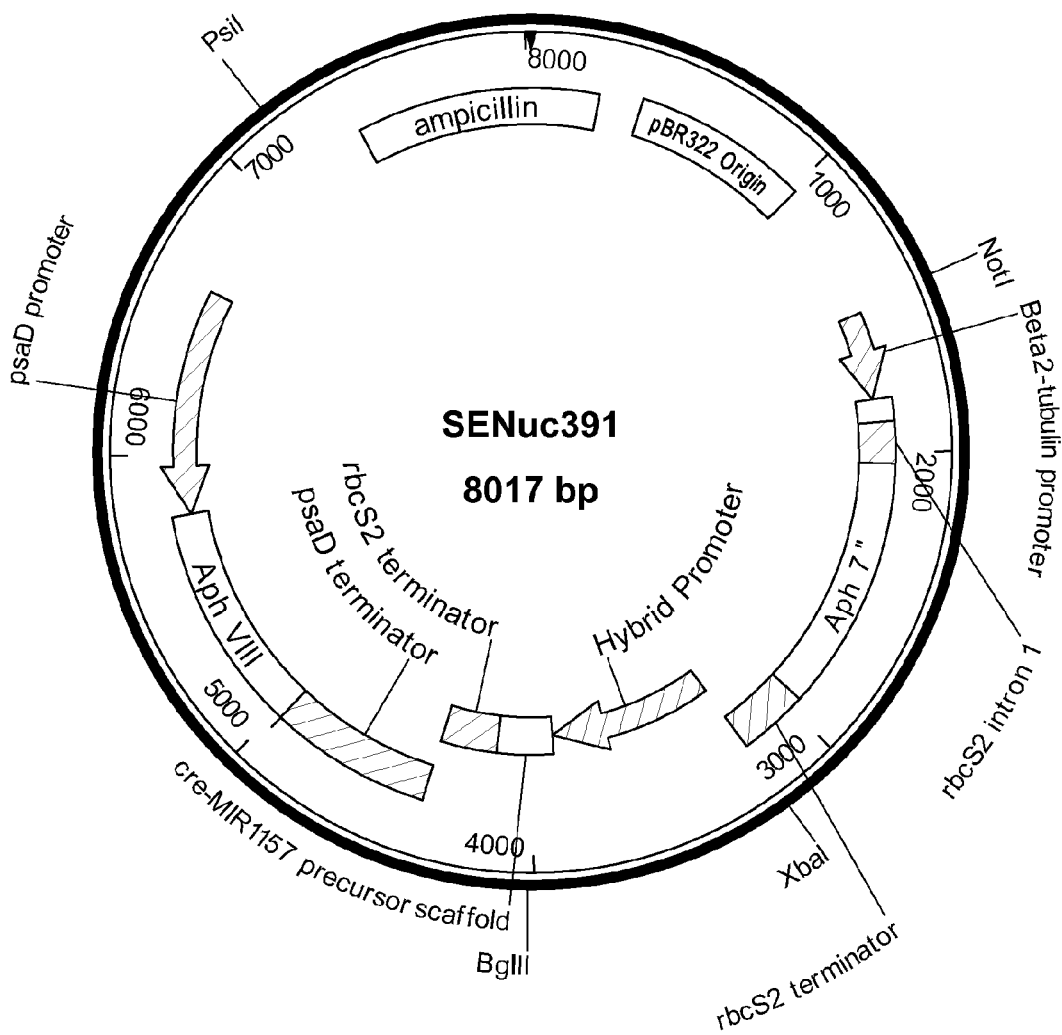
FIG. 52 shows a miRNA expression vector.

HPLC analysis of the MTBE extracted oil from, wild type *Chlamydomonas reinhardtii* and an SN03 knockdown line grown in the presence and absence of nitrogen demonstrates that some changes in lipid profile can still occur in the SN03 knockdown line upon nitrogen starvation. FIG. 51 shows four HPLC chromatograms. MTBE extracted oils were ran on reverse-phase HPLC on a C18 column. Mobile phase was Acetonitrile/water/THF run over 10 minutes and flow rate of 0.9 mL/min. Detection was via an Evaporative Light Scattering Detector (ELSD). The four chromatograms are labeled with sample names for an SN03 knockdown line (SN03 KD#1 +N) grown in the presence of nitrogen, wild type grown in the presence of nitrogen (WT +N), an SN03 knockdown line (SN03 KD#1 −N) grown in the absence of nitrogen, and wild type grown in the absence of nitrogen (WT −N). The y-axis is the ELSD signal representing abundance and the x axis is HPLC column retention time (in minutes). The peaks between 7 and 8.5 minutes retention time represent TAGs, which are present in both samples grown in the absence of nitrogen.

qPCR was used to demonstrate that the SN03 miRNA knockdown constructs are specific to the SN03 RNA. Wild-type *Chlamydomonas reinhardtii* cells and lines expressing the SN03 miRNA knockdown were grown in 10-100 mL of TAP media containing 7.5 mM $NH_4Cl$ in an air environment under constant light, until cells reached early log phase. The culture was centrifuged at 3000 to 5000×g for 5-10 minutes and one half of the culture was washed with 10-50 mL TAP, the other half with 10-50 mL TAP containing no nitrogen. After re-centrifugation, the cultures were resuspended in a volume equivalent to the starting culture volume. After 2-3 days of nitrogen starvation, cells were harvested by centrifugation. Total RNA was prepared from wild type and 3 SN03 knockdown lines. 0.25-1.0 ug of RNA was used for iScript cDNA synthesis (BioRad, USA) and standard qPCR using iQ SybrGreen (BioRad, USA) detection was performed. Relative RNA levels were determined by qPCR using primers that amplify the SN03. A positive control for nitrogen starvation was a stress induced protein kinase. Standard qPCR using SybrGreen detection was performed using *Chlamydomonas reinhardtii* ribosomal protein L11 for normalization between samples. FIG. 46B shows the levels of induction of the endogenous SN03 (gray column) and the stress induced protein kinase (black column) with the fold induction upon nitrogen starvation shown on the y axis. The x axis shows the strains used. Both SN03 and the protein kinase are induced in wild type, while the induction of SN03 is reduced in the knockdown lines where the protein kinase is unaffected. This demonstrates the effectiveness and specificity of the SN03 knockdown lines.

Example 18

Combining the Effects of SN03 with Other Traits

This example describes multiple methods to combine SN03 overexpression with other transgenic lines and/or modified strains that have phenotypes different from a wild type strain.

For example, one or more additional overexpression genes could be combined with SN03 overexpression, either by transforming the vector containing SN03 into a transgenic strain that already contains one or more overexpression genes, or by transforming one or more genes into a strain overexpressing SN03.

Another exemplary combination could be one or more knockdown, or knockout genes combined with SN03 overexpression, either by transforming the vector containing SN03 into a transgenic strain that already contains one or more knockdown, or knockouts, or by transforming one or more knockout or knockdown constructs into a strain overexpressing SN03.

Another method would be to transform SN03 into a strain that has been modified through mutagenesis or evolution to have a particular phenotype. Alternatively, a strain overexpressing SN03 could be mutagenized or evolved to produce an additional phenotype.

In these approaches, the additional phenotype that is combined with SN03 could be, for example, a lipid phenotype that produces additional lipid accumulation or additional lipid profile changes. Alternatively, the additional phenotype could be other than a lipid phenotype, such as a change in growth, a change in chlorophyll metabolism, resistance to some biotic or abiotic stress, or other.

One of skill in the art would be able to make numerous additional combinations, regarding the methods described above, in order to study the effects of combining the expression of SN03 with other traits.

Example 19

Using SN03 Knockdown to Identify Additional Gene(s) Involved in Nitrogen Starvation Pathway(s)

This example describes a method to identify genes involved in the nitrogen starvation phenotype using a transgenic line in which the SN03 gene is knocked down or knocked out. We expect that the genes whose expression is modified by knockdown of the endogenous SN03 will be a subset of the genes affected by nitrogen starvation. This data will help us understand what downstream pathways the SN03 protein is acting upon to produce more lipid and to alter the lipid profile.

One way to identify such genes is to grow wild type and an SN03 knockdown/out transgenic line in the presence and absence of nitrogen. An analysis of gene expression, protein levels and/or metabolic products could then be performed. One method to use for this analysis is the RNA-Seq methodology, which would produce lists of candidate genes based on which genes are up or down regulated in the samples.

There are many useful approaches to generating knockdown or knockouts of SN03. As mentioned above, the expression of an artificial miRNA led to a decrease in transcript levels. Other methods of RNA silencing involve the use of a tandem inverted repeat system (Rohr et al. *Plant J*, 40:611-621 (2004)) where a 100-500 bp region of the targeted gene transcript is expressed as an inverted repeat. The advantage of silencing is that there can be varying degrees in which the target transcript is knocked down. Oftentimes, expression of the transcript is necessary for the viability of the cell. Thus, there can exist an intermediate level of expression that allows for both viability and also the desired phenotype (e.g. lipid induction). Finding the specific level of expression that is necessary to produce the phenotype is possible through silencing.

Homologous recombination can be carried out by a number of methods and has been demonstrated in green algae (Zorin et al. *Gene*, 423:91-96 (2009); Mages et al., *Protist* 158:435-446 (2007)). A knock out can be obtained through homologous recombination where the gene product (e.g. mRNA transcript) is eliminated by gene deletion or an insertion of exogenous DNA that, disrupts the gene.

Gene Deletion

One such way is to PCR amplify two non-contiguous regions (from several hundred DNA base pairs to several thousand DNA base pairs) of the gene. These two non-contiguous regions are referred to as Homology Region 1 and Homology Region 2 are cloned into a plasmid. The plasmid can then be used to transform the host organism to create a knockout.

Gene Insertion

Another way is to PCR amplify two contiguous or two non-contiguous regions (from several hundred DNA base pairs to several thousand DNA base pairs) of the gene. A third sequence is ligated between the first and second regions, and the resulting construct is cloned into a plasmid. The plasmid can then be used to transform the host organism to create a knockout. The third sequence can be, for example, an antibiotic selectable marker cassette, an auxotrophic marker cassette, a protein expression cassette, or multiple cassettes.

Growth Rate

A substantial decrease in the growth rate of a transformed organism as compared to an untransformed organism is, for example, about 2%, about 4%, about 6%, about 8%, about 10%, about 12%, about 14%, about 16%, about 18%, about 20%, about 22%, about 24%, about 26%, about 28%, or about 30%.

A substantial decrease in the growth rate of a transformed organism as compared to an untransformed organism is, for example, at least 2%, at least 4%, at least 6%, at least 8%, at least 10%, at least 12%, at least 14%, at least 16%, at least 18%, at least 20%, at least 22%, at least 24%, at least 26%, at least 28%, or at least 30%.

Chlorophyll Breakdown

A substantial decrease in the breakdown of chlorophyll in a transformed organism as compared to an untransformed organism is, for example, about 2%, about 4%, about 6%, about 8%, about 30%, about 12%, about 14%, about 16%, about 18%, about 20%, about 22%, about 24%, about 26%, about 28%, or about 30%.

A substantial decrease in the breakdown of chlorophyll in a transformed organism as compared to an untransformed organism is, for example, at least 2%, at least 4%, at least 6%, at least 8%, at least 10%, at least 12%, at least 14%, at least 16%, at least 18%, at least 20%, at least 22%, at least 24%, at least 26%, at least 28%, or at least 30%.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A non-vascular photosynthetic organism transformed with a polynucleotide, wherein the polynucleotide comprises: (a) a nucleic acid sequence of SEQ ID NO: 9, SEQ ID NO: 12, or SEQ ID NO: 4; or (b) a nucleic acid sequence with at least 95%, at least 98%, or at least 99% sequence identity to the nucleic acid sequence of SEQ ID NO: 9, SEQ ID NO: 12, or SEQ ID NO: 4, wherein the transformed organism has an increased lipid content than the untransformed organism.

2. The transformed organism of claim 1, wherein the nucleic acid sequence encodes a polypeptide comprising an amino add sequence of SEQ ID NO: 52 or SEQ ID NO: 51, or at least 95%, at least 98%, or at least 99% sequence identity to the amino acid sequence of SEQ ID NO: 52 or SEQ ID NO: 51.

3. The transformed organism of claim 1, wherein the transformed organism is an alga or a photosynthetic bacterium.

4. The transformed organism of claim 3, wherein the photosynthetic bacterium is a cyanobacterium.

5. The transformed organism of claim 3, wherein the alga is a microalga.

6. The transformed organism of claim 1, wherein the increase is shown by a change in the amount of total lipids.

7. The transformed organism of claim 1, wherein the increase is shown by a change in the amount of total gravimetric lipids.

8. The transformed organism of claim 1, wherein the increase is shown by a change in percent lipids by use of hexane extraction.

9. The transformed organism of claim 1, wherein the increase is shown by a change in percent lipids by use of methyl tert-butyl ether (MTBE) extraction.

10. The transformed organism of claim 1, wherein the lipid is a triacylglycerol (TAG), a diacylglycerol (DAG), a glycosylglycerol, a neutral storage lipid, a polar lipid, a fat, a wax, a sterol, a fat-soluble vitamin, a monoglyceride, a diglyceride, a triglyceride, a phospholipid, a fatty acyl, a glycerolipid, a glycerophospholipid, a sphingolipid, a polyketide, a sterol lipid, a prenol lipid, a fatty acid, a fatty acid derivative, a sterol-containing metabolite, or a combination of any two or more thereof.

11. The transformed organism of claim 1, wherein the increase is determined by use of methyl-tert-butyl ether (MTBE) extraction.

12. The transformed organism of claim 1, wherein the increase is determined by use of a lipid dye.

13. The transformed organism of claim 12, wherein the lipid dye is Bodipy, LipidTOXgreen, or Nile Red.

14. The transformed organism of claim 1, wherein the lipid is stored in a lipid body, a cell membrane, an interthylakoid space, or a plastoglubuli of the transformed organism.

15. A method of increasing lipid content of a non-vascular photosynthetic organism, comprising: i) transforming the organism with a polynucleotide comprising a nucleotide sequence encoding a protein expressed in the transformed organism, wherein expression of the protein results in an increase in the lipid content of the transformed organism as compared to the untransformed organism, and wherein the nucleotide sequence comprises, (a) a nucleic acid sequence of SEQ ID NO: 9, SEQ ID NO: 12, or SEQ ID NO: 4, or (b) a nucleic acid sequence with at least 95%, at least 98%, or at least 99% sequence identity to the nucleic acid sequence of SEQ ID NO: 9, SEQ ID NO: 12, or SEQ ID NO: 4.

16. The method of claim 15, wherein the protein comprises an amino acid sequence of SEQ ID NO: 52 or SEQ ID NO: 51, or encodes a polypeptide comprising at least 95%, at least 98%, or at least 99% sequence identity to the amino acid sequence of SEQ ID NO: 52 or SEQ ID NO: 51.

17. The method of claim 15, further comprising determining the change increase by use of methyl-tert-butyl ether (MTBE) extraction or use of a lipid dye.

18. The transformed organism of claim 1, wherein said polynucleotide comprises: (a) a nucleic acid sequence of SEQ ID NO: 9, SEQ ID NO: 12, or SEQ ID NO: 4; or (b) a nucleic acid sequence with at least 95% 98% sequence identity to the nucleic acid sequence of SEQ ID NO: 9, SEQ ID NO: 12, or SEQ ID NO: 4.

19. The transformed organism of claim 2, wherein said nucleic acid sequence or nucleotide sequence encodes a polypeptide comprising an amino acid sequence of SEQ ID NO: 52 or SEQ ID NO: 51, or at least 98% sequence identity to the amino acid sequence of SEQ ID NO: 52 or SEQ ID NO: 51.

20. The method of claim 15, wherein nucleotide sequence comprises, (a) a nucleic acid sequence of SEQ ID NO: 9, SEQ ID NO: 12, or SEQ ID NO: 4, or (b) a nucleic acid sequence with at least 98% sequence identity to the nucleic acid sequence of SEQ ID NO: 9, SEQ ID NO: 12, or SEQ ID NO: 4.

21. The method of claim 16, wherein said comprising an amino acid sequence of SEQ ID NO: 52 or encodes a polypeptide comprising at least 98% sequence identity to the amino acid sequence of SEQ ID NO: 52.

22. The transformed organism of claim 1, wherein said polynucleotide comprises: (a) a nucleic acid sequence of SEQ ID NO: 9, SEQ ID NO: 12, or SEQ ID NO: 4; or (b) a nucleotide sequence with at least 99% sequence identity to the nucleic acid sequence of SEQ ID NO: 9, SEQ ID NO: 12, or SEQ ID NO: 4.

23. The transformed organism of claim 2, wherein said nucleic acid sequence or nucleotide sequence encodes a polypeptide comprising an amino acid sequence of SEQ ID NO: 52 or SEQ ID NO: 51, or at least 99% sequence identity to the amino acid sequence of SEQ ID NO: 52 or SEQ ID NO: 51.

24. The method of claim 15, wherein nucleotide sequence comprises, (a) a nucleic acid sequence of SEQ ID NO: 9, SEQ ID NO: 12, or SEQ ID NO: 4, or (h) a nucleic acid sequence with at least 99% sequence identify to the nucleic add sequence of SEQ ID NO: 9, SEQ ID NO: 12, or SEQ ID NO: 4.

25. The method of claim 16, wherein said polypeptide comprising an amino acid sequence of SEQ ID NO: 52 or at least 98% sequence identity to the amino acid sequence of SEQ ID NO: 52.

* * * * *